(12) United States Patent
Zhu et al.

(10) Patent No.: US 12,258,360 B2
(45) Date of Patent: Mar. 25, 2025

(54) COMPOSITIONS AND METHODS FOR TREATMENT OF ANTICANCER-DRUG RESISTANT CANCERS

(71) Applicant: THE GEORGE WASHINGTON UNIVERSITY, Washington, DC (US)

(72) Inventors: Wenge Zhu, Germantown, MD (US); Jing Li, Arlington, VA (US); Yiliang Li, Tianjin (CN)

(73) Assignee: The George Washington University, Washington, DC (US)

( * ) Notice: Subject to any disclaimer, the term of this patent is extended or adjusted under 35 U.S.C. 154(b) by 255 days.

(21) Appl. No.: 17/944,506

(22) Filed: Sep. 14, 2022

(65) Prior Publication Data

US 2023/0129381 A1 Apr. 27, 2023

Related U.S. Application Data

(63) Continuation of application No. PCT/US2021/026164, filed on Apr. 7, 2021.

(30) Foreign Application Priority Data

Apr. 7, 2020 (CN) .......................... 202010271412.4

(51) Int. Cl.
| | |
|---|---|
| *C07F 5/02* | (2006.01) |
| *A61K 31/69* | (2006.01) |
| *A61P 35/00* | (2006.01) |
| *C07D 311/02* | (2006.01) |

(52) U.S. Cl.
CPC .............. *C07F 5/025* (2013.01); *A61K 31/69* (2013.01); *A61P 35/00* (2018.01); *C07D 311/02* (2013.01)

(58) Field of Classification Search
CPC ....... A61P 35/00; A61K 31/69; C07D 311/02; C07F 5/025
See application file for complete search history.

(56) References Cited

U.S. PATENT DOCUMENTS

2018/0230169 A1 8/2018 Ramanujachary et al.

FOREIGN PATENT DOCUMENTS

| CN | 111333672 A | 6/2020 |
|---|---|---|
| WO | WO 2019140265 A1 | 7/2019 |

OTHER PUBLICATIONS

Zhang, J. et al., "The synthesis of benzoxaboroles and their applications in medicinal chemistry", Science china chemistry, 2013, vol. 56, No. 10, pp. 1372-1381.
Nocentini, A. et al., "Benzoxaborole compounds for therapeutic uses: a patent review (2010-2018)", Expert opinion on therapeutic patents, 2018, vol. 28, No. 6, pp. 493-504.
Zhang, Y.-K. et al., "Synthesis and structure-activity relationships of novel benzoxaboroles as a new class of antimalarial agents", Bioorganic & medicinal chemistry letters, 2011, vol. 21, No. 2, pp. 644-651.
Liu, C. T. et al., "The unique chemistry of benzoxaboroles: Current and emerging applications in biotechnology and therapeutic treatments", Bioorganic & medicinal chemistry, 2014, vol. 22, No. 16, pp. 4462-4473.

(Continued)

*Primary Examiner* — Savitha M Rao
(74) *Attorney, Agent, or Firm* — Kory D. Christensen

(57) ABSTRACT

Embodiments of the instant disclosure relate to novel methods and compositions for treating tumors resistant to one or more anticancer drugs, such as platinum-based chemotherapeutics.

18 Claims, 74 Drawing Sheets
(59 of 74 Drawing Sheet(s) Filed in Color)

(56) References Cited

OTHER PUBLICATIONS

Zhang, J. et al. "Design, Synthesis, and Structure-Activity Relationship of 7-Propanamide Benzoxaboroles as Potent Anticancer Agents." Journal of medicinal chemistry vol. 62, 14 (2019): 6765-6784. doi:10.1021/acs.jmedchem. 9b00736.

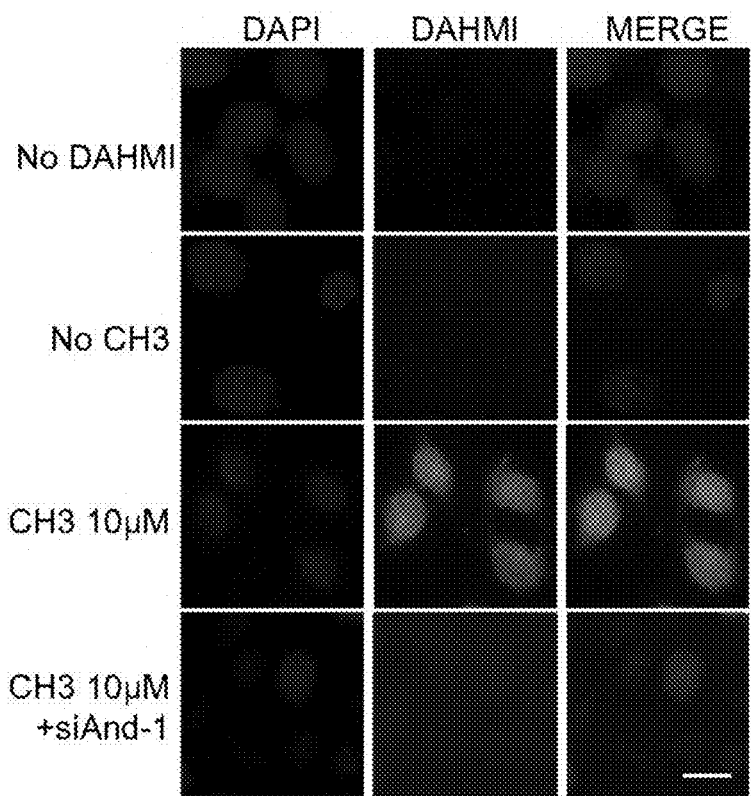
Fig. 16D
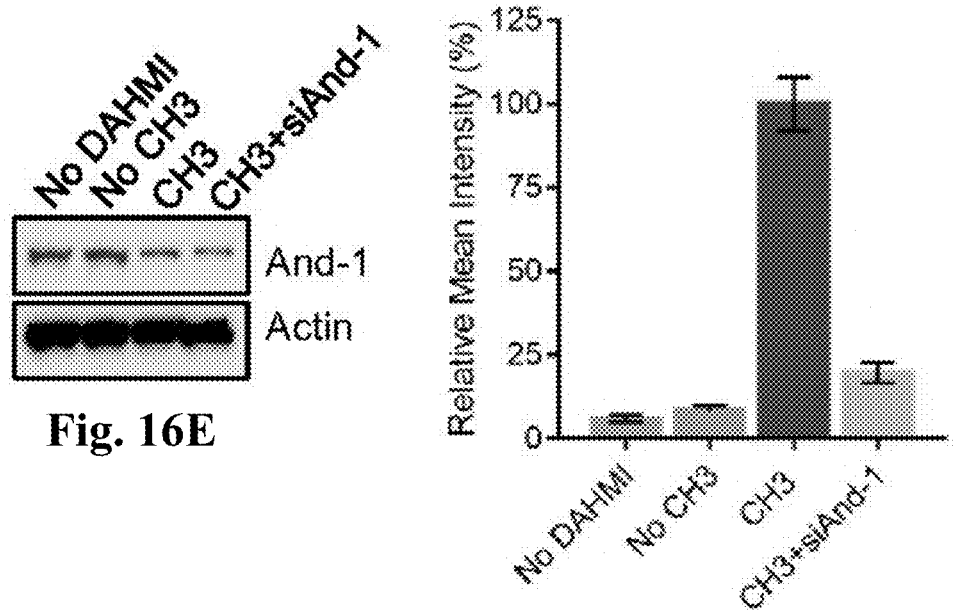
Fig. 16E
Fig. 16F

Fig. 22C  Fig. 22D

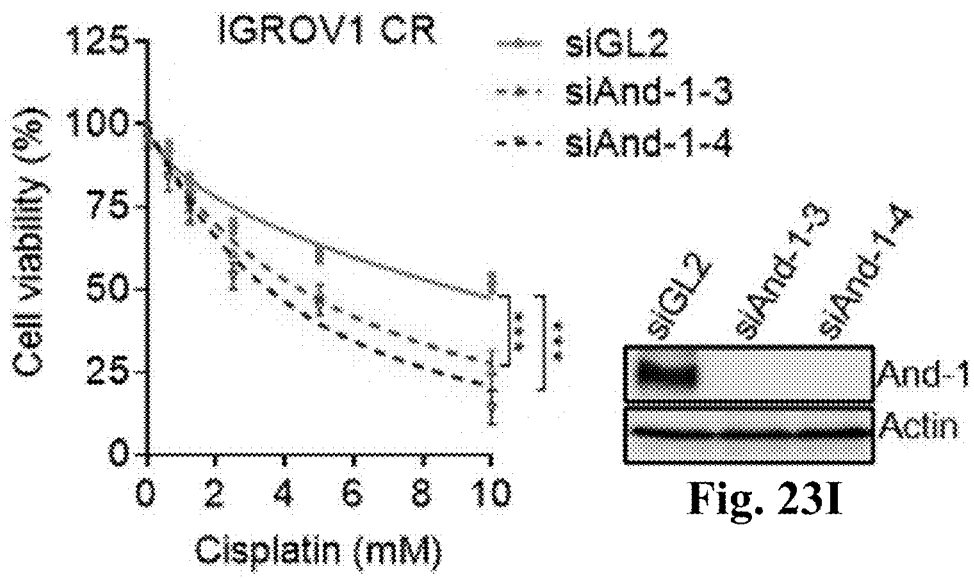
Fig. 23H
Fig. 23I
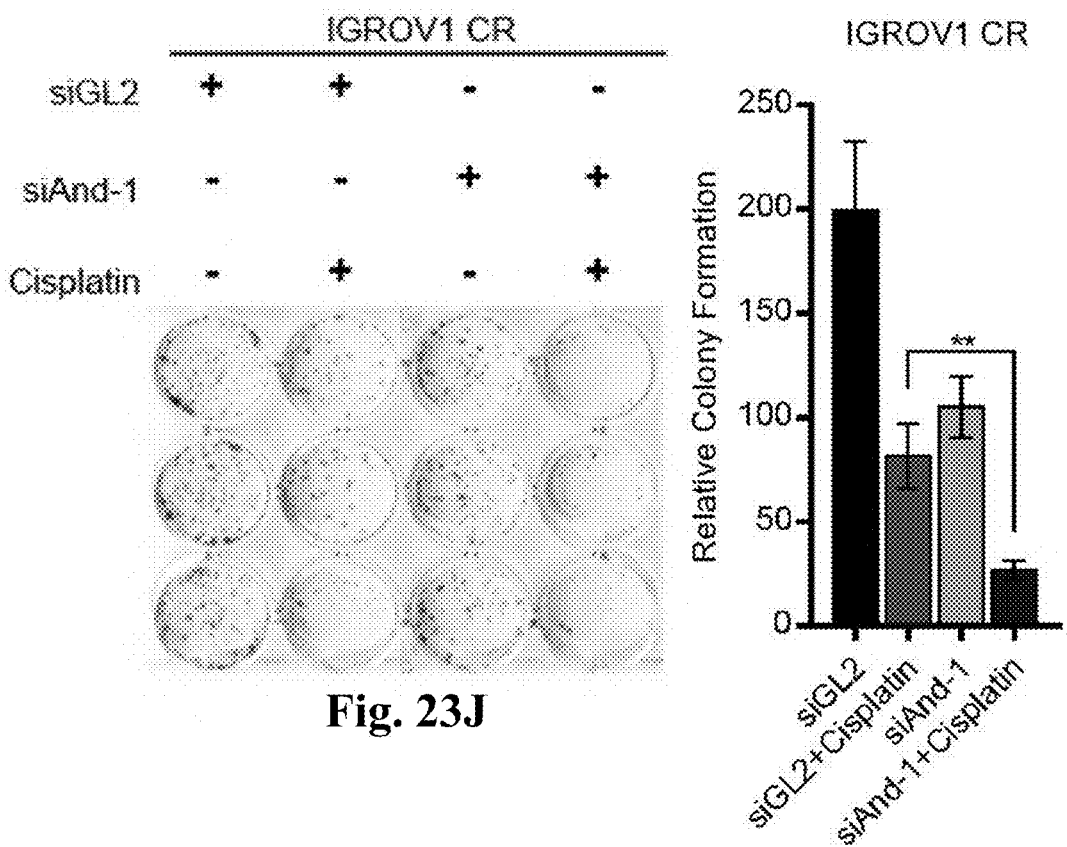
Fig. 23J
Fig. 23K

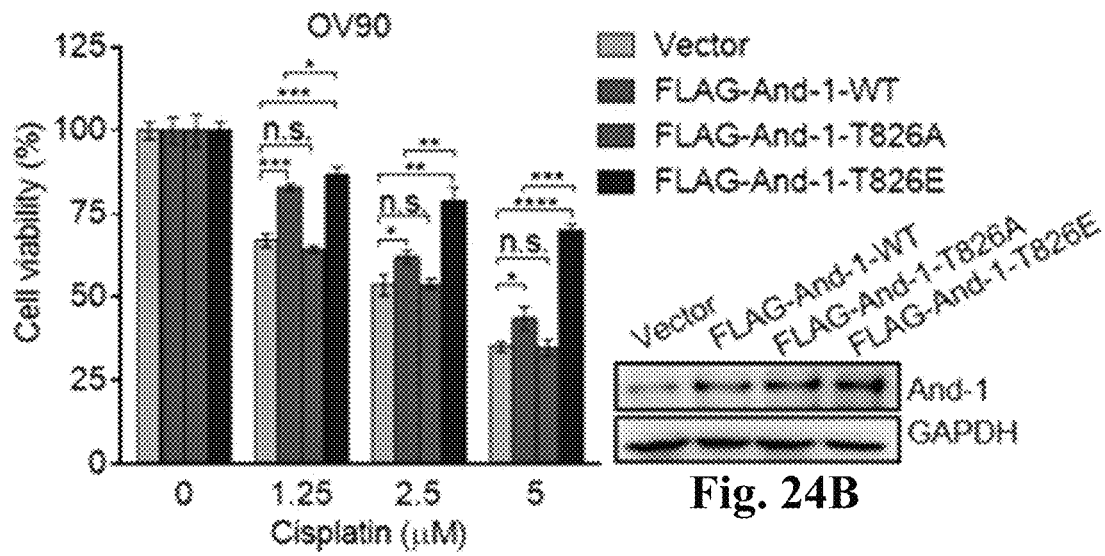
Fig. 24A
Fig. 24B
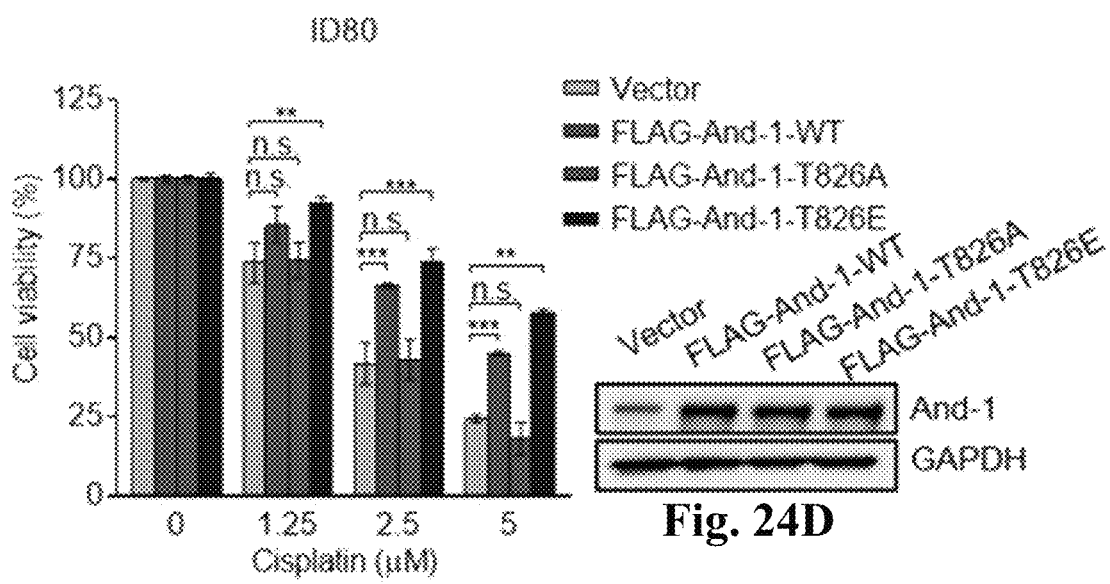
Fig. 24C
Fig. 24D

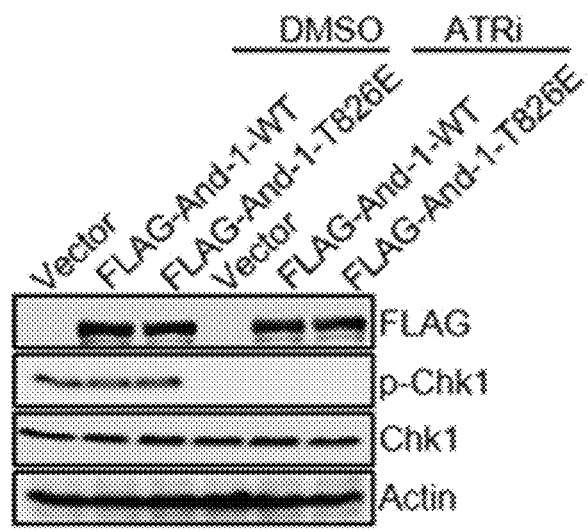
Fig. 24E
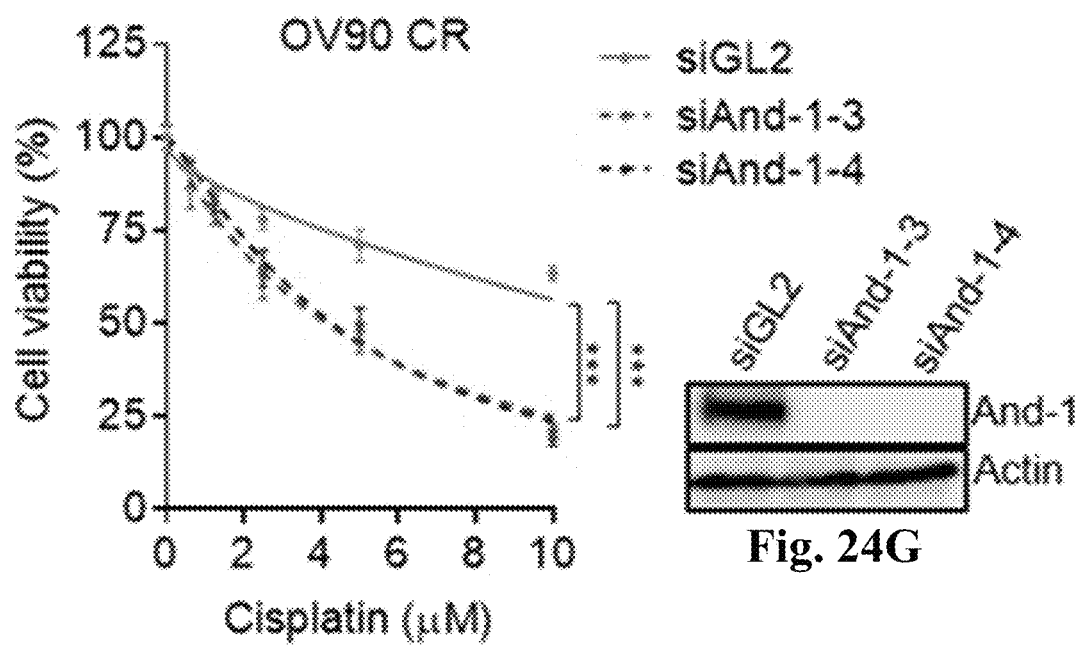
Fig. 24F
Fig. 24G

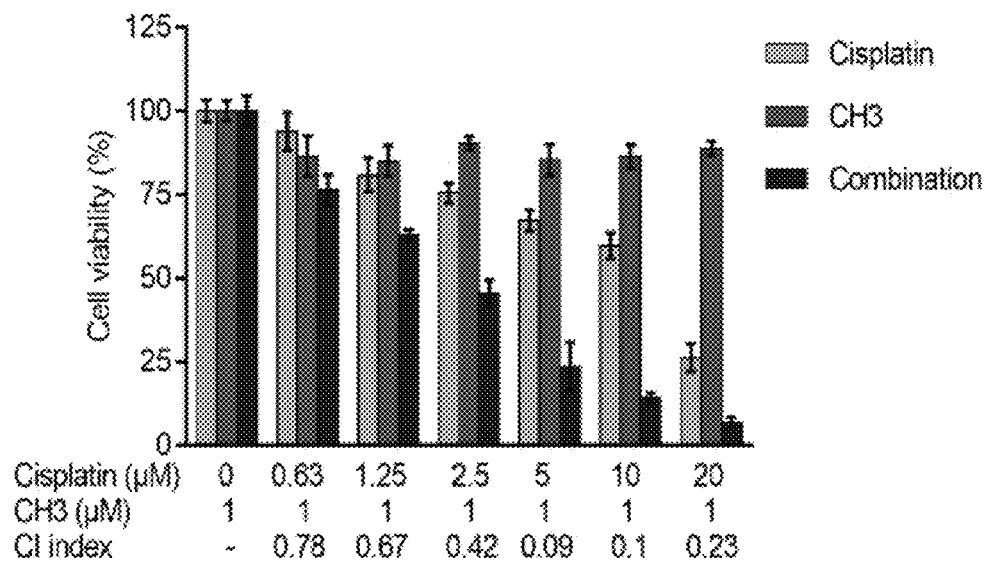
Fig. 30A
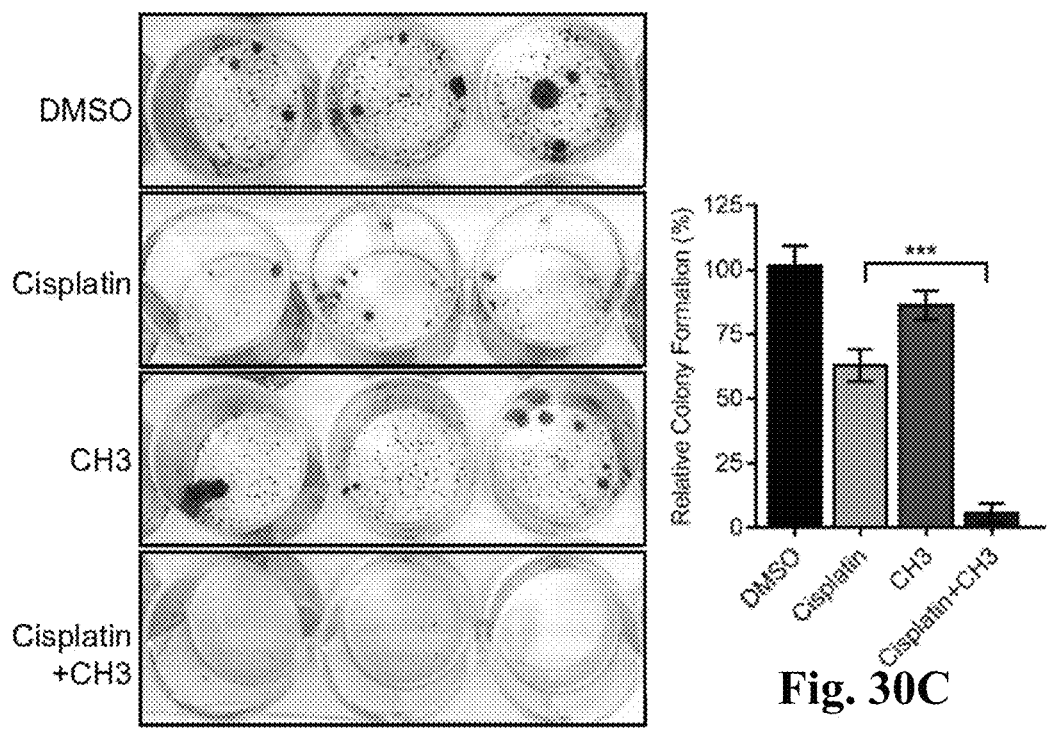
Fig. 30B
Fig. 30C

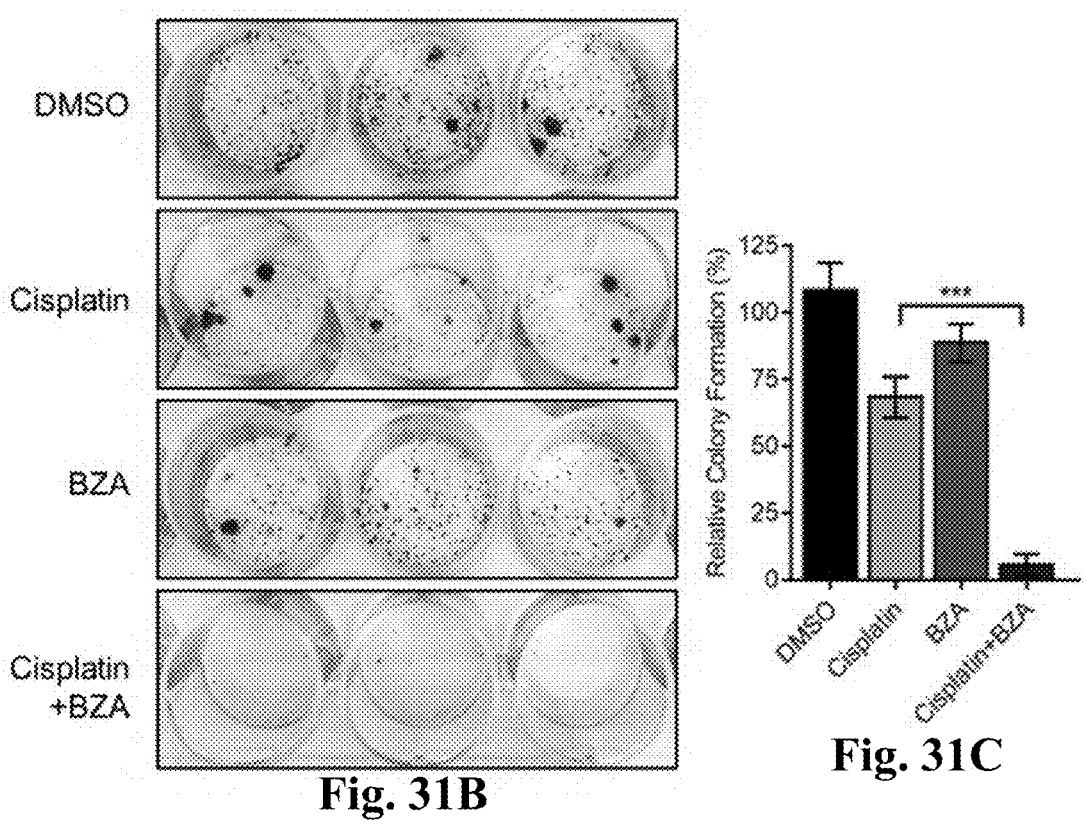
Fig. 31B
Fig. 31C
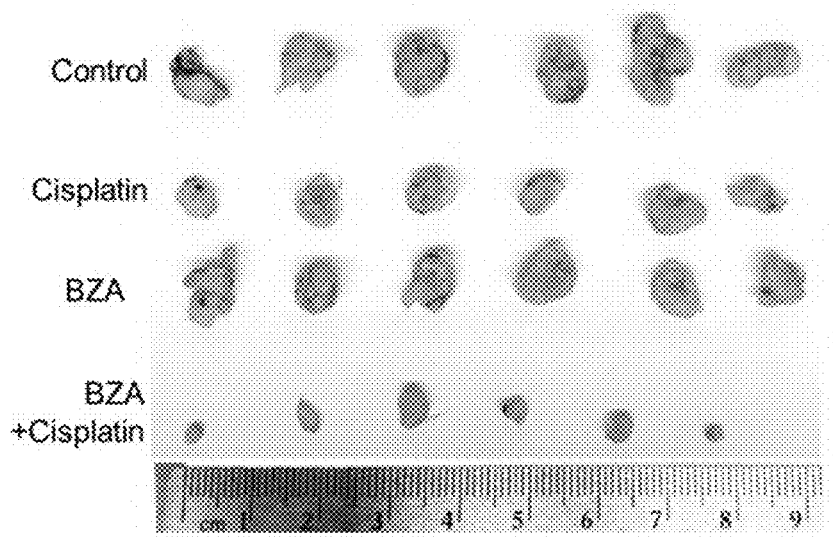
Fig. 31D

Benzoxaborole

Travaborole

COMPOSITIONS AND METHODS FOR TREATMENT OF ANTICANCER-DRUG RESISTANT CANCERS

CROSS-REFERENCE TO RELATED APPLICATION

This application is a continuation of PCT Application No. PCT/US2021/026164, filed on Apr. 7, 2021, which claims the benefit of Chinese Patent Application No. 202010271412.4, filed on Apr. 7, 2020, each of which is hereby incorporated by reference in its entirety.

GOVERNMENTAL RIGHTS

This invention was made with government support under CA184717 awarded by the National Institutes of Health. The government has certain rights in the invention.

FIELD

The present disclosure generally relates to compositions and methods for the treatment of cancer and tumor cells, prevention of tumor cell metastasis, and treatment and prevention of cancers and of cancers resistant to one or more anticancer drugs, such as platinum-based chemotherapeutics.

BACKGROUND

Anticancer drugs, such as platinum-based chemotherapy regimens, are frequently a standard of care for cancer patients, particularly those with late stage cancer and metastatic disease. A cancer that responds to a first anticancer drug treatment only to have the cancer return within a certain period is considered an anticancer drug-resistant cancer. For those with anticancer drug-resistant cancers, positive outcomes are very likely be low.

Several anticancer drugs work by producing excessive DNA damage that causes cell death directly or following DNA replication. However, DNA repair pathways can repair lesions induced by anticancer drugs, enabling cancerous tumor cells to survive and ultimately become resistant to the DNA damage that is induced by anticancer drug treatments. As such, there is a need in the art for cancer therapies that target the DNA repair pathways of cancerous cells. Once identified, cancer therapies capable of inhibiting DNA repair could be administered in combination with anticancer drugs to increase efficacy of their DNA-damaging effects in cancerous cells and tumors.

SUMMARY

Embodiments of the instant disclosure relate to novel methods and unique compositions for treating cancers, tumors (e.g., solid tumors), tumors resistant to anticancer drugs (e.g., platinum-based chemotherapy) and/or tumors suspected of developing anticancer drug resistance in a subject.

Certain embodiments of the present disclosure provide for compositions for treating cancer. In some embodiments, compositions for treating one or more cancers described herein can include at least one compound represented by formula I or a pharmaceutically acceptable salt thereof:

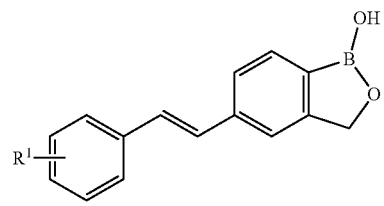

wherein, $R^1$ is independently mono- or poly-substituted with hydrogen, trifluoromethyl, trifluoromethoxy, nitro, cyano, halogen, C1-C10 alkyl, or —$OR^2$, wherein $R^2$ is independently selected from hydrogen or C1-C10 alkyl.

In some embodiments, compositions herein may have at least one compound represented by formula I or a pharmaceutically acceptable salt thereof wherein the compound of formula I may be selected from one or more compounds selected from the group consisting of:

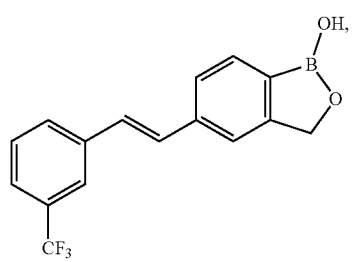

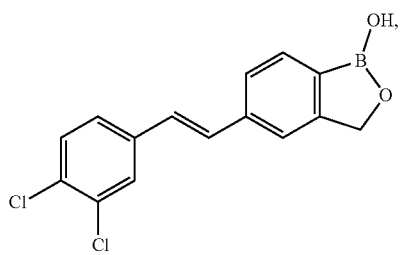

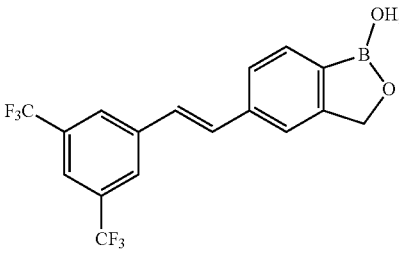

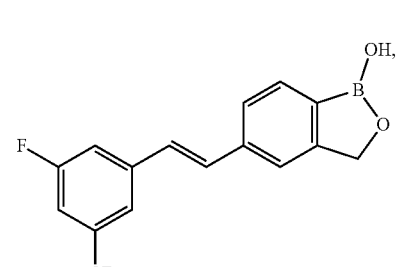

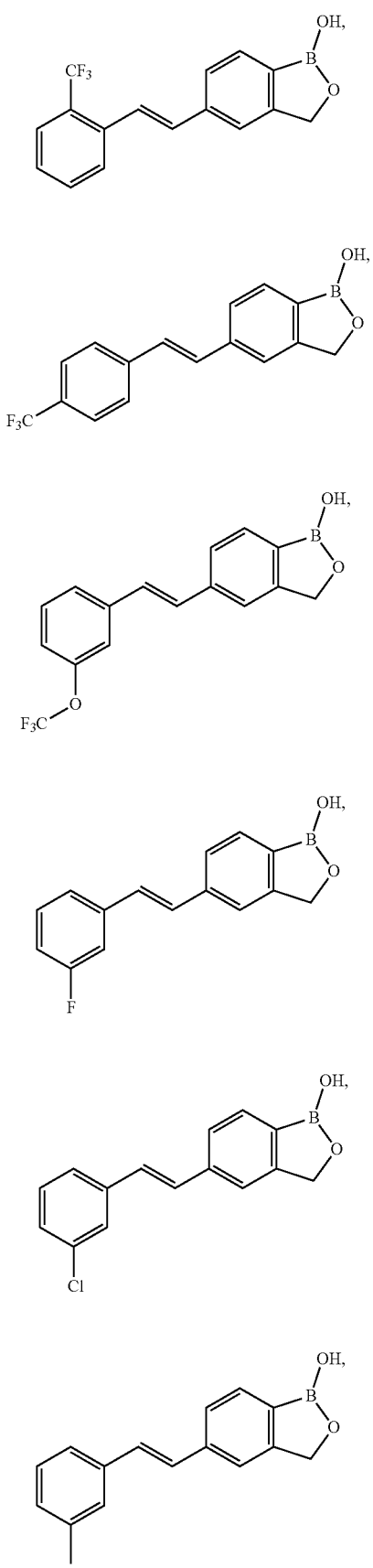
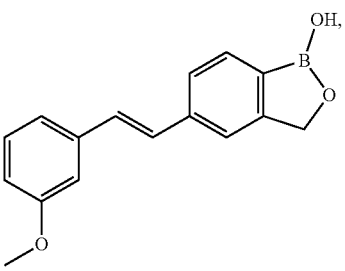
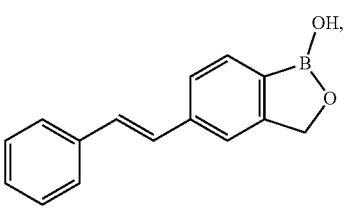

or any combination thereof. In some embodiments, compositions herein may comprise at least one compound represented by formula III.

In some embodiments, compositions for treating cancers as disclosed herein can further comprise one or more anti-cancer drugs. In some embodiments, compositions for treating cancers as disclosed herein can further comprise one or more platinum-based chemotherapeutics. In accordance with some embodiments herein, the one or more platinum-based chemotherapeutics may comprise one or more of cisplatin, carboplatin, nedaplatin, satraplatin, picoplatin, phenanthriplatin, triplatin tetranitrate, or any combination thereof. In some embodiments, compositions for treating cancers as disclosed herein can further comprise gemcitabine, methotrexate, vinblastine, adriamycin, or any combination thereof. In some embodiments, compositions for treating cancers as disclosed herein may further comprise one or more pharmaceutically acceptable excipients.

Certain embodiments of the present disclosure provides for compounds represented by formula I or a pharmaceutically acceptable salt thereof. In some embodiments, compounds of the present disclosure represented by formula I or a pharmaceutically acceptable salt thereof may be a compound selected from the group consisting of any one of the compounds represented by formulas II-XVI or any one of their pharmaceutically acceptable salts. In some embodiments, compounds of the present disclosure represented by formula I or a pharmaceutically acceptable salt thereof may be a compound represented by formula III. In some embodiments, a compound for use in the compostions and methods of the present disclosure may be (E)-5-(3,4-dichlorostyryl)benzo[c][1,2]oxaborol-1(3H)-ol.

In some embodiments, the present disclosure provides for pharmaceutical compositions comprising any one or more of the compounds or compositions disclosed herein. In some embodiments, pharmaceutical compositions disclosed herein may further include at least one pharmaceutically acceptable excipient.

Certain embodiments of the present disclosure provide for methods of delivering at least one of the compositions, compounds, and/or pharmaceutical compositions disclosed herein to a cell. Methods herein can include introducing the cell to any one of the compositions, compounds, and/or pharmaceutical compositions disclosed herein. In accordance with some embodiments herein, a cell to be introduced to any one of the compositions, compounds, and/or pharmaceutical compositions disclosed herein may be a cancer cell, a tumor cell, or any combination thereof.

Certain embodiments of the present disclosure provide for methods of delivering at least one of the compositions, compounds, and/or pharmaceutical compositions disclosed herein to a tumor. Methods herein can include introducing the tumor to any one of the compositions, compounds, and/or pharmaceutical compositions disclosed herein. In accordance with some embodiments herein, a tumor to be introduced to any one of the compositions, compounds, and/or pharmaceutical compositions disclosed herein may be a testicular tumor, ovarian tumor, cervical tumor, kidney tumor, bladder tumor, head-and-neck tumor, liver tumor, stomach tumor, lung tumor, endometrial tumor, esophageal tumor, breast tumor, cervical tumor, central nervous system tumor, germ cell tumor, prostate tumor, Hodgkin's lymphoma, non-Hodgkin's lymphoma, neuroblastoma, sarcoma, multiple myeloma, melanoma, mesothelioma, osteogenic sarcoma, or any combination thereof. In some examples, a tumor to be introduced to any one of the compositions, compounds, and/or pharmaceutical compositions disclosed herein may be a breast tumor, an ovarian tumor, or any combination thereof.

Certain embodiments of the present disclosure provide for methods of treating a tumor in a subject in need thereof. In some embodiments, methods disclosed herein for treating a tumor in a subject in need thereof may comprise administering to the subject at least one of the compositions, compounds, and/or pharmaceutical compositions disclosed herein.

In accordance with some embodiments herein, a subject in need thereof can be a subject undergoing or will undergo at least one anticancer drug therapy. In some embodiments, a subject in need thereof can be a subject undergoing or will undergo at least one or more platinum-based chemotherapeutics. In some embodiments, a subject may be in need of treating a tumor using the methods disclosed herein if the subject has a progressive cancer through the at least one anticancer drug therapy, or is resistant to the at least one anticancer drug therapy.

Certain embodiments of the present disclosure provide for methods of preparing the compounds disclosed herein. In some embodiments, methods of preparing at least one compound disclosed herein can have one or more of the following steps: (i) reacting a compound represented by Compound A with concentrated hydrochloric acid and paraformaldehyde to obtain a compound represented by Compound B; (ii) reacting a compound represented by Compound B with triphenylphosphonium in an aprotic solvent to obtain a compound represented by Compound C; (iii) producing a compound represented by Compound E from compounds represented by Compound C and Compound D under strong base conditions; (iv) reacting a compound represented by Compound E with trifluoromethanesulfonic anhydride in dichloromethane to obtain a compound represented by Compound F; (v) reacting a compound represented by Compound F with pinacol diboronic acid or diboronic acid under palladium salt catalyst to obtain a compound represented by Compound G; and (vi) reacting a compound represented by Compound G with a reducing agent such and adding acid to obtain a compound represented by Compound H, wherein the reducing agent comprises sodium borohydride, tetrahydroaluminum lithium, or any combination thereof;

wherein:

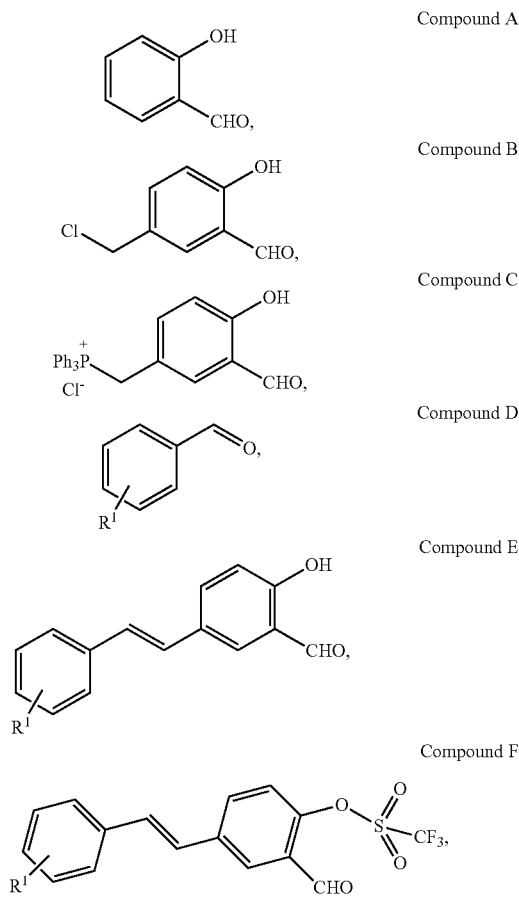

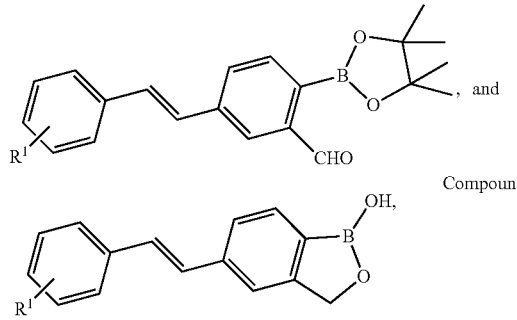

Compound G, and

Compound H wherein: $R^1$ is independently mono- or poly-substituted with hydrogen, trifluoromethyl, trifluoromethoxy, nitro, cyano, halogen, C1-C10 alkyl, or —$OR^2$, wherein $R^2$ is independently selected from hydrogen or C1-C10 alkyl.

In some embodiments, methods of preparing at least one compound disclosed herein can have strong base conditions of step (iii) that can be strong alkaline conditions comprising sodium methoxide, sodium ethoxide, sodium tert-butoxide, sodium isopropoxide, butyl lithium, sodium hydroxide, lithium hydroxide, potassium hydroxide, or any combination thereof. In some embodiments, methods of preparing at least one compound disclosed herein can have steps (iii) and (v) performed at about 80° C. In some embodiments, methods of preparing at least one compound disclosed herein can have steps (iv) and (vi) performed at about 0° C.

In some embodiments, methods of preparing at least one compound disclosed herein can comprise palladium salt catalyst in step (v). In some examples, the palladium salt catalyst may be palladium acetate, palladium chloride, tetrakis(triphenylphosphorus) palladium, bis(acetonitrile) palladium dichloride, bis(triphenylphosphorus) palladium chloride, 1,1'-[bis(diphenylphosphorus)ferrocene]palladium dichloride, bis(benzonitrile)palladium dichloride, 1,1'-[bis(di-tert-butylphosphorus)ferrocene] Palladium dichloride, bis(tricyclohexylphosphorus) palladium dichloride, bis(o-toluene) palladium dichloride, or any combination thereof.

In some embodiments, methods of preparing at least one compound disclosed herein may comprise step (v) performed under an alkaline condition, wherein the alkaline condition may be a base comprising sodium acetate, potassium acetate, sodium methoxide, sodium ethoxide, potassium methoxide, potassium ethoxide, sodium fluoride, potassium fluoride, or any combination thereof.

In some embodiments, methods of preparing at least one compound disclosed herein may comprise step (v) performed in a polar solvent, wherein the polar solvent may be N, N-dimethylformamide, dimethylsulfoxide, acetonitrile, acetone, methyl ethyl ketone, 1,4-dioxane, water, or any combination thereof.

In certain embodiments, kits are provided herein. In certain embodiments, compositions of the instant disclosure can be included in the kit, together or in separate containers. In certain embodiments, kits are provided for the practice of any one of the methods disclosed herein. In some embodiments, kits can include one or more of the compounds disclosed herein, one or more anticancer drugs (e.g., platinum-based chemotherapeutics), or a combination thereof.

BRIEF DESCRIPTION OF THE FIGURES

The patent or application file contains at least one drawing executed in color. Copies of this patent or patent application with color drawing(s) will be provided by the Office by request and payment of the necessary fee. The following drawings form part of the present specification and are included to further demonstrate certain aspects of the present disclosure, which can be better understood by reference to the drawings in combination with the detailed description of specific embodiments presented herein.

FIG. 13A shows a schematic depicting the establishment of GFP-based HEK293T-And-1-Luc cells. FIG. 13B shows a schematic diagram of And-1 inhibitor screening. FIG. 13C shows a representative immunoblot analysis of the And-1 expression in IGROV1 cells treated with resveratrol at indicated concentrations. FIG. 13D shows chemical structures of resveratrol and its analogs. FIGS. 13E-13H show immunoblot analyses of the And-1 expression in IGROV1 cells treated with the And-1 inhibitors DHS (FIG. 13E), CH3 (FIG. 13F), and BZA (FIG. 13G) at the indicated concentrations where FIG. 13G is a graph showing quantification of And-1 expression in FIGS. 13E-13G in response to And-1 inhibitor treatment.

FIGS. 15A-15D show flow cytometry analysis of propidium-iodide stained IGROV1 cells treated with DMSO (FIG. 15A), 1 µM of CH3 (FIG. 15B), 1 µM of BZA (FIG. 15C) and siAnd-1 (FIG. 15D) where "S" indicates S phase. FIG. 15E shows images of an immunofluorescence assay of CtIP co-localization with γH2AX after CH3 or BZA treatment where IGROV1 cells were treated with DMSO, 1 µM of CH3 or 1 µM of BZA and micro-irradiated and co-immunostained for γH2AX and CtIP 30 minutes post irradiation. For each experiment, 50 cells were counted and the percentage of γH2AX cells exhibiting CtIP foci was determined resulting in the graph shown in FIG. 15F (data represent means±standard deviation (SD) from three independent experiments). FIG. 15G shows a graph illustrating a HR reporter assay of HR repair efficiency in cells treated with CH3. In brief, IGROV1 cells treated with DMSO, 2 µM or 4 µM of CH3 were subjected to HR reporter assay and the percentage of GFP-positive cells was determined by flow cytometry 48 hours after I-SceI plasmid transfection. HR efficiency were normalized to those obtained from cells treated with DMSO. Data provided in the graph represent means±SD from three independent experiments. FIG. 15H shows a graph illustrating a HR reporter assay of HR repair efficiency in cells treated with BZA. In brief, IGROV1 cells treated with DMSO, 2 µM or 4 µM of BZA were subjected to HR reporter assay and the percentage of GFP-positive cells was determined by flow cytometry 48 hours after I-SceI plasmid transfection. HR efficiency were normalized to those obtained from cells treated with DMSO. Data provided in the graph represent means±SD from three independent experiments.

FIGS. 16A-16L depict schematics, images, and graphs illustrating And-1 inhibitor interaction with And-1 in accordance with embodiments of the present disclosure. FIGS. 16A-16C show graphs depicting thermal stability of And-1 in IGROV1 cells treated with DHS (FIG. 16A), CH3 (FIG. 16B), or BZA (FIG. 16C) with And-1. FIG. 16D shows images of fluorescent boron sensor DAHMI staining assays of CH3 distribution in live IGROV1 cells where siRNA was given to cells 24 hours before CH3 treatment and DAHMI was added to the cells 24 hours after CH3 treatment. FIG. 16E shows images of immunoblot analyses to determine the And-1 expression in the cells shown in FIG. 16D. FIG. 16F is a graph that depicts the quantification of fluorescent intensity in cells analyzed in FIG. 16D where the intensity was normalized to cells treated with 10 µM of CH3. FIG. 16G shows a schematic of And-1's domain organization. FIG. 16H shows images of a fluorescent boron sensor DAHMI staining assay of CH3 distribution in live And-1 knockout cells transfected with And-1 or its truncation mutant where And-1 plasmids were transfected in cells 24 hours before CH3 treatment and DAHMI was added to the cells 24 hours after 10 µM of CH3 treatment. FIG. 16I is a graph that depicts the quantification of fluorescent positive cells analyzed in FIG. 16D. FIG. 16J is a schematic depicting the docking position of CH3 in the WD40 domain of And-1 with a free energy of binding=−7.63 kcal/mol. FIG. 16K is a schematic depicting the amino acids of And-1 that contributed to CH3 interaction. FIG. 16K is a graph depicting thermal stability of FLAG-And-1-WT, FLAG-And-1-E18A, FLAG-And-1-R191A and FLAG-And-1-E18A-R191A in IGROV1 cells treated with CH3.

FIGS. 17A-17C show images depicting cellular thermal shift assays to examine interactions of DHS (FIG. 17A), CH3 (FIG. 17B) or BZA (FIG. 17C) with And-1 in IGROV1 cells where images depict And-1 stability as analyzed by using western blot against And-1 antibody. FIGS. 17D-17G show images depicting cellular thermal shift assays to examine interactions of CH3 with FLAG-And-1-WT (FIG. 17D), FLAG-And-1-E18A (FIG. 17E), FLAG-And-1-R191A (FIG. 17F) and FLAG-And-1-E18A-R191A (FIG. 17G) in IGROV1 cells where images depict And-1 stability as analyzed by western blot analysis against And-1 antibody.

FIG. 18A shows an image of an immunoblot analysis of And-1 expression in IGROV1 cells treated with 5 µM CH3 for 48 hours followed by MG132 treatment for 4 hours before harvesting. FIG. 18B shows an image of an immunoblot analysis of ubiquitinated And-1 in IGROV1 cells treated with CH3 where cell lysates were subjected to immunoprecipitation with antibody against And-1. FIG. 18C shows an image of an immunoblot analysis of And-1 expression in CUL4B knockdown IGROV1 cells treated with CH3 where siRNAs were transfected 24 hours before exposure to CH3 for another 48 hours. FIG. 18D shows a schematic of And-1's domain organization with predicted ubiquitination sites. FIG. 18E shows an image of an immunoblot analysis of ubiquitinated FLAG-And-1-WT, FLAG-And-1-K130R or FLAG-And-1-K811R in IGROV1 cells treated with CH3 where And-1 plasmids were transfected in IGROV1 cells 24 hours before CH3 treatment for another 48 hours followed by MG132 treatment for 4 hours and cell lysates were prepared and subjected to immunoprecipitation with antibody against FLAG. FIG. 18F shows an image of an immunoblot analysis of the FLAG-And-1-WT or FLAG-And-1-K811R expression in IGROV1 cells treated with CH3. FIG. 18G shows an image of an immunoblot analysis of the CUL4B interacted with FLAG-And-1-WT, FLAG-And-1-K130R or FLAG-And-1-K811R.

FIG. 19A shows an image of an immunoblot analysis of the full-length FLAG-And-1 and its truncation mutants' expression in cells treated with CH3. FIG. 19B shows an image of an immunoblot analysis of the full-length FLAG-And-1 expression in the presence of FLAG-And-1-1-330. FIG. 19C shows an image of an immunoblot analysis of the CUL4B interaction with FLAG-And-1-WT or FLAG-And-1-330-1129. FIG. 19D shows an image of an immunoblot analysis of HA-And-1 immunoprecipitated by FLAG-And-1 in cells treated with CH3. FIG. 19E shows an image of an immunoblot analysis of HA-And-1 immunoprecipitated by FLAG-And-1 in cells treated with CH3 at the indicated concentrations.

FIG. 20A shows an image of an immunoblot analysis of phosphorylated And-1 (p-And-1) expression in IGROV1 cells exposed to cisplatin where siRNAs were transfected 24 hours before cisplatin treatment for another 48 hours. FIG. 20B shows an image of an immunoblot analysis of the expression of indicated proteins in IGROV1 cells treated with 1 µM cisplatin for indicated time periods. FIG. 20C shows an image of an immunoblot analysis of the p-And-1 expression in IGROV1 cells treated with control, cisplatin or combination of cisplatin and ATR inhibitor (VE821). FIG. 20D shows an image of an immunoblot analysis of the expression of p-FLAG-And-1-WT or p-FLAG-And-1-T826A where pEFF-And-1 plasmids were transfected in IGROV1 cells 24 hours before 1 μM cisplatin treatment for another 48 hours and cell lysates were prepared and subjected to immuno-precipitation with antibody to FLAG.

FIG. 21A shows an image of an immunoblot analysis of the p-And-1 expression in 5 pairs of parental and cisplatin resistant OC cell lines. FIG. 21B shows a graph of a Kaplan-Meier analyses of 5-year overall survival rate (OS) based on clinical and molecular data for OC patients (n=512) where the patients were stratified by the expression levels in their tumors of the And-1 and ATR signature genes. FIGS. 21C-21D show images depicting phospho-And-1 expression in cisplatin sensitive and resistant tumor samples from eleven human patients where representative immunohistochemistry (IHC) images of the cisplatin-sensitive and resistant tumor samples from the same patient (P1-P3) are shown (FIG. 21D) and quantification was depicted as a graph (FIG. 21C). FIGS. 21E-21F show images depicting And-1 expression in cisplatin sensitive and resistant tumor samples from eleven human patients where representative IHC images of the cisplatin sensitive and resistant tumor samples from the same patient (P1-P3) are shown (FIG. 21F) and quantification was depicted as a graph (FIG. 21E). FIG. 21G shows a graph of scatter plots indicating a correlation between p-And-1 and And-1 levels in both sensitive and resistant patient tumors.

FIGS. 22A-22D depict images illustrating cisplatin treatment induced phospho-And-1 expression in both a dose- and a time course-dependent manner in ovarian cancer (OC) cells in accordance with embodiments of the present disclosure. FIGS. 22A-22B show images of immunoblot analyses of the expression of indicated proteins in PEO1 (FIG. 22A) and OV90 (FIG. 22B) cells treated with 1 μM cisplatin for indicated time periods. FIGS. 22C-22D show images of immunoblot analyses of the expression of indicated proteins in PEO1 (FIG. 22C) and OV90 (FIG. 22D) cells treated with cisplatin for 48 hours at indicated concentration.

FIGS. 23A-23K depict images and graphs illustrating And-1 phosphorylation contributed to cisplatin resistance in ovarian cancer (OC) cells in accordance with embodiments of the present disclosure. FIGS. 23A-23B show images depicting Sulforhodamine B (SRB) cell viability to cisplatin for 48 hours in IGROV1 cells overexpressed with FLAG-And-1-WT, FLAG-And-1-T826A or FLAG-And-1-T826E (FIG. 23B) and immunoblot analysis of the And-1 expression in the treated cells (FIG. 23A). FIG. 23C shows a graph illustrating SRB cell viability to cisplatin in IGROV1 cells overexpressed with Vector, FLAG-And-1-WT or FLAG-And-1-T826E where ATR inhibitor (1 μM of VE821) was given 24 hours before cisplatin treatment. FIGS. 23D-23E show images depicting a modified comet assay in IGROV1 WT and IGROV1 CR cells treated with 10 μM cisplatin for 2 hours and released into cisplatin free medium at indicated time followed by 20 gray (Gy) of ionizing radiation (IR) to introduce random DNA double strand breaks before harvesting (FIG. 23D) and the relative percentage of intrastrand and interstrand crosslinks (ICLs) in cells treated with cisplatin at indicated time points (FIG. 23E). Data points represent means±standard error and **, p<0.0001. FIGS. 23F-23G show images depicting a modified comet assay in cells IGROV1 WT transfected with siRNA 24 hours followed by plasmid transfection for another 24 hours (FIG. 23F) and relative percentage of ICLs (FIG. 23G). Data points represent means±standard error and *, p<0.001; ns=not significant. FIGS. 23H-23I show images depicting SRB cell viability to cisplatin in And-1 knockdown IGROV1 CR cells (FIG. 23H) and immunoblot analyses of the And-1 expression in the analyzed cells (FIG. 23I). FIGS. 23J-23K show images depicting colony formation in And-1 knockdown IGROV1 CR cells after cisplatin treatment where siRNAs were transfected 24 hours before cisplatin treatment and colonies were counted at the end of two weeks (FIG. 23J) and quantification of colony formation (FIG. 23K); **, p<0.01.

FIGS. 24A-24I depict images and graphs illustrating that up-regulated And-1 phosphorylation contributes to cisplatin resistance ovarian cancer (OC) cells in accordance with embodiments of the present disclosure. FIGS. 24A-24B show images depicting SRB cell viability to cisplatin for 48 hours in OV90 cells overexpressed with FLAG-And-1-WT, FLAG-And-1-T826A or FLAG-And-1-T826E (FIG. 24A) and immunoblot analysis of the And-1 expression in the treated cells (FIG. 24B). FIGS. 24C-24D show images depicting SRB cell viability to cisplatin for 48 hours in ID80 cells overexpressed with FLAG-And-1-WT, FLAG-And-1-T826A or FLAG-And-1-T826E (FIG. 24C) and immunoblot analysis of the And-1 expression in the treated cells (FIG. 24D). FIG. 24E shows an image of an immunoblot analysis of indicated protein expression in IGROV1 cells overexpressed with Vector, FLAG-And-1-WT or FLAG-And-1-T826E where ATR inhibitor (1 μM of VE821) was given 24 hours before cisplatin treatment. FIGS. 24F-24G show images depicting SRB cell viability analyses of And-1 knockdown OV90 CR cells exposed to cisplatin at indicated concentration for 48 hhours (FIG. 24F) and immunoblot analysis of the And-1 expression in cells analyzed (FIG. 24G). FIGS. 24H-24I show images depicting colony formation assay of And-1 knockdown OV90 CR cells after cisplatin treatment where siRNAs were transfected 24 hours before cisplatin treatment and colonies were counted at the end of two weeks (FIG. 24H) and quantification of colony formation (FIG. 24I), **, p<0.01.

FIGS. 28A-28I show graphs illustrating growth inhibition of NCI-60 cancer cell lines after exposure to CH3 at concentrations of 0.01 μM, 0.1 μM, 1 μM, 10 μM and 100 μM where the cell lines shown in FIG. 28A are the leukemia cell lines CCRF-CEM, HL-60 (TB), K-562, MOLT-4, and RPMI-8226; in FIG. 28B are the central nervous system (CNS) cancer cell lines SF-268, SF-295 (glioblastoma), SF-539 (gliosarcoma), SNB-19, SNB-75, and U251 (astroglioma); in FIG. 28C are the non-small cell lung cancer cell lines A549/ATCC, EKVX, HOP-62, HOP-92, NCI-H226, NCI-H23, NCI-H322M, NCI-H60, and NCI-H522; in FIG.

28D are the melanoma cell lines LOX IMVI, MALME-3M, M14, MDA-MB-435, SK-MEL-2, SK-MEL-28, SK-MEL-5, UACC-257, and UACC-62; in FIG. 28E are the colon cancer cell lines COLO 205, HCC-2998, HCT-116, HCT-15, HT29, KM12, and SW-620; in FIG. 28F are the ovarian cancer cell lines IGROV1, OVCAR-3, OVCAR-4, OVCAR-5, OVCAR-8, NCI/ADR-RES, and SK-OV-3; in FIG. 28G are the renal cancer cell lines 786-0, A498, ACHN, CAKI-1, RXF 393, SN12C, TK-10, and UO-31; in FIG. 28H are the prostate cancer cell lines PC-3 and DU-145; in FIG. 28I are the breast cancer cell lines MCF7, MDA-MB-231, HS 578T, BT-549, and T-47D. FIG. 28J shows growth curves of IGROV1 xenograft mice where data are represented as means±standard error of mean (SEM), ****, p<0.0001. FIG. 28O shows a bar graph depicting quantification of cleaved-caspase-3 expression detected by the IHC score in tumor samples analyzed in FIG. 28M.

FIGS. 29A-29D show graphs illustrating SRB cell viability to CH3 and BZA in IGROV1 (FIG. 29A), MCF7 (FIG. 29B), PK9 (FIG. 29C) and SW620 (FIG. 29D) cells. FIG. 29E shows an image of tumors from MCF7 xenograft mice treated with vehicle or CH3 (20 or 40 mg/kg/3 days intraperitoneally) for 3 weeks where the ruler scale is in cm. FIG. 29F shows growth curves of MCF7 xenograft mice where data are represented as means±SEM, ****, p<0.0001. FIG. 29G shows a graph depicting body weight changes of mice in each group where data are represented as means±SD, n=6 tumors/group. FIG. 29H shows images depicting H&E staining of paraffin-embedded, 3-μm-thick tissue sections of the tumor, heart, lung, liver and kidney, and IHC staining against And-1 and cleaved-caspase-3 antibodies of tumor samples from 3 groups of mice (Scale bar: 50 μm). FIG. 29I shows a bar graph depicting quantification of And-1 expression detected by the IHC score in tumor samples analyzed in FIG. 29H. FIG. 29J shows a bar graph depicting quantification of cleaved-caspase-3 expression detected by the IHC score in tumor samples analyzed in FIG. 29H.

FIGS. 30A-30H depict images and graphs illustrating that the And-1 inhibitor CH3 overcomes cisplatin resistance in Ovarian Cancer (OC) in accordance with embodiments of the present disclosure. FIG. 30A shows a graph illustrating SRB cell viability to cisplatin in IGROV1 CR cells treated with CH3 where synergies of each combination were indicated as combination index (CI) values. FIGS. 30B-30C are images showing colony formation in IGROV1 CR cells treated with DMSO, cisplatin, CH3 or a combination of cisplatin and CH3 (FIG. 30B), and quantification of colonies (FIG. 30C). FIG. 30D is an image showing tumors of IGROV1 CR xenograft mice treated with control (vehicle), cisplatin (8 mg/kg/day intraperitoneally), CH3 (20 mg/kg/3 days intraperitoneally), or combination of CH3 and cisplatin for 3 weeks where the ruler scale is in cm. FIG. 30E shows a graph depicting tumor size over time in IGROV1 CR xenograft mice. FIG. 30F shows a graph depicting body weight changes of mice in each group where data are represented as means±SD, n=7 tumors/group. FIG. 30G shows images depicting H&E staining of paraffin-embedded, 3-μm-thick tissue sections of the tumor, heart, lung, liver and kidney, and IHC staining against And-1 antibodies of tumor samples from 4 groups of mice (Scale bar: 50 μm). FIG. 30H shows a bar graph depicting quantification of And-1 expression detected by the IHC score in tumor samples analyzed in FIG. 30G.

FIGS. 31A-31H depict images and graphs illustrating that the And-1 inhibitor BZA overcomes cisplatin resistance in Ovarian Cancer (OC) in accordance with embodiments of the present disclosure. FIG. 31A shows a graph illustrating SRB cell viability to cisplatin in IGROV1 CR cells treated with BZA where synergies of each combination were indicated as CI values. FIGS. 31B-31C are images showing colony formation in IGROV1 CR cells treated with DMSO, cisplatin, BZA or combination of cisplatin and CH3 (FIG. 31B), and quantification of colonies (FIG. 31C). FIG. 31D is an image showing tumors of IGROV1 CR xenograft mice treated with control (vehicle), cisplatin (8 mg/kg/day intraperitoneally), BZA (2 mg/kg/3 days intraperitoneally), or combination of BZA and cisplatin for 3 weeks where the ruler scale is in cm. FIG. 31E shows a graphs depicting tumor size over time in IGROV1 CR xenograft mice. FIG. 31F shows a graph depicting body weight changes of mice in each group where data are represented as means±SD, n=7 tumors/group. FIG. 31G shows images depicting H&E staining of paraffin-embedded, 3-μm-thick tissue sections of the tumor, heart, lung, liver and kidney, and IHC staining against And-1 antibodies of tumor samples from 4 groups of mice (Scale bar: 50 μm). FIG. 31H shows a bar graph depicting quantification of And-1 expression detected by the IHC score in tumor samples analyzed in FIG. 31G.

DETAILED DESCRIPTION

Figure 1:
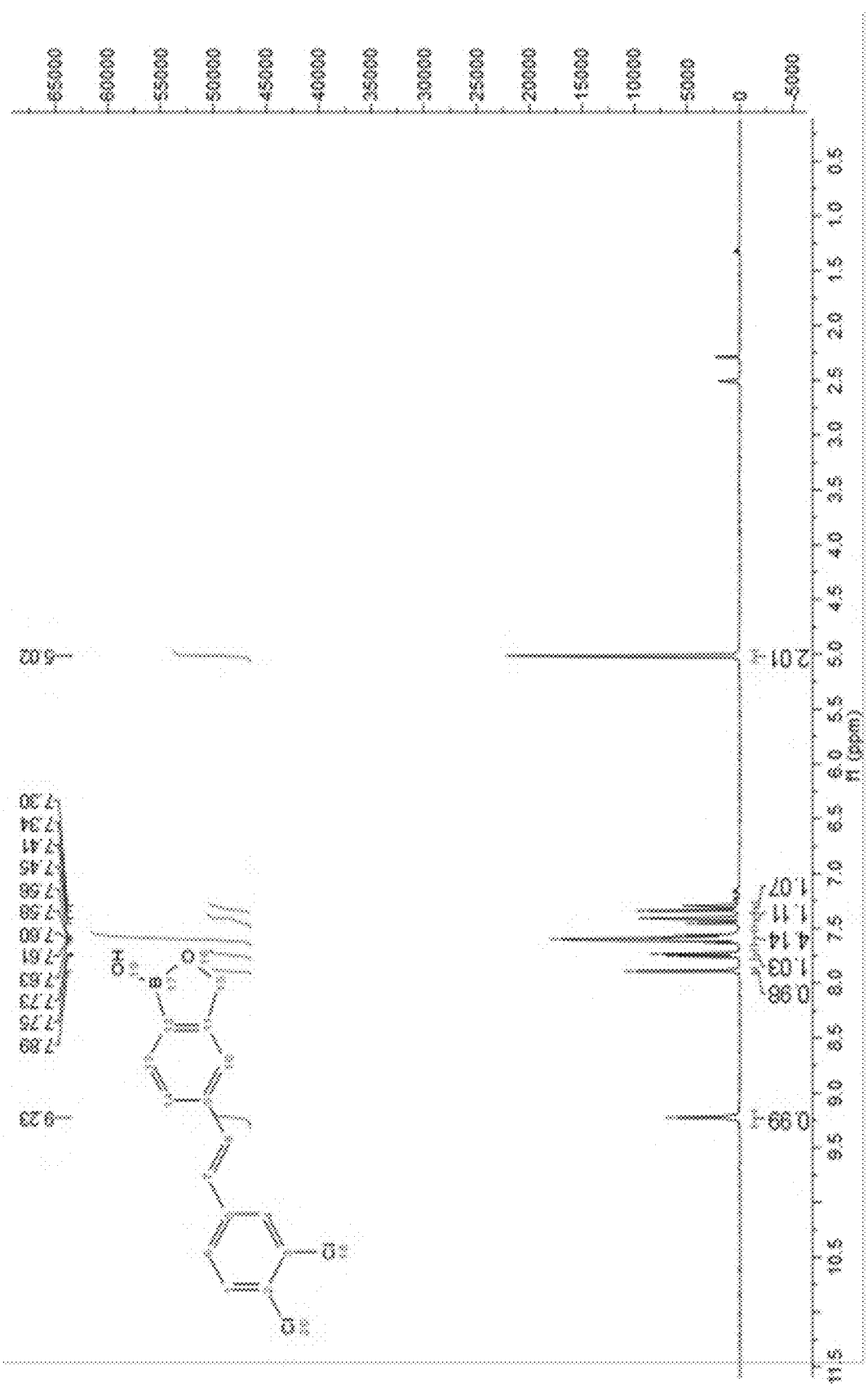
FIG. 1 is a proton nuclear magnetic resonance ($^1$H NMR) spectrum of (E)-5-(3,4-dichlorostyryl)benzo[c][1,2]oxaborol-1(3H)-ol (III) in accordance with embodiments of the present disclosure.

In the following sections, certain exemplary compositions and methods are described in order to detail certain embodiments of the invention. It will be obvious to one skilled in the art that practicing the certain embodiments does not require the employment of all or even some of the specific details outlined herein, but rather that concentrations, times and other specific details can be modified through routine experimentation. In some cases, well known methods, or components have not been included in the description.

Embodiments of the instant disclosure relate to novel methods and compositions for treating tumors resistant to or suspected of becoming resistant to one or more anticancer drugs, such as platinum-based chemotherapeutics. In some embodiments, a tumor subjected to the methods and compositions disclosed herein can be a solid tumor. In some embodiments, compositions and methods disclosed herein are designed to re-sensitize or sensitize a tumor in a subject to an anticancer drug to reduce costs, improve outcome, and reduce or eliminate patient exposure to anticancer therapy without significant effect.

I. Resveratrol Derivatives and And-1 Inhibitors

And-1, also known as WD repeat and HMG-box DNA binding protein 1 (WDHD1) and chromosome transmission fidelity factor 4 homolog (Ctf4), is an acidic nucleoplasmic DNA-binding protein containing N-terminal WD40 domains, a middle SepB domain, and a C-terminal high mobility group (HMG) domain. And-1 is important in regulating DNA replication, chromosome function, and DNA damage repair; however, a potent And-1 inhibitor is not known in the art. The present disclosure is based, at least in part, on the discovery of new resveratrol derivatives that can act as potent And-1 inhibitors and their use as anti-cancer agents.

In some embodiments, compounds of the present disclosure can be, resveratrol derivatives, And-1 inhibitors, or both. In some embodiments, compounds of the present disclosure can be represented by formula I or a pharmaceutically acceptable salt thereof.

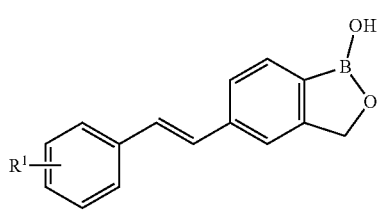

I wherein, $R^1$ is independently mono- or poly-substituted with hydrogen, trifluoromethyl, trifluoromethoxy, nitro, cyano, halogen, C1-C10 alkyl, or —$OR^2$, wherein $R^2$ is independently selected from hydrogen or C1-C10 alkyl.

As used herein, an alkyl is an aliphatic alkyl, which may be a linear or branched alkyl, and includes but is not limited to: methyl, ethyl, n-propyl, isopropyl, n-butyl, isobutyl, tert-butyl, etc. The expressions of the form "C1-C10" are intended to include those corresponding groups having 1, 2, 3, 4, 5, 6, 7, 8, 9, or 10 carbon atoms, for example, "C1-C10 alkyl" refers to an alkyl having 1, 2, 3, 4, 5, 6, 7, 8, 9 or 10 carbon atoms.

As used herein, a halogen refers to fluorine, chlorine, bromine or iodine. As used herein, "cyano" refers to a cyano functional group (e.g., —C≡N). As used herein, "nitro" refers to a nitro functional group (e.g., —$NO_2$).

Unless otherwise specified, the structure formula described herein are intended to include all tautomeric, optical, and stereoisomeric forms (e.g., enantiomers, diastereomers, geometric isomers, or conformers). For example, R and S configurations containing asymmetric centers, (Z), (E) isomers of double bonds and conformational isomers of (Z), (E). The individual stereochemical isomers, tautomers or enantiomers, diastereomers or geometric isomers or tautomers, or a mixture of conformers of the compounds herein belong to the scope of the present disclosure.

The term "tautomers" as used herein means that structural isomers with different energies can exceed low energy barriers and thus be converted into each other. For example, proton tautomers (i.e., proton shifts) include interconversions via proton migration, such as 1H-indazole and 2H-indazole, 1H-benzo[d]imidazole and 3H-benzo[d]imidazole. The valence tautomers can include interconversions by reorganization of some bonding electrons.

The pharmaceutically acceptable salts for use herein are not particularly limited, and preferably include: inorganic acid salts, organic acid salts, alkyl sulfonates, and aryl sulfonates; the inorganic acid salts include hydrochloride, hydrobromide, nitrate, sulfate, phosphate, etc.; the organic acid salts include formate, acetate, propionate, benzoate, maleate, fumarate, succinate, tartrate, citrate, etc.; the alkyl sulfonates include methyl sulfonate, ethyl sulfonate, etc.; and the aryl sulfonates include benzenesulfonate, p-toluenesulfonate, and the like.

In some embodiments, compounds of the present disclosure can be represented by formulas II-XVI or a pharmaceutically acceptable salt thereof, wherein formulas II-XVI include:

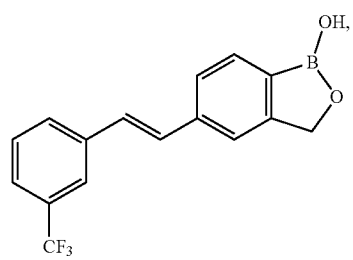

II

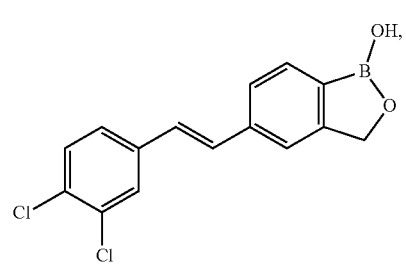

III

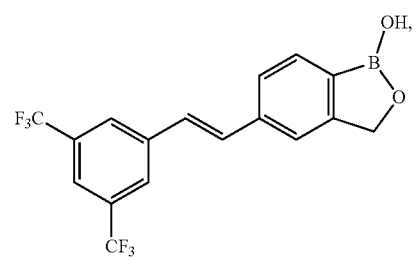

IV

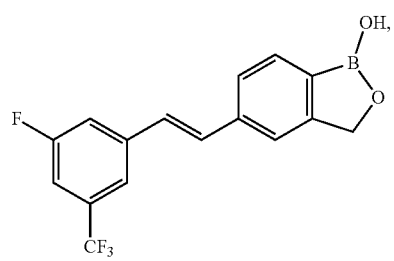

V

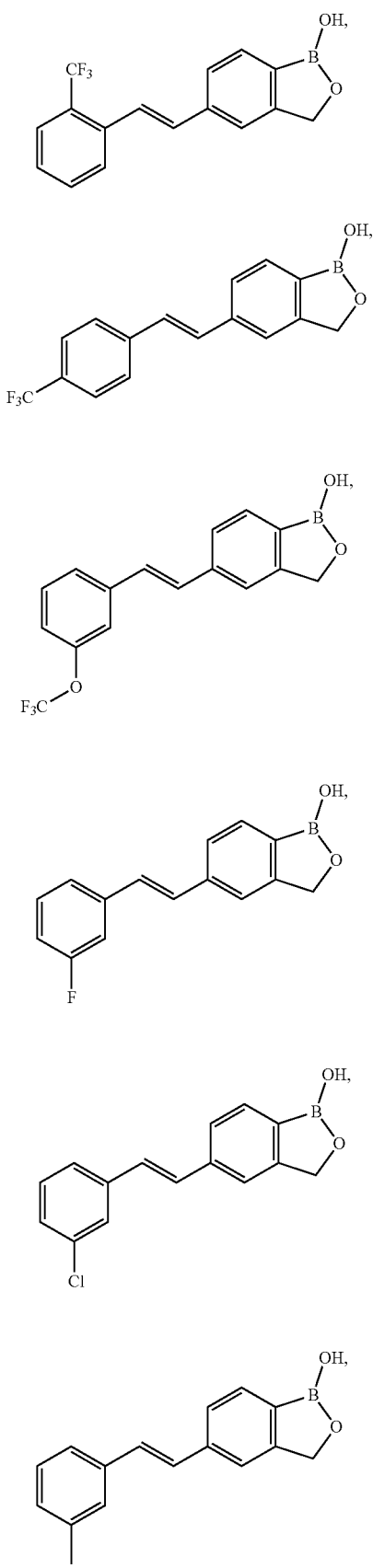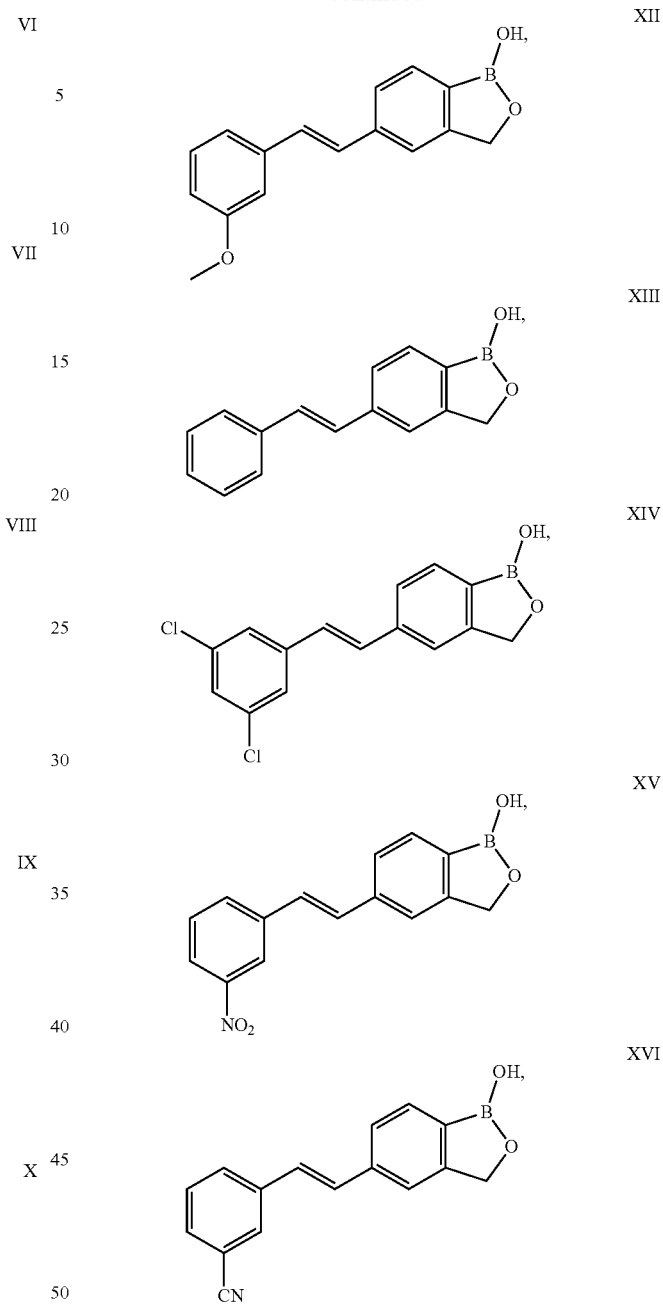

or any combination thereof.

The present disclosure also provides embodiments for methods of making any one of the compounds or pharmaceutically acceptable salts thereof as disclosed herein. Methods of making compounds of the present disclosure are further described below with reference to specific examples (e.g. Examples 1-5 herein). It should be understood that these examples are only used to illustrate the present invention and not to limit the scope of the present disclosure.

In certain embodiments, methods of making any one of the compounds or pharmaceutically acceptable salts thereof as disclosed herein may have one or more of the following steps: (i) reacting a compound represented by Compound A with concentrated hydrochloric acid and paraformaldehyde to obtain a compound represented by Compound B; (ii)

reacting a compound represented by Compound B with triphenylphosphonium in an aprotic solvent to obtain a compound represented by Compound C; (iii) producing a compound represented by Compound E from compounds represented by Compound C and Compound D under strong base conditions; (iv) reacting a compound represented by Compound E with trifluoromethanesulfonic anhydride in dichloromethane to obtain a compound represented by Compound F; (v) reacting a compound represented by Compound F with pinacol diboronic acid or diboronic acid under palladium salt catalyst to obtain a compound represented by Compound G; and (vi) reacting a compound represented by Compound G with a reducing agent such and adding acid to obtain a compound represented by Compound H, wherein the reducing agent comprises sodium borohydride, tetrahydroaluminum lithium, or any combination thereof; wherein:

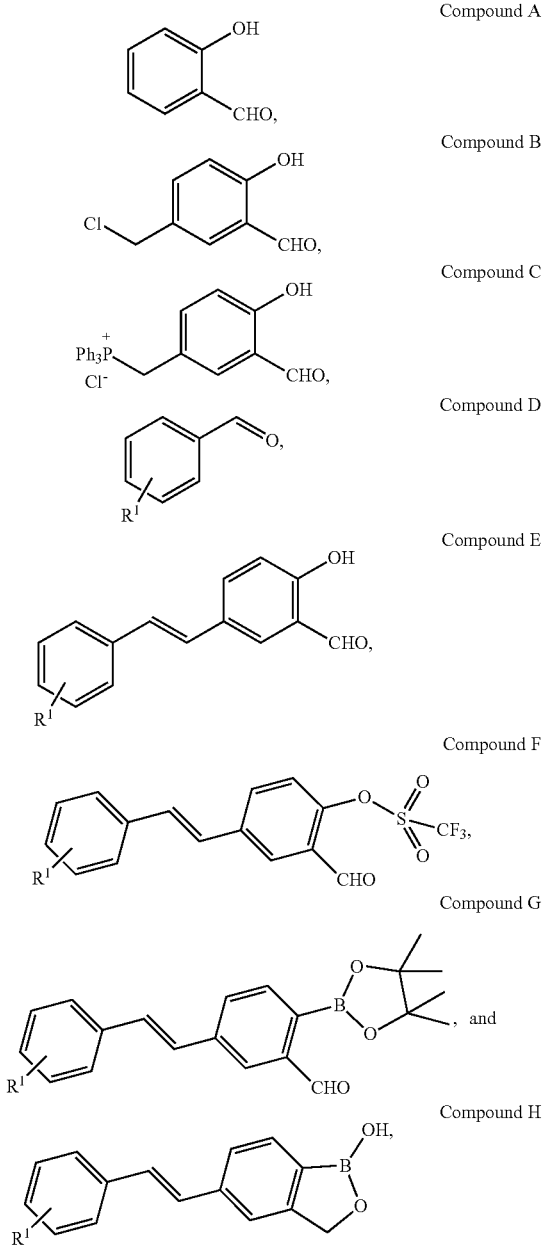

wherein: $R^1$ is independently mono- or poly-substituted with hydrogen, trifluoromethyl, trifluoromethoxy, nitro, cyano, halogen, C1-C10 alkyl, or —$OR^2$, wherein $R^2$ is independently selected from hydrogen or C1-C10 alkyl.

In some embodiments, methods of preparing at least one compound disclosed herein can have one or more steps that require a strong base condition. A strong base condition as used herein can require a step of the method herein be performed in the presence of one or more strong bases. Non-limiting examples of strong bases for use herein can be sodium methoxide, sodium ethoxide, sodium tert-butoxide, sodium isopropoxide, butyl lithium, sodium hydroxide, lithium hydroxide, potassium hydroxide, or any combination thereof. In some examples, methods of preparing at least one compound disclosed herein can include performing step (iii) as disclosed herein in a strong base condition.

In some embodiments, a strong base condition can be a strong alkaline condition. Non-limiting examples of bases for use in a strong alkaline condition can include sodium acetate, potassium acetate, sodium methoxide, sodium ethoxide, potassium methoxide, potassium ethoxide, sodium fluoride, potassium fluoride, or any combination thereof. In some examples, methods of preparing at least one compound disclosed herein may comprise step (v) herein performed under an alkaline condition.

In some embodiments, methods of preparing at least one compound disclosed herein can have one or more steps that require a temperature ranging from about −20° C. to about 100° C., about −10° C. to about 90° C., or about 0° C. to about 80° C. In some embodiments, methods of preparing at least one compound disclosed herein can have one or more steps that require a temperature of about −20° C., about −10° C., about 0° C., about 10° C., about 20° C., about 30° C., about 40° C., about 50° C., about 60° C., about 80° C., about 90° C., or about 100° C. In some examples, methods of preparing at least one compound disclosed herein can have one or more steps that require a temperature of about 0° C. In some other examples, methods of preparing at least one compound disclosed herein can have steps (iv) and (vi) herein performed at about 0° C. In some examples, methods of preparing at least one compound disclosed herein can have one or more steps that require a temperature of about 80° C. In some other examples, methods of preparing at least one compound disclosed herein can have steps (iii) and (v) herein performed at about 80° C.

In some embodiments, methods of preparing at least one compound disclosed herein can have one or more steps that utilize at least one palladium salt catalyst. Non-limiting examples of palladium salt catalysts suitable for use herein can include palladium acetate, palladium chloride, tetrakis(triphenylphosphorus) palladium, bis(acetonitrile) palladium dichloride, bis(triphenylphosphorus) palladium chloride, 1,1'-[bis(diphenylphosphorus)ferrocene]palladium dichloride, bis(benzonitrile)palladium dichloride, 1,1'-[bis(di-tert-butylphosphorus)ferrocene] Palladium dichloride, bis(tricyclohexylphosphorus) palladium dichloride, bis(o-toluene) palladium dichloride, or any combination thereof. In some examples, methods of preparing at least one compound disclosed herein can utilize a palladium salt catalyst in at least step (v) as disclosed herein.

In some embodiments, methods of preparing at least one compound disclosed herein can have one or more steps that utilize at least one polar solvent. Non-limiting examples of polar solvents for use herein can include N, N-dimethylformamide, dimethylsulfoxide, acetonitrile, acetone, methyl ethyl ketone, 1,4-dioxane, water, or any combination thereof. In some examples, methods of preparing at least one compound herein can utilize at least one polar solvent in step (v) as disclosed herein.

One of skill in the art would understand that the methods of making compounds disclosed herein can be modified to increase yield, purity, volume, solubility, crystallinity, and the like.

II. Pharmaceutical Compositions

In some embodiments, compounds disclosed herein for use according to the methods herein described may be provided per se or as part of a pharmaceutical composition, where compounds can be mixed with suitable carriers or excipients. In some embodiments, compositions disclosed herein can include one or more compounds disclosed herein. In some other embodiments, compositions disclosed herein can include one or more compounds disclosed herein and/or one or more anticancer drugs (e.g., one or more platinum-based chemotherapeutics). In certain embodiments, these compounds can be combined with a pharmaceutically acceptable carrier (excipient) to form a pharmaceutical composition for use in treating a cancer (e.g., a tumor) in a subject.

In some embodiments, compositions disclosed herein can include at least one compound represented by formula III or a salt thereof as disclosed herein. In some embodiments, compositions disclosed herein can include at least one compound represented by formula III or a salt thereof as disclosed herein and at least one anticancer drug. In some embodiments, compositions disclosed herein can include at least one compound represented by formula III or a salt thereof as disclosed herein and at least one platinum-based chemotherapeutic. In some embodiments, compositions disclosed herein can include at least one compound represented by formula III or a salt thereof as disclosed herein and cisplatin.

In some embodiments, compositions disclosed herein can include at least (E)-5-(3,4-dichlorostyryl)benzo[c][1,2]oxaborol-1(3H)-ol. In some embodiments, compositions disclosed herein can include at least (E)-5-(3,4-dichlorostyryl)benzo[c][1,2]oxaborol-1(3H)-ol and at least one anticancer drug. In some embodiments, compositions disclosed herein can include at least (E)-5-(3,4-dichlorostyryl)benzo[c][1,2]oxaborol-1(3H)-ol and at least one platinum-based chemotherapeutic. In some embodiments, compositions disclosed herein can include at least (E)-5-(3,4-dichlorostyryl)benzo[c][1,2]oxaborol-1(3H)-ol and cisplatin.

As used herein a "pharmaceutical composition" refers to a preparation of one or more of the active ingredients described herein (e.g., And-1 inhibitors) with other chemical components such as physiologically suitable carriers and excipients. A purpose of a pharmaceutical composition is to facilitate administration of a compound to an organism. Herein the term "active ingredient" refers to one or more of the compounds (e.g., And-1 inhibitors) disclosed herein, one or more anticancer drugs (e.g., platinum-based chemotherapeutics), or a combination thereof.

(i) Pharmaceutically Acceptable Carriers and Excipients

Hereinafter, the phrases "physiologically acceptable carrier" and "pharmaceutically acceptable carrier", which may be interchangeably used, refer to a carrier or a diluent that does not cause significant irritation to an organism and does not abrogate the biological activity and properties of the administered compound. An adjuvant is included under these phrases.

In various embodiments, compositions disclosed herein may further compromise one or more pharmaceutically acceptable diluent(s), excipient(s), or carrier(s). As used herein, a pharmaceutically acceptable diluent, excipient, or carrier, refers to a material suitable for administration to a subject without causing undesirable biological effects or interacting in a deleterious manner with any of the components of the composition in which it is contained. Pharmaceutically acceptable diluents, carriers, and excipients can include, but are not limited to, physiological saline, Ringer's solution, phosphate solution or buffer, buffered saline, and other carriers known in the art. Pharmaceutical compositions may also include stabilizers, anti-oxidants, colorants, other medicinal or pharmaceutical agents, carriers, adjuvants, preserving agents, stabilizing agents, wetting agents, emulsifying agents, solution promoters, salts, solubilizers, anti-foaming agents, antioxidants, dispersing agents, surfactants, and combinations thereof. Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols. Techniques for formulation and administration of drugs may be found in REMINGTON'S PHARMACEUTICAL SCIENCES, Mack Publishing Co., Easton, Pa., latest edition, which is incorporated herein by reference.

In various embodiments, pharmaceutical compositions described herein may be formulated in conventional manner using one or more physiologically acceptable carriers comprising excipients and auxiliaries to facilitate processing of genetically modified endothelial progenitor cells into preparations which can be used pharmaceutically. In other embodiments, any of the well-known techniques, carriers, and excipients may be used as suitable and as understood in the art.

In various embodiments, pharmaceutical compositions described herein may be an aqueous suspension comprising one or more polymers as suspending agents. In some aspects, polymers that may comprise pharmaceutical compositions described herein include: water-soluble polymers such as cellulosic polymers, e.g., hydroxypropyl methylcellulose; water-insoluble polymers such as cross-linked carboxyl-containing polymers; mucoadhesive polymers, selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran; or a combination thereof. In other aspects, compositions disclosed herein may comprise at least 5%, at least 10%, at least 20%, at least 25%, at least 30%, at least 35%, at least 40%, at least 45%, at least 50% total amount of polymers as suspending agent(s) by total weight of the composition.

In various embodiments, pharmaceutical compositions disclosed herein may comprise a viscous formulation. In some aspects, viscosity of the composition may be increased by the addition of one or more gelling or thickening agents. In other aspects, compositions disclosed herein may comprise one or more gelling or thickening agents in an amount to provide a sufficiently viscous formulation to remain on treated tissue. In still other aspects, compositions disclosed herein may comprise at least 5%, at least 10%, at least 20%, at least 25%, at least 30%, at least 35%, at least 40%, at least 45%, at least 50% total amount of gelling or thickening agent(s) by total weight of the composition. In yet other aspects, suitable thickening agents can be hydroxypropyl methylcellulose, hydroxyethyl cellulose, polyvinylpyrrolidone, carboxymethyl cellulose, polyvinyl alcohol, sodium chondroitin sulfate, sodium hyaluronate. In other aspects, viscosity enhancing agents can be acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose), or combinations thereof. In some embodiments, suitable thickening agent may be carboxymethylcellulose.

In various embodiments, pharmaceutical compositions disclosed herein may comprise additional agents or additives selected from a group including surface-active agents, detergents, solvents, acidifying agents, alkalizing agents, buffering agents, tonicity modifying agents, ionic additives effective to increase the ionic strength of the solution, antimicrobial agents, antibiotic agents, antifungal agents, antioxidants, preservatives, electrolytes, antifoaming agents, oils, stabilizers, enhancing agents, and the like. In some aspects, pharmaceutical compositions disclosed herein may comprise at least 5%, at least 10%, at least 20%, at least 25%, at least 30%, at least 35%, at least 40%, at least 45%, at least 50% total amount of one or more agents by total weight of the composition. In other aspects, one or more of these agents may be added to improve the performance, efficacy, safety, shelf-life and/or other property of the muscarinic antagonist composition of the present disclosure. In s aspects, additives will be biocompatible, and will not be harsh, abrasive, or allergenic.

In various embodiments, pharmaceutical compositions disclosed herein may comprise one or more acidifying agents. As used herein, "acidifying agents" refers to compounds used to provide an acidic medium. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art. In some aspects, any pharmaceutically acceptable organic or inorganic acid may be used. In other aspects, compositions disclosed herein may comprise at least 5%, at least 10%, at least 20%, at least 25%, at least 30%, at least 35%, at least 40%, at least 45%, at least 50% total amount of one or more acidifying agents by total weight of the composition.

In various embodiments, pharmaceutical compositions disclosed herein may comprise one or more alkalizing agents. As used herein, "alkalizing agents" are compounds used to provide alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art. In some aspects, any pharmaceutically acceptable organic or inorganic base can be used. In other aspects, compositions disclosed herein may comprise at least 5%, at least 10%, at least 20%, at least 25%, at least 30%, at least 35%, at least 40%, at least 45%, at least 50% total amount of one or more alkalizing agents by total weight of the composition.

In various embodiments, pharmaceutical compositions disclosed herein may comprise one or more antioxidants. As used herein, "antioxidants" are agents that inhibit oxidation and thus can be used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite and other materials known to one of ordinary skill in the art. In some aspects, compositions disclosed herein may comprise at least 5%, at least 10%, at least 20%, at least 25%, at least 30%, at least 35%, at least 40%, at least 45%, at least 50% total amount of one or more antioxidants by total weight of the composition.

In other embodiments, pharmaceutical compositions disclosed herein may comprise a buffer system. As used herein, a "buffer system" is a composition comprised of one or more buffering agents wherein "buffering agents" are compounds used to resist change in pH upon dilution or addition of acid or alkali. Buffering agents include, by way of example and without limitation, potassium metaphosphate, potassium phosphate, monobasic sodium acetate and sodium citrate anhydrous and dihydrate and other materials known to one of ordinary skill in the art. In some aspects, any pharmaceutically acceptable organic or inorganic buffer can be used. In another aspect, compositions disclosed herein may comprise at least 5%, at least 10%, at least 20%, at least 25%, at least 30%, at least 35%, at least 40%, at least 45%, at least 50% total amount of one or more buffering agents by total weight of the composition. In other aspects, the amount of one or more buffering agents may depend on the desired pH level of a composition. In some embodiments, pharmaceutical compositions disclosed herein may have a pH of about 6 to about 9. In other embodiments, pharmaceutical compositions disclosed herein may have a pH greater than about 8, greater than about 7.5, greater than about 7, greater than about 6.5, or greater than about 6. In a preferred embodiment, compositions disclosed herein may have a pH greater than about 6.8.

In various embodiments, pharmaceutical compositions disclosed herein may comprise one or more preservatives. As used herein, "preservatives" refers to agents or combination of agents that inhibits, reduces or eliminates bacterial growth in a pharmaceutical dosage form. Non-limiting examples of preservatives include Nipagin, Nipasol, isopropyl alcohol and a combination thereof. In some aspects, any pharmaceutically acceptable preservative can be used. In other aspects, pharmaceutical compositions disclosed herein may comprise at least 5%, at least 10%, at least 20%, at least 25%, at least 30%, at least 35%, at least 40%, at least 45%, at least 50% total amount of one or more preservatives by total weight of the composition.

In other embodiments, pharmaceutical compositions disclosed herein may comprise one or more surface-acting reagents or detergents. In some aspects, surface-acting reagents or detergents may be synthetic, natural, or semi-synthetic. In other aspects, compositions disclosed herein may comprise anionic detergents, cationic detergents, zwitterionic detergents, ampholytic detergents, amphoteric detergents, nonionic detergents having a steroid skeleton, or a combination thereof. In still other aspects, pharmaceutical compositions disclosed herein may comprise at least 5%, at least 10%, at least 20%, at least 25%, at least 30%, at least 35%, at least 40%, at least 45%, at least 50% total amount of one or more surface-acting reagents or detergents by total weight of the composition.

In various embodiments, pharmaceutical compositions disclosed herein may comprise one or more stabilizers. As used herein, a "stabilizer" refers to a compound used to stabilize an active agent against physical, chemical, or biochemical process that would otherwise reduce the therapeutic activity of the agent. Suitable stabilizers include, by way of example and without limitation, succinic anhydride, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art. In some aspects, pharmaceutical compositions disclosed herein may comprise at least 5%, at least 10%, at least 20%, at least 25%, at least 30%, at least 35%, at least 40%, at least 45%, at least 50% total amount of one or more stabilizers by total weight of the composition.

In other embodiments, pharmaceutical compositions disclosed herein may comprise one or more tonicity agents. As used herein, a "tonicity agents" refers to a compound that can be used to adjust the tonicity of the liquid formulation. Suitable tonicity agents include, but are not limited to, glycerin, lactose, mannitol, dextrose, sodium chloride, sodium sulfate, sorbitol, trehalose and others known to those or ordinary skill in the art. Osmolarity in a composition may be expressed in milliosmoles per liter (mOsm/L). Osmolarity may be measured using methods commonly known in the art. In preferred embodiments, a vapor pressure depression method is used to calculate the osmolarity of the compositions disclosed herein. In some aspects, the amount of one or more tonicity agents comprising a pharmaceutical composition disclosed herein may result in a composition osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L. In other aspects, a composition herein may have an osmolality ranging from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a pharmaceutical composition described herein has an osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L. In still other aspects, pharmaceutical compositions disclosed herein may comprise at least 5%, at least 10%, at least 20%, at least 25%, at least 30%, at least 35%, at least 40%, at least 45%, at least 50% total amount of one or more tonicity modifiers by total weight of the composition.

(ii) Dosage Formulations

Suitable routes of administration may, for example, include oral, rectal, transmucosal, especially transnasal, intestinal or parenteral delivery, including intramuscular, subcutaneous and intramedullary injections as well as, intravenous, intraperitoneal, intranasal injections.

One may administer the pharmaceutical compositions herein in a local or systemic manner, for example, via local injection of the pharmaceutical composition directly into a tissue region of a patient. In some embodiments, a pharmaceutical composition disclosed herein can be administered parenterally, e.g., by intravenous injection, intracerebroventricular injection, intra-cisterna magna injection, intra-parenchymal injection, or a combination thereof. In some embodiments, a pharmaceutical composition disclosed herein can administered to the human patient via at least two administration routes. In some examples, the combination of administration routes by be intramuscular injection and intravenous injection; subcutaneous injection and intravenous injection; intracerebroventricular injection and intravenous injection; intrathecal injection and intravenous injection; intra-cisterna magna injection and intravenous injection; and intra-parenchymal injection and intravenous injection. In some embodiments, a pharmaceutical composition disclosed herein can administered to a cancer cell, a tumor, or both. In some embodiments, a pharmaceutical composition disclosed herein can administered to a cancer cell, a tumor, or both by introducing the cancer cell, the tumor, or both to a pharmaceutical composition disclosed herein.

Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present disclosure may be formulated in conventional manner using one or more physiologically acceptable carriers comprising excipients and auxiliaries, which facilitate processing of the active ingredients (e.g., And-1 inhibitors and/or anticancer drugs) into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, tone or more active ingredients (e.g., And-1 inhibitors and/or anticancer drugs) may be in powder form for constitution with a suitable vehicle, e.g., sterile, pyrogen-free water based solution, before use.

Pharmaceutical compositions suitable for use in context of the present disclosure can include compositions wherein the active ingredients are contained in an amount effective to achieve the intended purpose. In some embodiments, a therapeutically effective amount means an amount of active ingredients (e.g., And-1 inhibitors and compounds disclosed herein) effective to prevent, slow, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the present disclosure, the therapeutically effective amount or dose can be estimated initially from in vitro and cell culture assays and or screening platforms disclosed herein. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in THE PHARMACOLOGICAL BASIS OF THERAPEUTICS, Ch. 1 p. 1).

Dosage amount and interval may be adjusted individually to brain or blood levels of the active ingredients and/or one of its metabolites are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc. Effective doses may be extrapolated from dose-responsive curves derived from in vitro or in vivo test systems.

III. Methods of Use

Embodiments of the instant disclosure relate to novel methods and compositions for treating cancers, tumors, or any combination thereof resistant to or suspected of becoming resistant to one or more anticancer drugs/therapies. As used herein an "anticancer drug" refers to any drug with an intended use for the treatment of malignant, or cancerous disease. Anticancer therapy refers to a treatment regimen for the treatment of malignant, or cancerous disease. Non-limiting examples of anticancer therapies can include administration of an anticancer drug, radiation, surgical methods, and the like. Anticancer drugs can be classified into three groups: cytotoxic drugs, hormones, and signal transduction inhibitors. Cytotoxic anticancer drugs suitable for use herein can include, but are not limited to: alkylating agents (e.g., nitrogen mustards and nitrosoureas); antimetabolites (e.g., folate antagonists, purine and pyrimidine analogues); antibiotics and other natural products (e.g., anthracyclines and *vinca* alkaloids); antibodies that improve drug specificity, and other generally cytotoxic drugs. In some embodiments, anticancer drugs herein can refer to platinum-based chemotherapeutics.

In some embodiments, a tumor subjected to the methods and compositions disclosed herein can be a solid tumor. In some embodiments, compositions and methods disclosed herein can re-sensitize or sensitize a tumor in a subject to one or more anticancer drugs (e.g., platinum-based chemotherapies). In some embodiments, compositions and methods disclosed herein can re-sensitize or sensitize a tumor in a subject to one or more anticancer drugs to reduce costs, improve outcome and reduce or eliminate patient exposure to an anticancer therapy without significant effect. In some embodiments, a subject can have an anticancer drug resistant cancer or be suspected of developing such a cancer where additional agents can be administered to re-sensitize or sensitize the cancer in a subject.

In some embodiments, a subject can have an anticancer drug resistant tumor or be suspected of developing such a tumor where additional agents can be administered to re-sensitize or sensitize a tumor in a subject wherein the tumor can include a solid tumor. In some embodiments, a solid tumor can be an abnormal mass of tissue that is devoid of cysts or liquid regions within the tumor. In some embodiments, solid tumors can be benign (not progressed to a cancer), a malignant or metastatic tumor. In some embodiments, a solid tumor herein can be a malignant cancer that has metastasized. In other embodiments, solid tumors contemplated herein can include, but are not limited to, sarcomas, carcinomas, lymphomas, gliomas or a combination thereof. In accordance with some embodiments herein, tumors resistant to anticancer drugs (e.g., platinum-based chemotherapies) can include, but are not limited to, a testicular tumor, ovarian tumor, cervical tumor, a kidney tumor, bladder tumor, head-and-neck tumor, liver tumor, stomach tumor, lung tumor, endometrial tumor, esophageal tumor, breast tumor, cervical tumor, central nervous system tumor, germ cell tumor, prostate tumor, Hodgkin's lymphoma, non-Hodgkin's lymphoma, neuroblastoma, sarcoma, multiple myeloma, melanoma, mesothelioma, osteogenic sarcoma or a combination thereof. In some embodiments, a targeted tumor contemplated herein can include a solid tumor such as an ovarian tumor, a breast tumor, or any combination thereof.

Some standards of care in the art for solid tumors include combination therapies but there has been limited success with combination therapies. Such combinations can lead to toxicity of the drugs, significant number of patients that are ineligible for cisplatin-based therapies, and a relatively small therapeutic survival benefit of about 5-15% when these combinations are used. Embodiments disclosed herein are designed to avoid such outcomes as there is a need in the art for new combination therapies that are equally or more effective than the current standard of care, and that offer patients a much more tolerable chemotherapeutic regimen. In some embodiments, methods of administering a combination therapy herein may include administration of any one of the compounds disclosed herein and at least one anticancer drug. In some embodiments, methods of administering a combination therapy herein may include administration of any one of the compounds disclosed herein and at least one anticancer drug wherein the compound and the anticancer drug are formulated into a single dosage form. In some embodiments, methods of administering a combination therapy herein may include administration of any one of the compounds disclosed herein and at least one anticancer drug simultaneously, subsequently, or at dosage intervals determined by one of skill in the art wherein the compound and the anticancer drug are each formulated into individual dosage forms.

In some embodiments, methods of administering any one of the compounds disclosed herein and at least one anticancer drug can have an additive effect on the efficacy of the compound (e.g., And-1 inhibitor), on the efficacy the anticancer drug, or on the efficacy both. In some embodiments, methods of administering any one of the compounds disclosed herein and at least one anticancer drug can have a synergistic effect on the efficacy of the compound (e.g., And-1 inhibitor), on the efficacy the anticancer drug, or on the efficacy both.

Studies have been performed and are currently continuing to identify biomarkers of anticancer drug-resistant cancers such as platinum-resistant cancers. Therapeutically actionable targets in treatment-resistant tumors have been hampered for example, by reliance on using simplistic techniques with tumor-derived cell line models. Embodiments of the present disclosure provides methods and compositions for treating cancers and tumors resistant to anticancer drugs (e.g., platinum-based chemotherapy) by, for example, identifying a subject having tumors with increased expression of And-1 and/or increased phosphorylation of And-1, and/or administering an effective amount of at least one compound (e.g., And-1 inhibitor) disclosed herein in combination with at least one anticancer drug (e.g., platinum-based chemotherapeutic) to the subject for treating a solid tumor depending on whether or not the subject was identified as an And-1 overexpresser, a phosphorylated And-1 protein overexpresser, or a combination thereof.

In some embodiments, compositions of use herein can include one or more compounds (e.g., And-1 inhibitors) or salts thereof. In some embodiments, concentrations of compounds herein or salts thereof for use in therapies disclosed herein can include about 1 mg to about 200 mg, about 5 mg to about 150 mg, about 10 mg to about 120 mg, about 20 mg about 30 mg, about 40 mg, about 60 mg, about 80 mg, about 100 mg, about 120 mg, about 140 mg, about 160 mg, about 180 mg, about 200 mg.

In some embodiments, compositions of use herein can include (E)-5-(3,4-dichlorostyryl)benzo[c][1,2]oxaborol-1(3H)-ol In some embodiments, concentrations of (E)-5-(3,4-dichlorostyryl)benzo[c][1,2]oxaborol-1(3H)-ol for use in therapies disclosed herein can include about 1 mg to about 200 mg, about 5 mg to about 150 mg, about 10 mg to about 120 mg, about 20 mg about 30 mg, about 40 mg, about 60 mg, about 80 mg, about 100 mg, about 120 mg, about 140 mg, about 160 mg, about 180 mg, about 200 mg.

In certain embodiments, compounds herein or salts thereof can be administered to a subject alone or in combination with an anticancer drug, daily, every other day, twice weekly, every other day, every other week, weekly or monthly or other suitable dosing regimen.

In some embodiments, other compositions which can be administered alone or in combination with an And-1 inhibitor-containing composition can include at least one anticancer drug, e.g., a platinum-based chemotherapeutic. As used herein, a "platinum-based chemotherapeutic" is a chemotherapeutic that is an organic compound which contains platinum as an integral part of the molecule. In some embodiments, compositions of use herein can contain one or more platinum-based chemotherapeutics including, but not limited to, cisplatin, carboplatin, nedaplatin, triplatin tetranitrate, phenanthriplatin, picoplatin, satraplatin or a combination thereof. In some embodiments, a platinum-based chemotherapeutic can be administered separately from the compounds disclosed herein. In some embodiments, compositions containing a platinum-based chemotherapeutic of use herein can contain a concentration of the platinum-based chemotherapeutic at about 1 mg/ml to about 100 mg/ml (e.g., about 1 mg/ml, about 5 mg/ml, about 10 mg/ml, about 20 mg/ml, about 30 mg/ml, about 40 mg/ml, about 50 mg/ml, about 60 mg/ml, about 80 mg/ml, about 100 mg/ml). In some embodiments, the platinum-based chemotherapeutic or salt thereof or derivative thereof includes cisplatin. In certain embodiments, platinum-based chemotherapeutic agents can be administered to a subject alone or in combination with at least one of the compounds disclosed herein (e.g., And-1 inhibitors), daily, every other day, twice weekly, every other day, every other week, weekly or monthly or other suitable dosing regimen.

In certain embodiments, compositions disclosed herein can treat and/or prevent cancer in a subject in need. In some embodiments, compositions disclosed herein can impair tumor growth compared to tumor growth in an untreated subject with identical disease condition and predicted outcome. In some embodiments, tumor growth can be stopped following treatment with compositions disclosed herein. In other embodiments, tumor growth can be impaired at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In other words, tumors in subject treated using a composition of the disclosure have tumors that grow at least 5% less (or more as described above) when compared to an untreated subject with identical disease condition and predicted outcome. In some embodiments, tumor growth can be impaired at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In some embodiments, tumor growth can be impaired at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated subject with identical disease condition and predicted outcome.

In some embodiments, treatment of tumors with compositions disclosed herein can result in a shrinking of a tumor in comparison to the starting size of the tumor. In some embodiments, tumor shrinking is at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% (meaning that the tumor is completely gone after treatment) compared to the starting size of the tumor.

In various embodiments, compositions disclosed herein can improve patient life expectancy compared to the cancer life expectancy of an untreated subject with identical disease condition and predicted outcome. As used herein, "patient life expectancy" is defined as the time at which 50 percent of subjects are alive and 50 percent have passed away. In some embodiments, patient life expectancy can be indefinite following treatment with a composition disclosed herein. In other aspects, patient life expectancy can be increased at least about 5% or greater to at least about 100%, at least about 10% or greater to at least about 95% or greater, at least about 20% or greater to at least about 80% or greater, at least about 40% or greater to at least about 60% or greater compared to an untreated subject with identical disease condition and predicted outcome. In some embodiments, patient life expectancy can be increased at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome. In some embodiments, patient life expectancy can be increased at least about 5% or greater to at least about 10% or greater, at least about 10% or greater to at least about 15% or greater, at least about 15% or greater to at least about 20% or greater, at least about 20% or greater to at least about 25% or greater, at least about 25% or greater to at least about 30% or greater, at least about 30% or greater to at least about 35% or greater, at least about 35% or greater to at least about 40% or greater, at least about 40% or greater to at least about 45% or greater, at least about 45% or greater to at least about 50% or greater, at least about 50% or greater to at least about 55% or greater, at least about 55% or greater to at least about 60% or greater, at least about 60% or greater to at least about 65% or greater, at least about 65% or greater to at least about 70% or greater, at least about 70% or greater to at least about 75% or greater, at least about 75% or greater to at least about 80% or greater, at least about 80% or greater to at least about 85% or greater, at least about 85% or greater to at least about 90% or greater, at least about 90% or greater to at least about 95% or greater, at least about 95% or greater to at least about 100% compared to an untreated patient with identical disease condition and predicted outcome.

In some embodiments, the methods of the present disclosure increase anti-tumor activity (e.g., reduce cell proliferation, tumor growth, tumor volume, and/or tumor burden or load or reduce the number of metastatic lesions over time) by at least about 10%, 20%, 25%, 30%, 40%, 50%, 60%, 70%, 75%, 80%, 85%, 90%, 95%, or more as compared to levels prior to treatment or in a control subject. In some embodiments, reduction is measured by comparing cell proliferation, tumor growth, and/or tumor volume in a subject before and after administration of the pharmaceutical composition. In some embodiments, the method of treating or ameliorating a cancer in a subject allows one or more symptoms of the cancer to improve by at least about 10%, 20%, 30%, 40%, 50%, 60%, 70%, 80%, 90%, 95%, or more. In some embodiments, before, during, and after the administration of the pharmaceutical composition, cancerous cells and/or biomarkers in a subject are measured in a biological sample, such as blood, serum, plasma, urine, peritoneal fluid, and/or a biopsy from a tissue or organ. In some embodiments, the methods include administration of the compositions of the invention to reduce tumor volume, size, load or burden in a subject to an undetectable size, or to less than about 1%, 2%, 5%, 10%, 20%, 25%, 30%, 40%, 50%, 60%, 70%, 75%, 80%, or 90% of the subject's tumor volume, size, load or burden prior to treatment. In other embodiments, the methods include administration of the compositions of the invention to reduce the cell proliferation rate or tumor growth rate in a subject to an undetectable rate, or to less than about 1%, 2%, 5%, 10%, 20%, 25%, 30%, 40%, 50%, 60%, 70%, 75%, 80%, or 90% of the rate prior to treatment.

In some embodiments, a subject to be treated by any of the methods and/or compositions herein can present with one or more cancerous solid tumors, metastatic nodes, of a combination thereof. In some embodiments, a subject herein can have a cancerous tumor cell source that can be less than about 0.2 $cm^3$ to at least about 20 $cm^3$ or greater, at least about 2 $cm^3$ to at least about 18 $cm^3$ or greater, at least about 3 $cm^3$ to at least about 15 $cm^3$ or greater, at least about 4 $cm^3$ to at least about 12 $cm^3$ or greater, at least about 5 $cm^3$ to at least about 10 $cm^3$ or greater, or at least about 6 $cm^3$ to at least about 8 $cm^3$ or greater.

In various embodiments, the compositions disclosed herein can be effective for treating at least one tumor cell in a solid tumor from a subject in need. In some embodiments, the amount of viable tumor cells is reduced by at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome.

In various embodiments, the compositions disclosed herein can reduce the amount of viable tumor cells by at least about 5% or greater, at least about 10% or greater, at least about 15% or greater, at least about 20% or greater, at least about 25% or greater, at least about 30% or greater, at least about 35% or greater, at least about 40% or greater, at least about 45% or greater, at least about 50% or greater, at least about 55% or greater, at least about 60% or greater, at least about 65% or greater, at least about 70% or greater, at least about 75% or greater, at least about 80% or greater, at least about 85% or greater, at least about 90% or greater, at least about 95% or greater, at least about 100% compared to an untreated subject with identical disease condition and predicted outcome.

Conventional methods, known to those of ordinary skill in the art of medicine, can be used to administer the compositions disclosed herein to a subject, depending upon the type of disease to be treated or the site of the disease. In some embodiments, compositions herein can be administered to a subject by intravenous infusion by subcutaneous administration, by inhalation, by intranasal administration or other mode of administration. In some embodiments, compositions herein can be administered to a subject orally.

In some embodiments, any of the methods disclosed herein can further include monitoring occurrence of one or more adverse effects in the subject. Exemplary adverse effects include, but are not limited to, hepatic impairment, hematologic toxicity, neurologic toxicity, cutaneous toxicity, gastrointestinal toxicity, or a combination thereof. When one or more adverse effects are observed, the method disclosed herein can further include reducing or increasing the dose of one or more of the disclosed compounds (e.g., And-1 inhibitors), the dose of one or more anticancer drugs (e.g., platinum-based chemotherapeutics) or both depending on the adverse effect or effects in the subject. For example, when a moderate to severe hepatic impairment is observed in a subject after treatment, compositions of use to treat the subject can be reduced in concentration or frequency of dosing with one or more disclosed compounds the dose or frequency of the platinum-based chemotherapeutic can be adjusted (e.g., cisplatin) or a combination thereof.

In some embodiments, one or more disclosed compounds (e.g., And-1 inhibitors) herein can be administered concurrently with the one or more anticancer drugs (e.g., platinum-based chemotherapeutics) by the same or different modes of administration. In some embodiments, one or more disclosed compounds (e.g., And-1 inhibitors) herein can be administered before, during or after the one or more anticancer drugs. In other embodiments, the one or more anticancer drugs can be administered systemically. In certain embodiments, the one or more anticancer drugs (e.g., platinum-based chemotherapeutics) can be administered locally directly to one or more tumors in the subject. In some embodiments, the one or more anticancer drugs can be administered by intravenous administration, e.g., as a bolus or by continuous infusion over a period of time, by intramuscular, intraperitoneal, intracerebrospinal, subcutaneous, intra-arterial, intra-articular, intrasynovial, intrathecal, intratumoral, oral, inhalation or topical routes. In other embodiments, the one or more anticancer drugs can be administered to the subject by intravenous infusion.

An effective amount of the pharmaceutical composition described herein can be administered to a subject (e.g., a human) in need of the treatment via a suitable route, systemically or locally. In some embodiments, one or more disclosed compounds (e.g., And-1 inhibitors) can be administered by intravenous administration, e.g., as a bolus or by continuous infusion over a period of time, by intramuscular, intraperitoneal, intracerebrospinal, subcutaneous, intra-arterial, intra-articular, intrasynovial, intrathecal, intratumoral, oral, inhalation or topical routes. In some embodiments, one or more disclosed compounds (e.g., And-1 inhibitors) can be administered orally.

In some embodiments, dosages for one or more disclosed compounds (e.g., And-1 inhibitors) and/or one or more anticancer drugs (e.g., platinum-based chemotherapeutics) as described herein are determined empirically in individuals who have been given one or more administration(s) of the one or more compounds herein and/or one or more platinum-based chemotherapeutics. Individuals are given incremental dosages of the one or more one or more disclosed compounds (e.g., And-1 inhibitors) and/or one or more anticancer drugs. To assess efficacy of the one or more disclosed compounds (e.g., And-1 inhibitors) and/or one or more anticancer drugs (e.g., platinum-based chemotherapeutics), an indicator of the disease/disorder can be followed.

In some embodiments, methods herein of treating a cancer with one or more disclosed compounds (e.g., And-1 inhibitors) and/or one or more platinum-based chemotherapeutics can further include treating a subject with at least one additional anti-cancer therapy, for example, chemotherapy, radiotherapy, immunotherapy, or surgery. In some embodiments, an additional anticancer drug can be administered to the subject including, but not limited to, one or more of gemcitabine, methotrexate, vinblastine, and/or adriamycin. In some embodiments, methods herein can be administered to a subject who has completed at least one anticancer therapy or who is currently undergoing at least anticancer therapy. In some embodiments, methods herein can be administered to a subject having received and/or currently receiving at least one immune-modulatory agent. Non-limiting examples of such immune-modulatory agents include, but are not limited to, anti-PD1, anti-PD-L1, anti-CTLA-4, anti-OX40, anti-CD137, etc. Non-limiting examples of PD-1 inhibitors include, but are not limited to, anti-PD-1 antibodies, such as pembrolizumab, nivolumab, and cemiplimab. Non-limiting examples of PD-L1 inhibitors can include atezolizumab, durvalumab, and avelumab. A non-limiting example of a CTLA-4 inhibitor is the anti-CTLA-4 antibody ipilimumab. In some embodiments, an immuno-modulatory agent can be one or more inhibitors that target a checkpoint molecule selected from CD40, GITR, LAG-3, OX40, TIGIT and TIM-3. In some embodiments, the additional one or more anticancer drugs can be one or more chemotherapeutics. In some examples, chemotherapeutics for use herein can include an antimetabolite, a microtubule inhibitor, or a combination thereof. Antimetabolites can include, for example, folic acid antagonist (e.g., methotrexate) and nucleotide analogs such as pyrimidine antagonist (e.g., 5-fluorouracil, foxuridine, cytarabine, capecitabine, and gemcitabine), purine antagonist (e.g., 6-mercaptopurine and 6-thioguanine), and adenosine deaminase inhibitor (e.g., cladribine, fludarabine and pentostatin).

In some embodiments, methods of treatment with at least one or more disclosed compounds (e.g., And-1 inhibitors) and/or one or more anticancer drugs (e.g., platinum-based chemotherapeutics) can depend on the cancer type, grade of cancer, stage or cancer or a combination thereof. In some embodiments, methods of treatment with at least one or more disclosed compounds (e.g., And-1 inhibitors) and/or one or more anticancer drugs (e.g., platinum-based chemotherapeutics) can depend on the stage of cancer as determined by the TNM system wherein "T" stands for tumor, "N" stands for node, and "M" stands for metastasis. When applying the TNM system, the following are considered: Tumor (T)—How large is the primary tumor? Where is it located?; Node (N)—Has the tumor spread to the lymph nodes? If so, where and how many?; and Metastasis (M)—Has the cancer spread to other parts of the body? If so, where and how much? In some embodiments, methods of treatment with at least one or more disclosed compounds (e.g., And-1 inhibitors) and/or one or more anticancer drugs (e.g., platinum-based chemotherapeutics) can depend on the stage of bladder cancer. One of skill in the art (i.e., a physician) can assign the stage of the cancer in a subject by combining the T, N, and M classifications.

In some embodiments, methods for measuring And-1 levels in a targeted tumor are disclosed where And-1 can be used as at least one biomarker, for example, to select or identify patients or subjects in need of aminopeptidase adjustment. In certain embodiments, And-1 levels can determine tumor burden, disease progression or projected response to treatment.

As used herein, "biomarker" can mean a distinctive biological or biologically derived indicator of a process, event or conditions. In some embodiments, the biomarker is a gene or gene product (e.g., a polypeptide). In some embodiments, a combination of biomarkers can be used as an indicator of a process, event or condition. In some embodiments, a combination of biomarkers used as an indicator of a process, event or condition can encompass at least two biomarkers. In some embodiments, a combination of biomarkers used as an indicator of a process, event or condition can encompass at least two biomarkers wherein one of the at least two biomarkers can be And-1.

As used herein, "predictive biomarker" can refer to a biomarker that can be used in advance of therapy to estimate the likelihood or predictability of response to a given therapeutic agent (e.g., anticancer drug) or class of therapeutic agents. In some embodiments, a combination of predictive biomarkers can be used in advance of therapy to estimate the likelihood or predictability of response to a given therapeutic agent or class of therapeutic agents. In some embodiments, a combination of predictive biomarkers used in advance of therapy to estimate the likelihood or predictability of response to a given therapeutic agent or class of therapeutic agents can have at least two predictive biomarkers. In some embodiments, a combination of predictive biomarkers used in advance of therapy to estimate the likelihood or predictability of response to a given therapeutic agent or class of therapeutic agents can have at least one predictive biomarkers wherein one of the predictive biomarkers can be And-1.

As used herein, the term "biological sample" can mean a sample obtained from a subject. A suitable biological sample can be obtained from a subject as described herein via routine practice. Non-limiting examples of biological samples include fluid samples such as blood (e.g., whole blood, plasma, or serum), urine, and saliva, and solid samples such as tissue (e.g., skin, lung, or nasal) and feces. Such samples can be collected using any method known in the art or described herein, e.g., buccal swab, nasal swab, venipuncture, biopsy, urine collection, or stool collection. In some embodiments, the biological sample can be a blood sample. In some other embodiments, the blood sample is a serum sample or a plasma sample. In some embodiments, a biological sample can be derived from a tissue and/or tumor biopsy collected from the subject e.g., patient-derived organotypic tumor spheroids prepared as described herein.

In some embodiments, methods herein of measuring And-1 levels in a biological sample of subject can be measured by routine practice. Methods for detecting and/or assessing an amount of gene expression of And-1 in a biological sample are well known in the art, and all suitable methods for detecting and/or assessing an amount of gene expression levels known to one of skill in the art are contemplated within the scope of the invention. In some embodiments, gene expression of And-1 in a biological sample can be measured by high-density expression array, DNA microarray, polymerase chain reaction (PCR), reverse transcriptase PCR (RT-PCR), real-time quantitative reverse transcription PCR (qRT-PCR), digital droplet PCR (ddPCR), serial analysis of gene expression (SAGE), Spotted cDNA arrays, GeneChip, spotted oligo arrays, bead arrays, RNA Seq, tiling array, northern blotting, hybridization microarray, in situ hybridization, or a combination thereof. In some aspects, gene expression of And-1 as disclosed herein can be measured by any known or future method suitable to assess gene expression.

Methods for detecting and/or assessing an amount of protein expression of And-1 and phosphorylated And-1 in a biological sample are well known in the art, and all suitable methods for detecting and/or assessing an amount of protein expression levels known to one of skill in the art are contemplated within the scope of the invention. In some embodiments, protein expression of And-1 in a biological sample can be measured by western blotting, enzyme-linked immunosorbent assay (ELISA), mass spectrometry, HPLC, flow cytometry, fluorescence-activated cell sorting (FACS), liquid chromatography-mass spectrometry (LC/MS), immunoelectrophoresis, translation complex profile sequencing (TCP-seq), protein microarray, protein chip, capture arrays, reverse phase protein microarray (RPPA), two-dimensional gel electrophoresis or (2D-PAGE), functional protein microarrays, electrospray ionization (ESI), matrix-assisted laser desorption/ionization (MALDI), or a combination thereof. In some aspects, protein expression of And-1 and phosphorylated And-1 as disclosed herein can be measured by any known or future method suitable to assess protein expression.

In some embodiments, a subject can be a human patient having an elevated level of And-1 relative to a control level. In some embodiments, a subject can be a human patient having an elevated level of phosphorylated And-1 protein relative to a control level. A control level can refer to the level of And-1 or the level of phosphorylated And-1 protein in a matched sample of a subject of the same species (e.g., human) who are free of the solid tumor. In some examples, the control level represents the level of And-1 or the level of phosphorylated And-1 protein in healthy subjects.

IV. Kits

In certain embodiments, the present disclosure provides kits for use in treating or alleviating a solid tumor described herein. Such kits can include one or more containers including one or more one or more disclosed compounds (e.g., And-1 inhibitors), e.g., any of those described. In some embodiments, kits can include one or more containers including one or more one or more disclosed compounds (e.g., And-1 inhibitors), e.g., any of those described and one or more platinum-based chemotherapeutic described herein (e.g., a cisplatin). In other embodiments, kits can include a control And-1 sample for assessing level of And-1 in a sample from a subject.

In some embodiments, the kits herein can include instructions for use in accordance with any of the methods described herein. The included instructions can have a description of administration of the one or more disclosed compounds (e.g., And-1 inhibitors), the one or more anti-cancer drugs (e.g., platinum-based chemotherapeutics), to treat, delay the onset, or alleviate a target disease as those described herein, or a combination thereof. In some embodiments, the kit can further include a description of selecting an individual suitable for treatment based on identifying whether that individual has the target disease, e.g., applying the diagnostic method as described herein. In still other embodiments, the instructions can have a description of administering any one of the compositions described herein to an individual at risk of the target disease.

In some embodiments, kit instructions relating to the use of one or more one or more disclosed compounds (e.g., And-1 inhibitors), one or more anticancer drugs (e.g., platinum-based chemotherapeutics) described herein (e.g., a cisplatin), or a combination thereof can generally include information as to dosage, dosing schedule, and route of administration for the intended treatment. The containers can be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating the solid tumor. In some embodiments, instructions are provided for practicing any of the methods described herein. In some embodiments, instructions are provided for assessing And-1 as a biomarker of disease (e.g., cancer).

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. In some embodiments, a kit has a sterile access port (for example the container can be an intravenous solution bag or a vial having a stopper pierceable by a hypodermic injection needle). In some embodiments, the container also has a sterile access port (for example the container is an intravenous solution bag or a vial having a stopper pierceable by a hypodermic injection needle). At least one active agent in the composition is at least one or more disclosed compounds (e.g., And-1 inhibitors).

In some embodiments, kits herein can optionally provide additional components such as buffers and interpretive information. Normally, the kit comprises a container and a label or package insert(s) on or associated with the container. In some embodiments, the invention provides articles of manufacture comprising contents of the kits described above.

EXAMPLES

The following examples are included to demonstrate preferred embodiments of the disclosure. It should be appreciated by those of skill in the art that the techniques disclosed in the examples that follow represent techniques discovered by the inventors to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Example 1: Synthesis of 5-(chloromethyl)-2-hydroxybenzaldehyde (B)

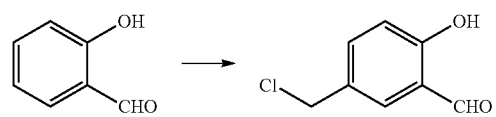 [SMILES: O=Cc1ccccc1O ; O=Cc1cc(CCl)ccc1O]

A solution of paraformaldehyde (24.40 grams (g), 0.20 moles (mol)) in concentrated hydrochloric acid (80 milliliters (mL)) was stirred at room temperature for 10 minutes, and then salicylaldehyde (17.95 g, 0.60 mol) was added dropwise over 30 minutes. The reaction solution was stirred at room temperature for 24 hours to give a white solid. Filtration, washing the filter cake with cold water, and drying to obtain a crude product. Recrystallization from n-hexane (310 mL) gave white crystals (16.80 g, 49.4%). $^1$H NMR (400 megahertz (MHz), DMSO-$d_6$) δ 10.91 (s, 1H), 10.27 (s, 1H), 7.72 (d, J=2.4 Hz, 1H), 7.59 (dd, J=8.5, 2.4 Hz, 1H), 7.03 (d, J=8.5 Hz, 1H), 4.76 (s, 2H).

Example 2: Synthesis of (3-formyl-4-hydroxybenzyl)triphenylphosphonium chloride (C)

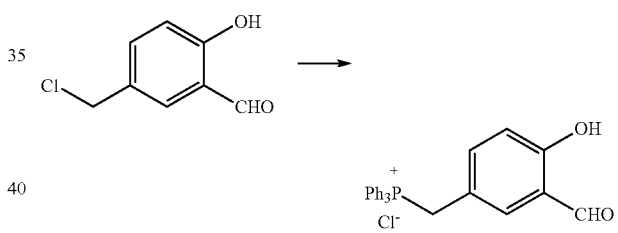

5-(chloromethyl)-2-hydroxybenzaldehyde (15.50 g, 91.2 mmol) and triphenylphosphine (30.98 g, 118.1 mmol) were dissolved in 220 mL of dry acetonitrile. The reaction solution was stirred at 80° C. for 3 hours under a nitrogen atmosphere. The acetonitrile was evaporated to dryness under reduced pressure, and the residue was washed with petroleum ether (100 mL×3) to afford white powder (38.52 g, 97.8%).

Example 3: Synthesis of (E)-5-(3,5-dichlorostyryl)-2-hydroxybenzaldehyde (E1)

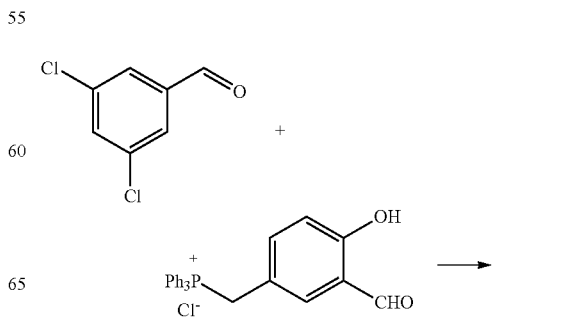

-continued

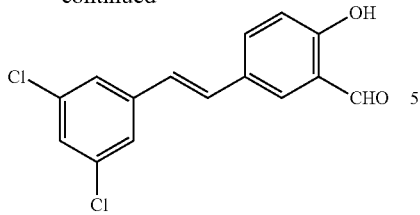

Sodium (0.19 g, 8.26 mmol) was dissolved in absolute ethanol (30 ml) under nitrogen. The phosphonium salt (1.20 g, 2.78 mmol) was added to this sodium ethoxide solution until the reaction mixture became dark yellow, and 3,5-dichlorobenzaldehyde (0.57 g, 3.26 mmol) was added. The reaction solution was stirred at 75° C. for 3 hours. The reaction was withdrawn, cooled to room temperature, clarified and then turbid with water, and the pH was adjusted to be acidic with dilute hydrochloric acid to precipitate a yellow solid. Filtration, drying and recrystallization from tetrahydrofuran afforded yellow crystals (0.387 g, 44.4%). $^1$H NMR (400 MHz, DMSO-$d_6$) δ 10.97 (s, 1H), 10.31 (s, 1H), 7.87 (d, J=2.2 Hz, 1H), 7.79 (dd, J=8.7, 2.3 Hz, 1H), 7.67 (d, J=1.8 Hz, 2H), 7.46 (d, J=16.5 Hz, 1H), 7.45 (t, J=1.8 Hz, 1H), 7.13 (d, J=16.5 Hz, 1H), 7.06 (d, J=8.6 Hz, 1H).

By performing the steps described in Example 3, the following intermediates were prepared:

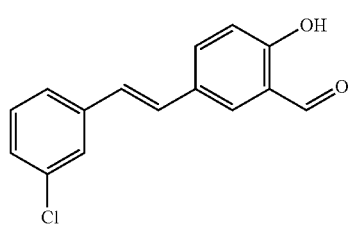 [SMILES: O=Cc1cc(/C=C/c2cccc(Cl)c2)ccc1O]

(E)-5-(3-fluorostyryl)-2-hydroxybenzaldehyde $^1$H NMR (400 MHz, DMSO-$d_6$) δ 10.91 (s, 1H), 10.31 (s, 1H), 7.87 (d, J=1.9 Hz, 1H), 7.80 (dd, J=8.6, 1.9 Hz, 1H), 7.49-7.36 (m, 3H), 7.32 (d, J=16.4 Hz, 1H), 7.14 (d, J=16.4 Hz, 1H), 7.07 (dd, J=14.4, 6.6 Hz, 2H). $^{13}$C NMR (101 MHz, DMSO-$d_6$) δ 191.56, 164.30, 161.89, 161.09, 140.39, 140.31, 134.54, 130.99, 130.91, 129.28, 128.79, 127.59, 126.19, 126.16, 123.15, 123.13, 122.87, 118.29, 114.52, 114.30, 112.88, 112.67;

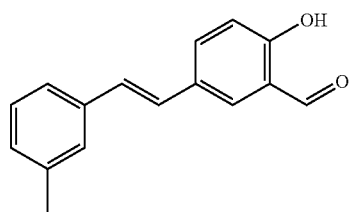 [SMILES: Cc1cccc(/C=C/c2ccc(O)c(C=O)c2)c1]

(E)-5-(3-chlorostyryl)-2-hydroxybenzaldehyde $^1$H NMR (400 MHz, DMSO-$d_6$) δ 10.94 (s, 1H), 7.87 (d, J=2.0 Hz, 1H), 7.81 (dd, J=8.6, 2.1 Hz, 1H), 7.68 (s, 1H), 7.54 (d, J=7.8 Hz, 1H), 7.35 (dt, J=17.0, 7.9 Hz, 3H), 7.14 (d, J=16.5 Hz, 1H), 7.05 (d, J=8.6 Hz, 1H);

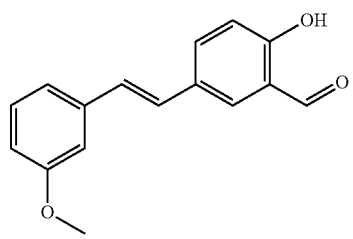 [SMILES: COc1cccc(/C=C/c2ccc(O)c(C=O)c2)c1]

(E)-2-hydroxy-5-(3-methylstyryl)benzaldehyde $^1$H NMR (400 MHz, DMSO-$d_6$) δ 10.86 (s, 1H), 10.30 (s, 1H), 7.84 (d, J=2.2 Hz, 1H), 7.80 (dd, J=8.6, 2.3 Hz, 1H), 7.44-7.34 (m, 2H), 7.29-7.17 (m, 2H), 7.14-7.01 (m, 3H), 2.32 (s, 3H);

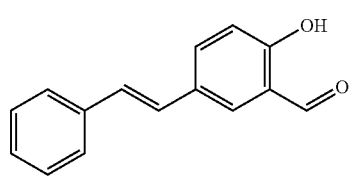

(E)-2-hydroxy-5-(3-methoxystyryl)benzaldehyde $^1$H NMR (400 MHz, DMSO-$d_6$) δ 10.89 (s, 1H), 10.31 (s, 1H), 7.93-7.75 (m, 2H), 7.39-7.22 (m, 2H), 7.14 (dd, J=16.7, 12.2 Hz, 3H), 7.04 (d, J=8.6 Hz, 1H), 6.88-6.79 (m, 1H), 3.79 (s, 3H);

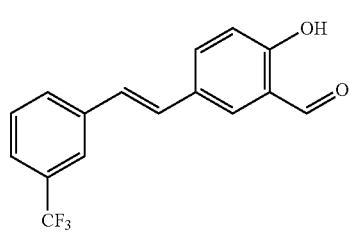 [SMILES: O=Cc1cc(/C=C/c2cccc(C(F)(F)F)c2)ccc1O]

(E)-2-hydroxy-5-styrylbenzaldehyde $^1$H NMR (400 MHz, DMSO-$d_6$) δ 10.88 (s, 1H), 10.31 (s, 1H), 7.86 (s, 1H), 7.84-7.78 (m, 1H), 7.59 (d, J=7.7 Hz, 2H), 7.37 (t, J=7.6 Hz, 2H), 7.30-7.20 (m, 2H), 7.14 (d, J=16.5 Hz, 1H), 7.04 (d, J=8.6 Hz, 1H);

(E)-2-hydroxy-5-(3-(trifluoromethyl)styryl)benzaldehyde

¹H NMR (400 MHz, DMSO-d₆) δ 10.93 (s, 1H), 10.31 (s, 1H), 7.95 (s, 1H), 7.90 (t, J=4.3 Hz, 2H), 7.83 (dd, J=8.7, 2.3 Hz, 1H), 7.65-7.55 (m, 2H), 7.44 (d, J=16.5 Hz, 1H), 7.26 (d, J=16.5 Hz, 1H), 7.06 (d, J=8.6 Hz, 1H);

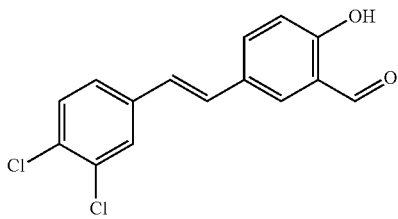 [SMILES: O=Cc1cc(/C=C/c2ccc(Cl)c(Cl)c2)ccc1O]

(E)-5-(3,4-dichlorostyryl)-2-hydroxybenzaldehyde

¹H NMR (400 MHz, DMSO-d₆) δ 10.92 (s, 1H), 10.31 (s, 1H), 7.87 (d, J=1.9 Hz, 2H), 7.80 (dd, J=8.6, 2.3 Hz, 1H), 7.65-7.52 (m, 2H), 7.37 (d, J=16.5 Hz, 1H), 7.13 (d, J=16.5 Hz, 1H), 7.05 (d, J=8.6 Hz, 1H). ¹³C NMR (101 MHz, DMSO-d₆) δ 191.43, 161.22, 138.63, 134.57, 131.94, 131.13, 130.08, 129.72, 128.62, 128.24, 127.64, 126.74, 124.79, 122.88, 118.30;

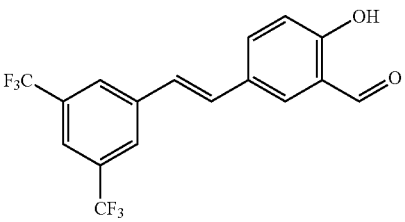

(E)-5-(3,5-bis(trifluoromethyl)styryl)-2-hydroxybenzaldehyde

¹H NMR (400 MHz, DMSO-d₆) δ 11.02 (s, 1H), 10.32 (s, 1H), 8.29 (s, 2H), 7.93 (d, J=2.0 Hz, 1H), 7.91 (s, 1H), 7.83 (dd, J=8.6, 2.1 Hz, 1H), 7.67 (d, J=16.6 Hz, 1H), 7.37 (d, J=16.5 Hz, 1H), 7.07 (d, J=8.6 Hz, 1H);

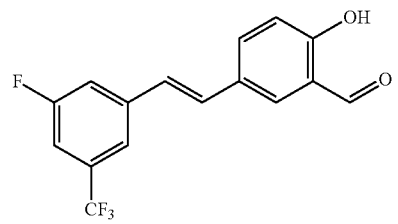 [SMILES: O=Cc1cc(/C=C/c2cc(F)cc(C(F)(F)F)c2)ccc1O]

(E)-5-(3-fluoro-5-(trifluoromethyl)styryl)-2-hydroxybenzaldehyde

¹H NMR (400 MHz, DMSO-d₆) δ 11.00 (s, 1H), 10.31 (s, 1H), 7.89 (d, J=2.2 Hz, 1H), 7.84-7.74 (m, 3H), 7.59-7.48 (m, 2H), 7.26 (d, J=16.5 Hz, 1H), 7.06 (d, J=8.6 Hz, 1H);

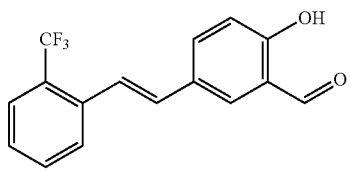 [SMILES: O=Cc1cc(/C=C/c2ccccc2C(F)(F)F)ccc1O]

(E)-2-hydroxy-5-(2-(trifluoromethyl)styryl)benzaldehyde

¹H NMR (400 MHz, DMSO-d₆) δ 11.01 (s, 1H), 10.31 (s, 1H), 7.98 (d, J=7.9 Hz, 1H), 7.85 (d, J=2.2 Hz, 1H), 7.80 (dd, J=8.6, 2.3 Hz, 1H), 7.74 (d, J=7.8 Hz, 1H), 7.69 (t, J=7.6 Hz, 1H), 7.48 (t, J=7.6 Hz, 1H), 7.35 (d, J=16.1 Hz, 1H), 7.24 (dd, J=16.2, 2.1 Hz, 1H), 7.08 (d, J=8.6 Hz, 1H);

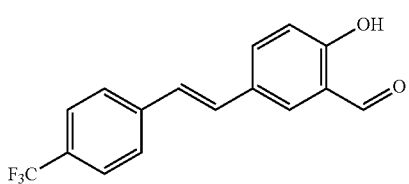

(E)-2-hydroxy-5-(4-(trifluoromethyl)styryl)benzaldehyde

¹H NMR (400 MHz, DMSO-d₆) δ 10.98 (s, 1H), 10.31 (s, 1H), 7.90 (d, J=2.2 Hz, 1H), 7.85 (dd, J=8.6, 2.2 Hz, 1H), 7.79 (d, J=8.2 Hz, 2H), 7.71 (d, J=8.3 Hz, 2H), 7.43 (d, J=16.5 Hz, 1H), 7.24 (d, J=16.5 Hz, 1H), 7.05 (d, J=8.6 Hz, 1H); and

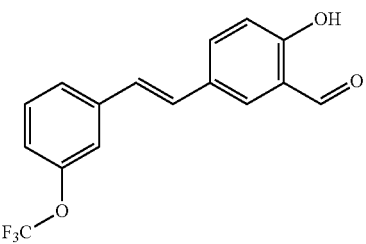

(E)-2-hydroxy-5-(3-(trifluoromethoxy)styryl)benzaldehyde

¹H NMR (400 MHz, DMSO-d₆) δ 10.90 (s, 1H), 10.31 (s, 1H), 7.89 (d, J=2.2 Hz, 1H), 7.82 (dd, J=8.6, 2.3 Hz, 1H), 7.66-7.56 (m, 2H), 7.49 (t, J=8.0 Hz, 1H), 7.38 (d, J=16.5 Hz, 1H), 7.21 (t, J=12.3 Hz, 2H), 7.05 (d, J=8.6 Hz, 1H).

Example 4: Synthesis of (E)-4-(3,5-dichlorostyryl)-2-formylphenyl trifluoromethanesulfonate (F1)

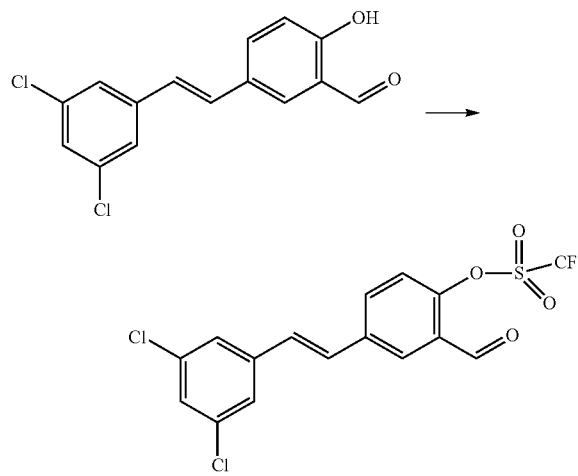

(E)-5-(3,5-dichlorostyryl)-2-hydroxybenzaldehyde (0.557 g, 1.90 mmol) and pyridine (0.750 g, 9.49 mmol) were dissolved in anhydrous dichloromethane (25 mL), and the mixture was stirred at 0° C. A solution of trifluoromethanesulfonic anhydride (0.810 g, 2.87 mmol) in dichloromethane was added dropwise. After the reaction solution was stirred for 40 minutes in an ice bath, it was monitored by Thin layer Chromatography (TLC) to determine when reactants were consumed and a new product was formed. The reaction mixture was poured into ice water, and the mixture was adjusted to pH 2 with dilute aqueous hydrochloric acid, washed with saturated brine, dried over anhydrous sodium sulfate and evaporated to dryness. The residue was purified by column chromatography (petroleum ether: ethyl acetate 4:1). A white solid (0.775 g, 96.3%) was obtained. $^1$H NMR (400 MHz, DMSO-$d_6$) δ 10.11 (s, 1H), 8.28 (s, 1H), 8.03 (d, J=8.6 Hz, 1H), 7.71 (s, 2H), 7.65 (d, J=8.6 Hz, 1H), 7.60 (d, J=16.5 Hz, 1H), 7.50 (s, 1H), 7.41 (d, J=16.5 Hz, 1H). $^{13}$C NMR (101 MHz, DMSO-$d_6$) δ 189.15, 147.29, 140.62, 138.38, 134.99, 134.27, 131.74, 129.48, 129.21, 128.85, 127.78, 125.79, 123.84, 123.43, 120.24, 117.06, 113.87.

By performing the steps described in Example 4, the following intermediates were prepared:

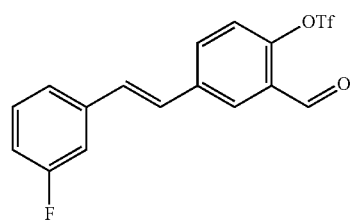 [SMILES: O=Cc1cc(/C=C/c2cccc(F)c2)ccc1OS(=O)(=O)C(F)(F)F]

(E)-4-(3-fluorostyryl)-2-formylphenyl trifluoromethanesulfonate $^1$H NMR (400 MHz, DMSO-$d_6$) δ 10.17 (s, 1H), 8.39 (d, J=2.3 Hz, 1H), 8.11 (dd, J=8.6, 2.3 Hz, 1H), 7.70 (d, J=8.5 Hz, 1H), 7.63-7.46 (m, 5H), 7.26-7.15 (m, 1H);

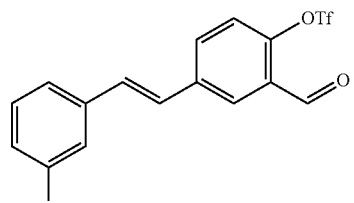

(E)-4-(3-chlorostyryl)-2-formylphenyl trifluoromethanesulfonate $^1$H NMR (400 MHz, DMSO-$d_6$) δ 10.11 (s, 1H), 8.33 (d, J=2.3 Hz, 1H), 8.06 (dd, J=8.6, 2.3 Hz, 1H), 7.76 (s, 1H), 7.63 (dd, J=18.5, 8.1 Hz, 2H), 7.53 (d, J=16.5 Hz, 1H), 7.50-7.35 (m, 3H);

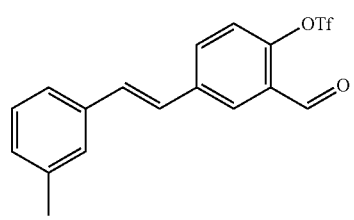

(E)-2-formyl-4-(3-methylstyryl)phenyl trifluoromethanesulfonate $^1$H NMR (400 MHz, DMSO-$d_6$) δ 10.11 (s, 1H), 8.34 (d, J=2.3 Hz, 1H), 8.06 (dd, J=8.6, 2.3 Hz, 1H), 7.62 (d, J=8.6 Hz, 1H), 7.52-7.39 (m, 4H), 7.31 (t, J=7.6 Hz, 1H), 7.16 (d, J=7.5 Hz, 1H), 2.35 (s, 3H);

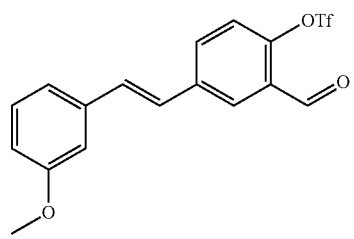 [SMILES: COc1cccc(/C=C/c2ccc(OS(=O)(=O)C(F)(F)F)c(C=O)c2)c1]

(E)-2-formyl-4-(3-methoxystyryl)phenyl trifluoromethanesulfonate $^1$H NMR (400 MHz, DMSO-$d_6$) δ 10.11 (s, 1H), 8.34 (d, J=1.9 Hz, 1H), 8.06 (dd, J=8.6, 2.0 Hz, 1H), 7.64 (d, J=8.5 Hz, 1H), 7.45 (s, 2H), 7.34 (t, J=7.9 Hz, 1H), 7.23 (d, J=7.3 Hz, 2H), 6.99-6.86 (m, 1H), 3.82 (s, 3H);

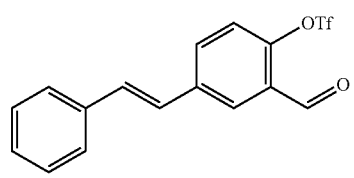 [SMILES: O=Cc1cc(/C=C/c2ccccc2)ccc1OS(=O)(=O)C(F)(F)F]

(E)-2-formyl-4-styrylphenyl trifluoromethanesulfonate

¹H NMR (400 MHz, DMSO-d₆) δ 10.12 (s, 1H), 8.35 (d, J=2.3 Hz, 1H), 8.07 (dd, J=8.6, 2.3 Hz, 1H), 7.65 (dd, J=14.2, 8.0 Hz, 3H), 7.53-7.39 (m, 4H), 7.34 (t, J=7.3 Hz, 1H);

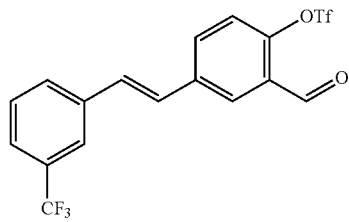 [SMILES: O=Cc1cc(/C=C/c2cccc(C(F)(F)F)c2)ccc1OS(=O)(=O)C(F)(F)F]

(E)-2-formyl-4-(3-(trifluoromethyl)styryl)phenyl trifluoromethanesulfonate

¹H NMR (400 MHz, DMSO-d₆) δ 10.12 (s, 1H), 8.36 (d, J=2.3 Hz, 1H), 8.09 (dd, J=8.6, 2.3 Hz, 1H), 8.03 (s, 1H), 7.96 (d, J=6.7 Hz, 1H), 7.72-7.54 (m, 5H);

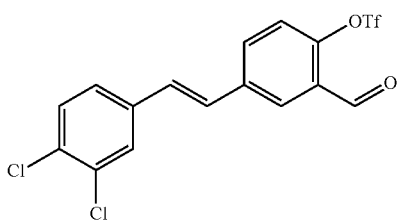

(E)-4-(3,4-dichlorostyryl)-2-formylphenyl trifluoromethanesulfonate

¹H NMR (400 MHz, DMSO-d₆) δ 10.11 (s, 1H), 8.28 (d, J=2.1 Hz, 1H), 8.02 (dd, J=8.6, 2.2 Hz, 1H), 7.90 (d, J=1.4 Hz, 1H), 7.68-7.56 (m, 3H), 7.51 (d, J=16.5 Hz, 1H), 7.41 (d, J=16.5 Hz, 1H). ¹³C NMR (101 MHz, DMSO-d₆) δ 189.20, 147.11, 138.55, 137.70, 134.14, 132.10, 131.71, 131.33, 130.92, 129.79, 128.83, 128.79, 128.23, 127.42, 123.77, 120.24, 117.05;

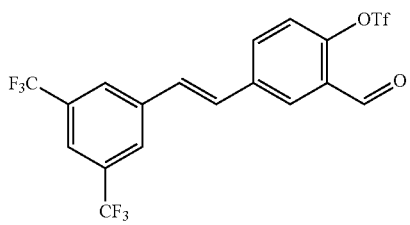 [SMILES: O=Cc1cc(/C=C/c2cc(C(F)(F)F)cc(C(F)(F)F)c2)ccc1OS(=O)(=O)C(F)(F)F]

(E)-4-(3,5-bis(trifluoromethyl)styryl)-2-formylphenyl trifluoromethanesulfonate

¹H NMR (400 MHz, DMSO-d₆) δ 10.12 (s, 1H), 8.47-8.28 (m, 3H), 8.09 (dd, J=8.6, 2.1 Hz, 1H), 8.03 (s, 1H), 7.84 (d, J=16.6 Hz, 1H), 7.69 (dd, J=12.3, 10.5 Hz, 2H);

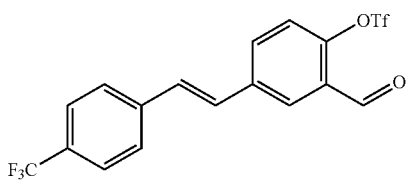 [SMILES: O=Cc1cc(/C=C/c2ccc(C(F)(F)F)cc2)ccc1OS(=O)(=O)C(F)(F)F]

(E)-2-formyl-4-(4-(trifluoromethyl)styryl)phenyl trifluoromethanesulfonate

¹H NMR (400 MHz, DMSO-d₆) δ 10.12 (s, 1H), 8.38 (s, 1H), 8.11 (dd, J=8.6, 1.9 Hz, 1H), 7.87 (d, J=8.0 Hz, 2H), 7.78 (d, J=7.5 Hz, 2H), 7.66 (dd, J=8.5, 2.0 Hz, 1H), 7.64-7.52 (m, 2H); and

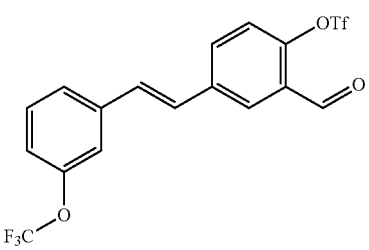

(E)-2-formyl-4-(3-(trifluoromethoxy)styryl)phenyl trifluoromethanesulfonate

¹H NMR (400 MHz, DMSO-d₆) δ 10.12 (s, 1H), 8.35 (d, J=2.3 Hz, 1H), 8.08 (dd, J=8.7, 2.4 Hz, 1H), 7.73-7.62 (m, 3H), 7.60-7.48 (m, 3H), 7.35-7.29 (m, 1H).

Example 5: Synthesis of (E)-5-(3,5-dichlorostyryl)benzo[c][1,2]oxaborol-1(3H)-ol (XIV)

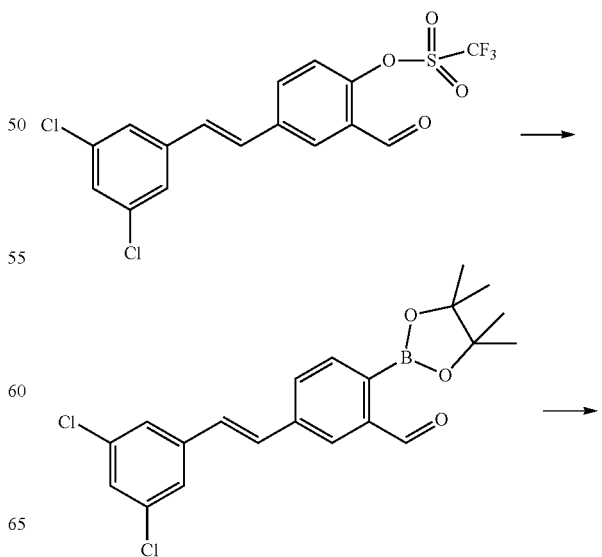

-continued

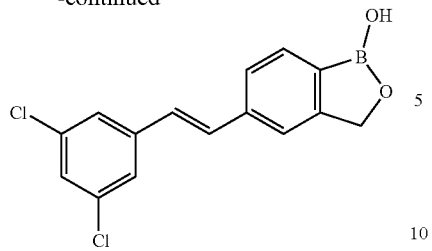

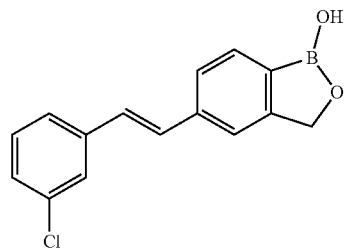 [SMILES: OB1OCc2cc(/C=C/c3cccc(Cl)c3)ccc21]

(E)-5-(3-chlorostyryl)benzo[c][1,2]oxaborol-1(3H)-ol (X)

B₂(Pin)₂ (0.870 g, 3.43 mmol) and potassium acetate (0.510 g, 5.19 mmol) were added to dry 1,4-dioxane (18 mL) under nitrogen atmosphere. (E)-4-(3,5-dichlorostyryl)-2-formylphenyl trifluoromethanesulfonate (0.725 g, 1.71 mmol) and Pd(dppf)Cl₂ (0.140 g, 0.17 mmol) were then added. The mixture was stirred at 80° C. for two hours. After the dioxane was removed under reduced pressure, the residue was purified by flash column chromatography to obtain a crude product, which was directly used in the next reaction. The crude product was dissolved in a mixed solution of 4 mL methanol and 3 mL tetrahydrofuran, and NaBH₄ (0.280 g, 7.41 mmol) was added in portions at 0° C. After the mixture was stirred for one hour, part of the solvent was removed under reduced pressure, 15 mL of water was added, and the pH was adjusted to 3 with dilute hydrochloric acid. After extraction with ethyl acetate, the organic phase was dried over anhydrous sodium sulfate and evaporated to dryness under reduced pressure. The residue was first purified by column chromatography and then recrystallized from toluene to obtain 0.250 g of white solid. The two-step yield was 48.2%. ¹H NMR (400 MHz, DMSO-d₆) δ 9.23 (s, 1H), 7.76 (d, J=7.6 Hz, 1H), 7.72 (d, J=1.7 Hz, 2H), 7.65-7.57 (m, 2H), 7.54 (d, J=16.5 Hz, 1H), 7.50 (s, 1H), 7.33 (d, J=16.4 Hz, 1H), 5.04 (s, 2H). ¹³C NMR (101 MHz, DMSO-d₆) δ 155.02, 141.25, 139.06, 134.92, 132.22, 131.27, 127.20, 127.15, 126.26, 125.47, 119.81, 70.29.

Figure 7:
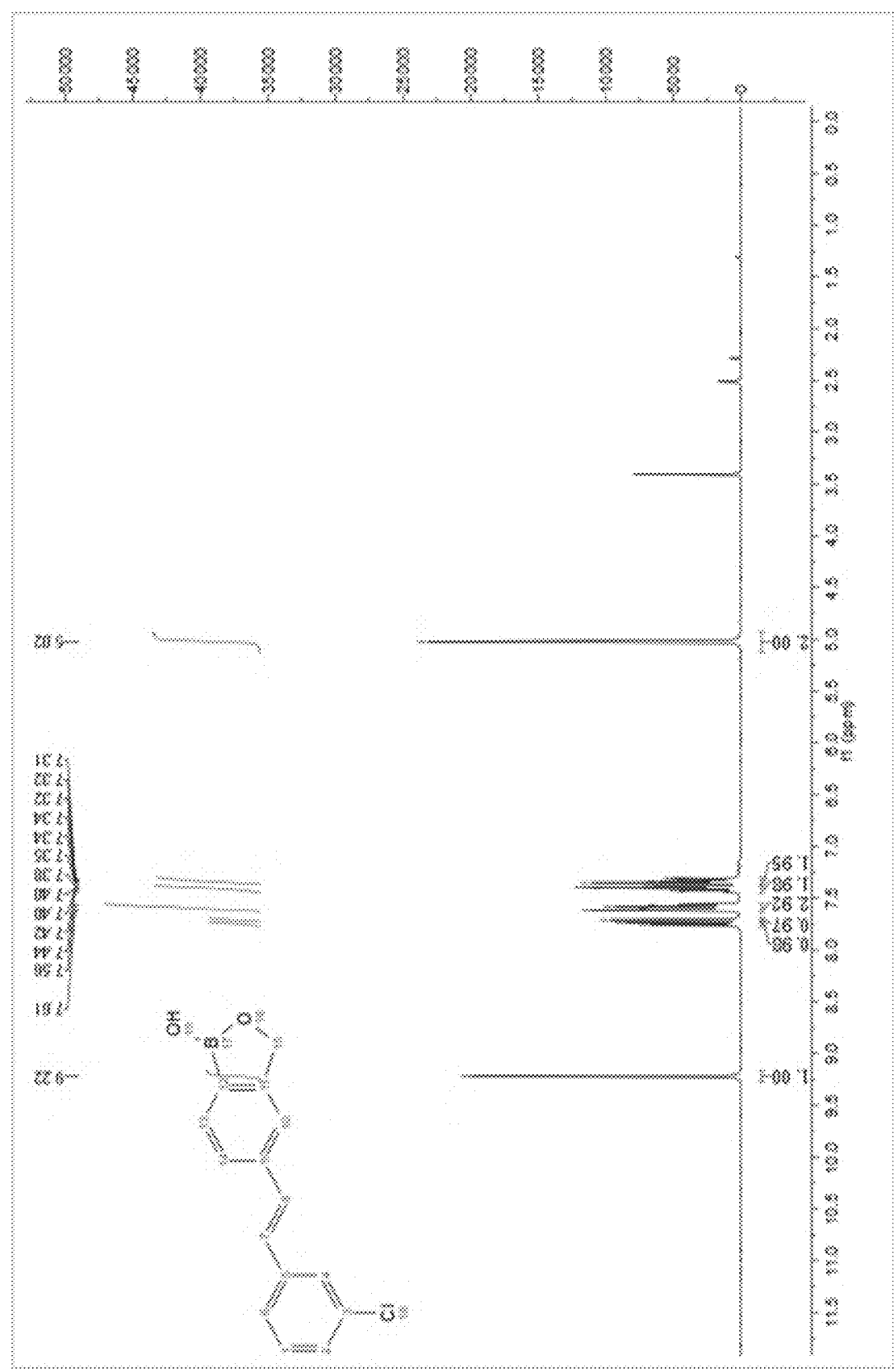
FIG. 7 is a $^1$H NMR spectrum of (E)-5-(3-chlorostyryl)benzo[c][1,2]oxaborol-1(3H)-ol (X) in accordance with embodiments of the present disclosure.
Figure 8:
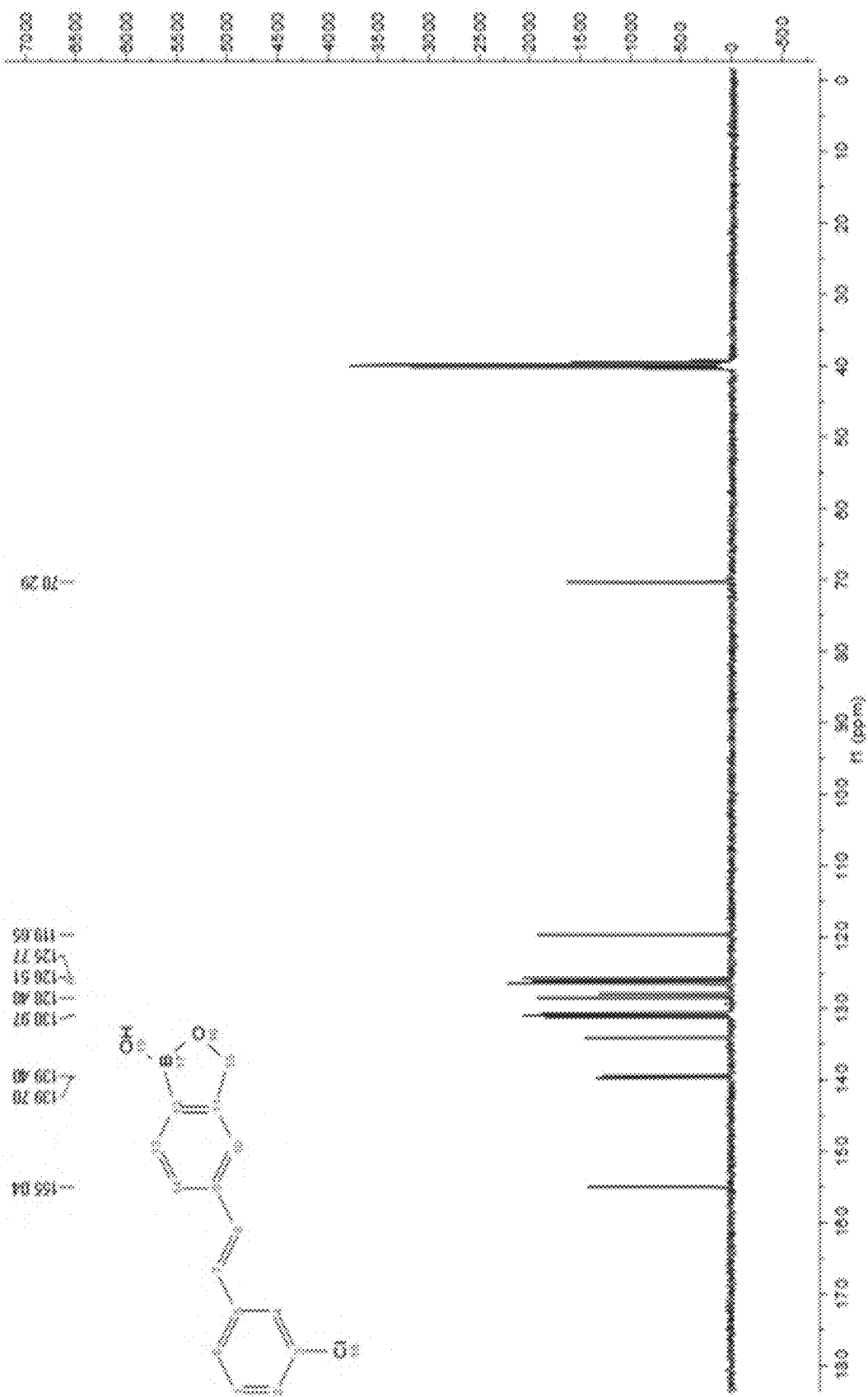
FIG. 8 is a $^{13}$C NMR spectrum of (E)-5-(3-chlorostyryl)benzo[c][1,2]oxaborol-1(3H)-ol (X) in accordance with embodiments of the present disclosure.

By performing the steps described in Example 5, the following intermediates were prepared:

¹H NMR (400 MHz, DMSO-d₆) δ 9.22 (s, 1H), 7.75 (d, J=7.6 Hz, 1H), 7.71 (s, 1H), 7.59 (dd, J=13.9, 6.6 Hz, 3H), 7.46-7.37 (m, 2H), 7.37-7.30 (m, 2H), 5.02 (s, 2H) (FIG. 7). ¹³C NMR (101 MHz, DMSO-d₆) δ 155.04, 139.70, 139.40, 134.09, 131.26, 130.97, 130.62, 128.48, 127.92, 126.51, 126.14, 125.77, 119.65, 70.29 (FIG. 8);

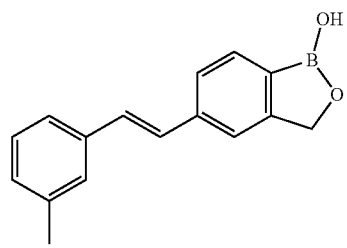 [SMILES: Cc1cccc(/C=C/c2ccc3c(c2)COB3O)c1]

(E)-5-(3-methylstyryl)benzo[c][1,2]oxaborol-1(3H)-ol (XI)

Figure 9:
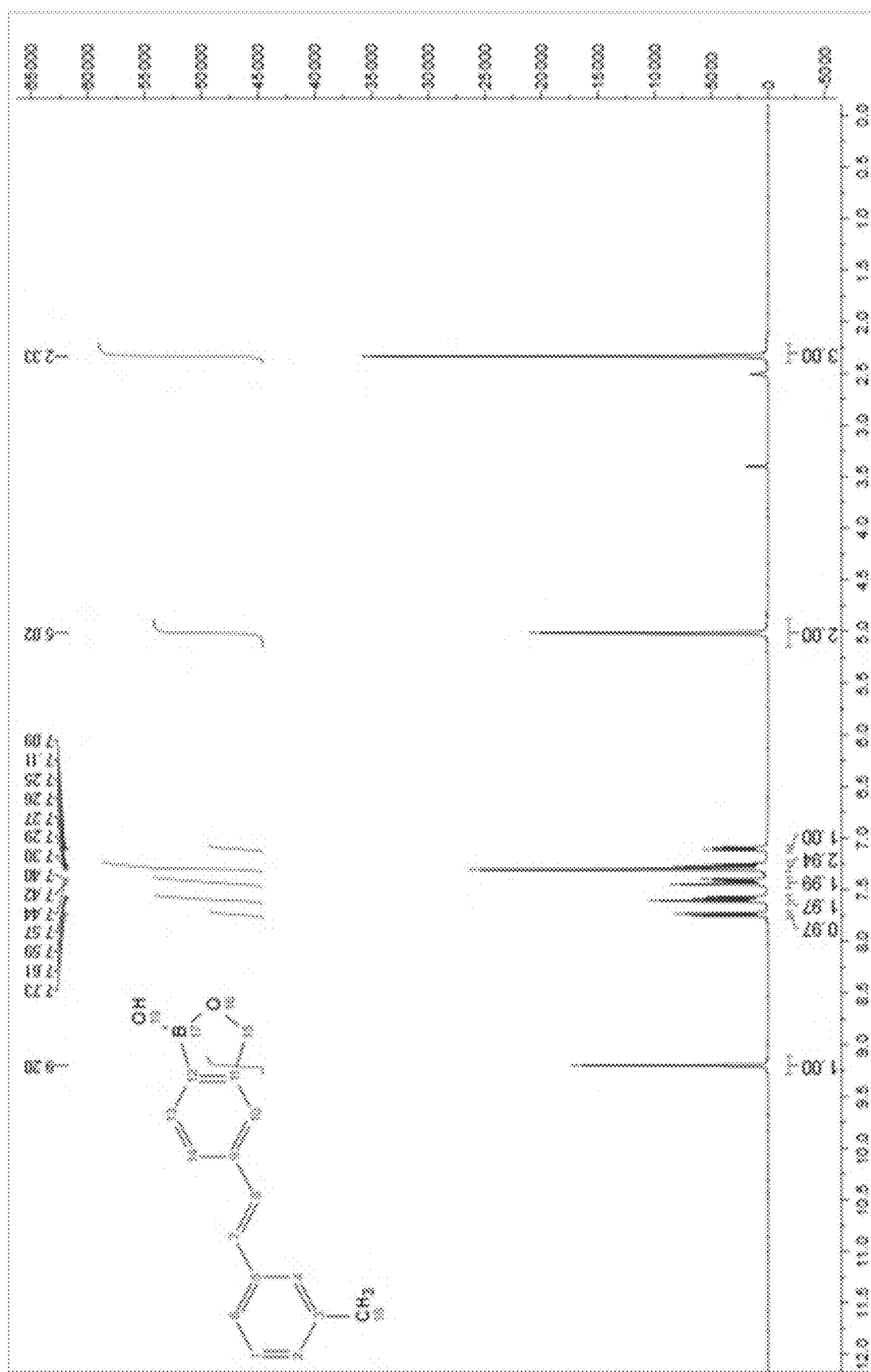
FIG. 9 is a $^1$H NMR spectrum of (E)-5-(3-methylstyryl)benzo[c][1,2]oxaborol-1(3H)-ol (XI) in accordance with embodiments of the present disclosure.
Figure 10:
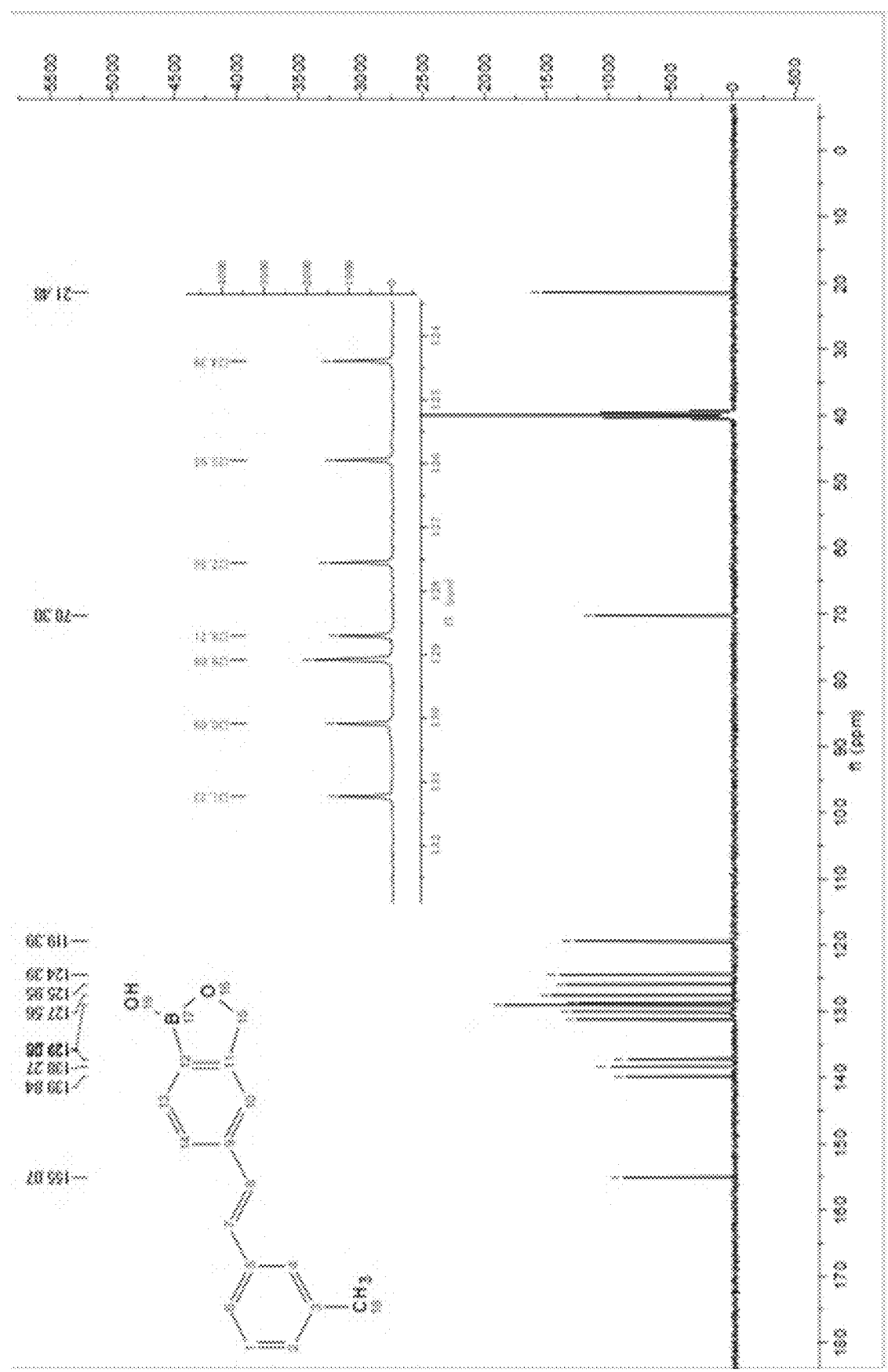
FIG. 10 is a $^{13}$C NMR spectrum of (E)-5-(3-methylstyryl)benzo[c][1,2]oxaborol-1(3H)-ol (XI) in accordance with embodiments of the present disclosure.

¹H NMR (400 MHz, DMSO-d₆) δ 9.20 (s, 1H), 7.74 (d, J=7.6 Hz, 1H), 7.64-7.54 (m, 2H), 7.47-7.38 (m, 2H), 7.33-7.22 (m, 3H), 7.10 (d, J=7.5 Hz, 1H), 5.02 (s, 2H), 2.33 (s, 3H) (FIG. 9). ¹³C NMR (101 MHz, DMSO-d₆) δ 155.07, 139.84, 138.27, 137.25, 131.23, 130.09, 129.08, 128.71, 127.56, 125.95, 124.39, 119.39, 70.30, 21.48 (FIG. 10);

(E)-5-(3-methoxystyryl)benzo[c][1,2]oxaborol-1(3H)-ol (XII)

¹H NMR (400 MHz, DMSO-d₆) δ 9.21 (s, 1H), 7.74 (d, J=7.6 Hz, 1H), 7.66-7.55 (m, 2H), 7.37-7.26 (m, 3H), 7.20 (d, J=6.3 Hz, 2H), 6.87 (dd, J=8.0, 1.8 Hz, 1H), 5.02 (s, 2H), 3.80 (s, 3H). ¹³C NMR (101 MHz, DMSO-d₆) δ 160.08, 155.06, 139.75, 138.80, 131.24, 130.19, 129.97, 129.21, 126.00, 119.67, 119.46, 114.11, 112.19, 70.29, 55.53;

(E)-5-(3-fluorostyryl)benzo[c][1,2]oxaborol-1(3H)-ol (IX)

¹H NMR (400 MHz, DMSO-d₆) δ 9.21 (s, 1H), 7.75 (d, J=7.3 Hz, 1H), 7.66-7.56 (m, 2H), 7.50 (d, J=10.6 Hz, 1H), 7.46-7.32 (m, 4H), 7.12 (s, 1H), 5.03 (s, 2H);

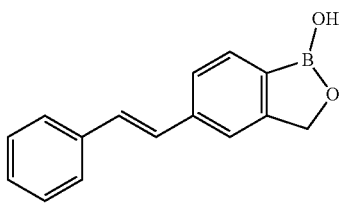 [SMILES: OB1OCc2cc(/C=C/c3ccccc3)ccc21]

(E)-5-styrylbenzo[c][1,2]oxaborol-1(3H)-ol (XIII)

Figure 5:
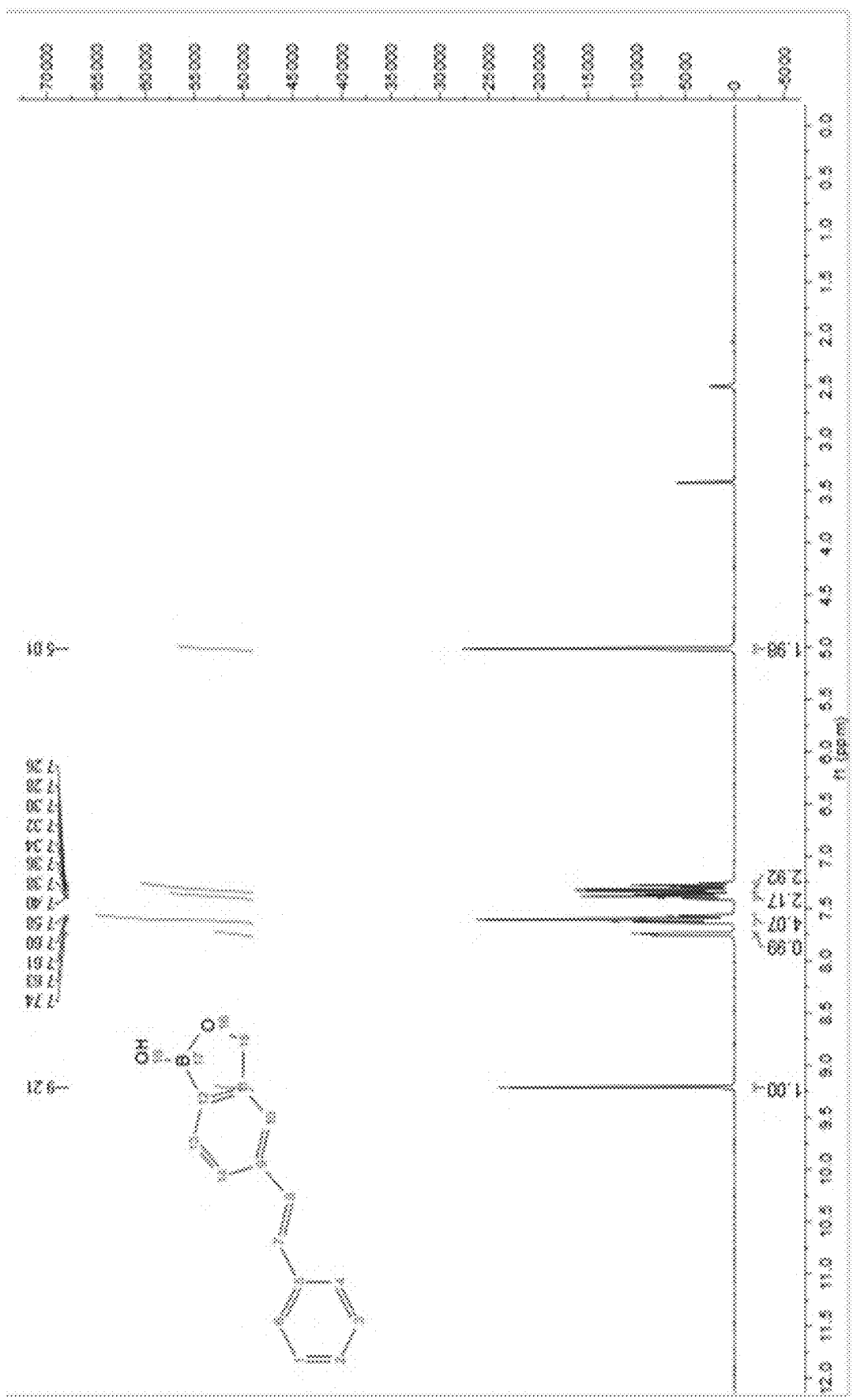
FIG. 5 is a $^1$H NMR spectrum of (E)-5-styrylbenzo[c][1,2]oxaborol-1(3H)-ol (XIII) in accordance with embodiments of the present disclosure.
Figure 6:
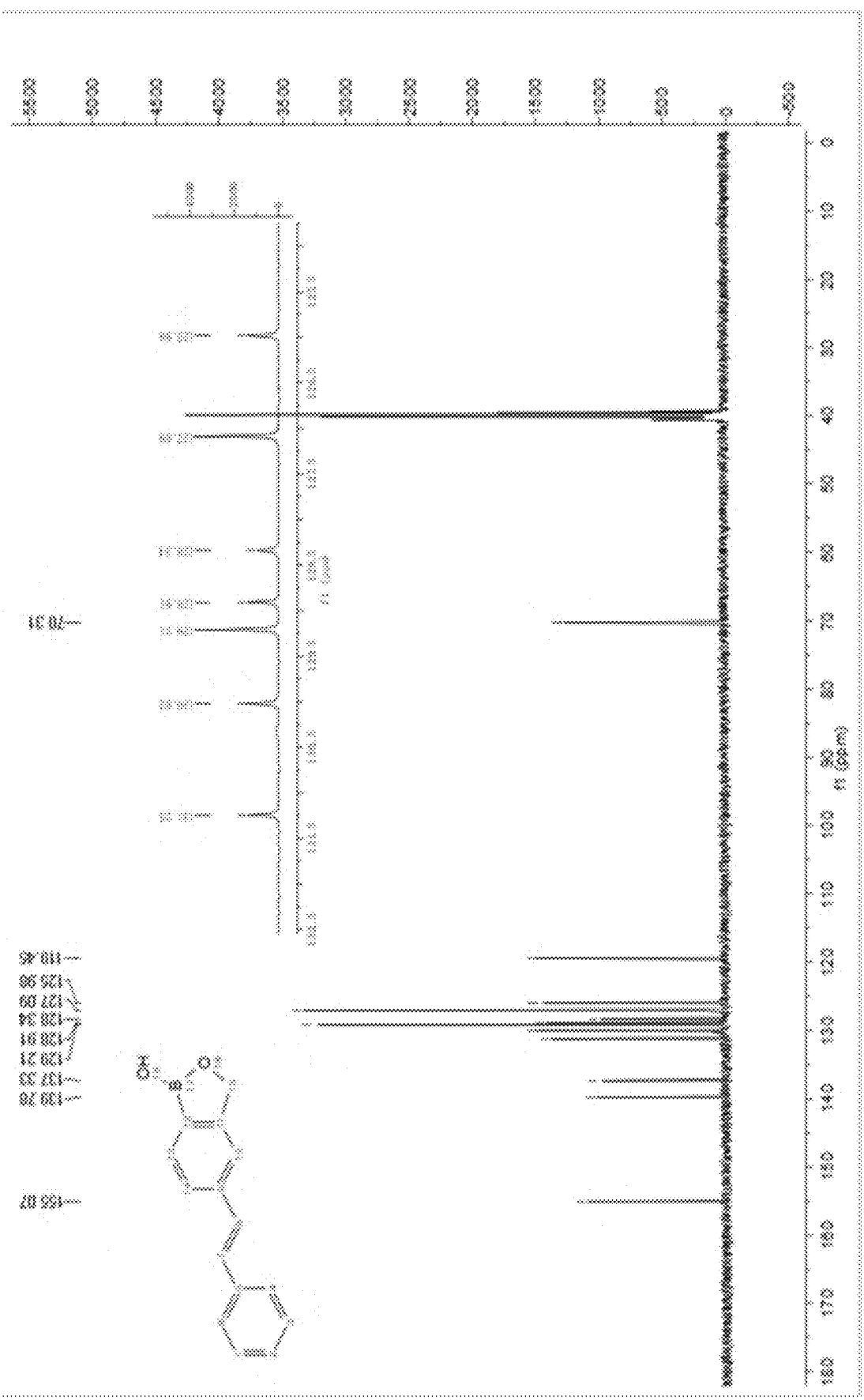
FIG. 6 is a $^{13}$C NMR spectrum of (E)-5-styrylbenzo[c][1,2]oxaborol-1(3H)-ol (XIII) in accordance with embodiments of the present disclosure.

$^1$H NMR (400 MHz, DMSO-$d_6$) δ 9.21 (s, 1H), 7.75 (d, J=7.6 Hz, 1H), 7.60 (dd, J=12.1, 7.7 Hz, 4H), 7.38 (t, J=7.6 Hz, 2H), 7.35-7.24 (m, 3H), 5.01 (s, 2H) (FIG. 5). $^{13}$C NMR (101 MHz, DMSO-$d_6$) δ 155.07, 139.78, 137.33, 131.25, 130.02, 129.21, 128.91, 128.34, 127.09, 125.98, 119.45, 70.31 (FIG. 6);

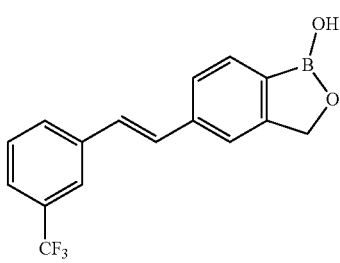 [SMILES: OB1OCc2cc(/C=C/c3cccc(C(F)(F)F)c3)ccc21]

(E)-5-(3-(trifluoromethyl)styryl)benzo[c][1,2]oxaborol-1(3H)-ol (II)

Figure 11:
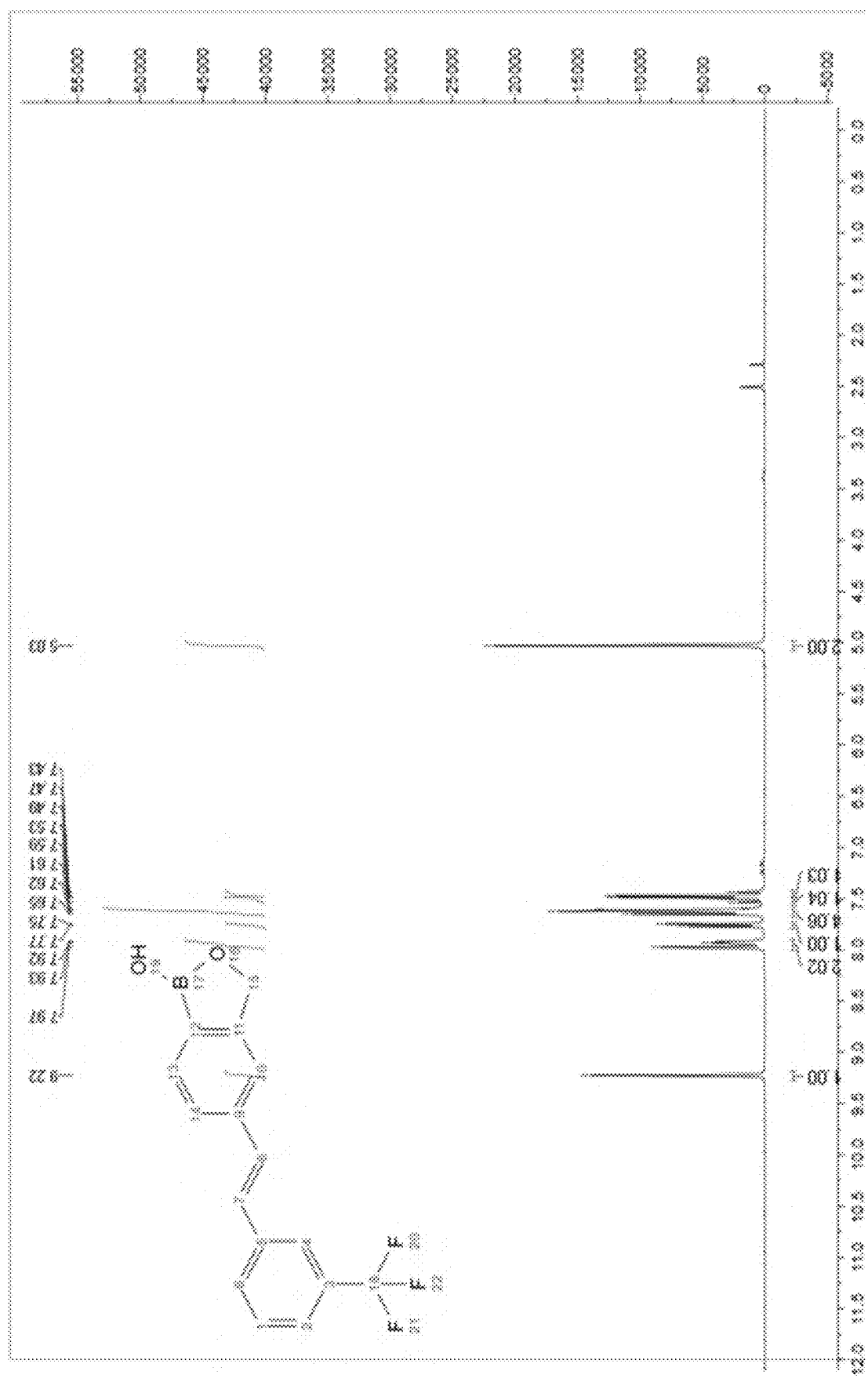
FIG. 11 is a $^1$H NMR spectrum of (E)-5-(3-(trifluoromethyl)styryl) benzo[c][1,2]oxaborol-1(3H)-ol (II) in accordance with embodiments of the present disclosure.
Figure 12:
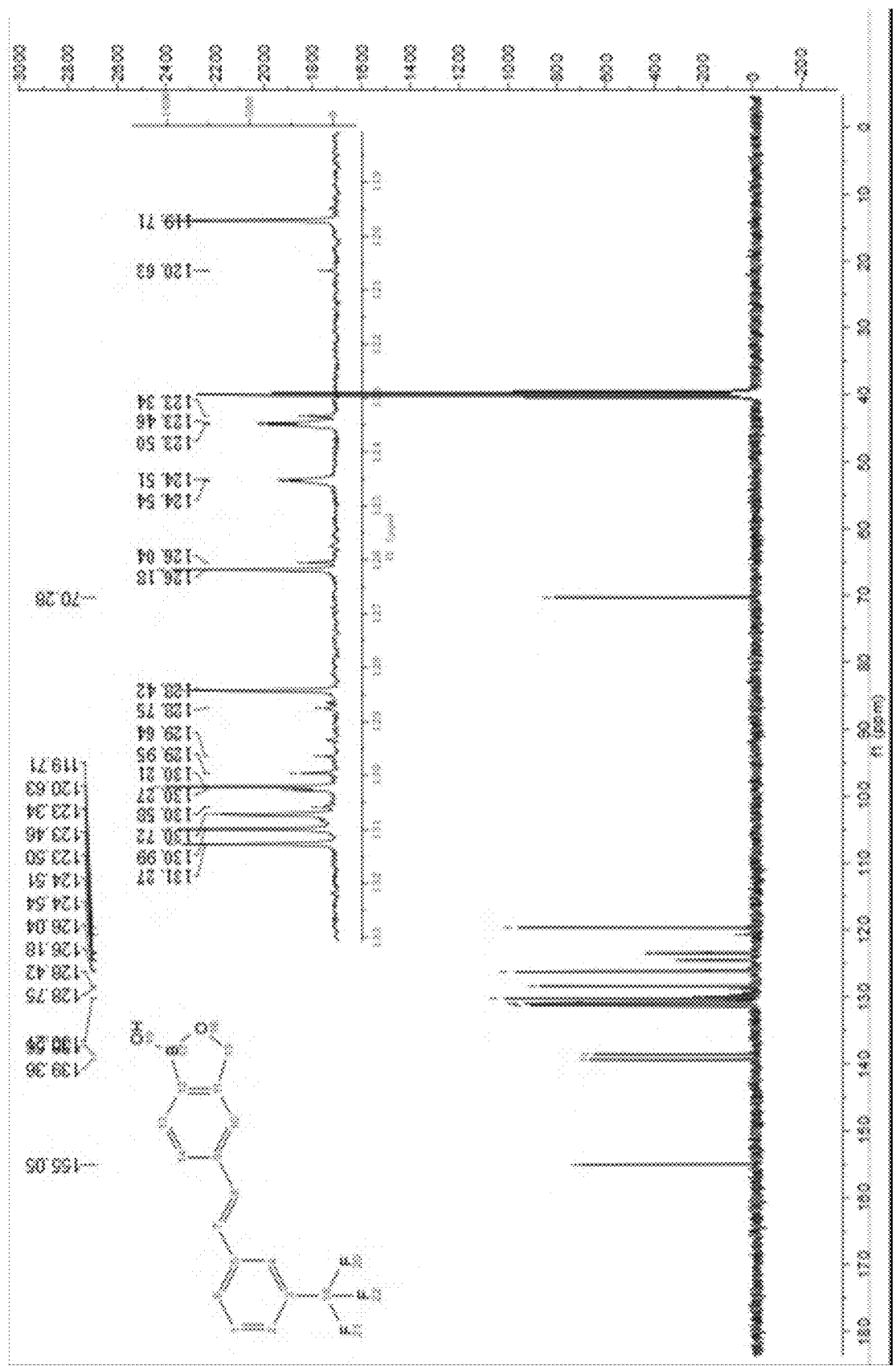
FIG. 12 is a 13C NMR spectrum of (E)-5-(3-(trifluoromethyl)styryl) benzo[c][1,2]oxaborol-1(3H)-ol (II) in accordance with embodiments of the present disclosure.

$^1$H NMR (400 MHz, DMSO-$d_6$) δ 9.22 (s, 1H), 7.94 (dd, J=12.7, 8.8 Hz, 2H), 7.76 (d, J=7.6 Hz, 1H), 7.62 (dd, J=14.5, 8.9 Hz, 4H), 7.51 (d, J=16.5 Hz, 1H), 7.45 (d, J=16.5 Hz, 1H), 5.03 (s, 2H) (FIG. 11). $^{13}$C NMR (101 MHz, DMSO-$d_6$) δ 155.05, 139.36, 138.56, 131.27, 130.99, 130.72, 130.21, 130.11 (q, $^2J_{C-F}$=31.4 Hz), 128.42, 126.18, 124.69 (q, $^1J_{C-F}$=273.4 Hz), 124.53 (d, $^3J_{C-F}$=3.5 Hz), 123.48 (d, $^3J_{C-F}$=3.7 Hz), 119.71, 70.28 (FIG. 12);

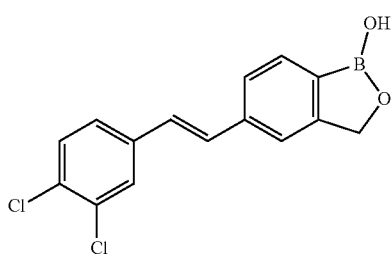 [SMILES: OB1OCc2cc(/C=C/c3ccc(Cl)c(Cl)c3)ccc21]

(E)-5-(3,4-dichlorostyryl)benzo[c][1,2]oxaborol-1(3H)-ol (III)

Figure 2:
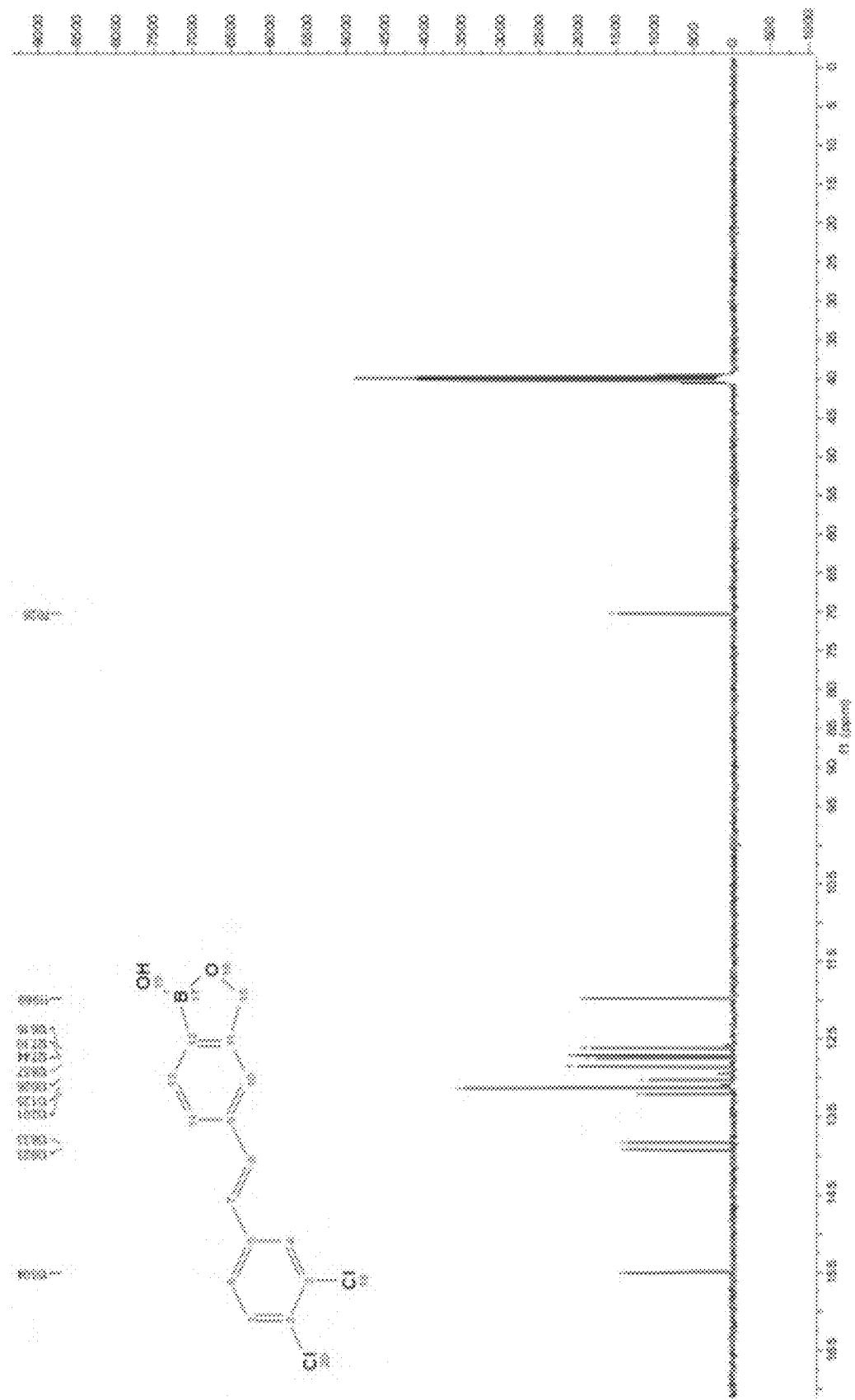
FIG. 2 is a carbon-13 nuclear magnetic resonance ($^{13}$C NMR) spectrum of (E)-5-(3,4-dichlorostyryl)benzo[c][1,2]oxaborol-1(3H)-ol (III) in accordance with embodiments of the present disclosure.

$^1$H NMR (400 MHz, DMSO-$d_6$) δ 9.23 (s, 1H), 7.89 (s, 1H), 7.74 (d, J=7.6 Hz, 1H), 7.65-7.54 (m, 4H), 7.43 (d, J=16.5 Hz, 1H), 7.32 (d, J=16.5 Hz, 1H), 5.02 (s, 2H) (FIG. 1). $^{13}$C NMR (75 MHz, DMSO-$d_6$) δ 155.05, 139.25, 138.35, 132.02, 131.28, 130.27, 128.58, 127.46, 127.13, 126.18, 119.70, 70.28 (FIG. 2);

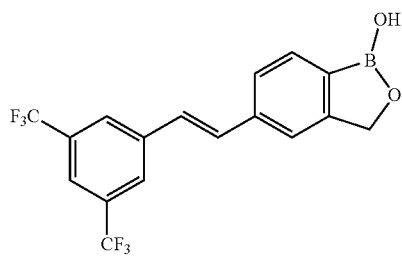 [SMILES: OB1OCc2cc(/C=C/c3cc(C(F)(F)F)cc(C(F)(F)F)c3)ccc21]

(E)-5-(3,5-bis(trifluoromethyl)styryl)benzo[c][1,2]oxaborol-1(3H)-ol (IV)

Figure 3:
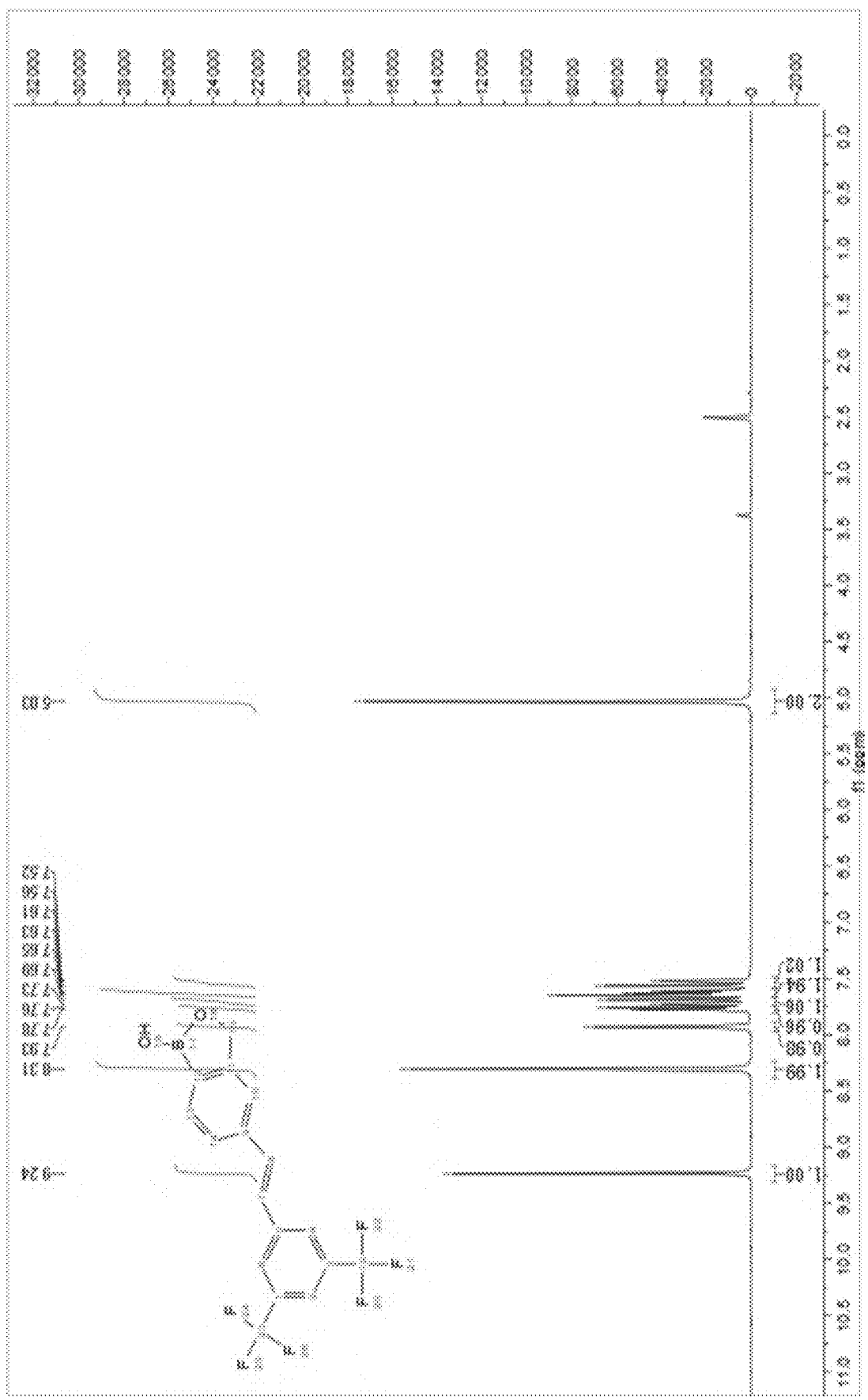
FIG. 3 is a $^1$H NMR spectrum of (E)-5-(3,5-bis(trifluoromethyl) styryl)benzo[c][1,2]oxaborol-1(3H)-ol (IV) in accordance with embodiments of the present disclosure.
Figure 4:
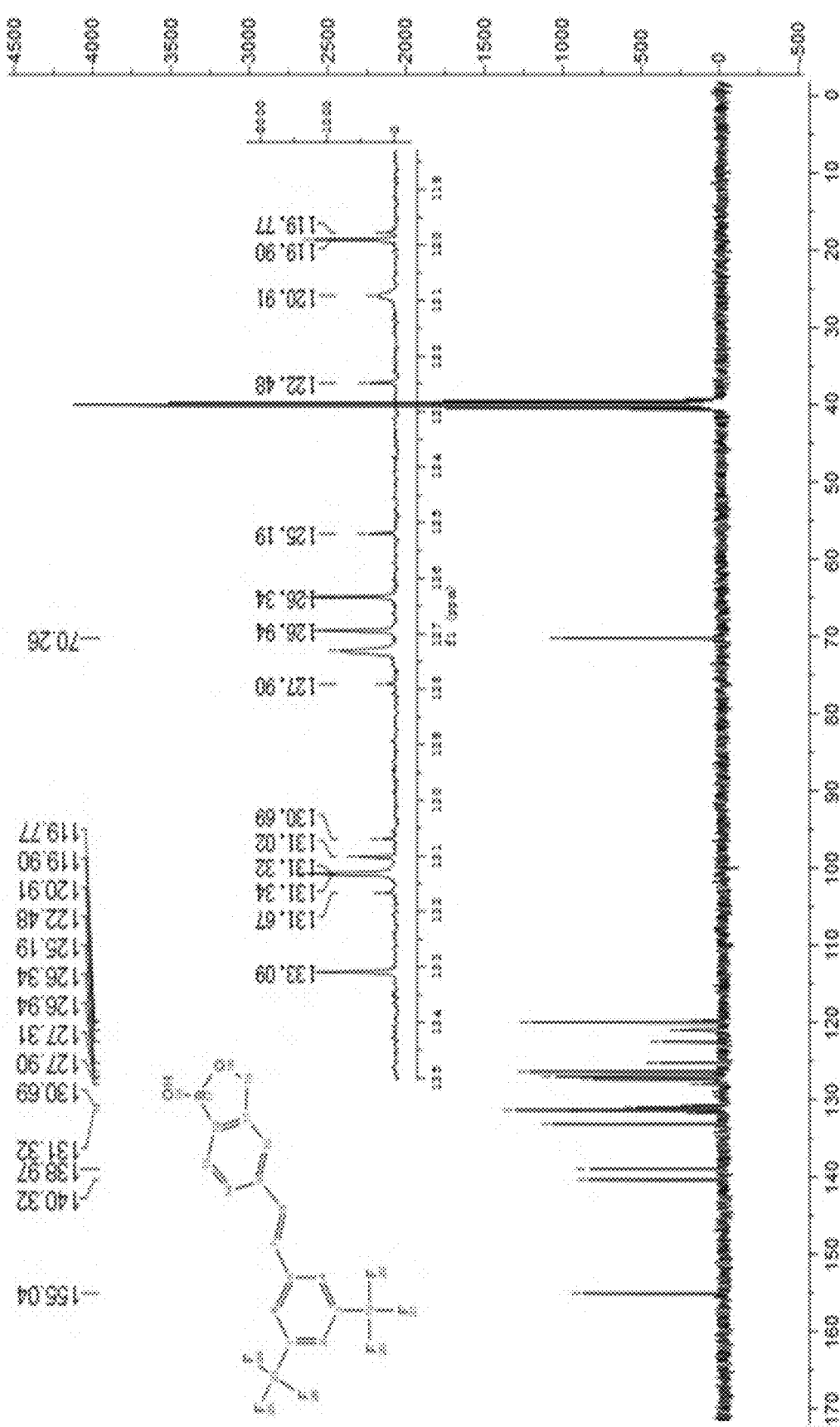
FIG. 4 is a $^{13}$C NMR spectrum of (E)-5-(3,5-bis(trifluoromethyl) styryl)benzo[c][1,2]oxaborol-1(3H)-ol (IV) in accordance with embodiments of the present disclosure.

$^1$H NMR (400 MHz, DMSO-$d_6$) δ 9.24 (s, 1H), 8.31 (s, 2H), 7.93 (s, 1H), 7.77 (d, J=7.6 Hz, 1H), 7.71 (d, J=16.5 Hz, 1H), 7.67-7.59 (m, 2H), 7.54 (d, J=16.5 Hz, 1H), 5.03 (s, 2H) (FIG. 3). $^{13}$C NMR (101 MHz, DMSO-$d_6$) δ 155.04, 140.32, 138.97, 133.09, 131.34, 131.17 (q, $^2J_{C-F}$=35.8 Hz), 127.31, 126.94, 126.34, 123.84 (q, $J_{C-F}$=273.9 Hz), 120.91, 119.90, 70.26 (FIG. 4);

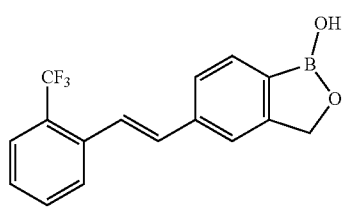 [SMILES: OB1OCc2cc(/C=C/c3ccccc3C(F)(F)F)ccc21]

(E)-5-(2-(trifluoromethyl)styryl)benzo[c][1,2]oxaborol-1(3H)-ol (VI)

$^1$H NMR (400 MHz, DMSO-$d_6$) δ 9.24 (s, 1H), 8.00 (d, J=7.8 Hz, 1H), 7.74 (dt, J=20.2, 7.7 Hz, 3H), 7.62 (s, 1H), 7.57 (d, J=7.5 Hz, 1H), 7.54-7.47 (m, 1H), 7.41 (t, J=14.1 Hz, 2H), 5.03 (s, 2H). $^{13}$C NMR (101 MHz, DMSO-$d_6$) δ 155.18, 139.00, 135.91, 133.76, 133.25, 131.44, 128.48, 127.86, 126.39 (q, $^2J_{C-F}$=29.7 Hz), 126.36, 125.40 (q, $^1J_{C-F}$=182.7 Hz), 119.74, 70.33;

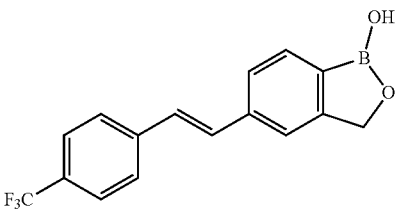 [SMILES: OB1OCc2cc(/C=C/c3ccc(C(F)(F)F)cc3)ccc21]

(E)-5-(4-(trifluoromethyl)styryl)benzo[c][1,2]oxaborol-1(3H)-ol (VII)

$^1$H NMR (400 MHz, DMSO-$d_6$) δ 9.24 (s, 1H), 7.95-7.31 (m, 9H), 5.02 (s, 2H). $^{13}$C NMR (101 MHz, DMSO-$d_6$) δ 155.05, 141.43, 139.18, 131.76, 131.28, 128.42, 128.17 (q, $^2J_{C-F}$=31.1 Hz), 127.55, 126.28, 126.01, 119.83, 70.28; and

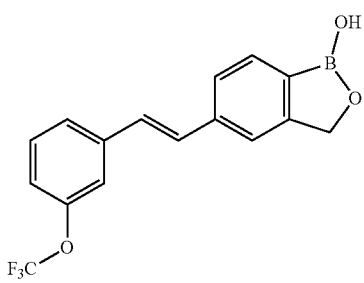 [SMILES: OB1OCc2cc(/C=C/c3cccc(OC(F)(F)F)c3)ccc21]

(E)-5-(3-(trifluoromethoxy)styryl)benzo[c][1,2]oxaborol-1(3H)-ol (VIII)

$^{1}$H NMR (400 MHz, DMSO-d$_6$) δ 9.18 (s, 1H), 7.75 (d, J=7.6 Hz, 1H), 7.71-7.58 (m, 4H), 7.53 (t, J=8.0 Hz, 1H), 7.50-7.36 (m, 2H), 7.31-7.24 (m, 1H), 5.03 (s, 2H). $^{13}$C NMR (101 MHz, DMSO-d$_6$) δ 155.06, 149.41, 140.01, 139.35, 131.25, 131.05, 130.96, 128.45, 126.19, 126.08, 120.61 (q, $^{1}J_{C-F}$=257.3 Hz), 120.36, 119.69, 119.21, 70.28.

Example 6: Identification of And-1 Inhibitors by High Throughput Screen Assay

Figure 13A:
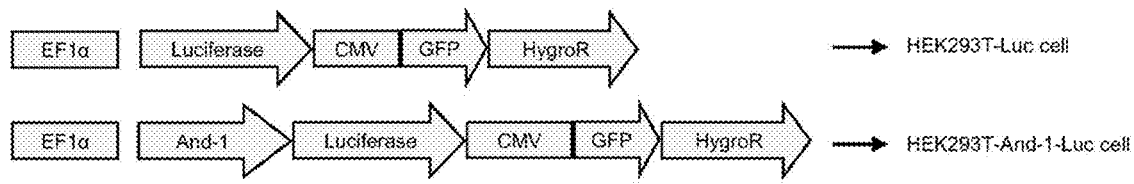
FIGS. 13A-13H depict schematics, images, and graphs illustrating the identification of And-1 inhibitors in accordance with embodiments of the present disclosure.
Figure 13B:
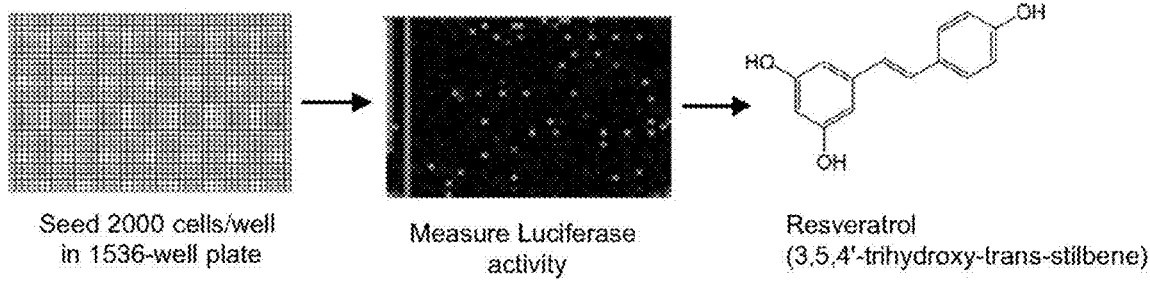

To identify And-1 specific pharmacologic inhibitors, a high-throughput screening (HTS) assay was established to identify small molecules that can inhibit And-1 by inducing its degradation. For this assay, two stable cell lines, a HEK293T-And-1-Luc cell expressing And-1 protein fused to a luciferase reporter gene, and a HEK293T-Luc cell expressing luciferase only were generated (FIG. 13A). HEK293T-And-1-Luc cells allowed for assessment of And-1 protein levels by measuring luciferase activity in a high throughput manner. Using these cell lines, a screening for And-1 inhibitors against a LOPAC (Library of Pharmacologically Active Compounds) small molecule library was conducted using a quantitative HTS (qHTS). From this screening, it was identified that resveratrol that could reduce And-1 levels with an IC$_{50}$ at 18.91 μM (FIG. 13B, Table 1).

TABLE 1

IC$_{50}$ values for HTS assay

| Sample Name | IC50 (μM) 1 | IC50 (μM) 2 | IC50 (μM) average |
|---|---|---|---|
| Methotrexate hydrate | 0.08 | 0.16 | 0.12 |
| Diphenyleneiodonium chloride | 0.84 | 0.03 | 0.43 |
| AC-93253 iodide | 1.09 | 0.44 | 0.76 |
| PD-166285 hydrate | 3.33 | 2.73 | 3.03 |
| Thapsigargin | 13.27 | 0.63 | 6.95 |
| Calcimycin | 6.10 | 10.54 | 8.32 |
| NSC 95397 | 11.17 | 7.68 | 9.42 |
| Resveratrol | 14.89 | 22.93 | 18.91 |
| Cilnidipine | 22.93 | 19.30 | 21.11 |
| PAC-1 | 18.75 | 23.83 | 21.29 |
| Gemcitabine hydrochloride | 0.02 | inactive | |
| (S)-(+)-Camptothecin | 0.73 | inactive | |
| 2-methoxyestradiol | 1.67 | inactive | |
| Topotecan hydrochloride hydrate | 0.61 | inactive | |

Figure 13C:
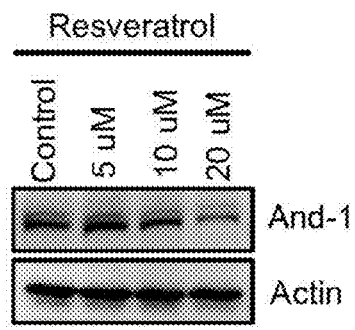
Figure 13D:
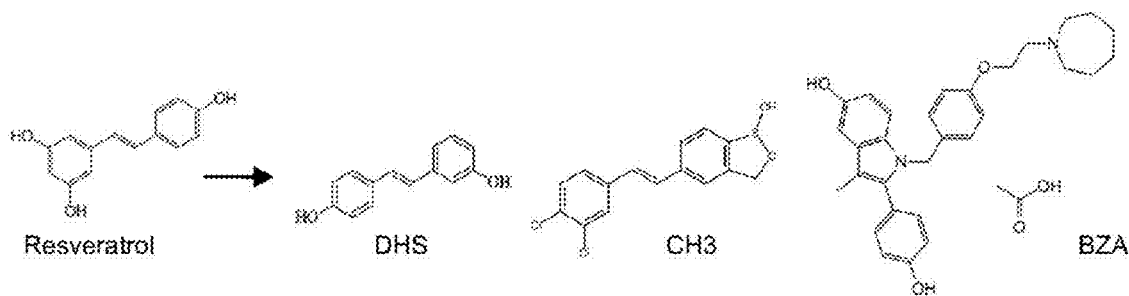
Figure 13E:
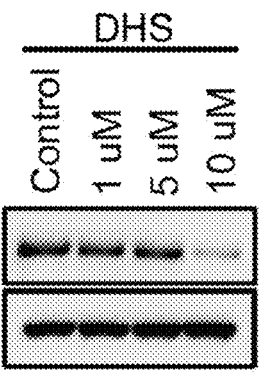
Figure 13F:
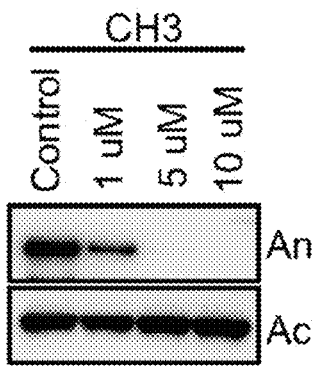
Figure 13G:
Figure 13H:
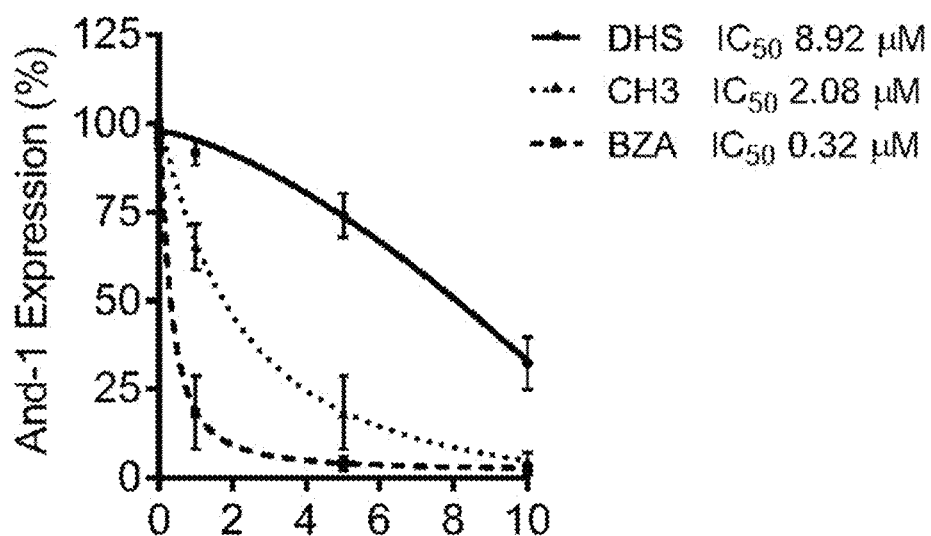
Figure 14:
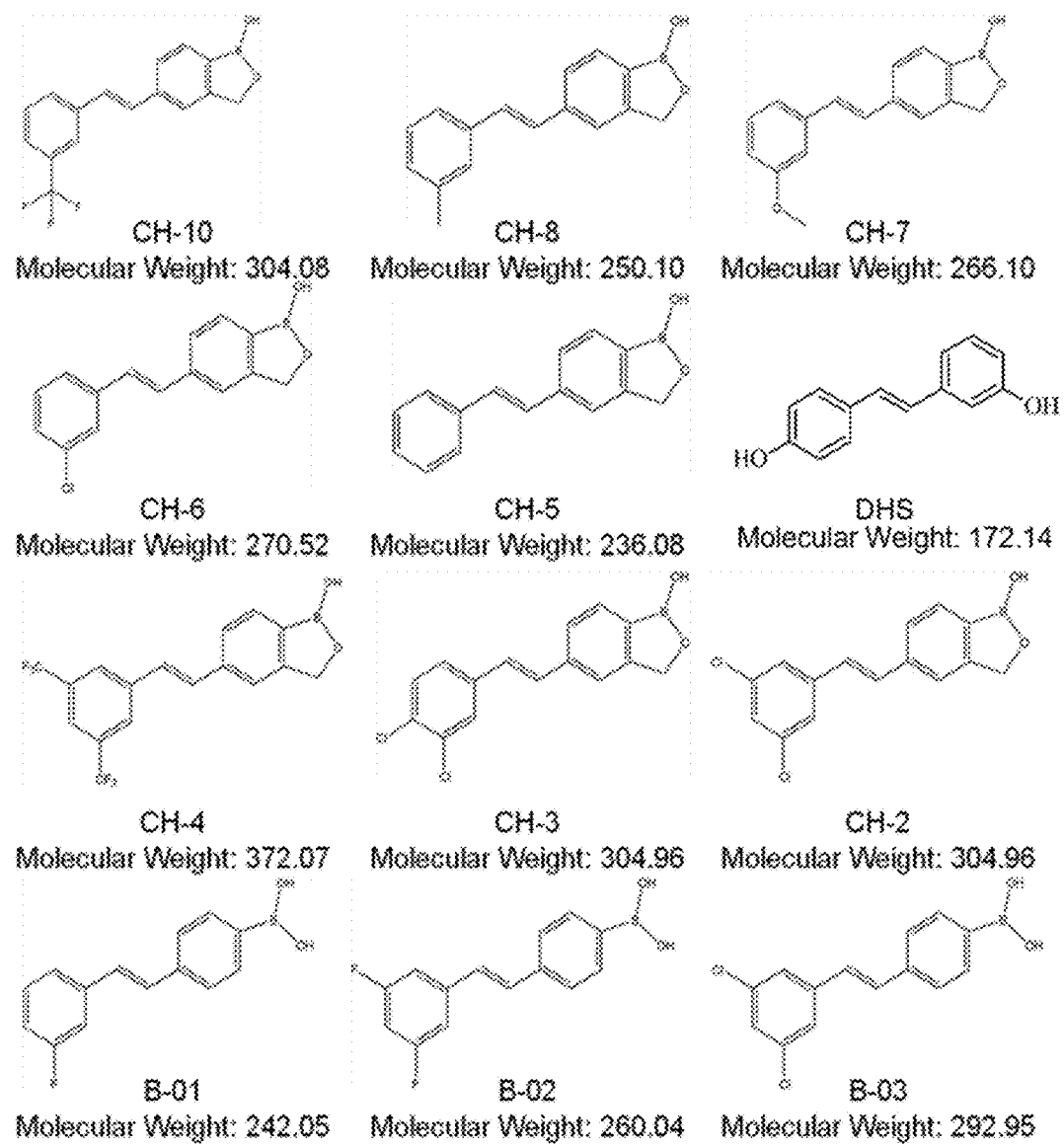
FIG. 14 depicts chemical structures of resveratrol analogs disclosed herein and their molecular weights in accordance with embodiments of the present disclosure.

Using a human ovarian cancer cell line (IGROV1 cells), it was confirmed that resveratrol could inhibit And-1 expression with relative high IC$_{50}$ value (FIG. 13C, IC$_{50}$=16.70 μM). The high IC$_{50}$ of resveratrol compromises its potential clinical application; therefore, resveratrol was used as a lead compound to screen 12 analogs of resveratrol for potent compounds that can inhibit And-1 (FIG. 14). In brief, immunoblot analysis of And-1 expression in IGROV1 cells treated with the 12 analogs of resveratrol was performed to identify which of the analogs inhibited And-1 expression. To perform immunoblot analyses, cells were first treated with increasing concentrations of the 12 analogs. After treatment, the cells were harvested and then lysed with RIPA buffer protease inhibitor and phosphatase inhibitor cocktail. Protein concentration was determined by the BCA protein assay. Equal amounts of whole cell lysates were separated on sodium dodecyl sulfate polyacrylamide gel electrophoresis (SDS-PAGE) and transferred onto nitrocellulose membranes. Membranes were then incubated in blocking solution (5% non-fat milk in 20 mM TRIS-HCl, 150 mM NaCl, 0.1% Tween-20) (TBST), followed by incubation with the indicated antibodies at 4° C. overnight. The membranes were then washed in TBST and incubated with HRP-conjugated secondary antibodies for 1 hour at room temperature (21° C.±2° C.). Antibody detection was performed with an enhanced chemiluminescence reaction. From these 12 analogs, three compounds, DHS, CH3 and BZA (FIG. 13D) were found to inhibit And-1 expression in IGROV1 cells with IC$_{50}$ of 8.92 μM, 2.08 μM, and 0.32 μM respectively (FIGS. 13E-13H).

Next, flow cytometry analysis (specifically, fluorescence-activated cell sorting (FACS)) was performed on propidium-iodide stained IGROV1 cells treated with either DMSO, 1 μM of CH3, 1 μM of BZA, and siAnd-1. FACS analyses indicated that both CH3 and BZA reduced the percentage of cells in the S-phase in a manner similar to those in And-1 depleted cells (FIGS. 15A-15D).

H2AX (H2A histone family member X) becomes phosphorylated on serine 139 (wherein the phosphorylated form is then called γH2AX) as a reaction on DNA double-strand breaks (DSB). And-1 regulates DSB end resection by establishing a condition or acting as a platform for recruitment of the tumor suppressor protein CtIP—a CtBP (carboxy-terminal binding protein)-interacting protein, to the DSB sites. To determine if the 12 analogs of resveratrol disrupted this complex, an immunofluorescence assay of CtIP co-localization with γH2AX after CH3 or BZA treatment was performed. In brief, IGROV1 cells were cultured on coverslips coated with 0.01% of poly-L-lysine. After treatment, the cells were then washed once with PBS, then pre-extracted with 0.5% Triton X-100 extraction buffer (10 mM PIPES pH 7.0, 100 mM NaCl, 3 mM MgCl$_2$ and 300 mM sucrose) on ice for 5 minutes. After washing with PBS, cells were fixed with 4% paraformaldehyde in PBS for 15 minutes. Cells were then washed and incubated for 10 minutes in blocking buffer (PBS containing 3% BSA and 0.02% Tween-20) and subsequently incubated for 1 hour with a primary antibody at room temperature. Cells were washed three times with PBS-T (PBS containing 0.02% Tween-20) and then incubated with a secondary antibody (e.g., rabbit Alexa Fluor-594 and mouse Alexa Fluor-488). After washing with PBS-T, cells were mounted with Fluoromount G containing DAPI (4',6-diamidino-2-phenylindole—a fluorescent stain that binds strongly to adenine-thymine-rich regions in DNA). Slides were then imaged using a Nikon Eclipse 80i microscope.

Figure 15A:
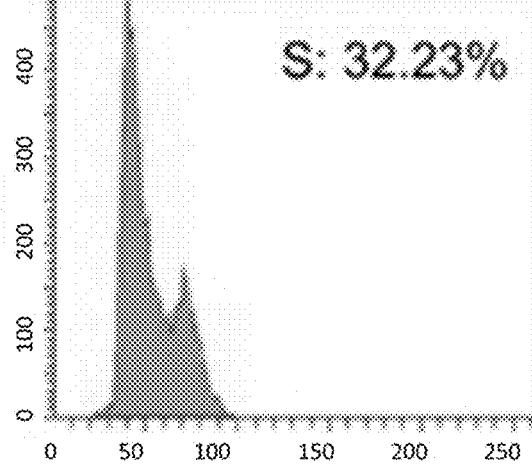
FIGS. 15A-15H depict schematics, images, and graphs illustrating effects of CH3 and BZA treatment of cells in accordance with embodiments of the present disclosure.
Figure 15B:
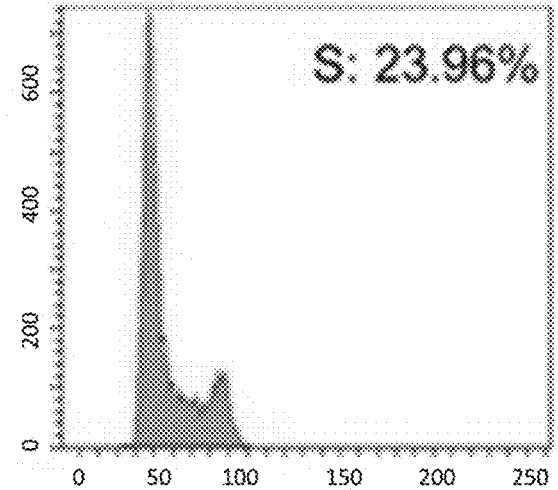
Figure 15C:
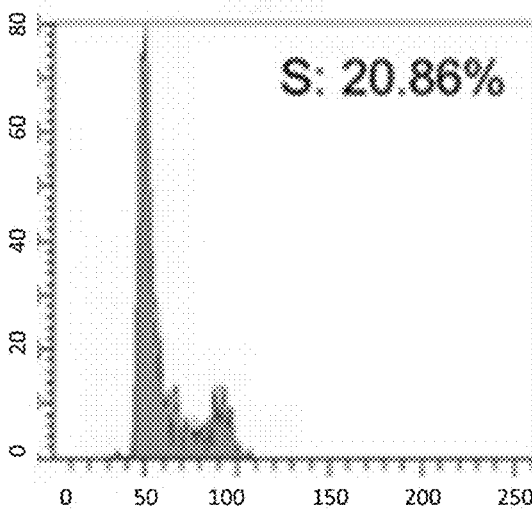
Figure 15D:
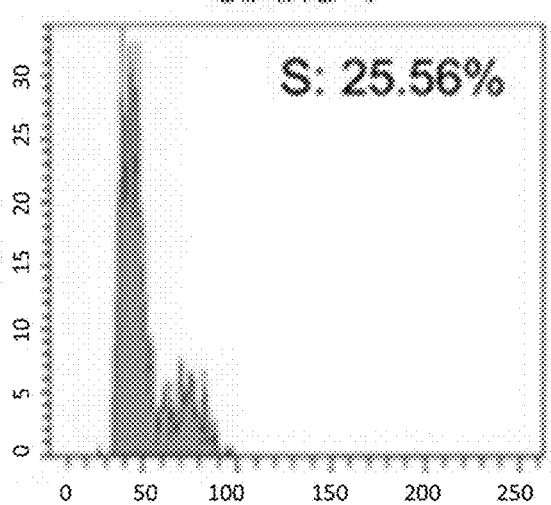
Figure 15E:
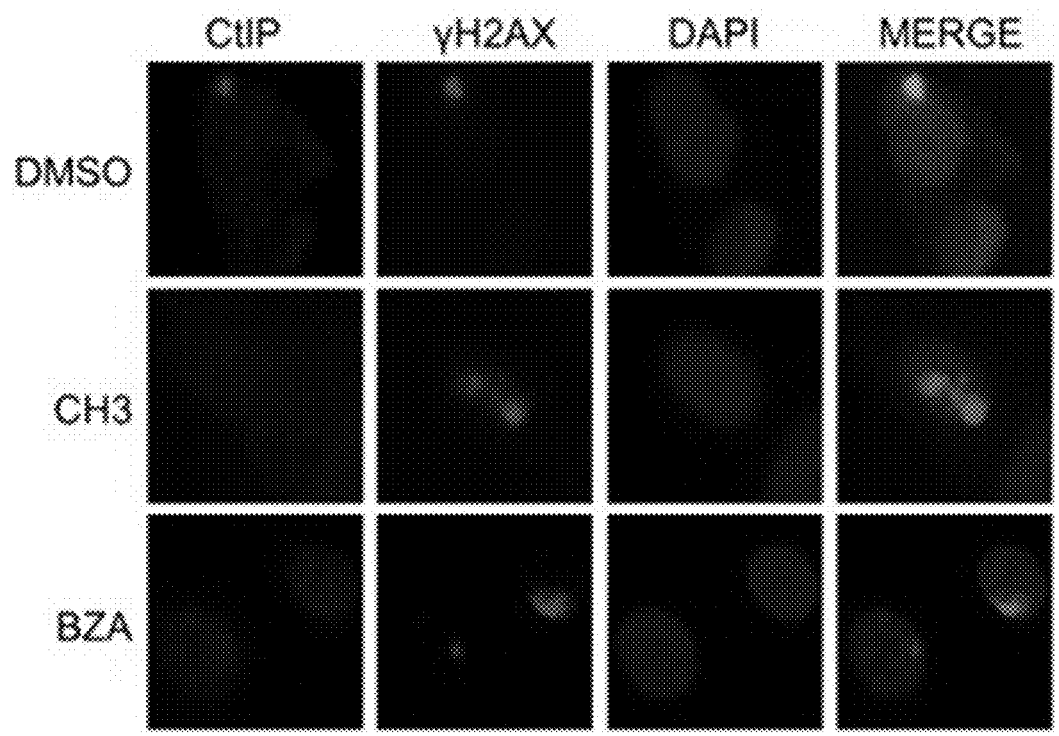
Figure 15F:
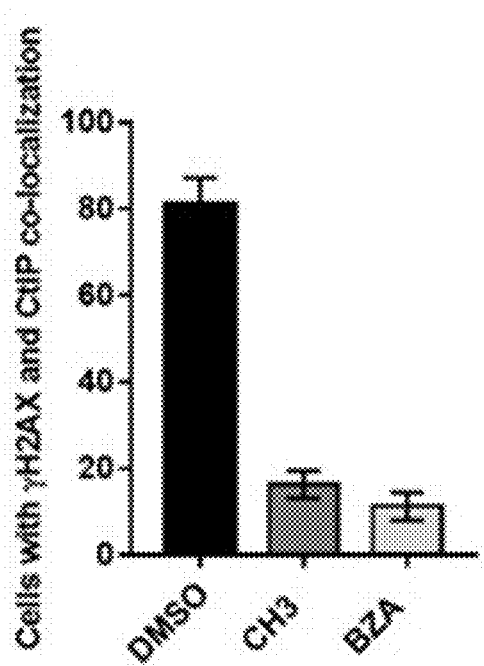

IGROV1 cells treated with DMSO, 1 μM of CH3 or 1 μM of BZA were micro-irradiated and co-immunostained for γH2AX and CtIP 30 minutes post irradiation. Briefly, cells were labeled with 10 μM BrdU for 48-72 h. Cells were then washed with PBS and covered by a micropore membrane (Isopore 5 μM, Millipore), followed by exposure to UVC lamp at a dose of 30 J/m$^2$ (Hitachi, Germicidal lamp, GL-15). After the exposure, cells were incubated in culture medium for 30 minutes and then subjected to immunofluorescence. For each experiment, 50 cells were counted and the percentage of γH2AX cells exhibiting CtIP foci was determined. Consistently, CH3 and BZA treatment significantly decreased the recruitment of CtIP to DSB sites induced by micro-irradiation (FIGS. 15E and 15F).

Figure 15G:
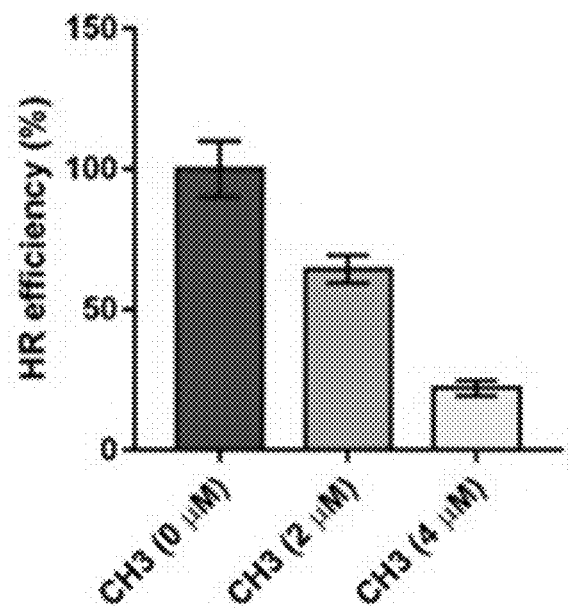
Figure 15H:
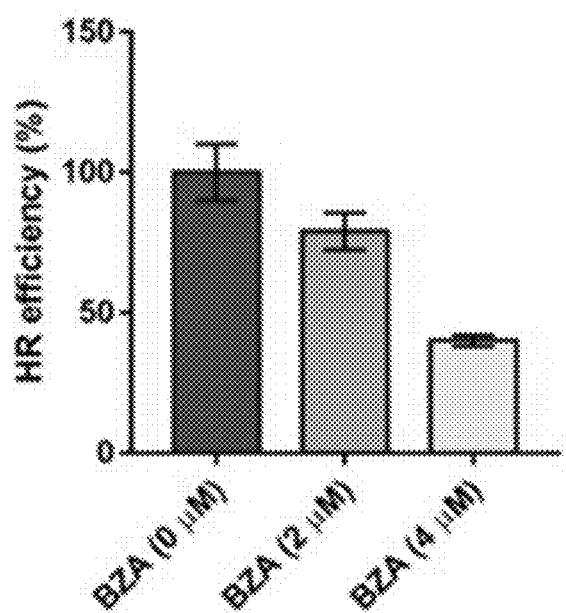

Homologous recombination (HR) reporter assays were performed to determine HR repair efficiency in cells treated with CH3. HR reporter assays were performed using methods similar to those described in Nakanishi et al., *Methods Mol Biol.* 2011; 745:283-291, the disclosure of which is incorporated herein in its entirety. Briefly, IGROV1 cells treated with DMSO, 2 μM or 4 μM of CH3, or 2 μM or 4 μM of BZA were subjected to HR reporter assays and the percentage of GFP-positive cells was determined by flow cytometry 48 hours after I-SceI plasmid transfection. HR efficiency was normalized to that obtained from cells treated with DMSO. HR reporter assays showed that inhibition of And-1 by BZA profoundly reduced HR efficiency and delayed DSB repair (FIGS. 15G and 15H). Together, these data clearly demonstrated that CH3 and BZA significantly inhibited And-1 activity.

Example 7: And-1 Inhibitors Directly Interacted with And-1

To explore whether And-1 inhibitors directly bind to And-1, cellular thermal shift assays were performed in which a small molecule binds to a protein resulting in thermal stabilization of the protein. Briefly, cells were incubated with MG132 (10 μM), DHS, CH3, CH10 or DMSO for 8 hours. After washing with ice-cold PBS (suppled with Protease Inhibitor Cocktail), cells were aliquoted into PCR tubes (100 μL each) and then incubated at different temperatures (from 25° C. to 71° C.) for 4 minutes. After the cells were frozen and thawed twice using liquid nitrogen, proteins were isolated from the cells after centrifugation and incubated at 70° C. for 10 minutes for analysis by western blotting. From this analysis, it was found that at higher temperatures, And-1 protein was stabilized upon treatment with DHS, CH3 or BZA (FIGS. 16A-16C and FIGS. 17A-17C) compared to DMSO treatment.

Boron-containing compounds can be visualized using a fluorescent boron sensor DAHMI. To determine the binding specificity of CH3 to And-1, the distribution of CH3 in live cells was examined using DAHMI. As shown in FIGS. 16D-16F, CH3 was detected in nuclei 1 minute after DAHMI treatment in IGROV1 cells. And-1 depletion by siRNA significantly reduced the amount of CH3 in nuclei, indicating that And-1 is bona fide specific target of CH3 in living cells.

Figure 16A:
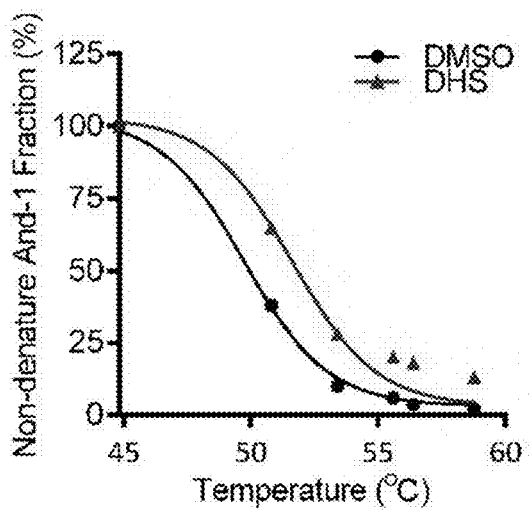
Figure 16B:
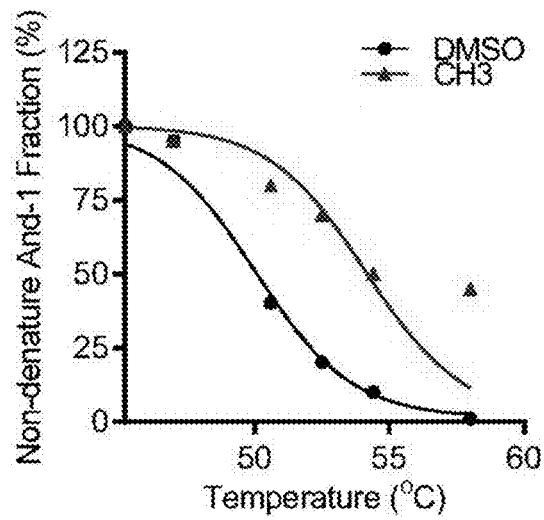
Figure 16C:
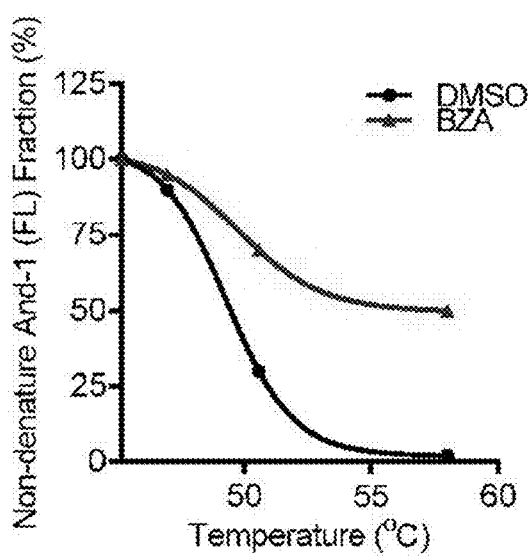
Figure 16G:
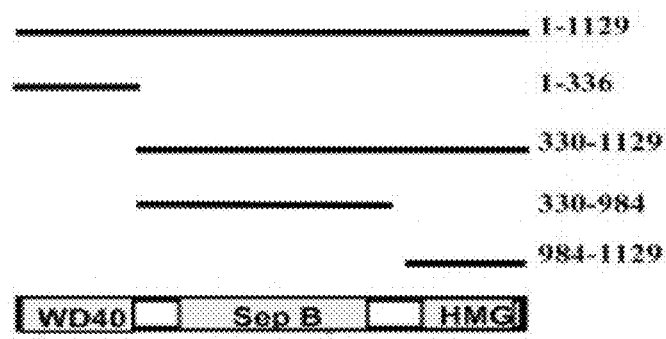
Figure 16H:
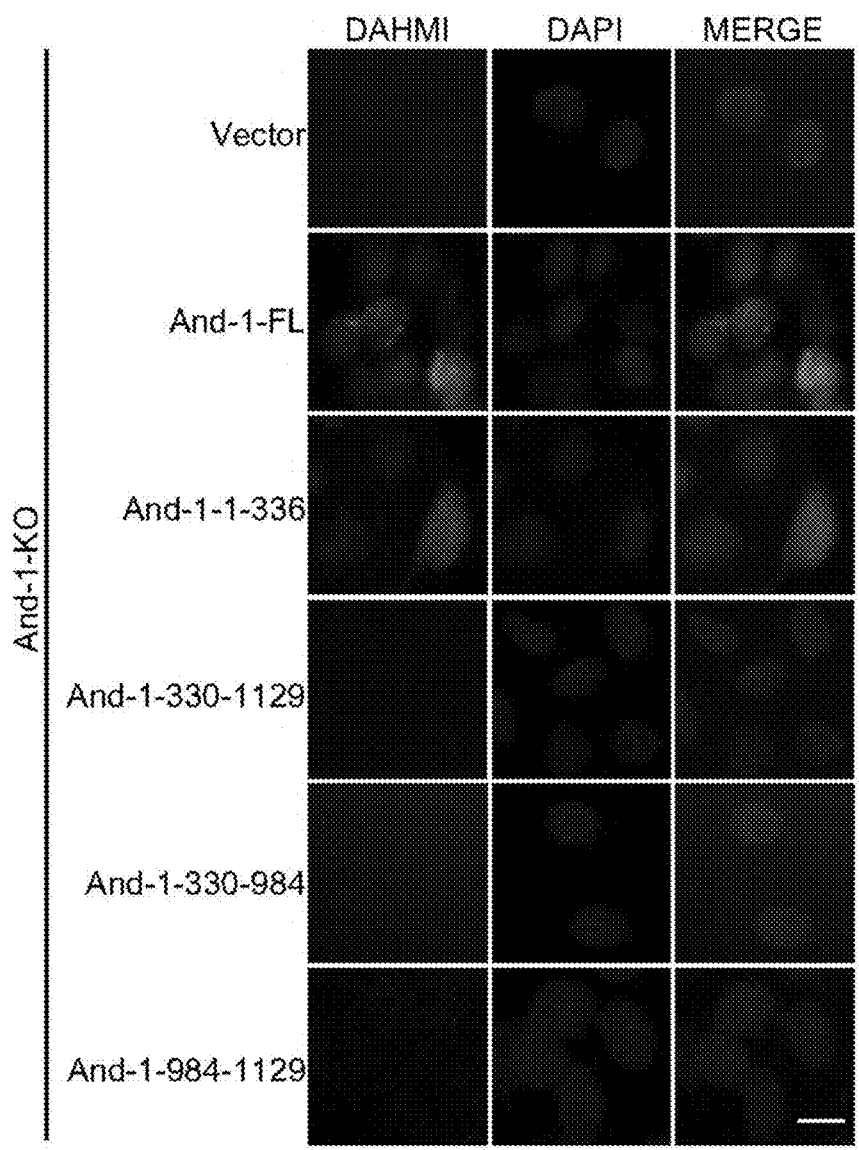
Figure 16I:
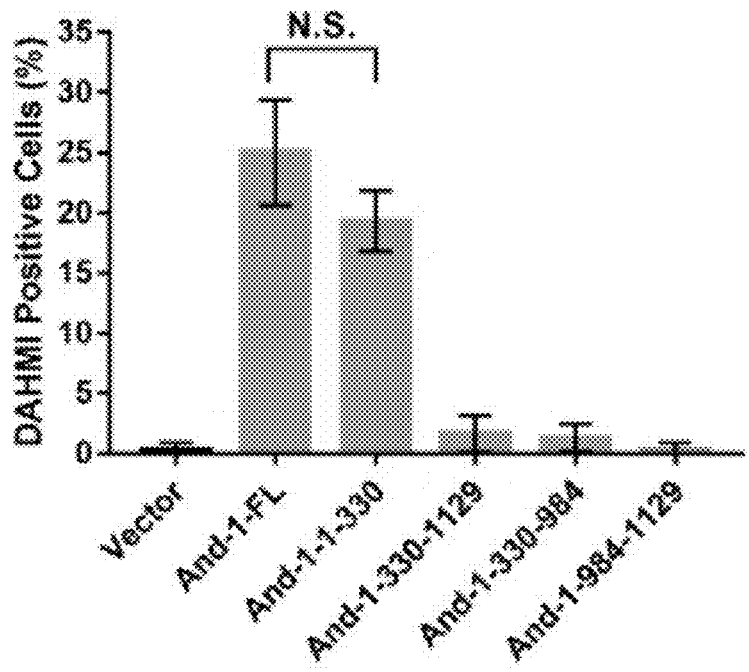
Figure 16J:
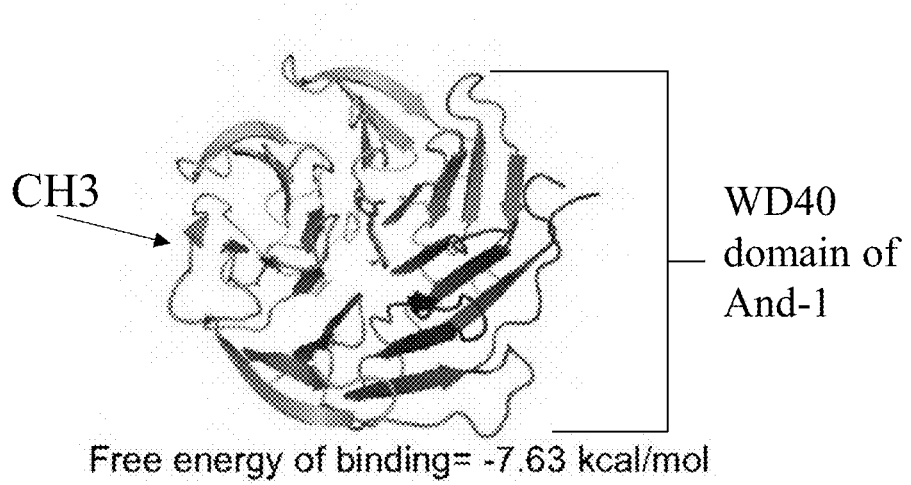
Figure 16K:
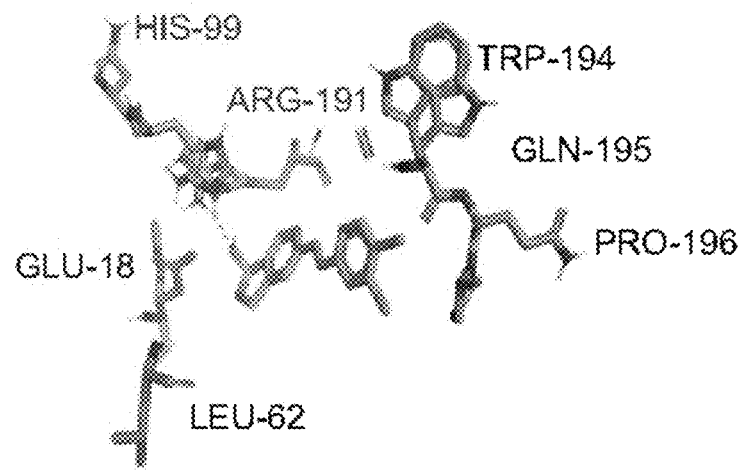
Figure 16L:
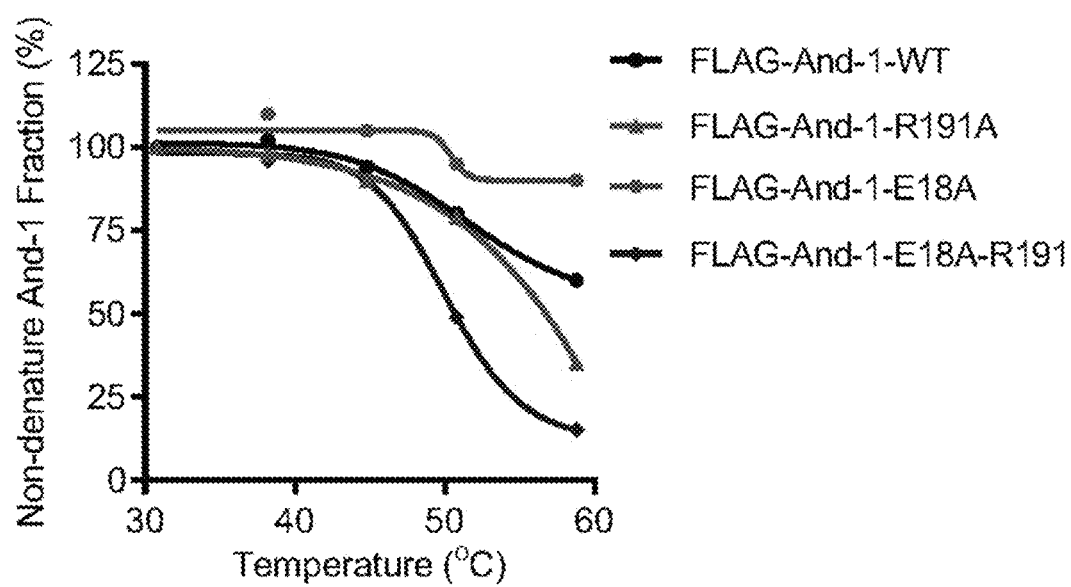
Figure 17A:
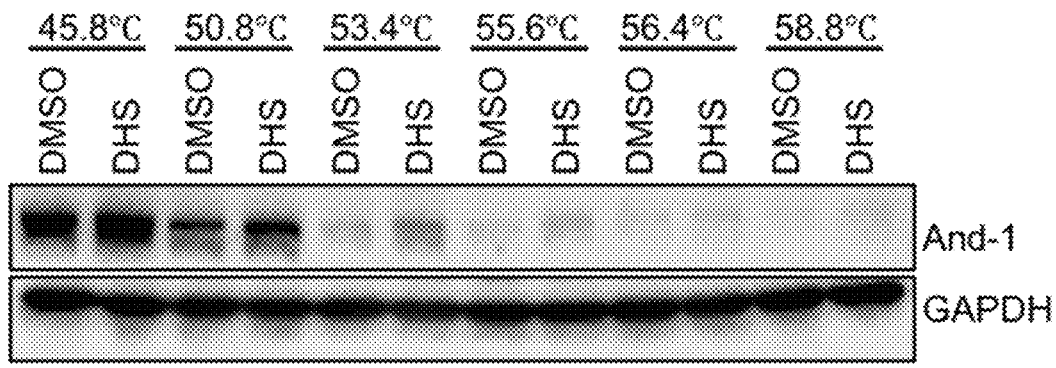
FIGS. 17A-17G depict images illustrating And-1 inhibitor interaction with And-1 in accordance with embodiments of the present disclosure.
Figure 17B:
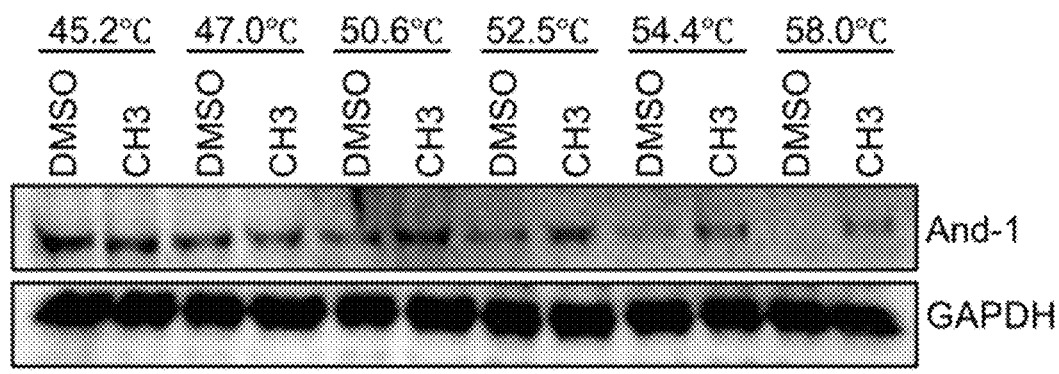
Figure 17C:
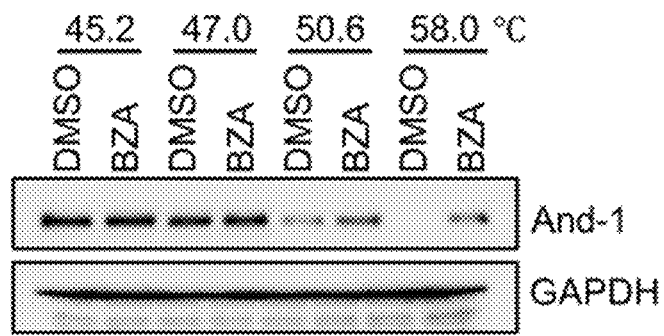
Figure 17D:
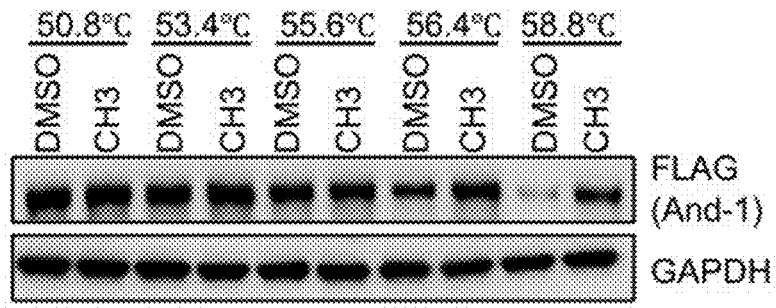
Figure 17E:
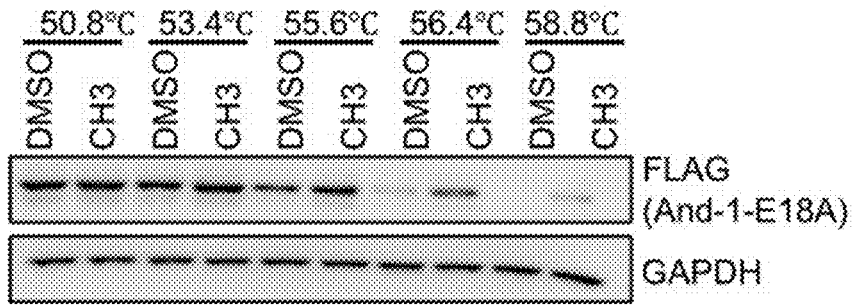
Figure 17F:
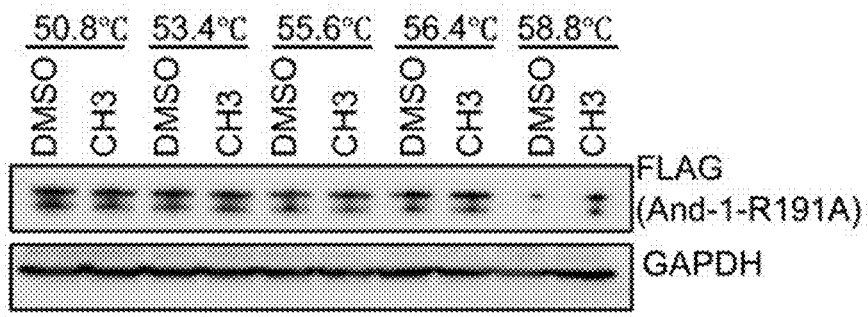
Figure 17G:
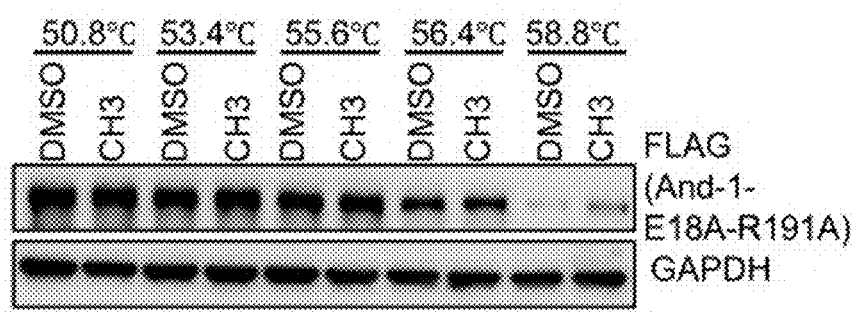

To identify the CH3-binding region on And-1, the DAHMI system was used in And-1 knockout U20S cells to analyze the binding affinity of CH3 with ectopically expressed And-1 and its truncation mutants, including And-1(1-330) containing the WD40 domain, And-1 (330-1129) containing SepB and HMG domain, And-1 (330-984) containing Sep domain and And-1 (984-1129) containing HMG domain (FIG. 2G). As shown in FIGS. 16H and 16I, wild type And-1 and And-1(1-330) but not other And-1 mutants exhibited binding affinity to CH3, suggesting CH3 binds to the N-terminal region of And-1. Consistently, by analyzing binding energy between CH3 and And-1 domains using virtual ligand-protein docking, it was found that WD40 domain was the potential binding domain for CH3 because it exhibited the lowest free energy of binding (FIG. 16J). The binding energy of each binding site on And-1 was further examined with CH3 and it was found that Arginine-191 and Glutamic acid-18 had the lowest binding energy with CH3 and BZA (FIG. 16K and Table 2), suggesting that both amino acids were potential critical binding sites for the And-1 inhibitors.

TABLE 2

Decomposed interaction energy of top 5 amino acids of And-1 contributed to CH3 interaction.

| Interaction | Decomposed interaction energies in kcal/mol |
| --- | --- |
| ARG-191 | −0.8965 |
| GLU-18 | −0.5906 |
| TRP-194 | −0.4597 |
| PRO-196 | −0.3958 |
| HIS-99 | −0.2848 |

Indeed, the thermoshift assay indicated that either the R191A or E18A mutation slightly reduced And-1 thermostability, but mutation of both R191A and E18A significantly impaired the thermostability of And-1 in response to CH3 treatment (FIG. 16L and FIGS. 17D-17G). Together, these results indicated that CH3 was directly bound to the WD40 domain of And-1.

Figure 18A:
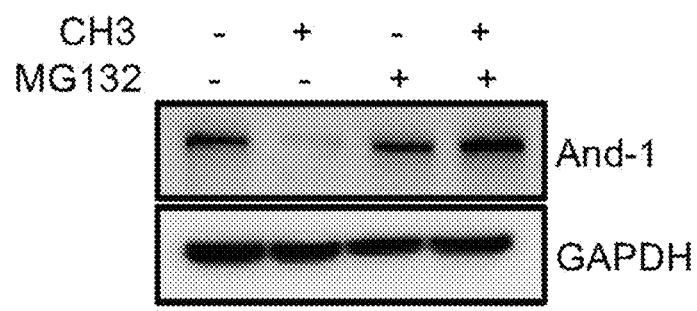
FIGS. 18A-18G depict schematics and images illustrating And-1 inhibitor induction of And-1 degradation via a CUL4B-mediated proteasome degradation pathway in accordance with embodiments of the present disclosure.
Figure 18B:
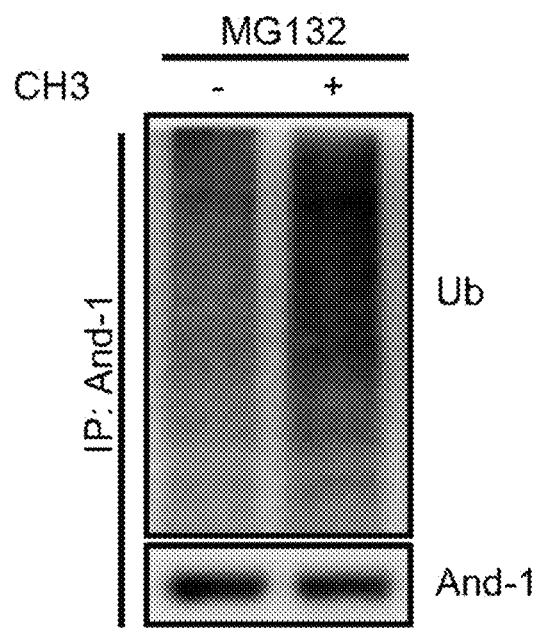

Example 8. And-1 Inhibitors Induced And-1 Degradation Via CUL4B-Mediated Proteasome Degradation Pathway To investigate the molecular mechanism by which And-1 inhibitors induced And-1 degradation, it was first determined whether the ubiquitin-mediated proteasome pathway was involved in CH3-induced And-1 degradation. IGROV1 cells were treated with CH3 in the absence and presence of the 26S proteasome inhibitor MG132 (Benzyl N-[(2S)-4-methyl-1-[[(2S)-4-methyl-1-[[(2S)-4-methyl-1-oxopentan-2-yl]amino]-1-oxopentan-2-yl]amino]-1-oxopentan-2-yl] carbamate). As shown in FIG. 18A, CH3 treatment reduced And-1 protein levels, and reduced And-1 levels were restored by MG132, suggesting that CH3-induced And-1 degradation was regulated by proteasome pathway. Protein degradation through the proteasome requires conjugation of one or more ubiquitin molecules to the target. To address whether And-1 was modified by ubiquitin in IGROV1 cells treated with CH3, And-1 protein was immunoprecipitated and probed with anti-ubiquitin antibody. As shown in FIG. 18B, the discrete slower-migrating ubiquitinated And-1 bands were increased in cells treated with CH3, indicating that CH3 induced And-1 degradation through a ubiquitin-mediated proteasome pathway.

Figure 18C:
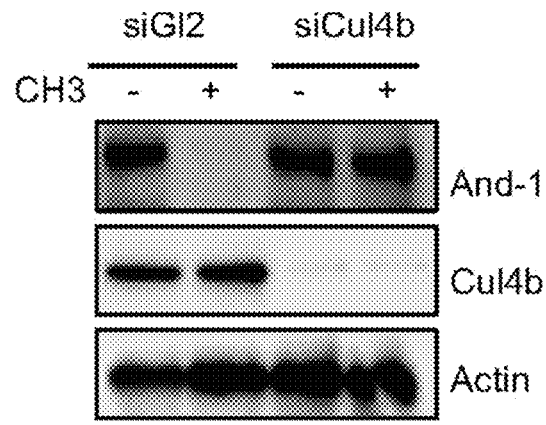
Figure 18D:
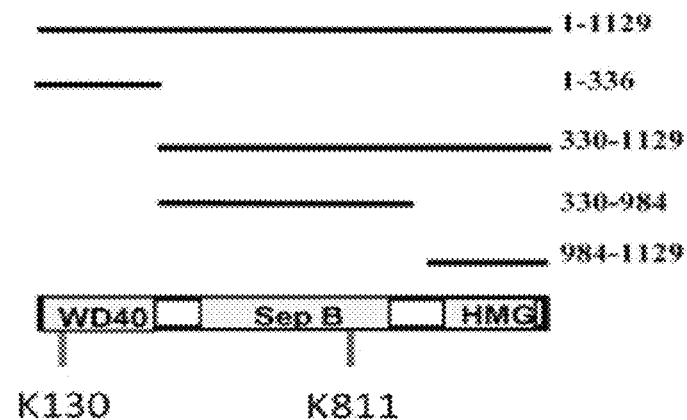
Figure 18E:
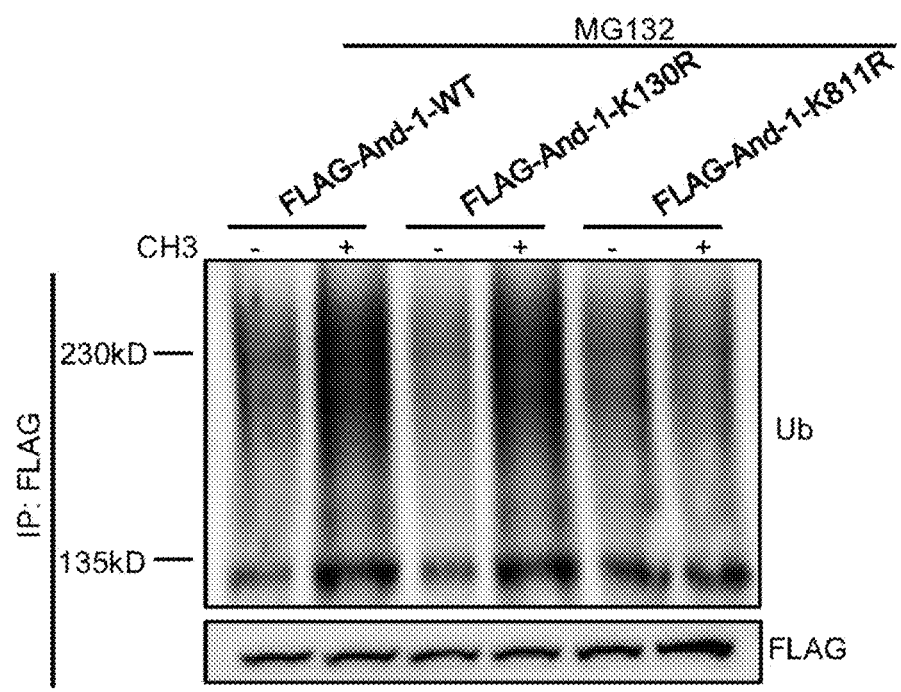
Figure 18F:
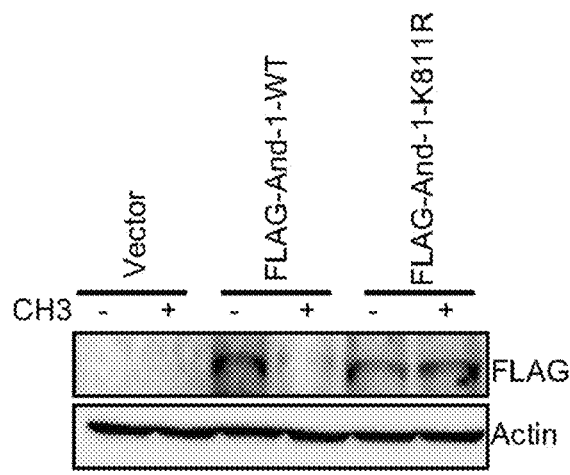
Figure 18G:
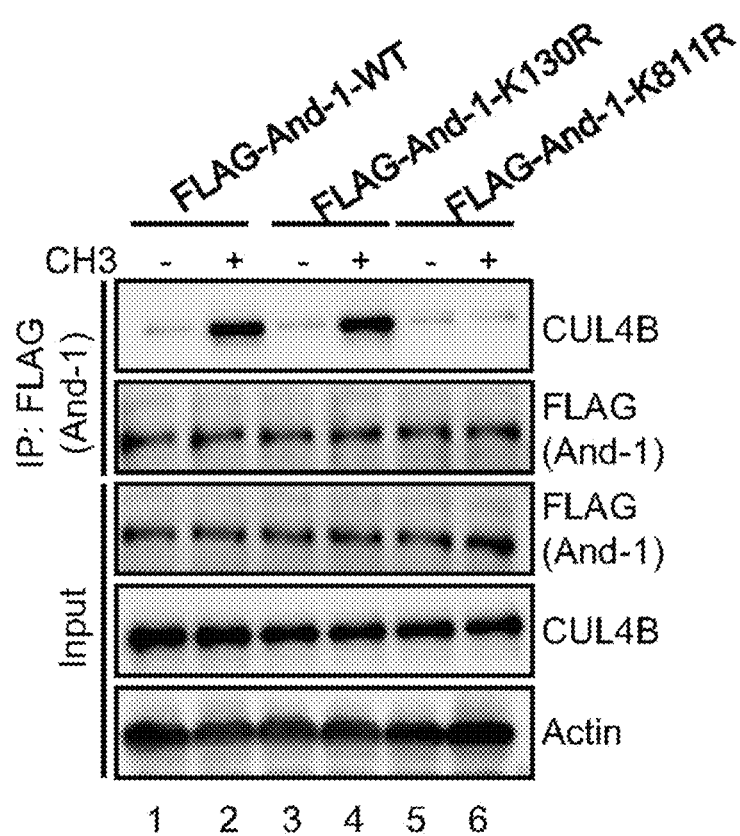

Previous studies in yeast cells indicated that the E3 ligase Rtt101 interacts with Ctf4. Since the human analogue of Rtt101 is Cul4, the Cul4 expression in IGROV1 cells was knockeddown by siRNA to determine of Cul4 was the E3 ligase responsible for And-1 degradation. Indeed, knockdown of CUL4B by siRNA dramatically restored And-1 protein levels in cells treated with CH3, indicating that And-1 was a substrate of CUL4B for ubiquitination by CH3 (FIG. 18C). To determine the ubiquitination sites of And-1, the proteomic analysis program neXtProt (neXtProt release 2021-02-18) was used and Lysine 130 and Lysine 811 were identified as potential ubiquitination sites. Significantly, a K811R mutation but not a K130R mutation in the amino acid sequence of And-1 abolished the ubiquitination of And-1 induced by CH3 (FIGS. 18D and 18E), indicating that K811 was the bona-fide ubiquitin site. Consistently, a FLAG-And-1-K811R mutant was stabilized in cells treated with CH3 (FIG. 18F). In agreement with CUL4B-mediated the degradation of And-1, CH3 treatment increased the interaction between FLAG-And-1 and CUL4B (FIG. 18G, see lane 1 and 2). Interestingly, the interaction between CUL4B and FLAG-And-1-K811R was not induced by CH3, indicating Lysine 811 of And-1 was required for And-1-CUL4B interaction induced by CH3 (FIG. 18G, see lane 5 and 6).

Figure 19A:
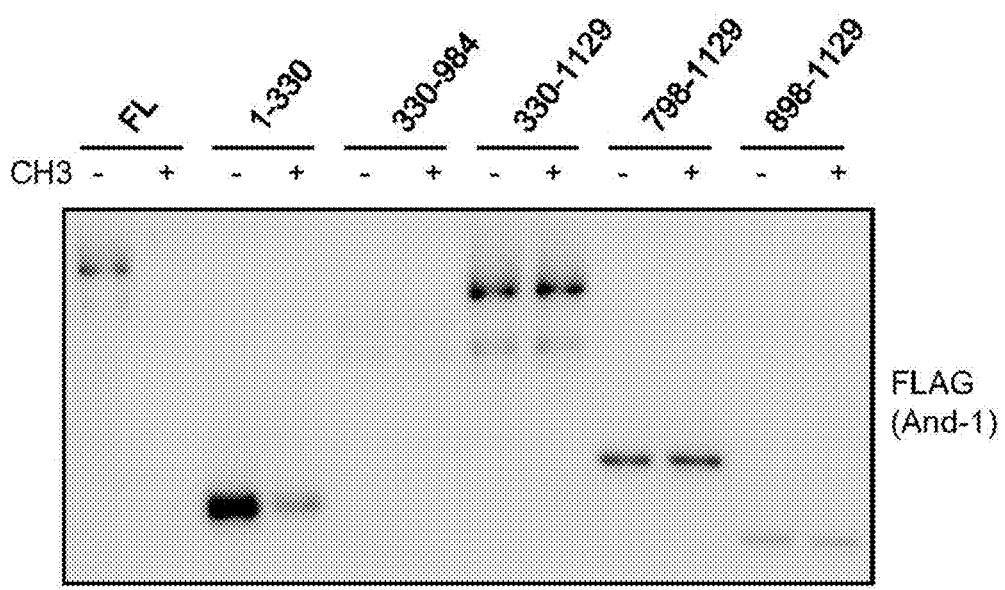
FIGS. 19A-19E depict images illustrating And-1 inhibitor promotion of And-1 and CUL4B interaction through altering And-1 conformation in accordance with embodiments of the present disclosure.
Figure 19B:
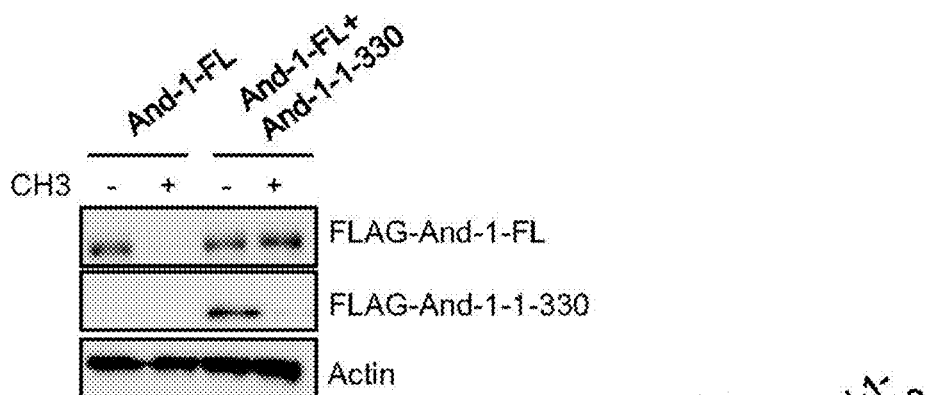
Figure 19C:
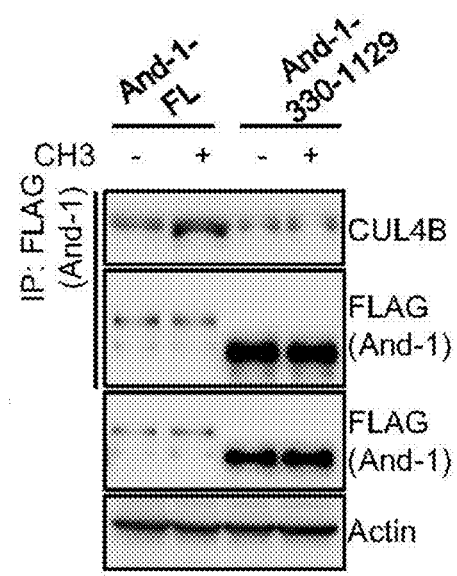

Example 9. And-1 Inhibitors Promoted And-1 and CUL4B Interaction by Affecting And-1 Conformation Given that the WD40 domain of And-1 mediated the interaction of And-1 with CH3 as shown in the Examples above, it was assumed that And-1 mutants that lack a WD40 domain should not be degraded by CH3. Indeed, the And-1-330-1129 mutant was not degraded in response to CH3 (FIG. 19A). Consistently, overexpression of the WD40 domain of And-1 prevented full-length And-1 from degradation by CH3 (FIG. 19B). Together, the WD40 domain of And-1 was required for And-1 degradation by CH3. It was next tested whether the WD40 domain was required for efficient And-1-CUL4B interaction. As shown in FIG. 19C, CH3 induced the interaction of CUL4B with full-length And-1 but not with the And-1-330-1129 mutant, indicating that the WD40 domain was required for CH3-induced And-1-CUL4B interaction.

Figure 19D:
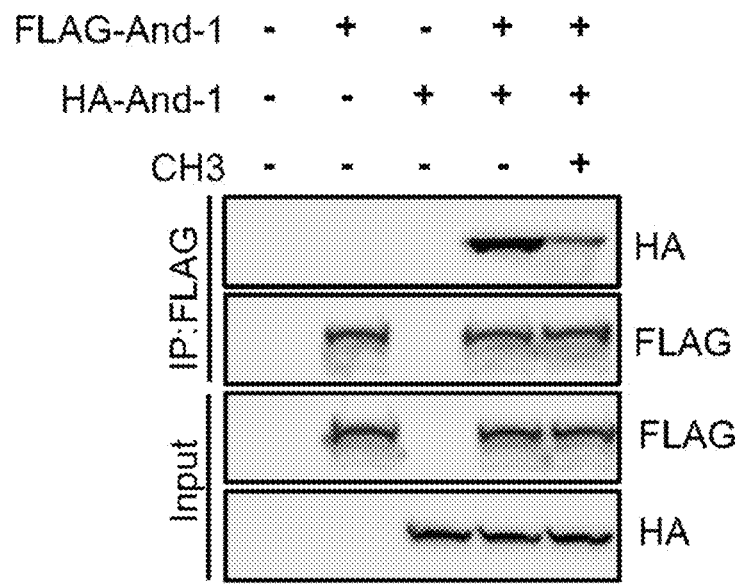
Figure 19E:
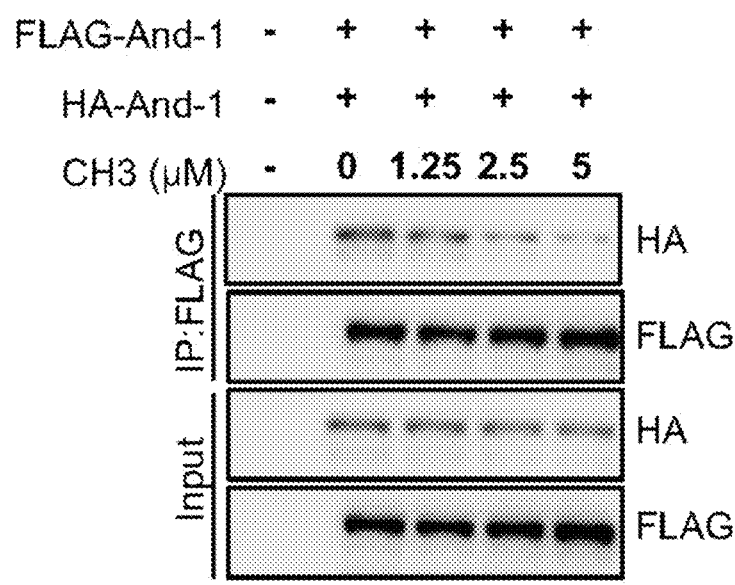

Human And-1 exists as a homotrimer mediated by the SepB domain. To determine whether the interaction of CH3 with the WD40 domain can disrupt And-1 polymerization, resulting in exposure of CUL4B binding site on And-1 to CUL4B, both FLAG-And-1 and HA-And-1 were transfected into U2OS cells and the protein-protein interaction was examined in the presence of CH3. As shown in FIGS. 19D and 19E, CH3 treatment significantly decreased the interaction between HA-And-1 and FLAG-And-1 in a dose dependent manner, demonstrating that CH3 indeed disrupted the polymerization of And-1, resulting in its gradation.

Figure 20A:
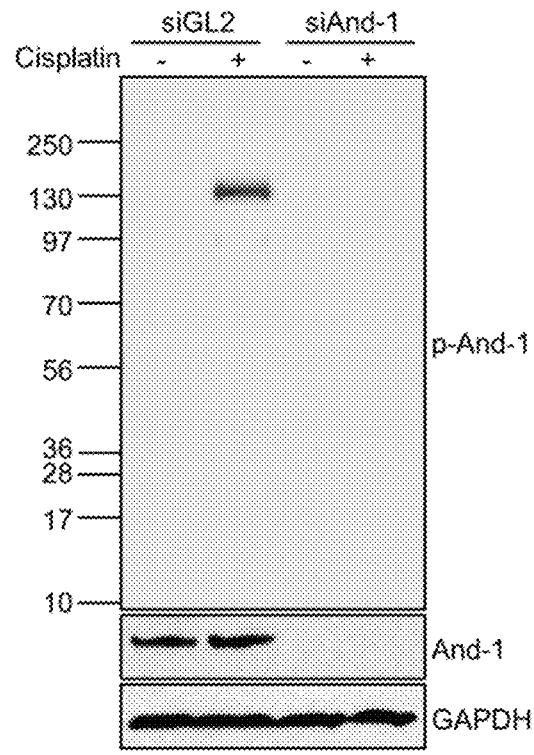
FIGS. 20A-20D depict images illustrating phosphorylation of And-1 at amino acid residue T826 in cells treated with cisplatin in a time dependent manner in accordance with embodiments of the present disclosure.
Figure 20B:
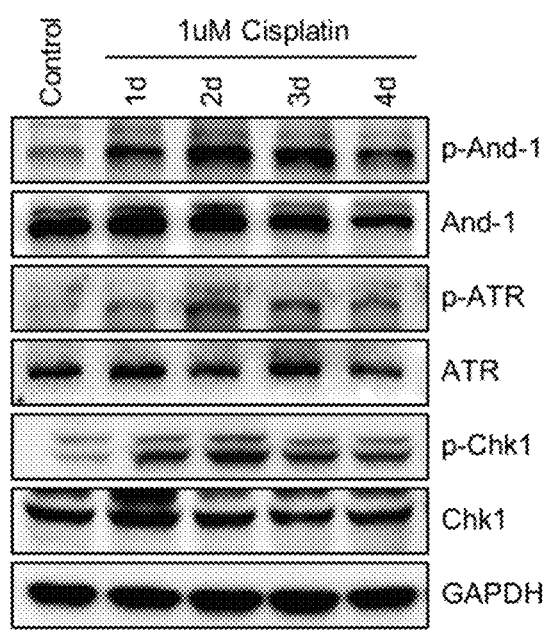
Figure 20C:
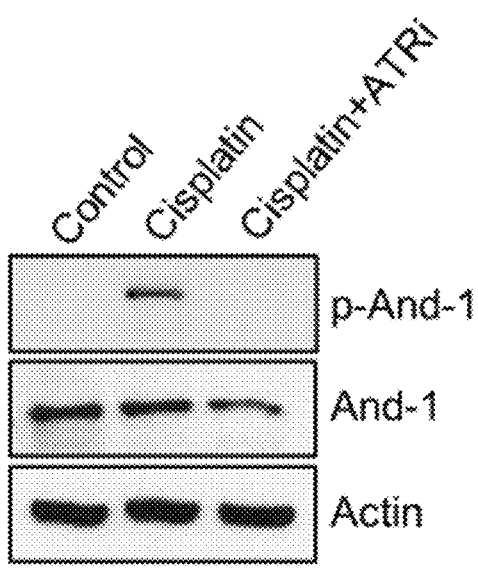
Figure 20D:
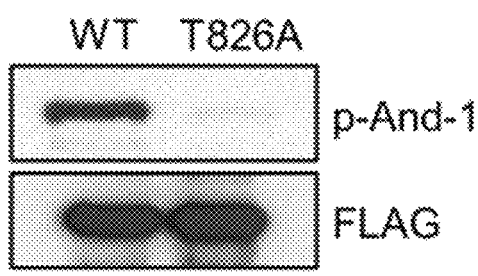

Example 10. And-1 Phosphorylation was Upregulated in Cisplatin Resistant Ovarian Cancer Cisplatin causes cell death by introducing DNA crosslinks that inhibits DNA replication and transcription. ATR (ataxia telangiectasia and Rad3-related) is an essential DNA damage response (DDR) kinase that phosphorylates And-1 at amino acid residue T826 under replication stress. To explore the physiological significance of And-1 phosphorylation at T826, an antibody that specifically detects the And-1 phosphorylated protein phosphorylated at T826 (referred to herein interchangeably as "phospho-And-1 antibody" or "p-And-1") was developed. This antibody specifically recognized phosphorylation of And-1 at T826 in cells treated with cisplatin in a time dependent manner (FIGS. 20A and 20B). Inhibition of ATR by using its specific inhibitor, VE821, abolished expression of p-And-1 in response to cisplatin, suggesting that this antibody specifically recognized phosphorylation caused by ATR (FIG. 20C). To validate the specificity of p-And-1 antibody, FLAG-And-1-WT or FLAG-And-1-T826A was transfected into HEK293T cells followed by cisplatin treatment. As shown in FIG. 20D, p-And-1 antibody could detect phosphorylation of FLAG-And-1-WT but not FLAG-And-1-T826A, indicating that the p-And-1 antibody was specific for detection of phosphorylated And-1 at T826.

The expression level of p-And-1 protein was examined the in five paired human ovarian cancer (OC) cell lines, including IGROV1, cisplatin resistant IGROV1 (IGROV1 CR), PEO1, PEO4, OV90, OV90 CR, PEO14, PEO23, OV433 and OV433 CR. Briefly, the human OC PEO1 and PEO4 cells were cultured in RPMI-1640 with 10% Fetal Bovine Serum (FBS). IGROV1 cells were cultured in DMEM with 10% FBS. OV433 cells were cultured in DMEM with 10% FBS. OV90 cells were cultured in the growth medium containing 1:1 MCDB 105 and M199 supplemented with 10% FBS. All the cells were cultured at 37° C. in a humidified incubator containing 5% CO2. Cisplatin resistant ("CR") cells were generated by first treating wild-type with cisplatin for six cycles (4 hours of cisplatin treatment, followed by release to cisplatin free medium for three weeks). In the next cycle, cisplatin treatment was repeated with an increased concentration of cisplatin. After five months of treatment (6 cycles), cisplatin resistant cell lines IGROV1 CR, OV90 CR and OV433 CR were obtained. Only early-passage (<10 passages) resistant cell lines were used for the Examples herein.

Figure 21A:
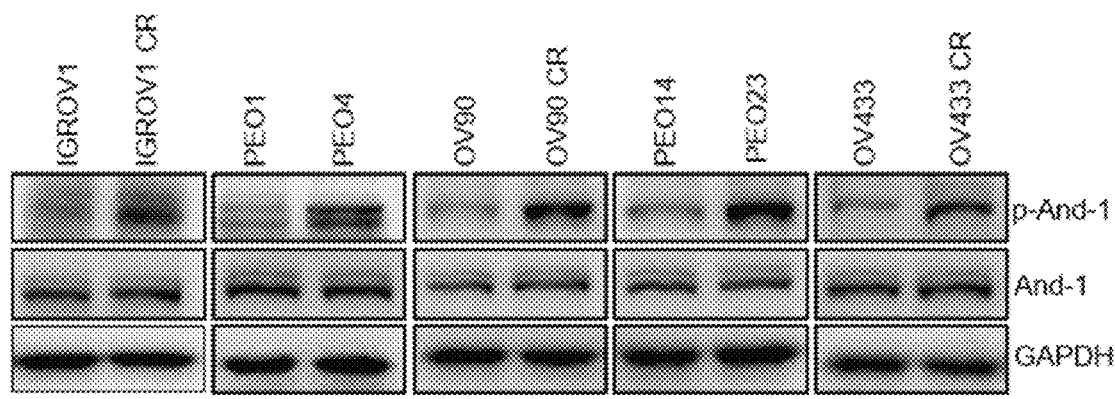
FIGS. 21A-21G depict images and graphs illustrating phosphorylation of And-1 in correlation with cisplatin resistance in ovarian cancer (OC) patients in accordance with embodiments of the present disclosure.
Figure 21B:
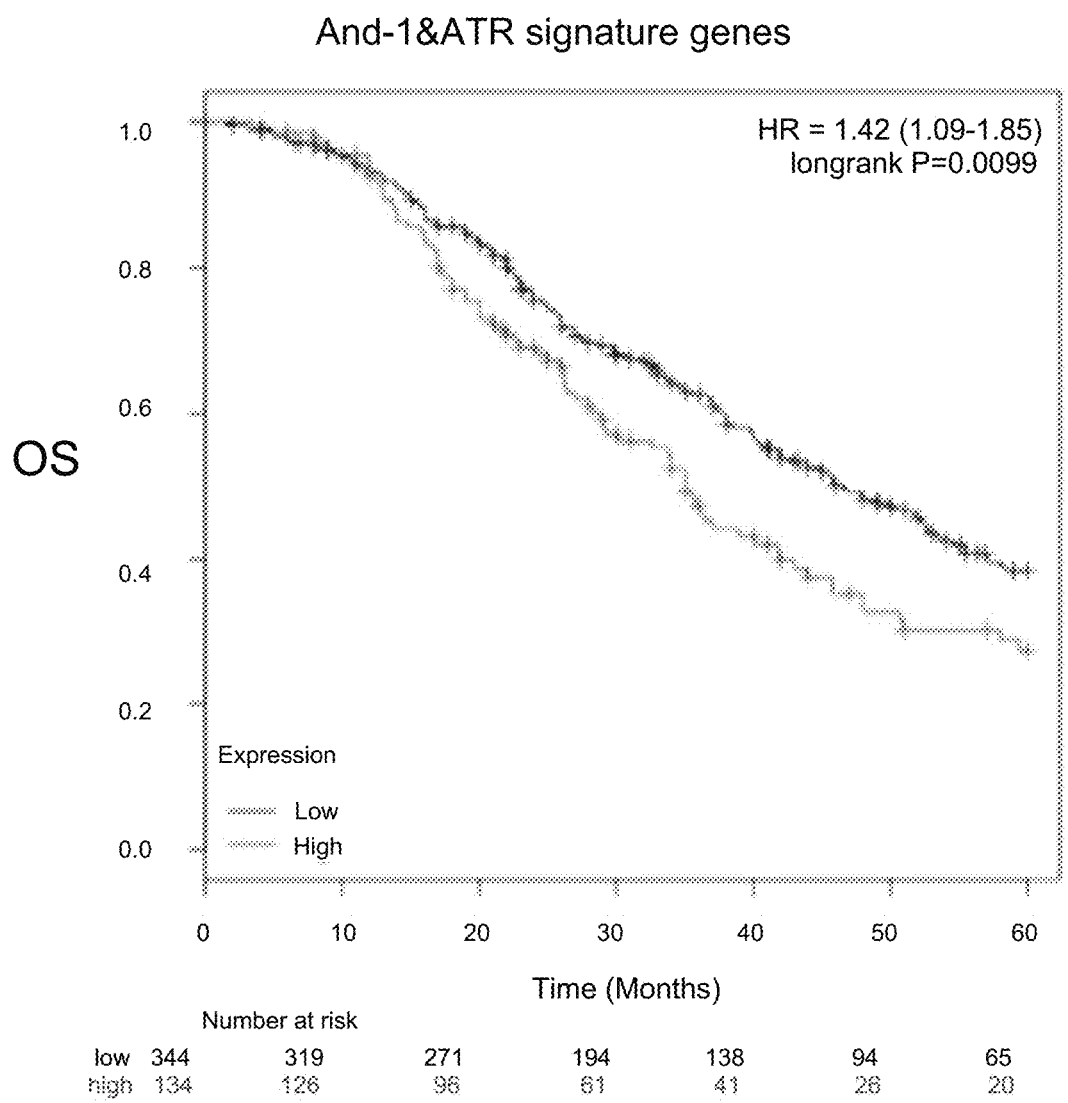

Significantly, p-And-1 levels were increased in all cisplatin resistant cells compared to their sensitive counterparts (FIG. 21A). Consistently, cisplatin treatment induced p-And-1 expression in both dose- and time course-dependent manner in OC cells (FIGS. 22A-22D). To investigate and confirm the role of And-1 phosphorylation in platinum drug resistance of OC patients, the correlation of overall survival rate (OS) with And-1 was analyzed using large scaled OC data bases (See Kaplan-Meier Plotter for Ovarian Cancers, as described in Gyorffy et al., *Endocrine-Related Cancer.* 2012 Apr. 10; 19(2):197-208, the disclosure of which is incorporated herein in its entirety.) Since And-1 phosphorylation but not proteins levels were up-regulated in cisplatin resistant cells, the correlation of OS with And-1 and ATR signature genes was examined in patients who had been treated with platinum drugs. Significantly, patients with high expression levels of And-1 and ATR signature genes exhibited a poor prognosis of overall survival (FIG. 21B), suggesting phosphorylation of And-1 is negatively correlated with prognosis.

To directly evaluate p-And-1 expression in response to chemotherapy, phosphorylated And-1 protein expression levels in the samples from the same patient before platinum treatment and after acquired drug resistance were examined. The specimens of chemosensitive and matched recurrent or chemoresistant tumor tissues from OC patients were kept as formalin-fixed paraffin-embedded (FFPE) samples. The histological types, disease stages, and cancer cell contents in each FFPE sections were examined by experienced pathologists. Platinum-sensitive was defined as patients who have a total response to platinum-based therapy and no recurrence within 6 months. Platinum resistance means patients who had the recurrence occur within 6 months following the completion of platinum-based therapy.

Figure 21C:
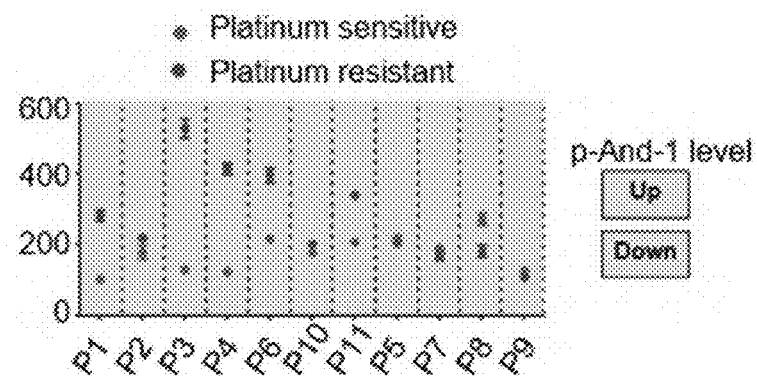
Figure 21D:
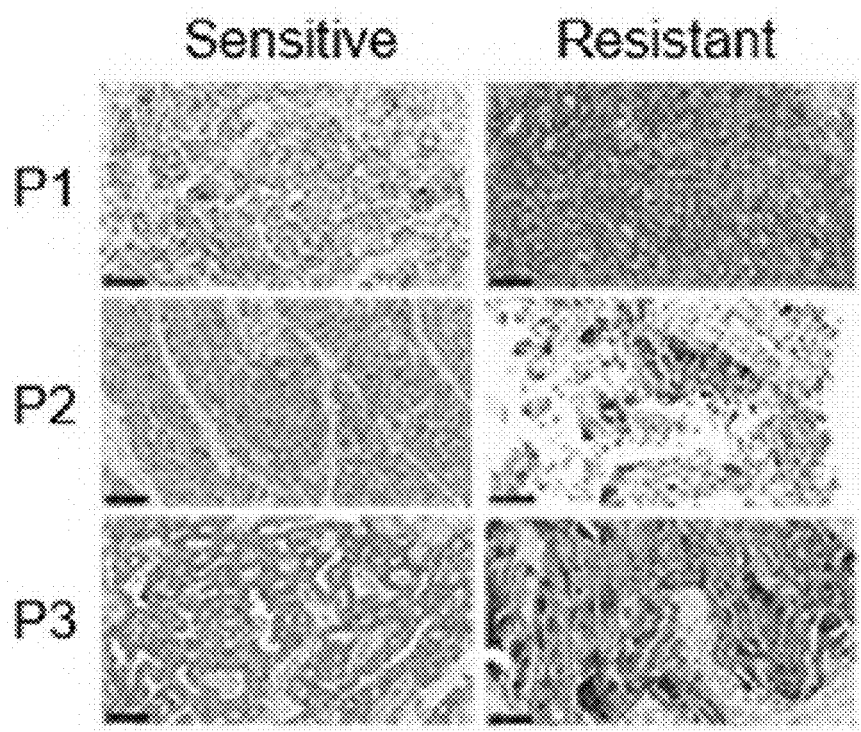
Figure 21E:
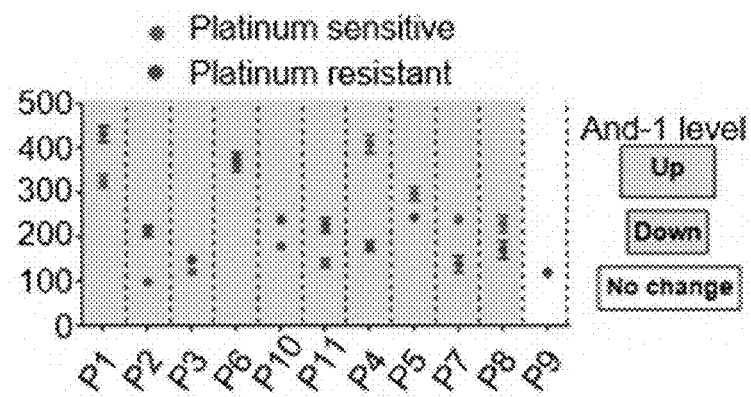
Figure 21F:
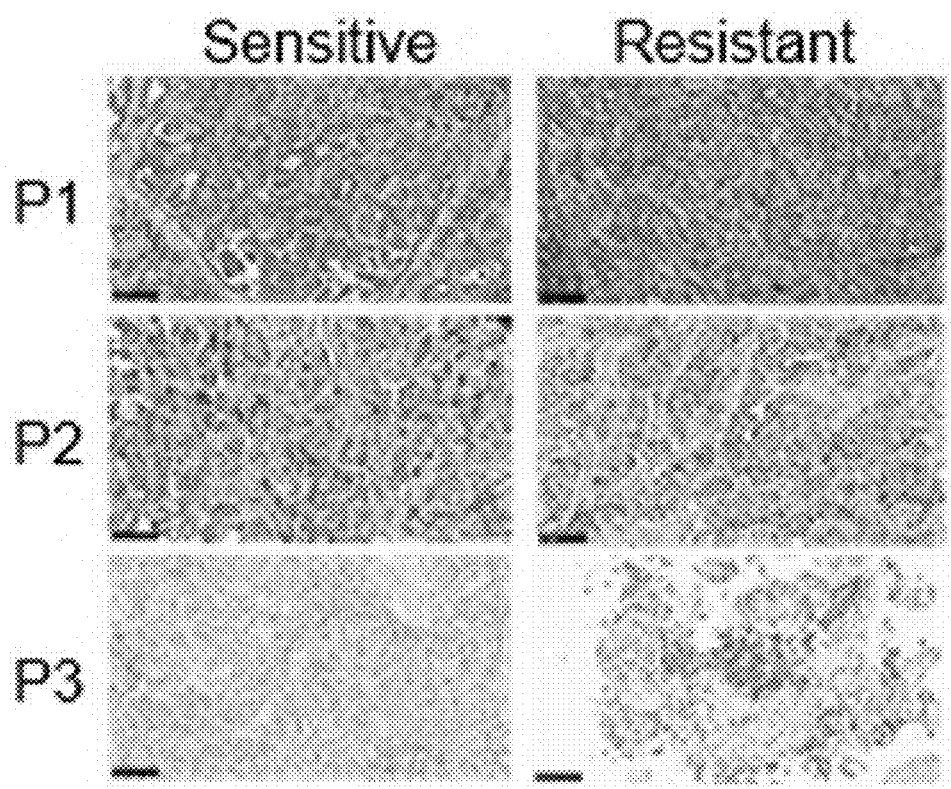
Figure 21G:
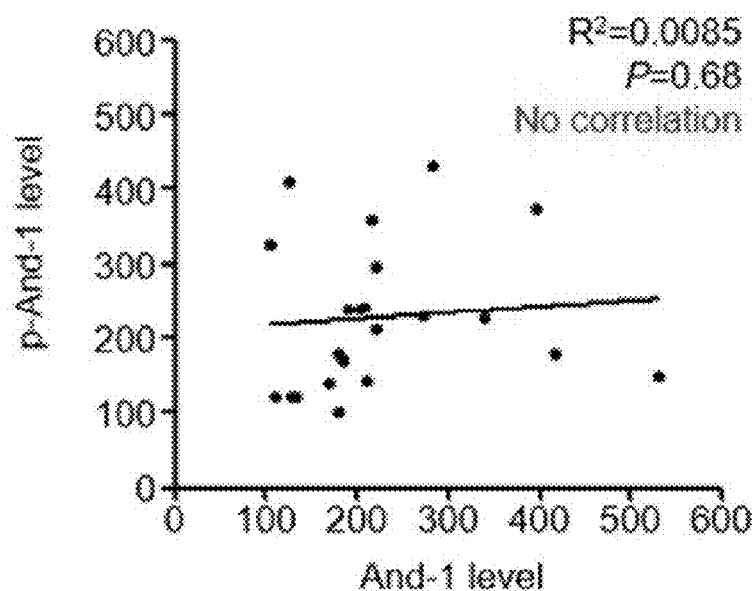
Figures 22A, 22B:
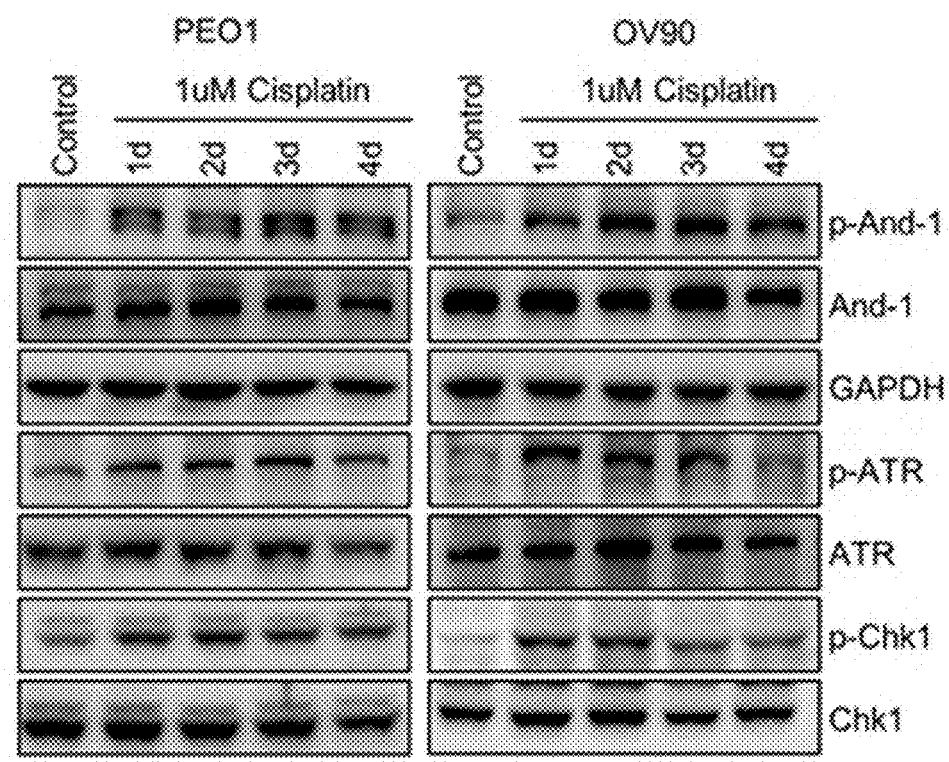

Strikingly, 7 out of 11 patients showed upregulated p-And-1 protein level after developing platinum drug resistance (FIGS. 21C and 21D). Importantly, there was no correlation between p-And-1 and total And-1 expression in these patients (FIGS. 21E-21G), suggesting And-1 phosphorylation was positively correlated with platinum resistance in OC patients. Thus, anti-And-1 was a potential approach for treatment of platinum drug resistant OC.

Figure 23A:
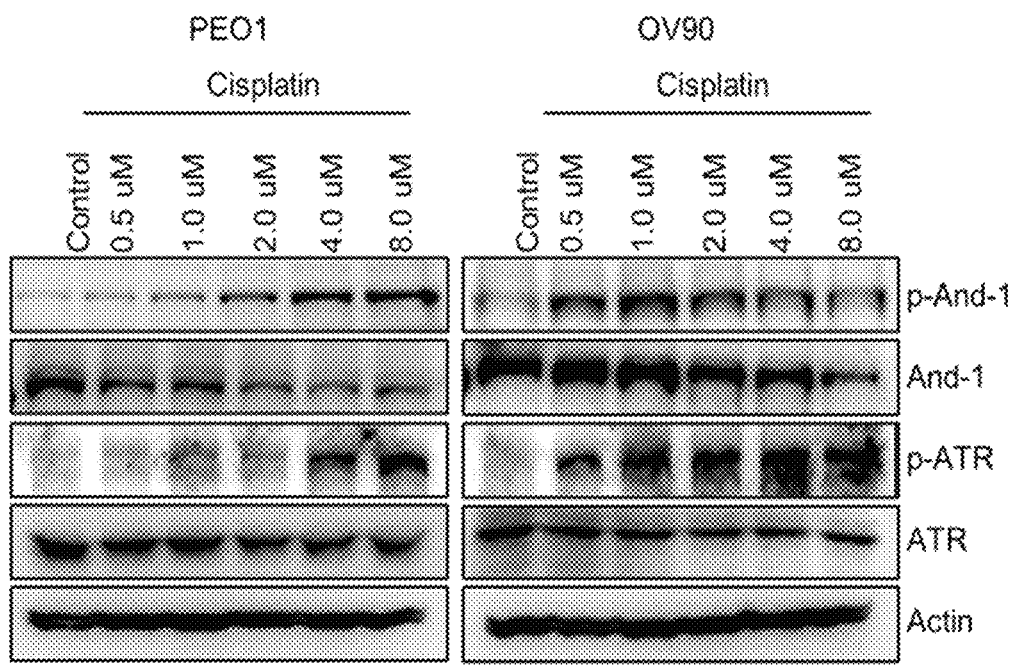
Figure 23A:
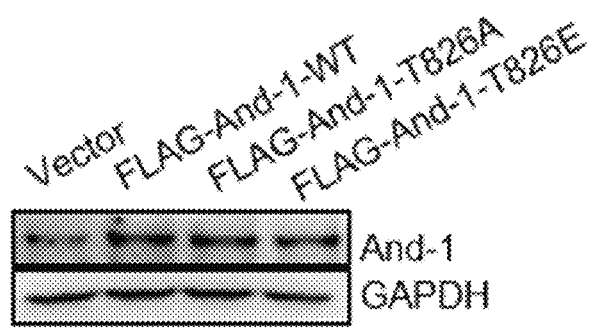
Figure 23B:
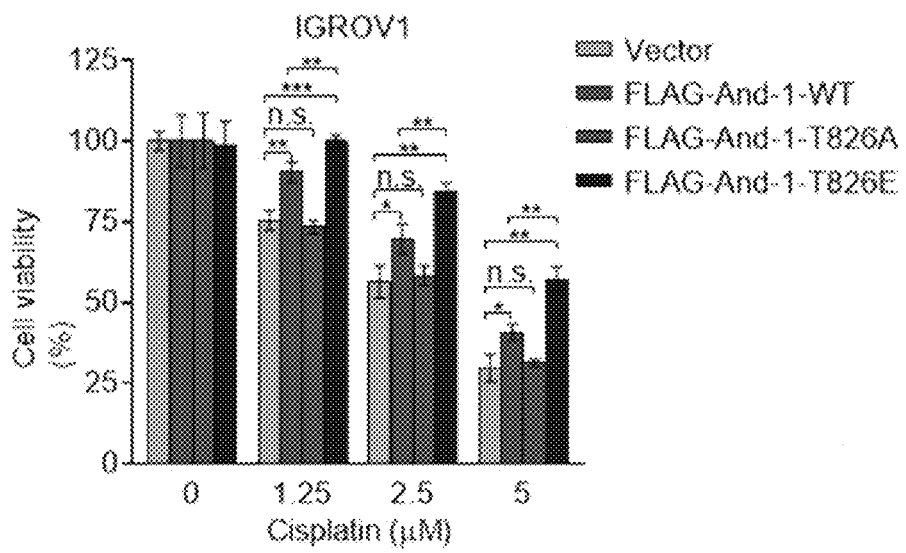
Figure 23C:
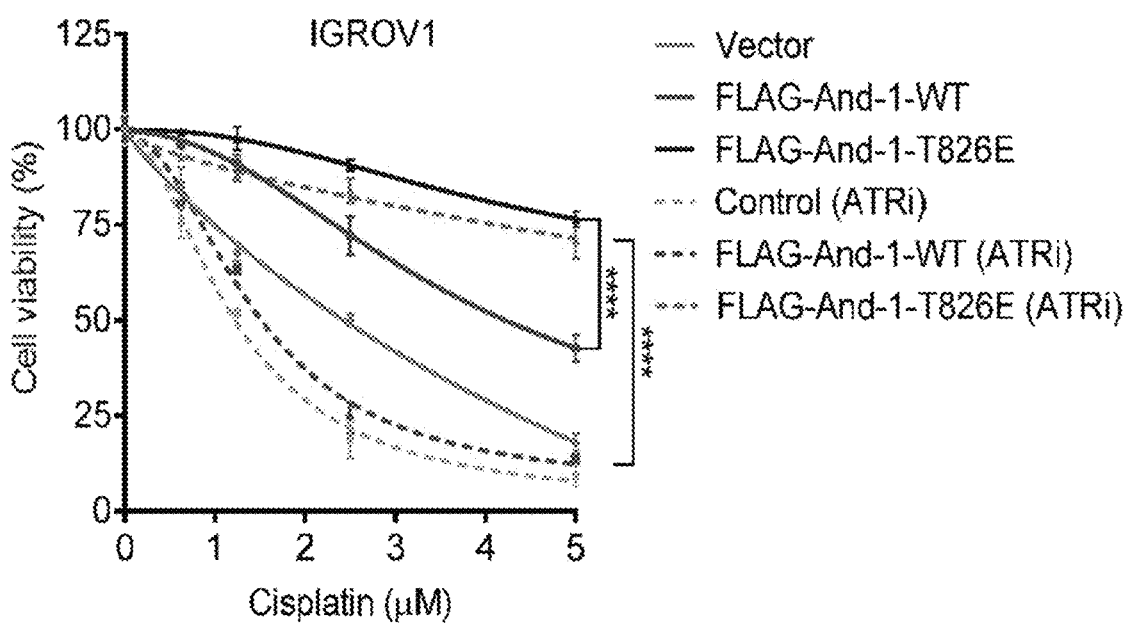
Figure 24I:
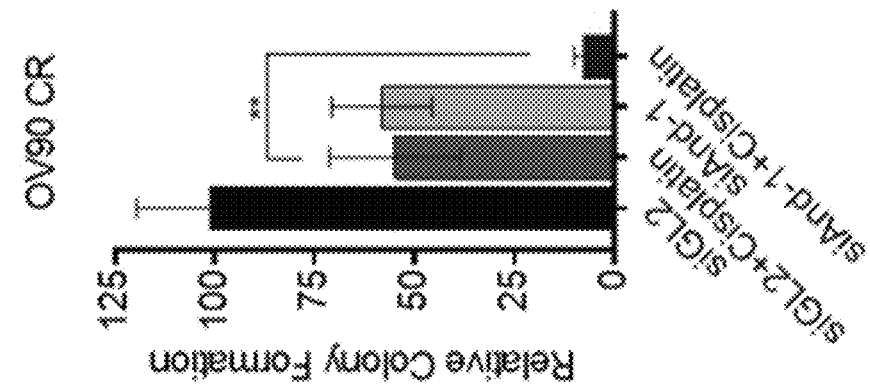
Figure 24H:
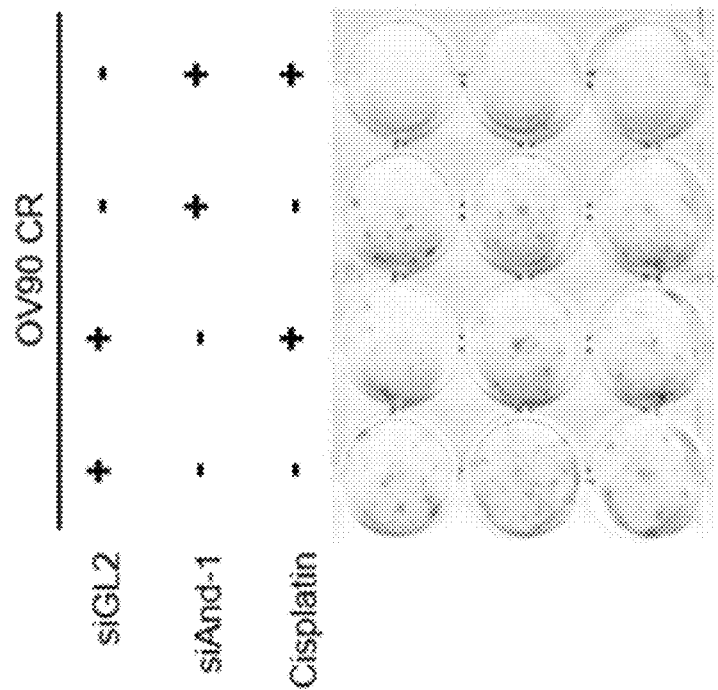
Figure 25A:
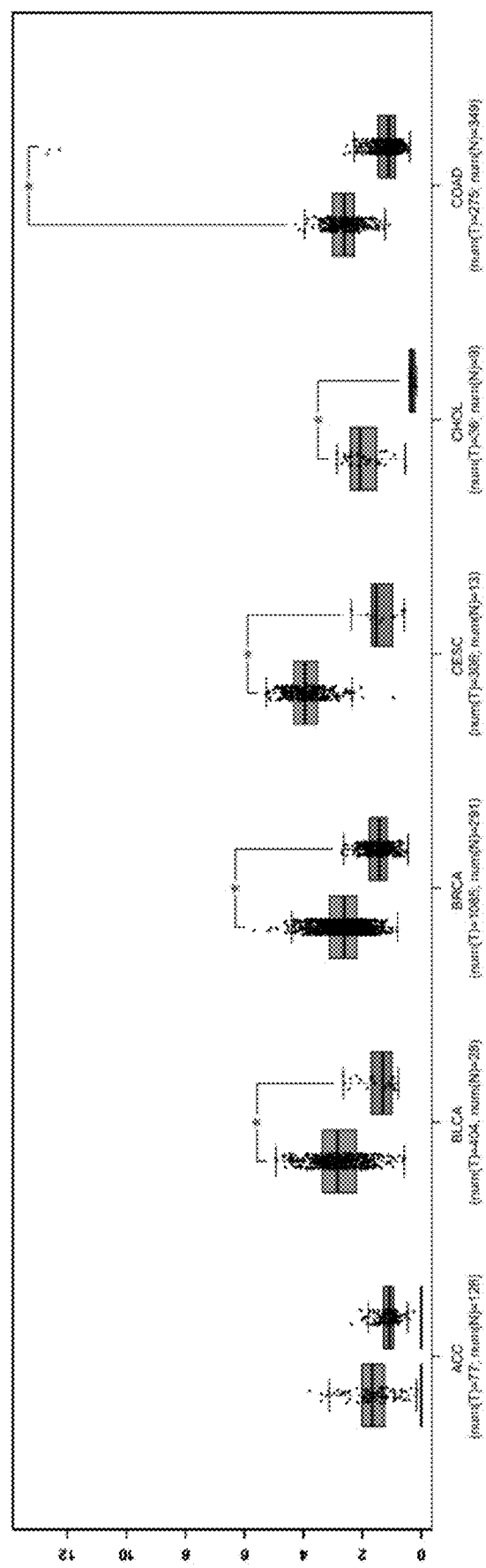
FIGS. 25A-25E depict graphs illustrating TCGA data which indicated that expression levels of And-1/WDHD1 were significantly upregulated in most of the tested cancers but not normal tissues in accordance with embodiments of the present disclosure.
Figure 25B:
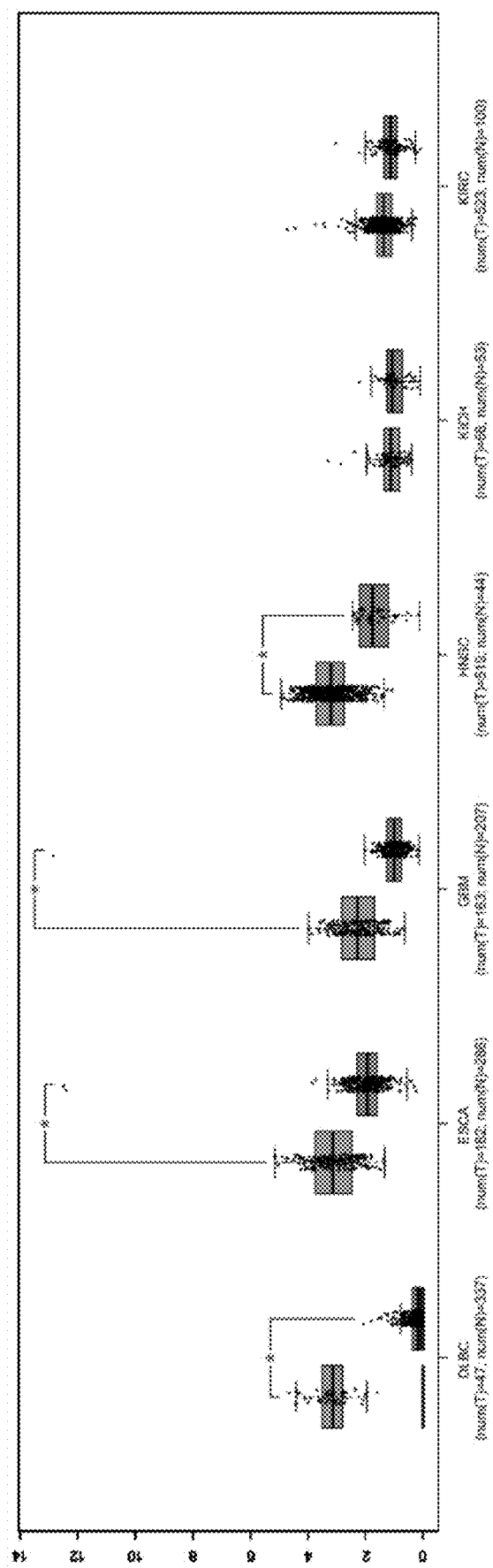
Figure 25C:
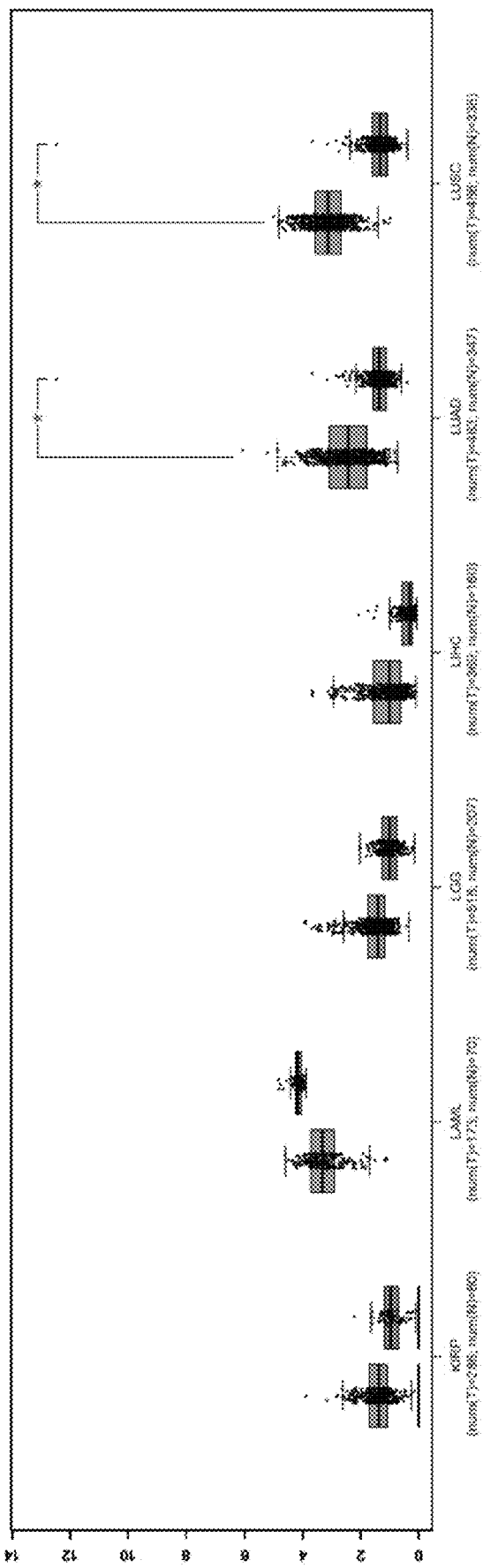
Figure 25D:
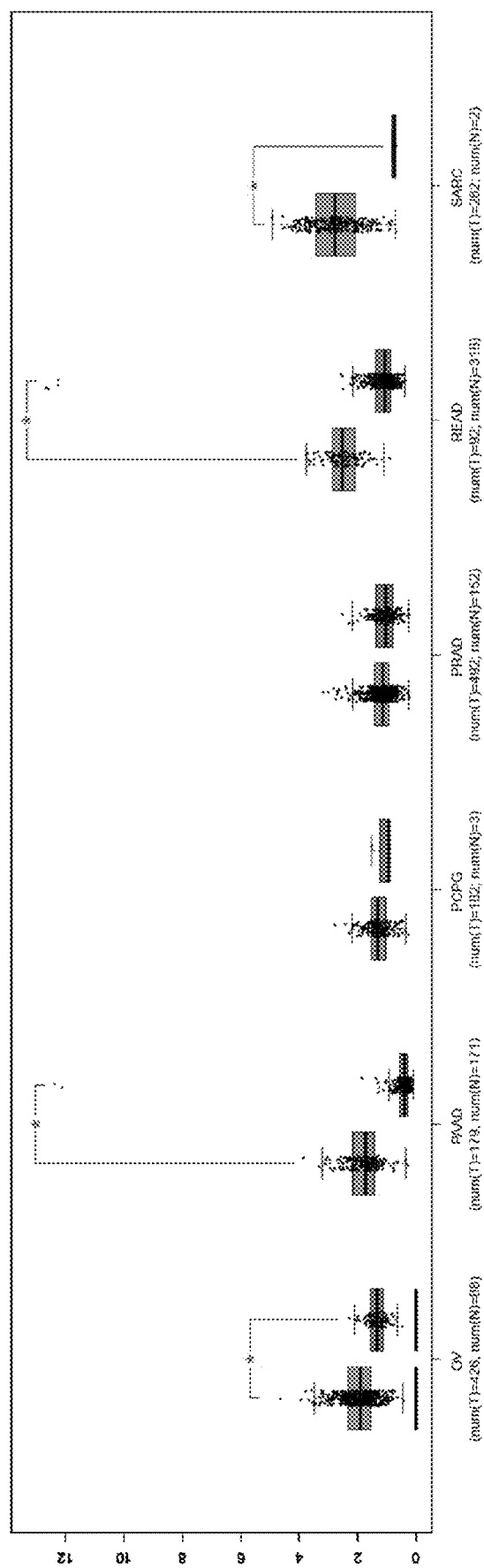
Figure 25E:
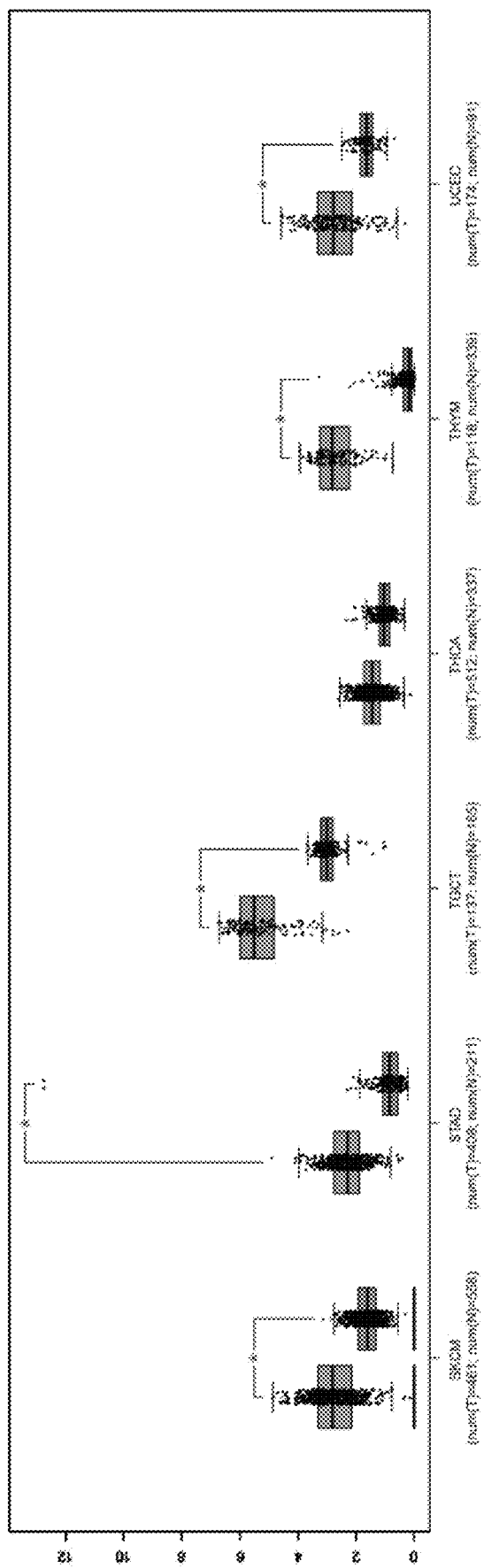

Example 11. Up-Regulated And-1 Phosphorylation Contributed to Cisplatin Resistance in OC Given that And-1 phosphorylation was positively correlated with cisplatin resistance in OC according the Examples above, it was next determined whether And-1 phosphorylation contributes to cell survival in response to cisplatin. The cell viability to cisplatin in IGROV1, OV90 and mice ID80 cells overexpressed with FLAG-And-1-WT, FLAG-And-1-T826A and phosphomimetic FLAG-And-1-T826E was examined. In brief, cells were seeded in 96-well plate at a density of 3,000-5,000 cells per well and treated with indicated reagents for different concentration. Three days after treatment, the cell viability was measured by Sulforhodamine B (SRB) assay. The $IC_{50}$ values and CI index were further determined by compusyn software. Every experiment was done in triplicate and repeated three times. Compared to cells transfected with FLAG-And-1-WT, overexpression of FLAG-And-1-T826E significantly increased cell resistance to cisplatin, while overexpression of non-phosphorylatable FLAG-And-1-T826A failed to restore resistance (FIGS. 23A-23B and FIGS. 24A-24D), indicating And-1 phosphorylation indeed promoted cisplatin resistance in OC cells. To confirm And-1 was the primary target of ATR to promote platinum-resistance, the sensitivity of IGROV1 cells to cisplatin was examined using genetic analyses. As shown in FIG. 23C and FIG. 24E, in the presence of ATR inhibitor, expression of FLAG-And-1-WT failed to rescue cell resistance to cisplatin, whereas FLAG-And-1-T826E successfully increased cell viability to cisplatin as compared to that in cells without VE821 treatment, suggesting that And-1 phosphorylation at T826 mediated ATR-dependent cisplatin resistance in OC cells.

To determine if increased And-1 phosphorylation at T826 upregulated repair of crosslinks, thus resulting in cisplatin resistance, the levels of crosslink DNA was measured using modified comet assay. In brief, the experiment was performed according to the manufacture's instruction of CometAssay Kit (Trevigen) where the modified comet assay was performed in cells treated with 10 μM cisplatin for 2 hours and released into cisplatin free medium at indicated times followed by 20 Gy of ionizing radiation (IR) to introduce random DNA double strand breaks before harvesting. For transfections, cells were transfected with siRNA 24 hours before plasmid transfection for another 24 hours. Cells were then subjected to modified comet assay.

Figure 23D:
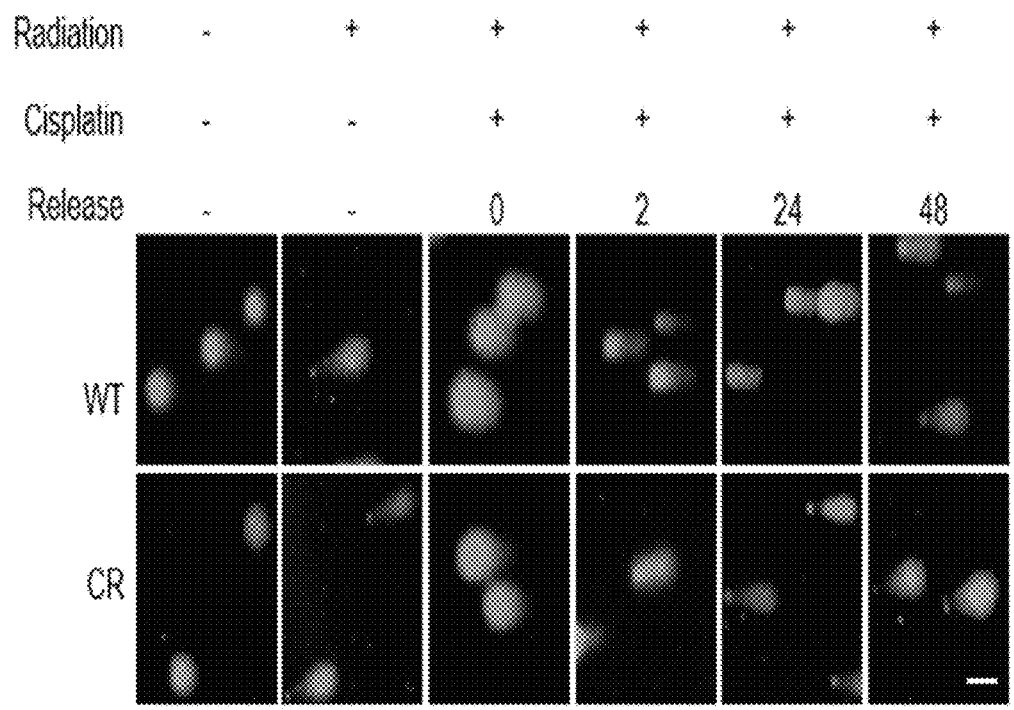
Figure 23E:
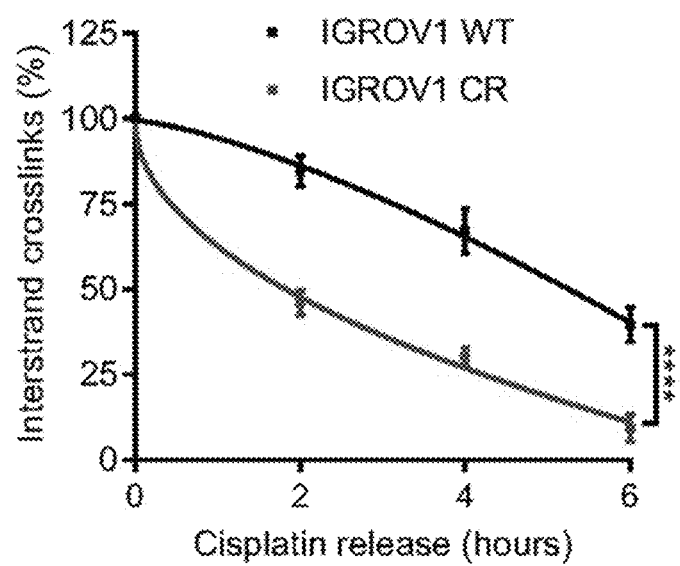
Figure 23F:
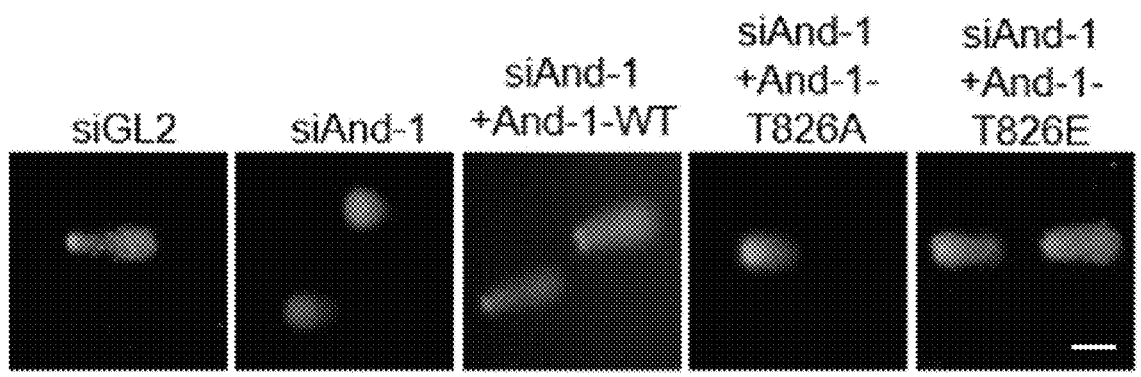
Figure 23G:
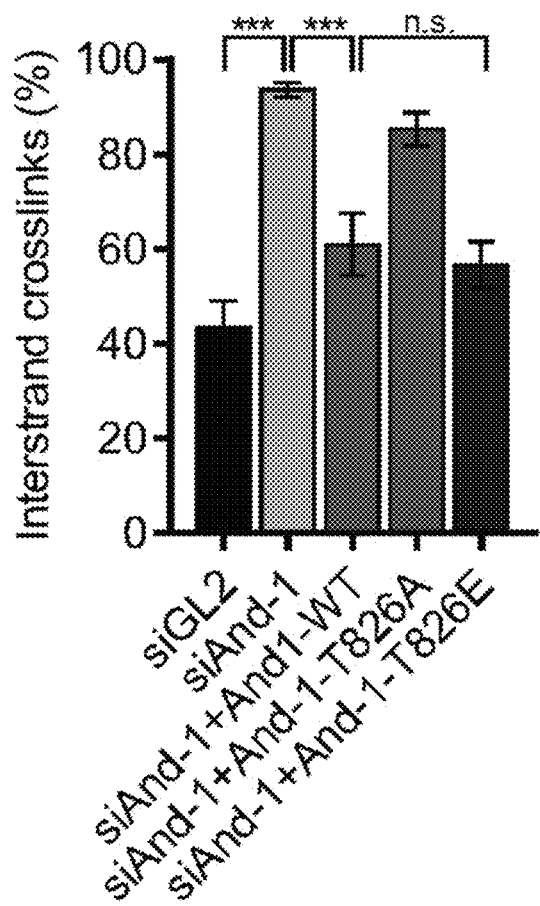

As shown in FIGS. 23D and 23E, cells treated with 20 μM cisplatin were released into cisplatin-free medium for 0, 2, 24 and 48 hours followed by 20 Gy of ionizing radiation (IR) to introduce random DNA double strand breaks. Significantly, it was observed that IGROV1 CR cells exhibited much more tail moments especially at 2 hour and 24-hour time points, indicating efficiency of ICL repair was elevated in cisplatin resistant OC cells. Next, it was tested whether And-1 or And-1 phosphorylation played a role in ICL repair induced by cisplatin. As shown in FIGS. 23F and 23G, And-1 depletion significantly increased ICLs retention, suggesting that And-1 promoted cisplatin generated ICL repair in OC cells. Compared to FLAG-And-1-WT complementation, non-phosphorylatable FLAG-And-1-T826A failed to rescue ICL repair whereas phosphomimetic FLAG-And-1-T826E ectopic expression resulted in efficient ICL repair, indicating And-1 phosphorylation was important for And-1 contribution in cisplatin induced ICL repair.

Although ATR inhibition resulted in elevated sensitivity to cisplatin in OC cells, the unpredictable side effects generated by variety of ATR-related pathways are undesirable for chemotherapy. As such, it was determined whether And-1 inhibition could overcome cisplatin resistance in OC cells. To this end, And-1 depletion by siRNAs significantly increased the cell sensitivity to cisplatin in both IGROV1 CR and OV90 CR cells (FIGS. 23H-23I and FIGS. 24F-24G).

Clonogenic survival assays were also performed. In brief, cells were seeded in 6-well dishes at a density of 500 cells per dish then treated with the cisplatin at the indicated concentrations (See FIGS. 23 and 24). Cells were then kept in the incubator for 10-14 days to allow colony formation. Colonies were visualized by crystal violet staining. Colonies with >50 cells were counted. Consistently, using clonogenic survival assay, it was further confirmed that And-1 knockdown sensitized IGROV1 CR and OV90 CR cells to cisplatin (FIGS. 23J-23K and FIGS. 24H-24I). Together, these data clearly demonstrated that And-1 inhibition was an approach to overcome platinum resistance in OC.

Example 12. And-1 Inhibitors Inhibited Cancer Cell Survival and Tumor Growth

Figure 26:
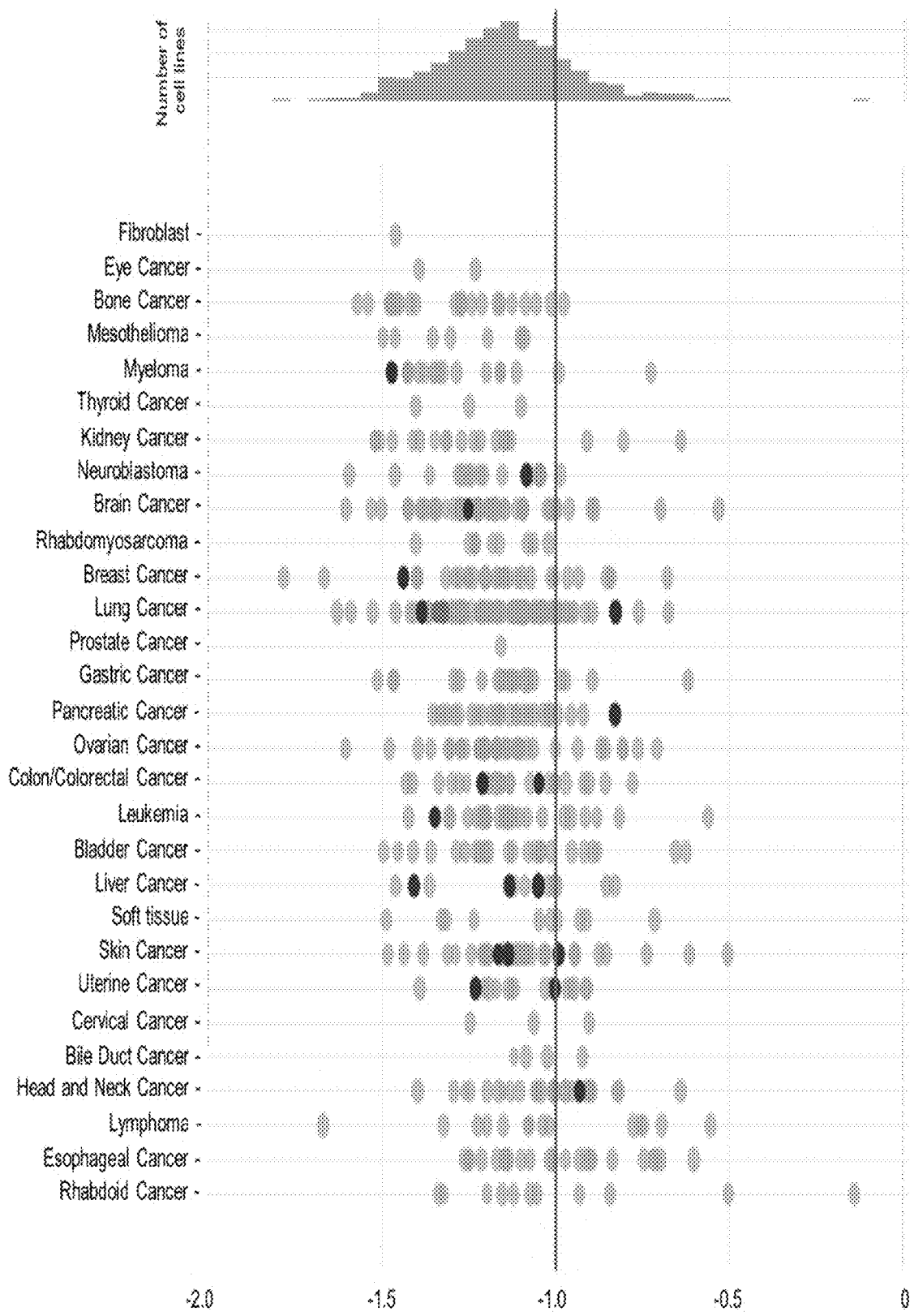
FIG. 26 depicts a graph illustrating dependency score analysis of WDHD1 by DepMap in accordance with embodiments of the present disclosure.
Figure 27:
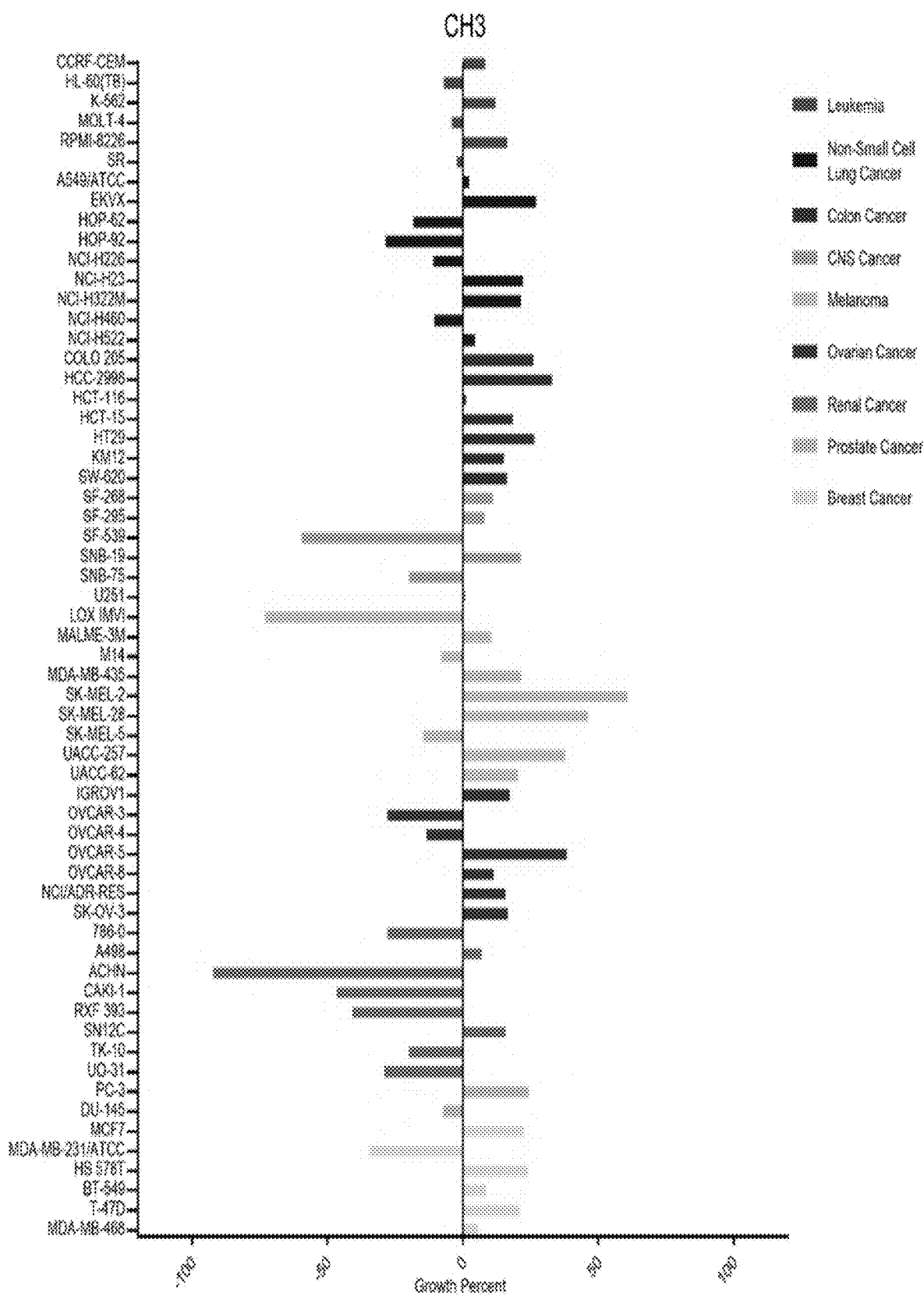
FIG. 27 depicts a graph illustrating growth inhibition by CH3 at 10 μM in a NCI-60 cancer cell lines panel in accordance with embodiments of the present disclosure.
Figure 28A:
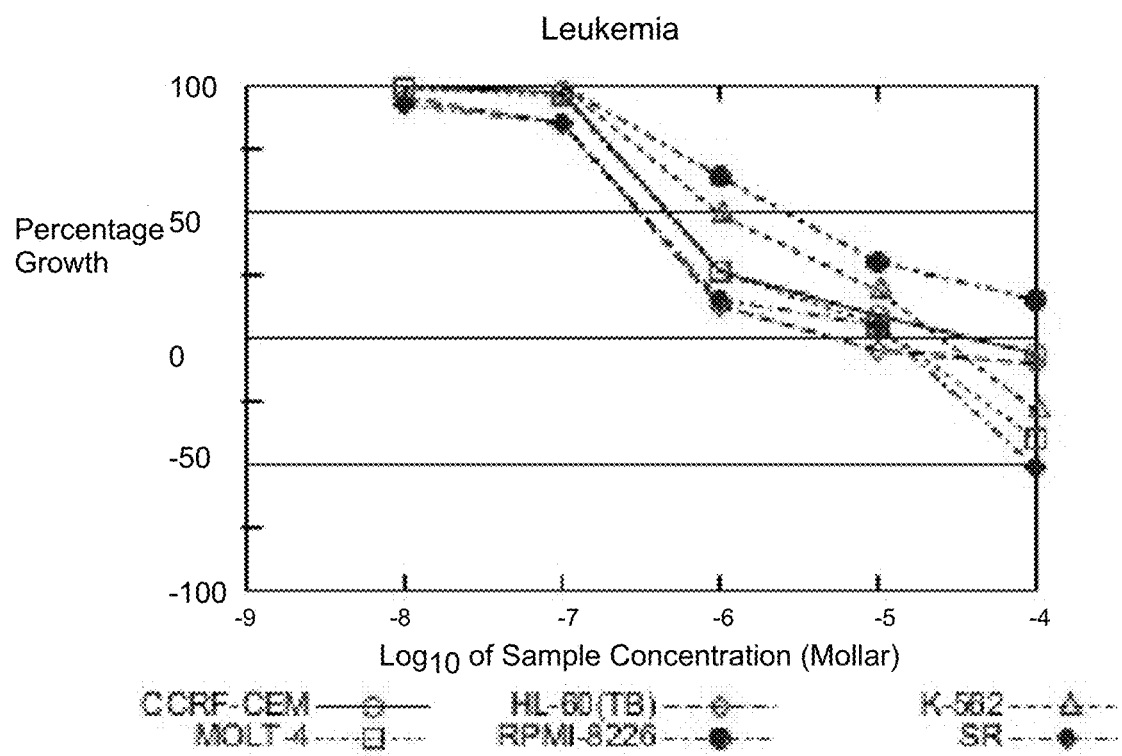
FIGS. 28A-28O depict images and graphs illustrating that And-1 inhibitors inhibit cancer cell survival and tumor growth in accordance with embodiments of the present disclosure.
Figure 28B:
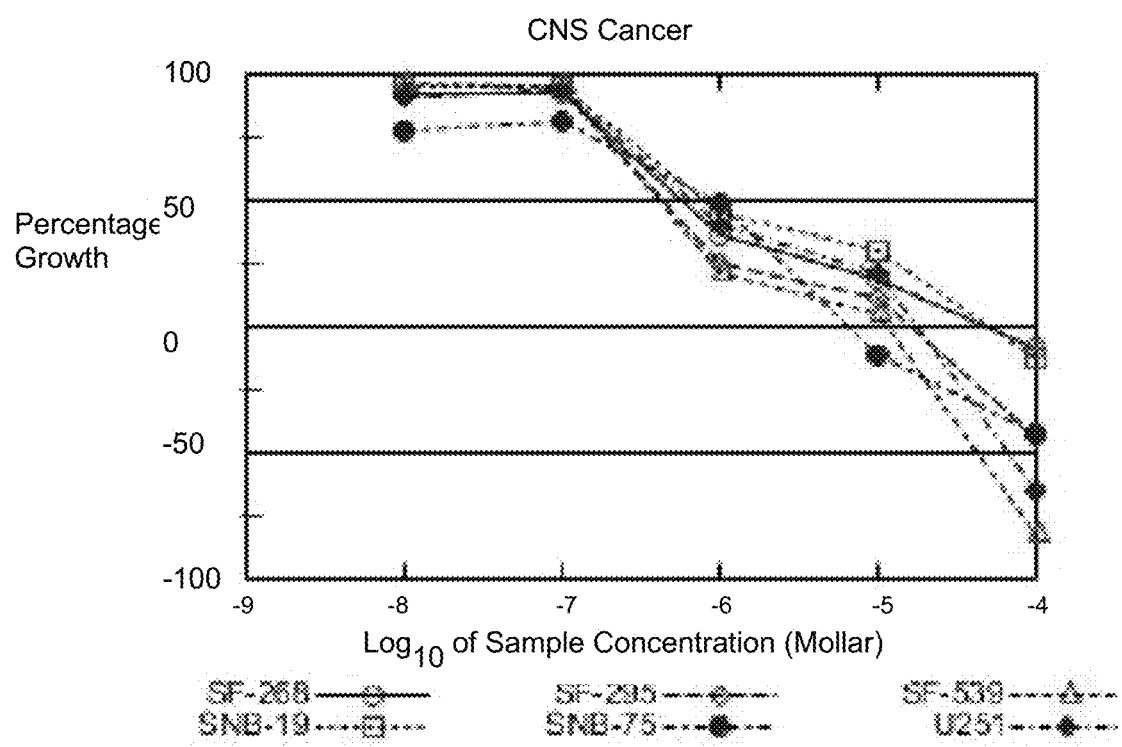
Figure 28C:
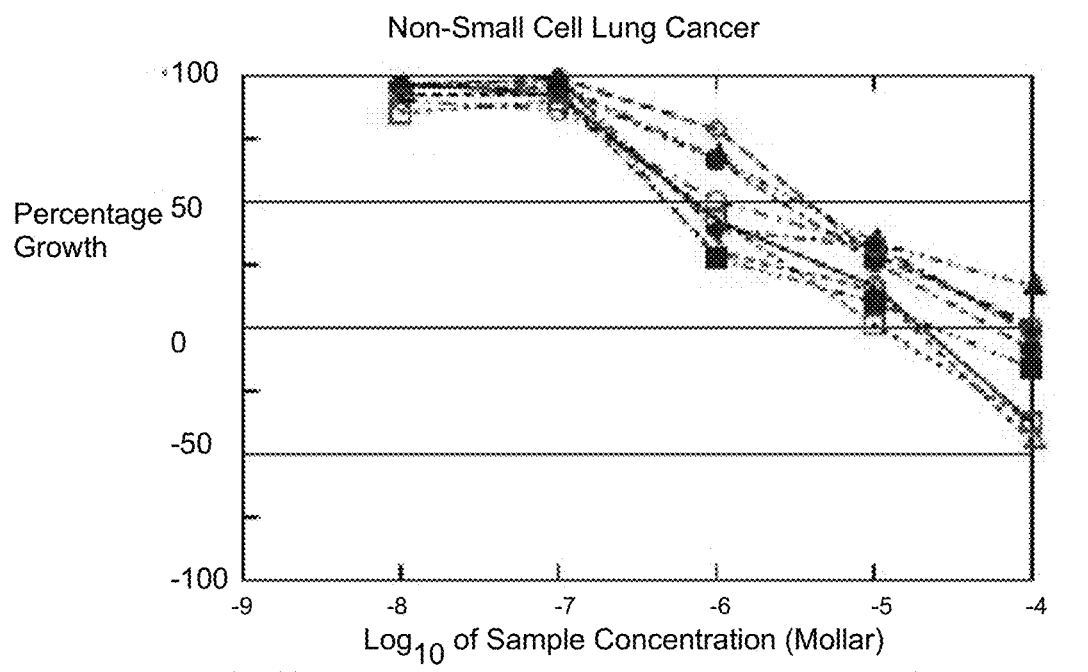
Figure 28D:
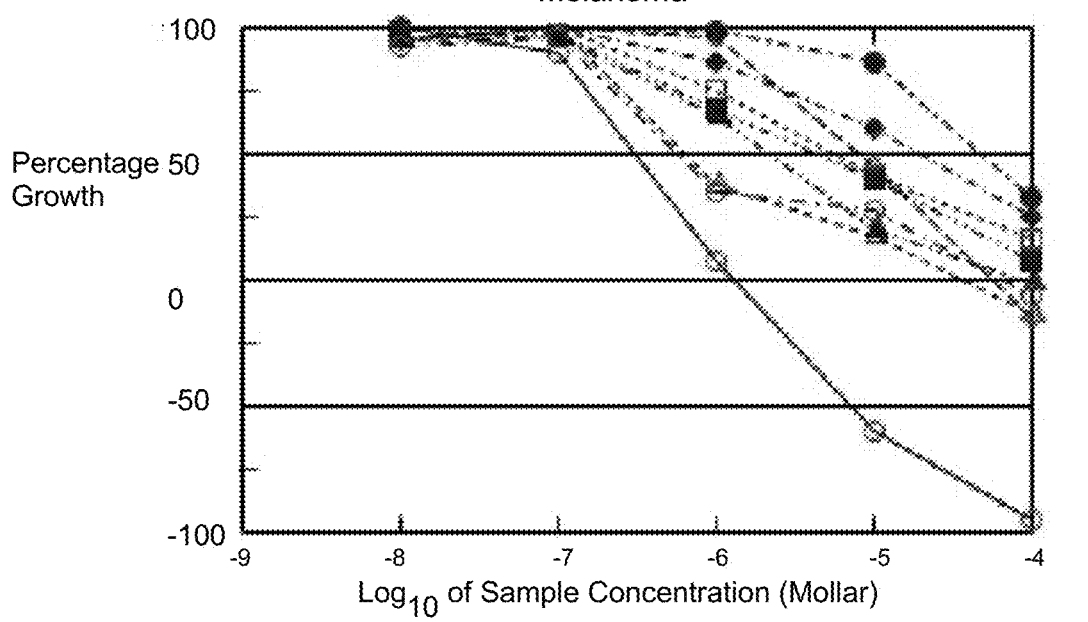
Figure 28E:
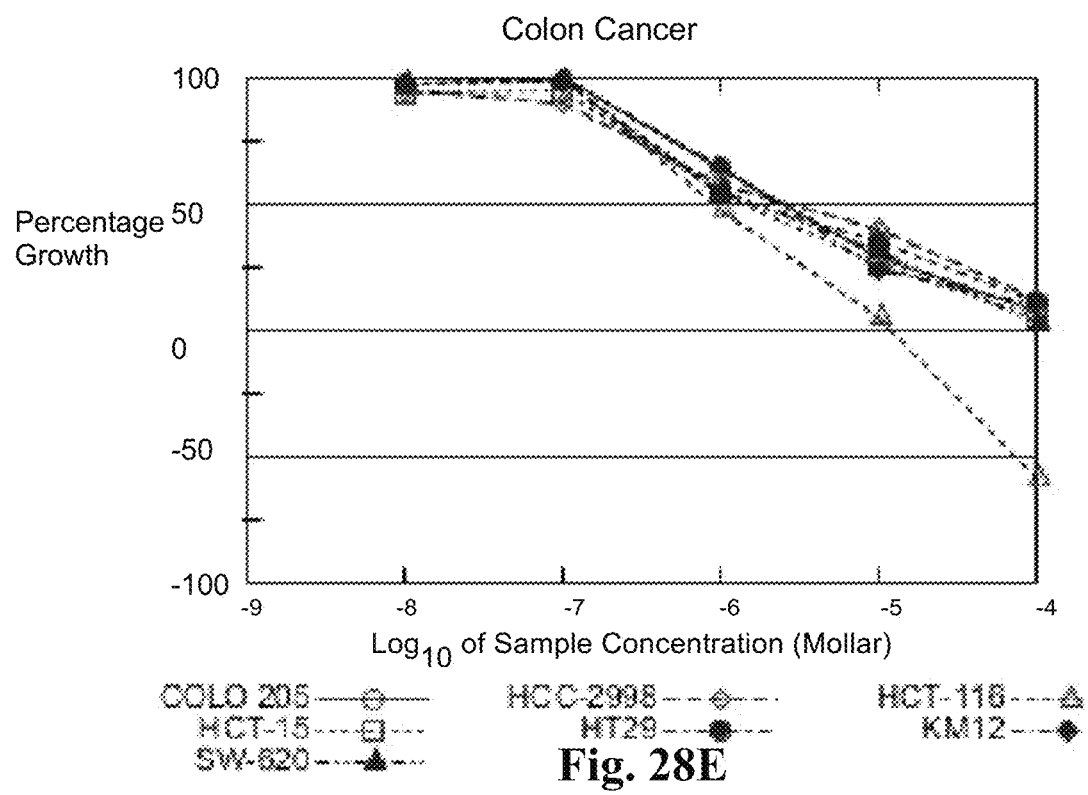
Figure 28F:
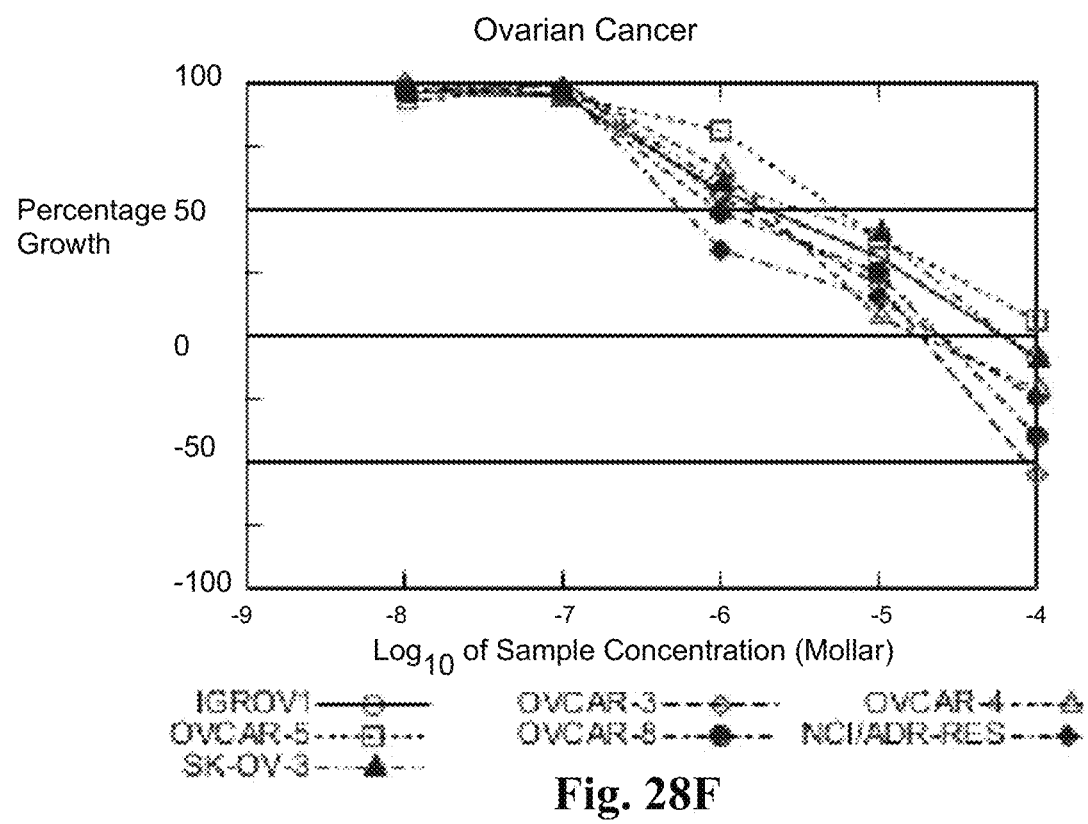
Figure 28G:
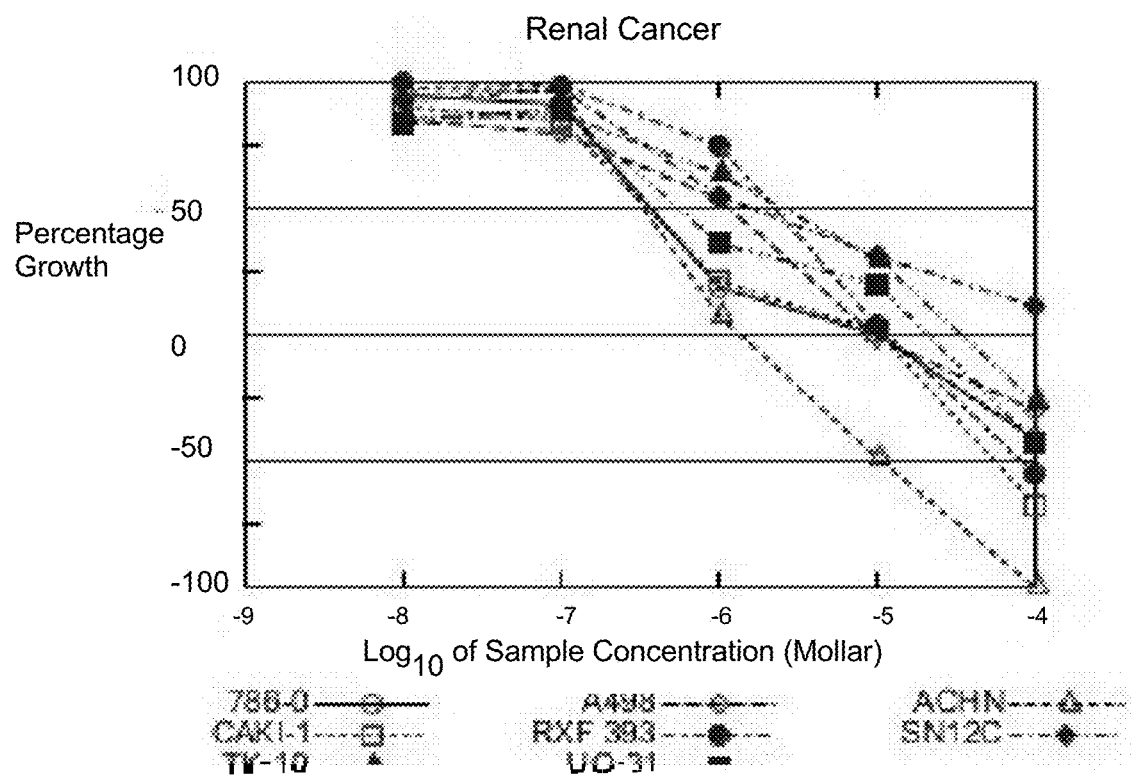
Figure 28H:
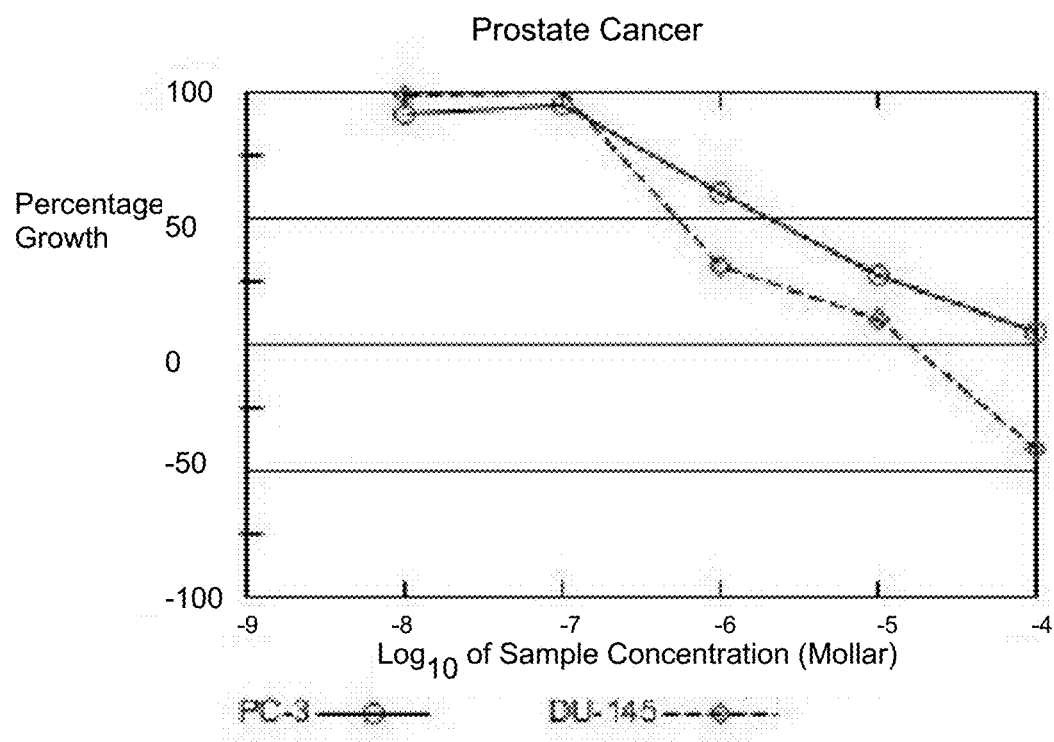
Figure 28I:
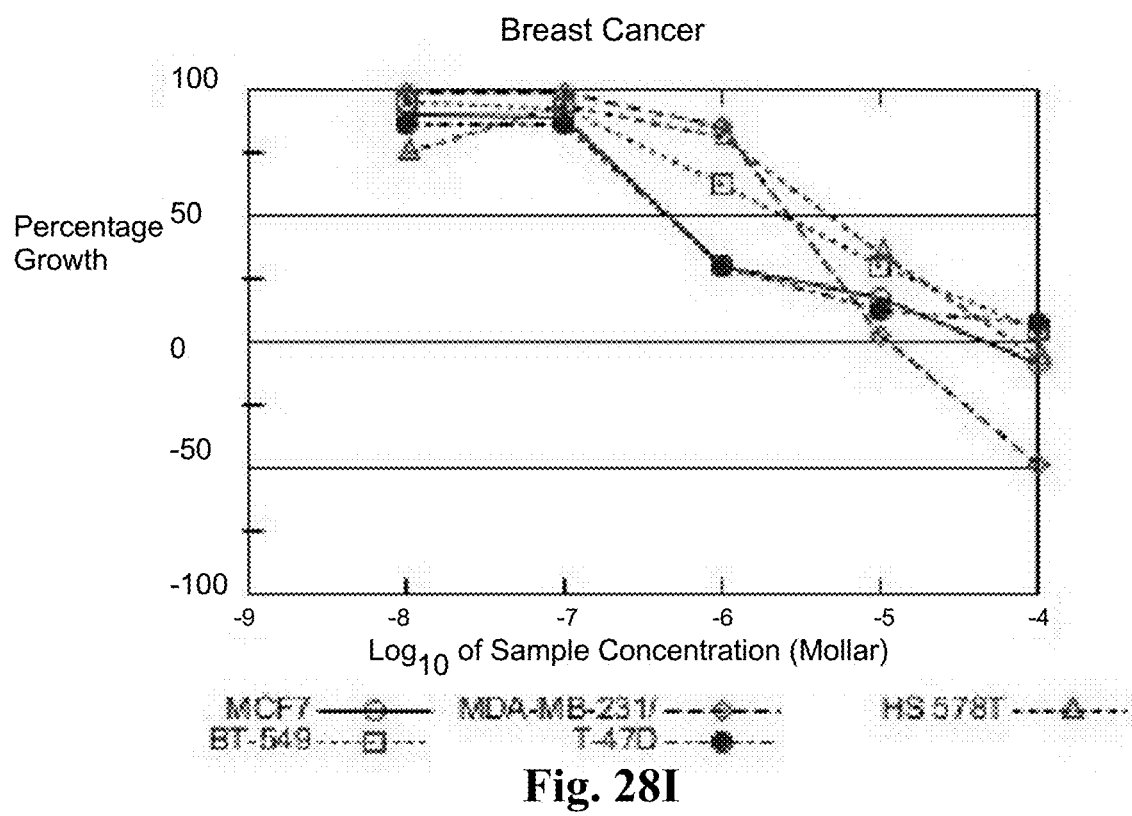
Figure 28J:
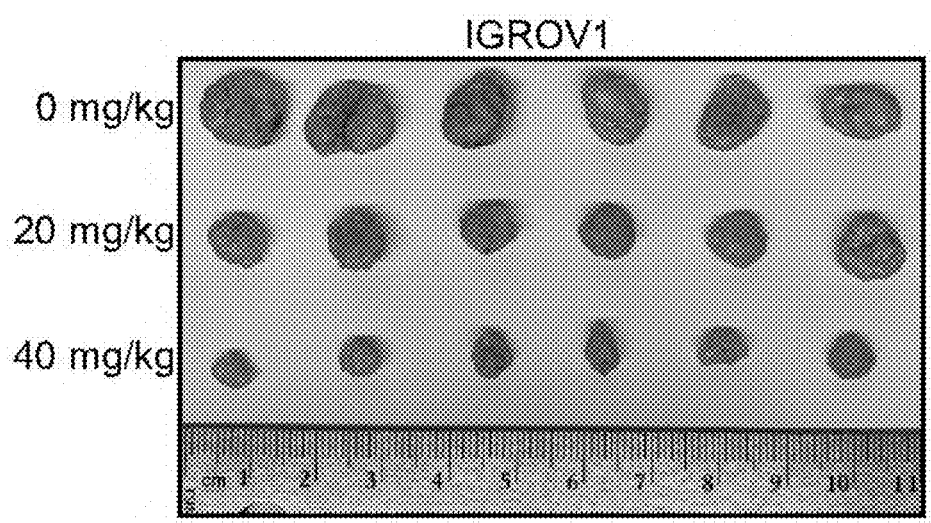
FIG. 28J shows an image of tumors of IGROV1 xenograft mice treated with vehicle or CH3 (20 or 40 mg/kg/3 days intraperitoneally) for 3 weeks where the ruler scale is in centimeters (cm).
Figure 28K:
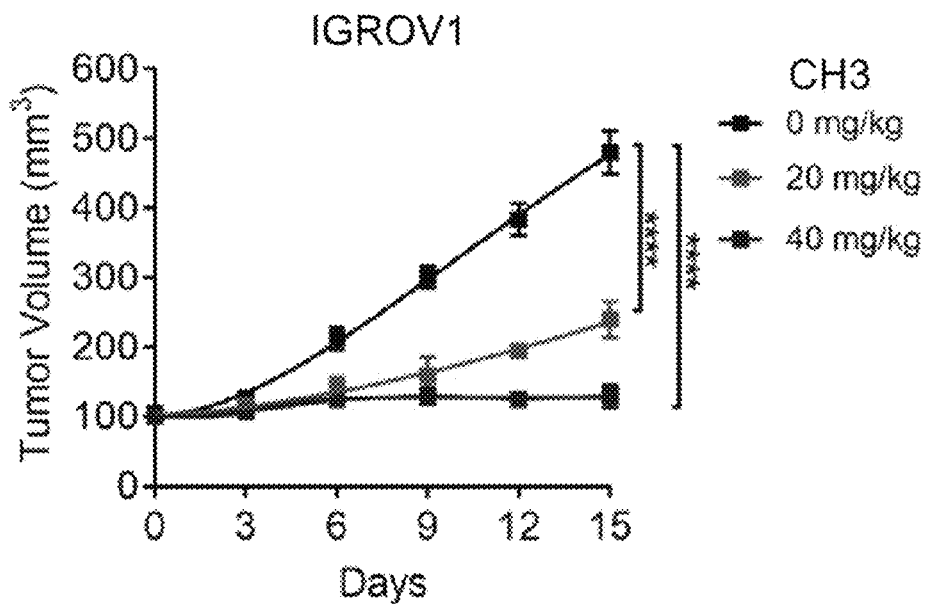
Figure 28L:
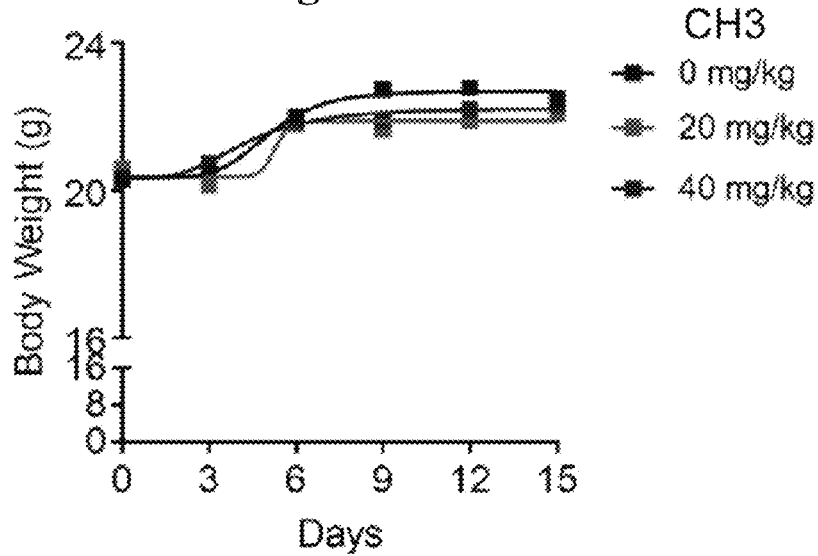
FIG. 28L shows a graph depicting body weight changes of mice in each group where data are represented as means±SD, n=6 tumors/group.
Figure 28M:
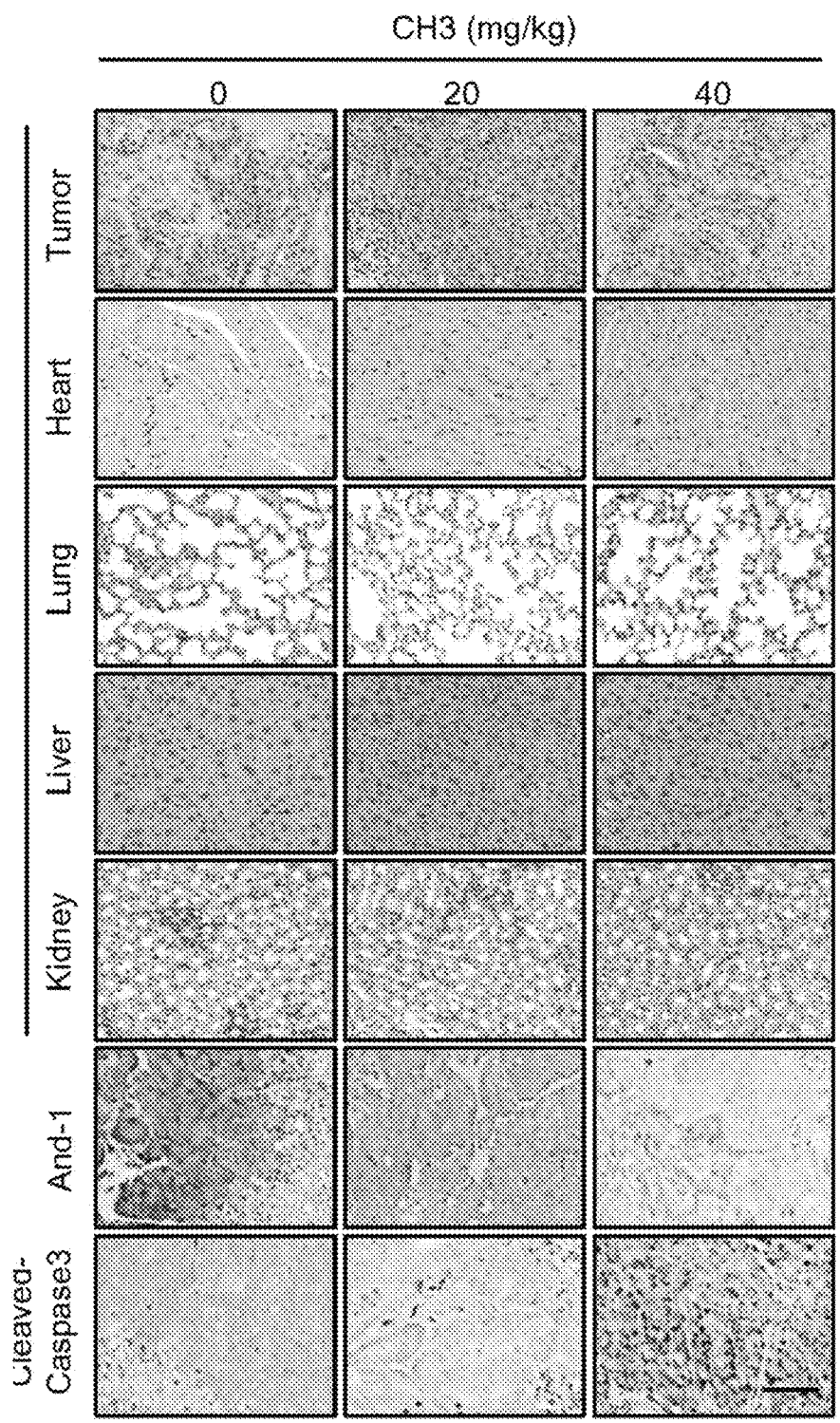
FIG. 28M shows images depicting H&E staining of paraffin-embedded, 3-μm-thick tissue sections of the tumor, heart, lung, liver and kidney, and IHC staining against And-1 and cleaved-caspase-3 antibodies of tumor samples from 3 groups of mice (Scale bar: 50 μm).
Figure 28N:
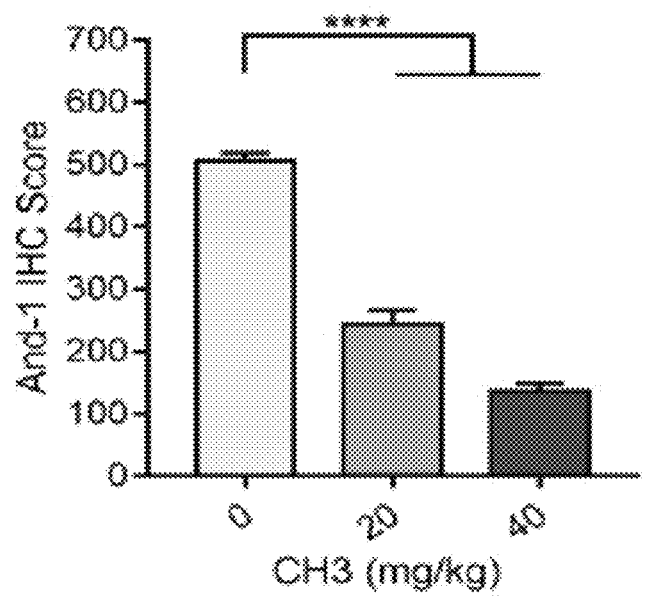
FIG. 28N shows a bar graph depicting quantification of And-1 expression detected by the IHC score in tumor samples analyzed in FIG. 28M
Figure 28O:
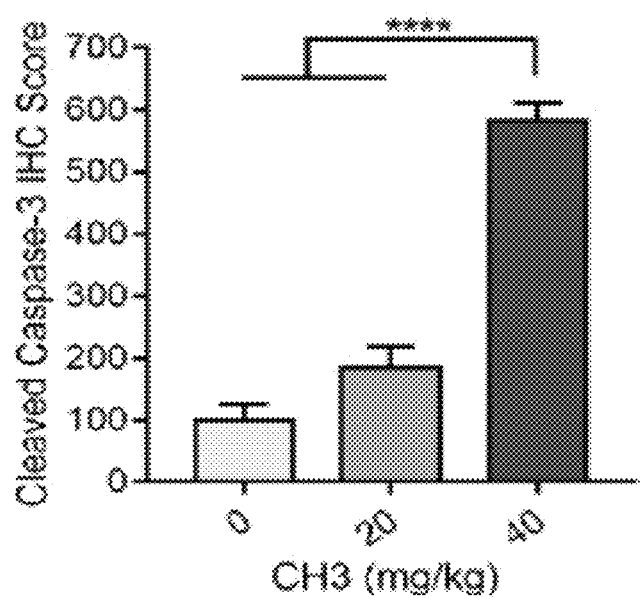
Figure 29A:
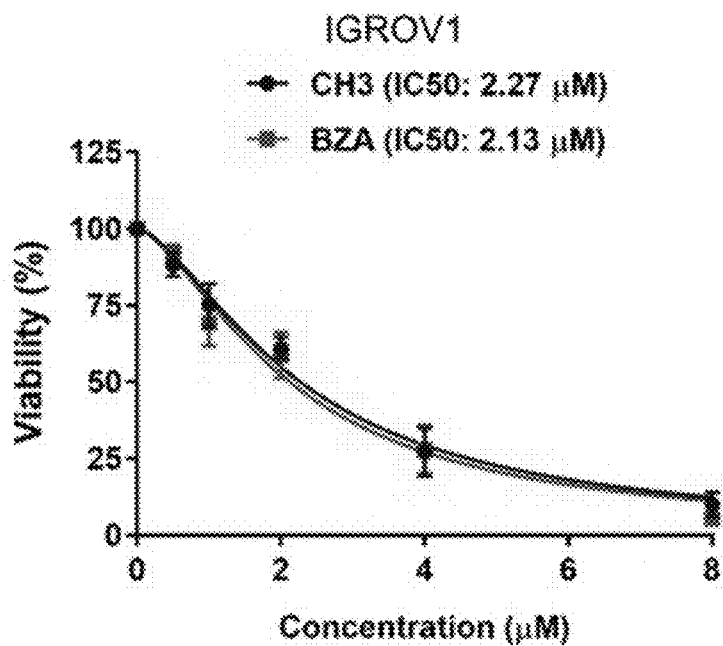
FIGS. 29A-29J depict images and graphs illustrating that both CH3 and BZA inhibited the survival of multiple cancer cells in accordance with embodiments of the present disclosure.
Figure 29B:
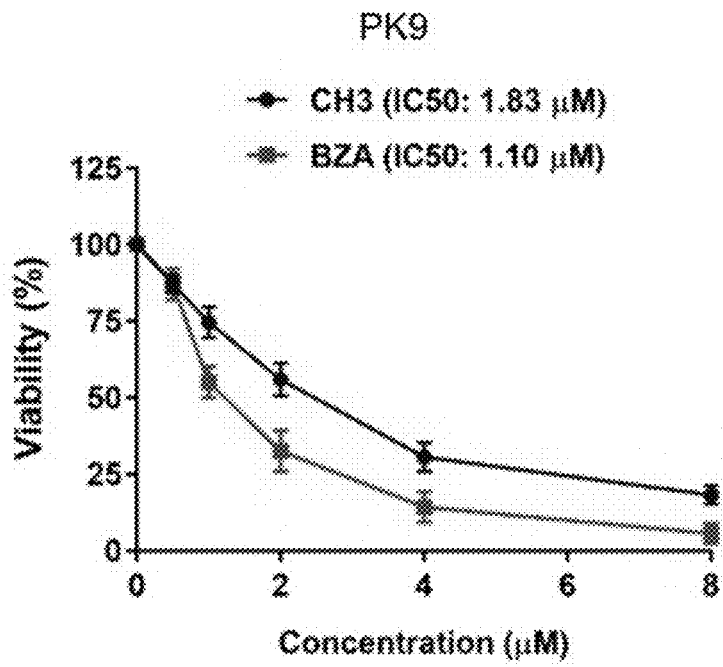
Figure 29C:
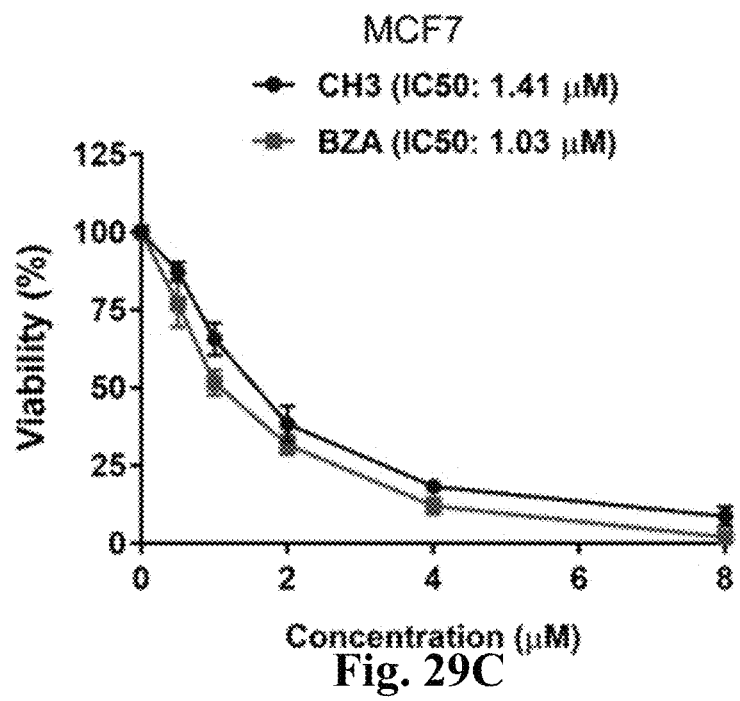
Figure 29D:
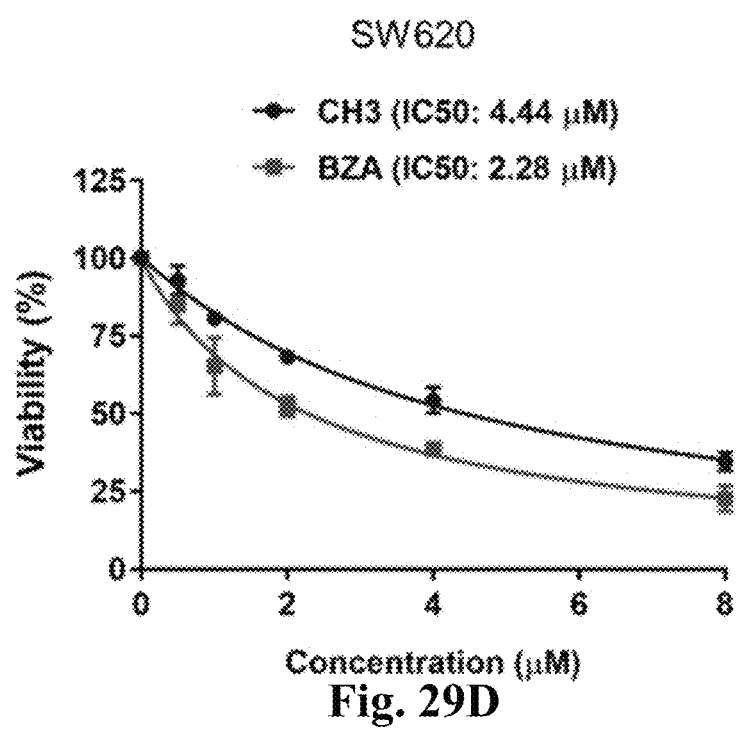
Figure 29E:
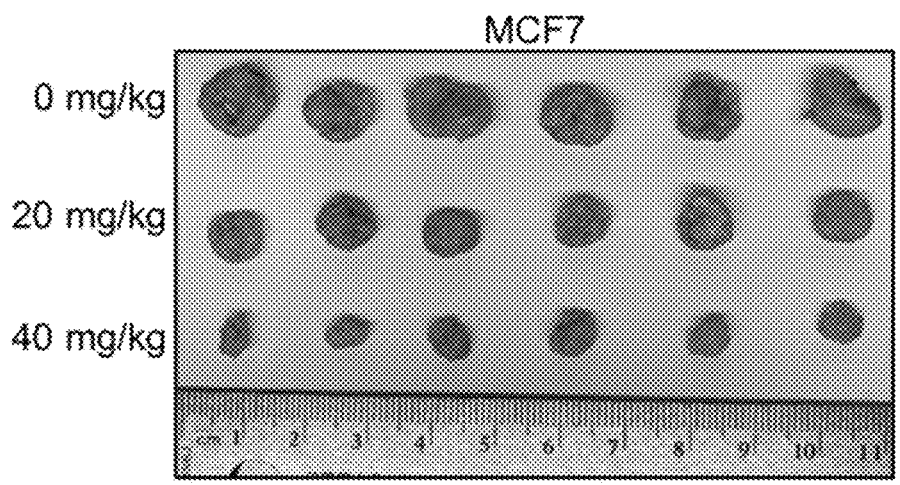
Figure 29F:
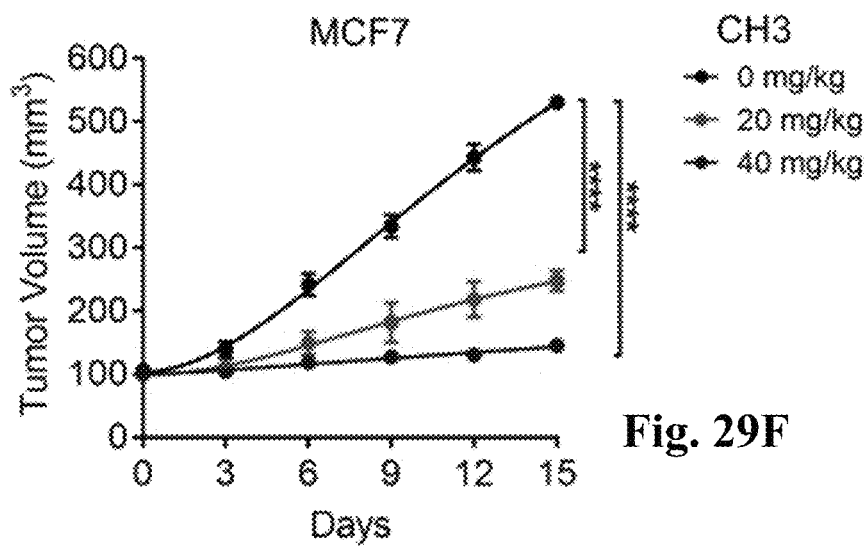
Figure 29G:
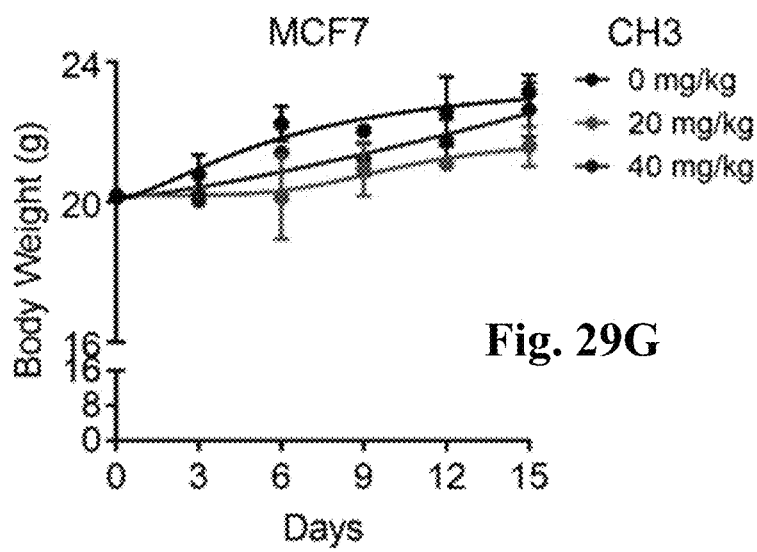
Figure 29H:
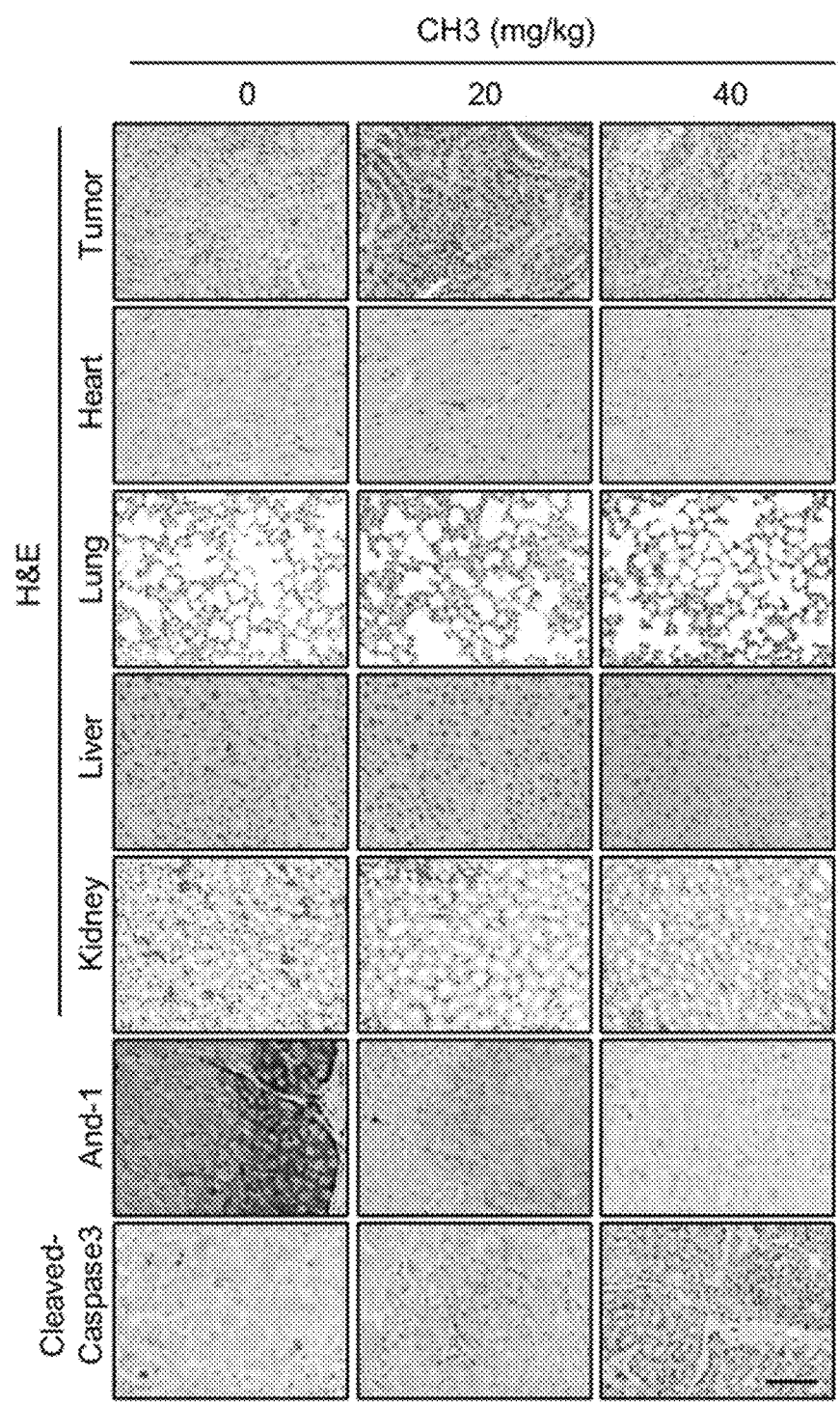
Figure 29I:
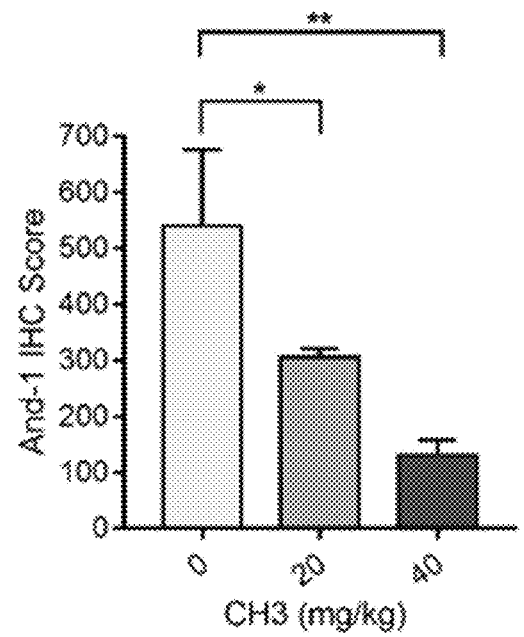
Figure 29J:
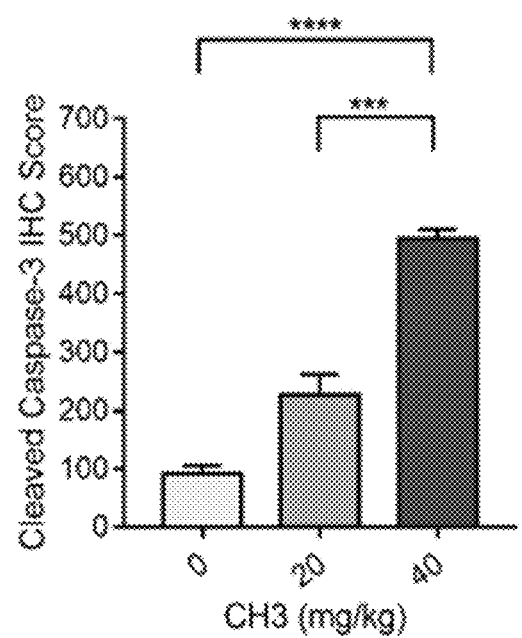

Analyses using data from The Cancer Genome Atlas (TCGA) indicated that expression levels of And-1/WDHD1 were significantly upregulated in most of the tested cancers but not normal tissues (FIGS. 25A-25D). Importantly, dependency score analysis by DepMap showed a highly negative dependency score of WDHD1 in all major types of cancer, implying that WDHD1 was essential for cell growth and proliferation across pan-cancer cells (FIG. 26). These results strongly indicated that And-1 inhibitors may have efficacy against broad-spectrum types of cancer. To test this hypothesis, inhibition of CH3 on cancer cells was evaluated by using NCI 60 tumor cell lines. The one dose anti-cancer assay, which reported compound as a mean graph of the percent growth of the treated cells when compared to the untreated control cells, showed that CH3 had a mean growth percentage of 1.84% at 10 μM against 60 tumor cell lines (FIG. 27). Moreover, CH3 inhibited cancer cell growth in all 60 tumor cell lines in a dose dependent manner (FIGS. 28A-28I). It was then confirmed that both CH3 and BZA inhibited the survival of multiple cancer cells including IGROV1 (OC), MCF7 (breast cancer), PK9 (pancreatic cancer) and SW620 (colon cancer) cells with the $IC_{50}$ range between 1.03 and 4.44 μM (FIGS. 29A-29D). Taken together, the results demonstrated that And-1 inhibitors were potent against a variety types of cancer.

To evaluate the potency of And-1 inhibitors in vivo, IGROV1 or MCF7 cells were subcutaneously implanted into nude mice to form ovarian or breast tumors, respectively. In brief, 5-6 week-old female BALB/c athymic nude mice (CByJ.Cg-Foxn1nu/J, weighting 20-25 grams) were inoculated subcutaneously by injecting the OC cells, cisplatin resistant OC cells or breast cancer cells suspended in 100 μl ice-cold Matrigel/PBS (1:1, V:V; $5 \times 10^6$/mouse) into the dorsal flank of each mouse. When the average tumor volume reached 100-150 mm³, the mice were randomized into subsequent experiment groups. For tumors treated with CH3 only, CH3 was given at 0 mg/kg, 20 mg/kg and 40 mg/kg via intraperitoneal injection twice a week for three weeks. For combinational treatment, cisplatin, CH3, and BZA were then given intraperitoneally at 8 mg/kg, 20 mg/kg and 2 mg/kg respectively twice a week for three weeks. The relative tumor volumes were calculated using the formula: $a \times (b^2)/2$, for which a and b represented the longest and shortest diameters, respectively. During the drug treatment, the tumor volume and body weight were measured. Tumor samples were collected 4 days after final administration of the drug.

As shown in FIGS. 28J-28K and FIGS. 29E-29F, CH3 significantly reduced tumor growth in IGROV1 and MCF7 xenografts. By assessing body weight and H&E staining of heart, liver, kidney and lung tissues, systemic toxicity or obvious side effects were not observed in evaluated organs (FIGS. 28L-28M and FIGS. 29G-29H). The immunohistochemistry (IHC) analysis of tumor tissues against And-1 and cleaved caspase-3 antibodies demonstrated that CH3 inhibited And-1 expression and induced apoptosis in tumor (FIGS. 28N-28O and FIGS. 29H-29J). These results demonstrated that CH3 was a potential potent and safe compound for treatment of different cancers.

Example 13. Andi Inhibitor Overcame Cisplatin Resistance in OC

Figure 30D:
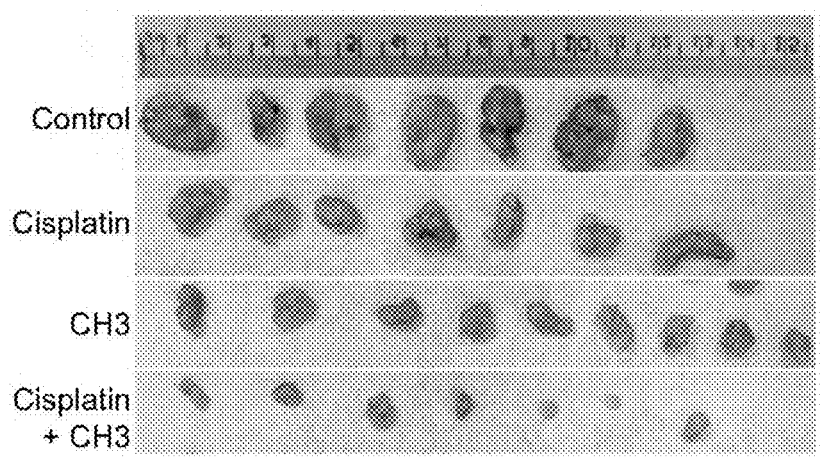
Figure 30E:
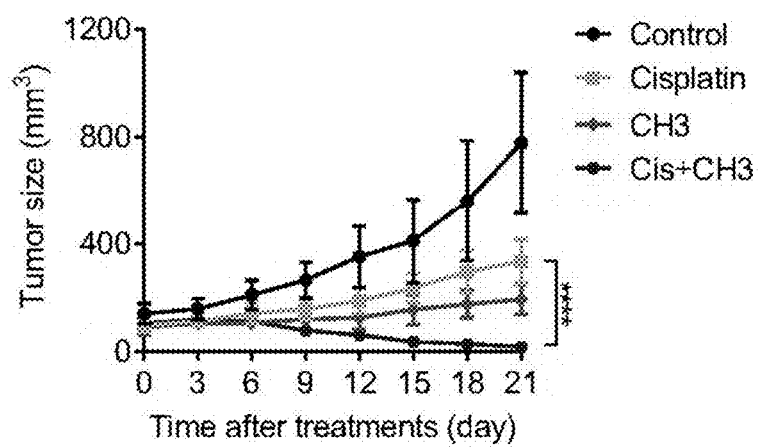
Figure 30F:
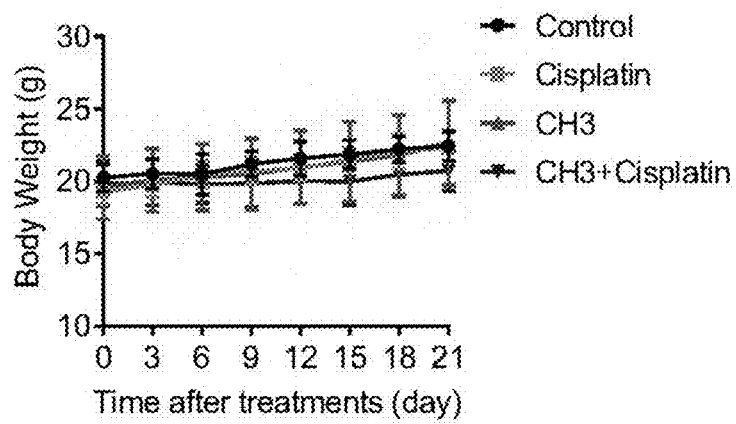
Figure 30G:
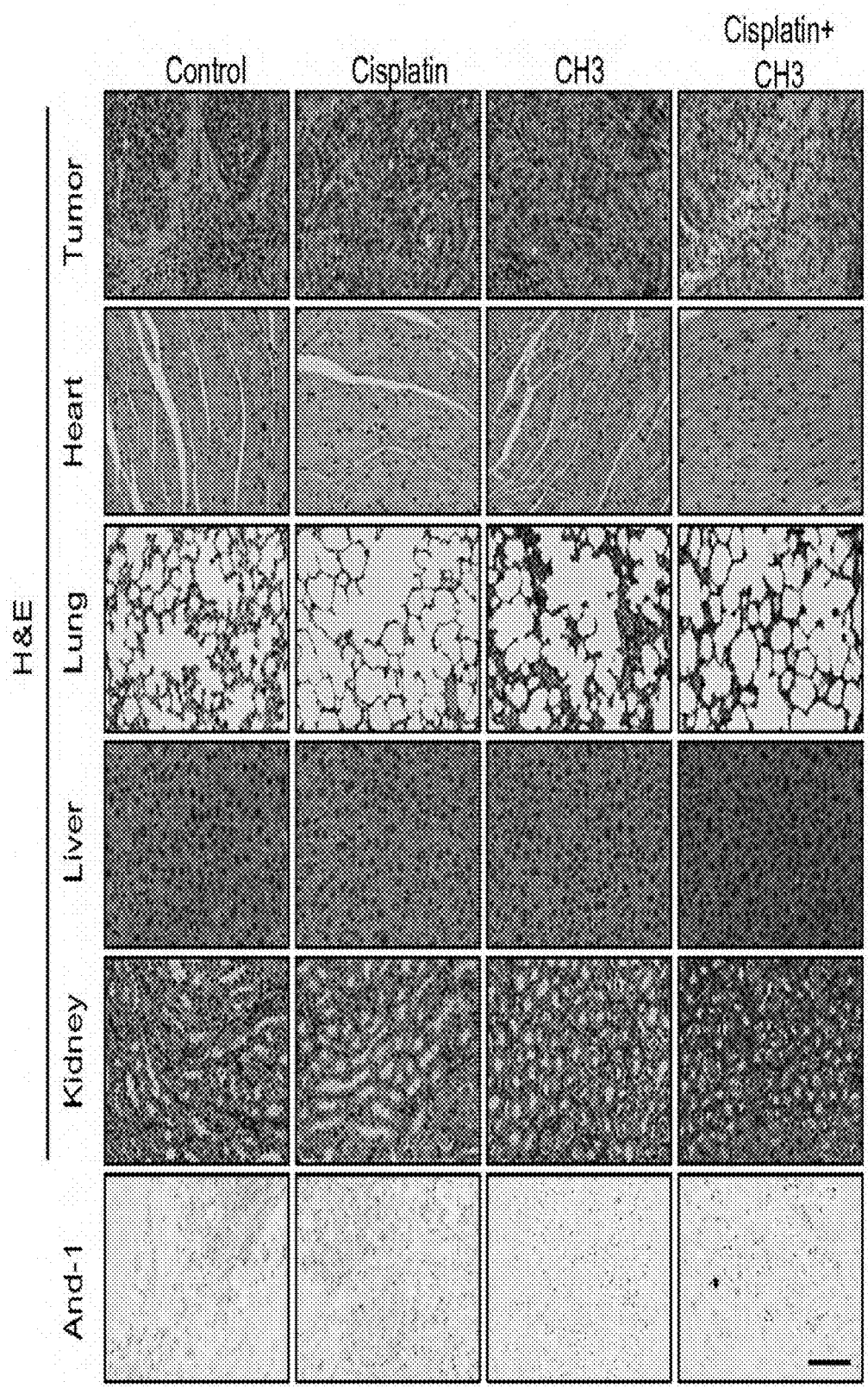
Figure 30H:
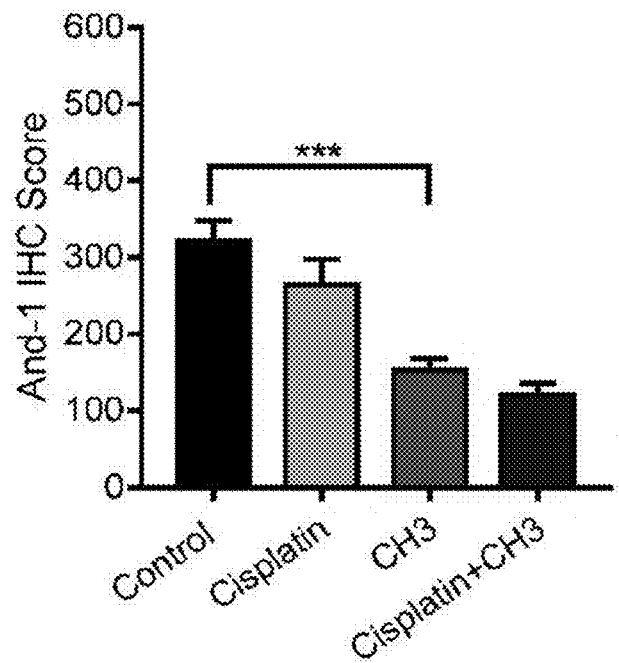
Figure 31A:
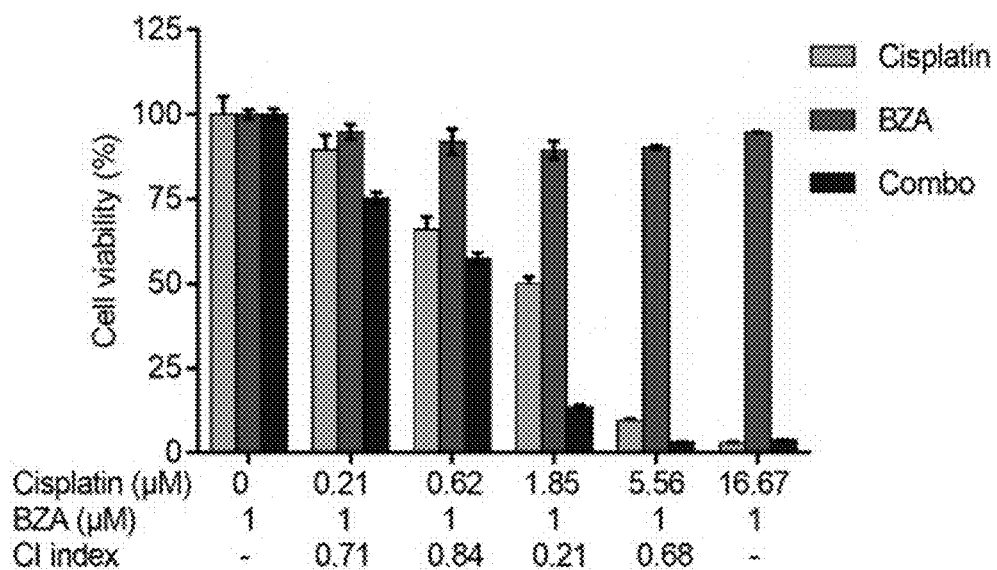
Figure 31E:
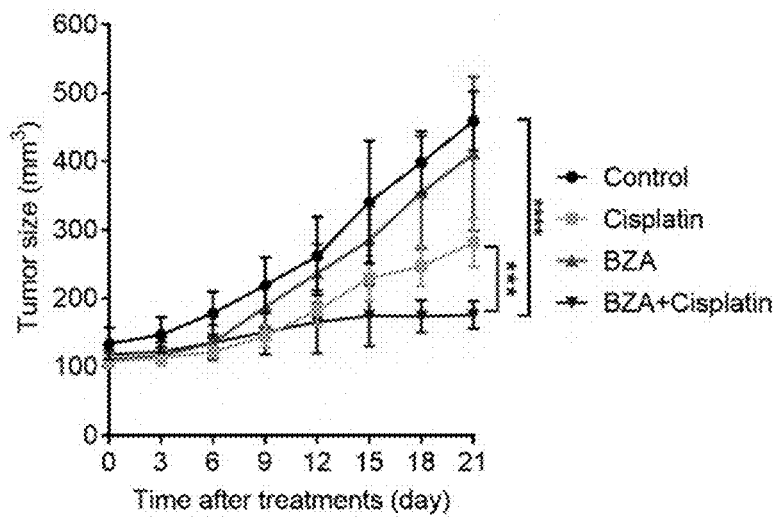
Figure 31F:
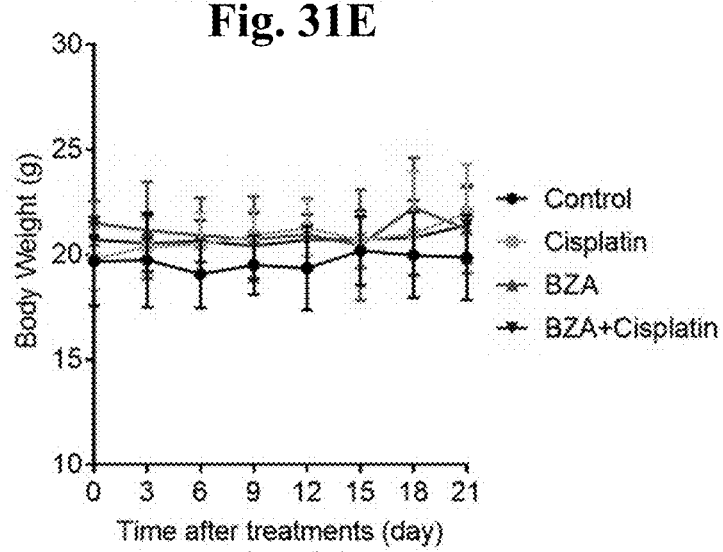
Figure 31G:
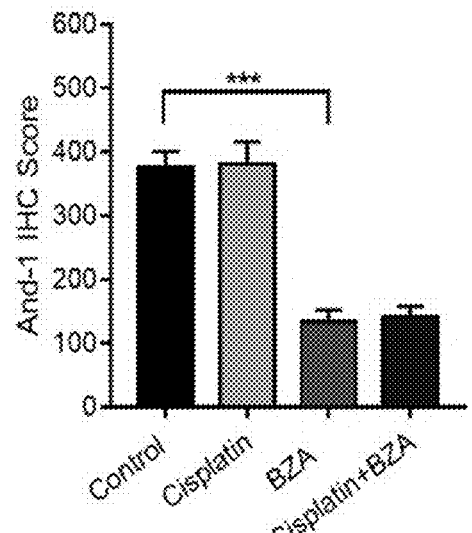
Figure 31H:
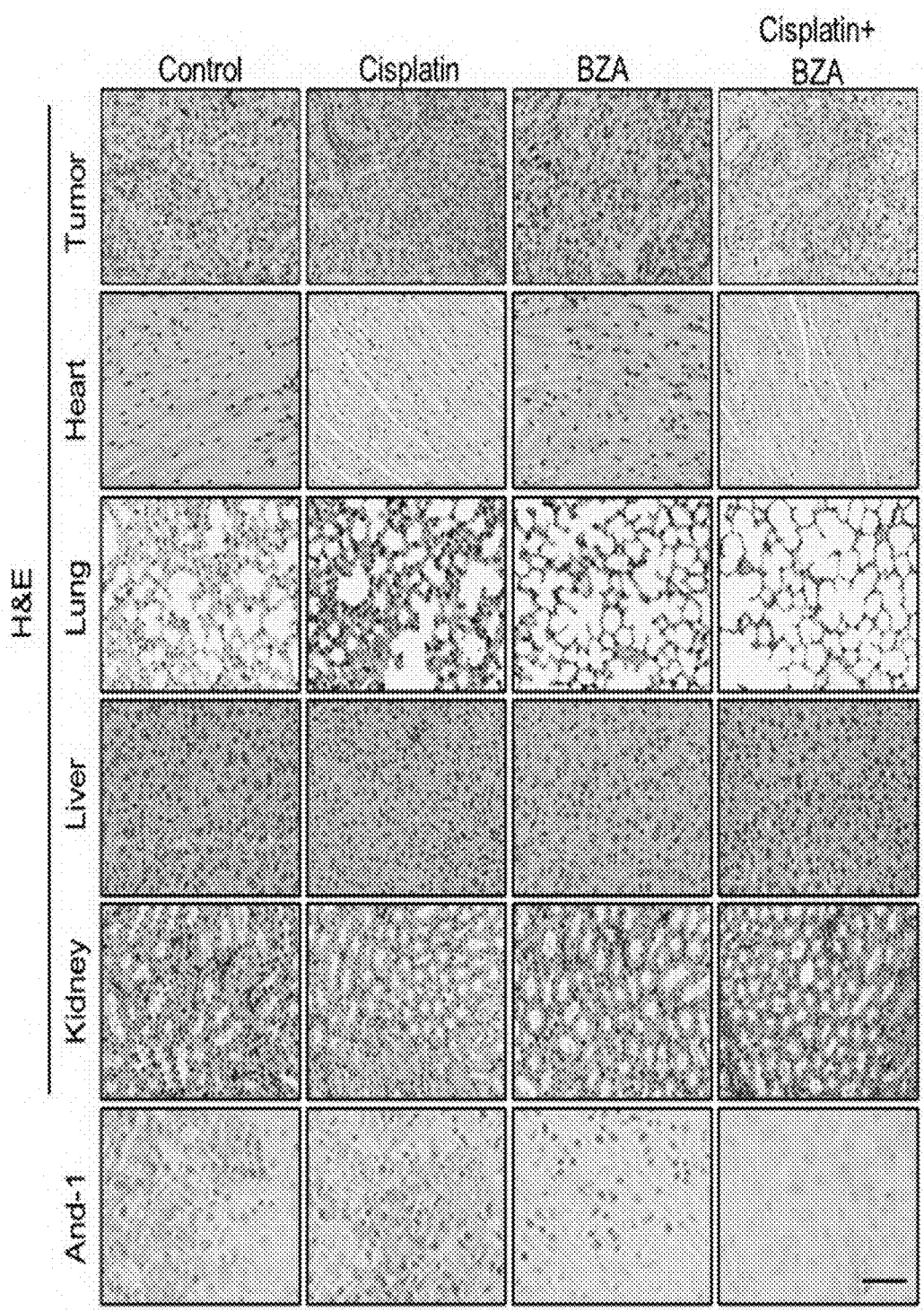

To determine whether And-1 inhibitors can overcome cisplatin resistance in OC cells, the synergy of And-1 inhibitors and cisplatin in IGROV1 CR cells was examined. As shown in FIG. 30A and FIG. 31A, CH3 and BZA exhibited significant synergy with cisplatin to inhibit cell proliferation in IGROV1 CR cells indicated by combination index (CI) (synergism: CI<1; additive effect: CI=1; and antagonism CI>1). Consistently, the clonogenic assays (performed as described in the Examples above) demonstrated that CH3 and BZA have synergy with cisplatin to reduce clonogenic capacity of IGROV1 CR cells (FIGS. 30B-30C and FIGS. 31B-31C).

To assess the efficacy of combination therapy with And-1 inhibitor and cisplatin in vivo, an IGROV1 CR xenograft was treated with vehicle, And-1 inhibitors, cisplatin or combination of cisplatin and And-1 inhibitor via intraperitoneal injection. Similar to cell-based assay result, it was found that the combinational treatments of CH3 and cisplatin, or BZA and cisplatin had excellent synergy in reducing tumor growth as compared to cisplatin treatment alone (FIGS. 30D-30E and FIGS. 31D-31E). Importantly, body weight assessment and H&E staining of heart, liver, kidney, and lung did not show a significant difference between these groups, indicating that combination of CH3 or BZA and cisplatin had no obvious systemic toxicity or side effect on these organs (FIGS. 30F-30G and FIGS. 31F-31G).

IHC analysis of tumor samples showed that CH3 and BZA suppressed expression of And-1, indicating that CH3 and BZA indeed targeted And-1 in vivo (FIGS. 30G-30H and FIGS. 31G-31H). Together these results demonstrated that inhibition of And-1 was a promising therapeutic approach to overcome platinum-resistance in OC.

Example 14. Stability Test

The liquid chromatography conditions of reference substance BF-175:

The chromatograph is Essentia LC-16 high performance liquid chromatograph, Dionex UltiMate 3000 liquid chromatograph; chromatographic column is XAqua Ph 5 μM 100 A 4.6×250 mm; column temperature is 35° C.; mobile phase is acetonitrile/water 70:30; flow rate is 1.000 mL/min; injection volume 10 μL; detection wavelength 315 nm. Pipette 20 μL of 1 mg/mL acetonitrile stock solution into 4 10 mL volumetric flasks, add 4 mL 0.1M hydrochloric acid (or 4 mL 0.1M sodium hydroxide) to each, keep in a 37° C. water bath, respectively take out at 5 min, 1 h, and dilute with acetonitrile To the mark, mix well, filter, and inject. The stability of the sample in 0.1M hydrochloric acid and sodium hydroxide was investigated.

Compound Liquid Chromatography Conditions:

The chromatograph is Essentia LC-16 high performance liquid chromatograph, Dionex UltiMate 3000 liquid chromatograph; chromatographic column is XAqua Ph 5 μM 100 A 4.6×250 mm; column temperature is 35° C.; mobile phase is acetonitrile/water 60:40; flow rate is 1.000 mL/min; injection volume 10 μL; detection wavelength 313 nm. Pipette 200 μL of 0.1 mg/mL acetonitrile stock solution into 8 10 mL volumetric flasks, add 4 mL 0.1M hydrochloric acid (or 4 mL 0.1M sodium hydroxide) to each, keep in a 37° C. water bath, and take them out at 5 min, 2 h, 5 h, 19 h respectively. Dilute to volume with acetonitrile, mix well, filter, and inject. The stability of the sample in 0.1M hydrochloric acid and 0.1M sodium hydroxide was investigated.

Figure 32:
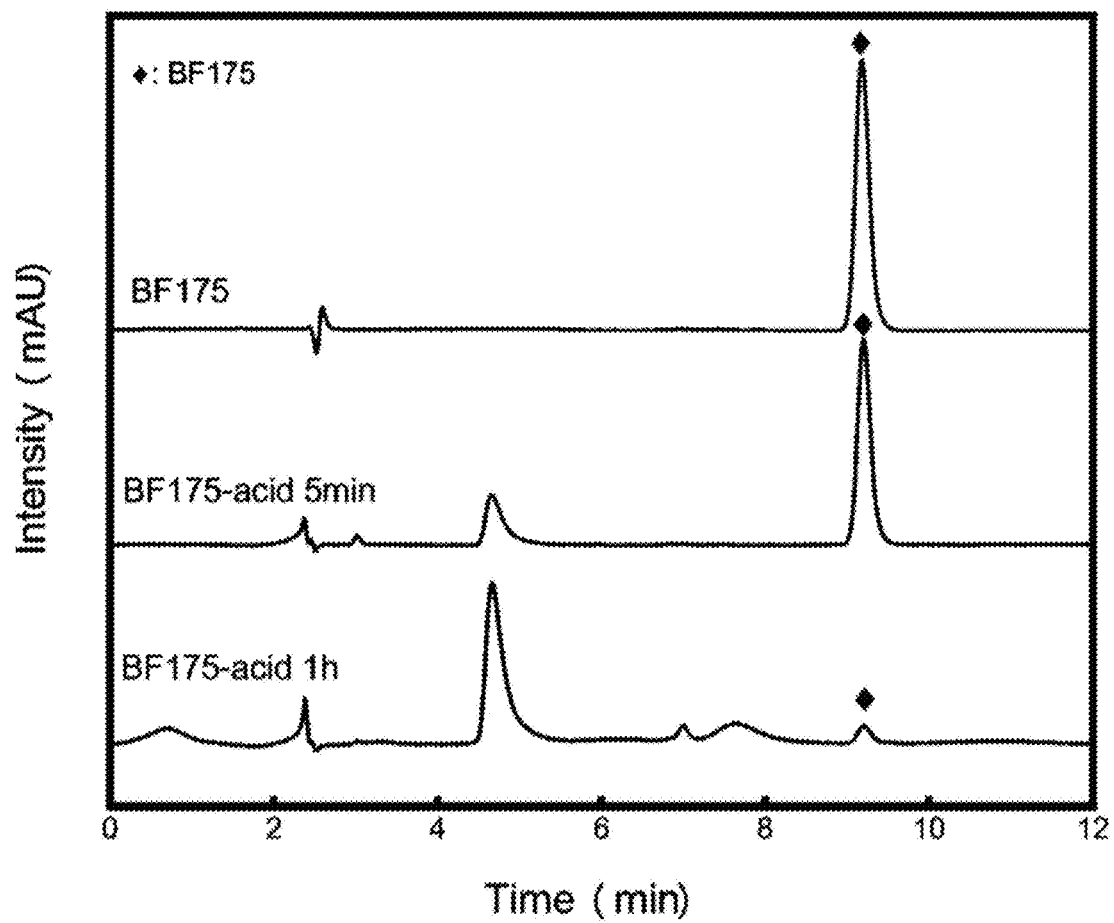
FIG. 32 shows HPLC results of BF-175 and its derivatives.

The results are detailed in FIG. 32 of the description: HPLC results of BF-175 and its derivatives. (A): HPLC analysis result of BF-175; (B): HPLC analysis result of BF-175 in 0.1M hydrochloric acid for 5 minutes; (C): BF-175 in 0.1M hydrochloric acid for 5 minutes HPLC analysis results.

The above results prove that BF-175 is extremely unstable under acidic conditions, while its derivatives are stable under the same conditions.

Example 15. RT-PCR Detection Assay

1. Experimental reagent
2. The experimental steps are as follows:
2.1 AN3CA cell recovery and culture (10% serum 1% double antibody in MEM medium);
2.2 passages (passage at a ratio of 1:2);
2.3 Place 6 well plates when the cell status is good, $5 \times 10^5$ Well, culture overnight;
2.4 adding medicine: diluting the final concentration of the drug with a culture medium to 10 μM, 2 mL/well;
2.5 adding medicine for 48 h, and then extracting RNA;
2.5.1 removing the culture medium, adding 0.5 mL/hole Trizol to lyse the cells, repeatedly blowing and beating the cells by a pipette after 5 min, completely lysing the cells, transferring the cells into a 1.5 mL EP tube without RNase, and standing the tube for 5 min;
2.5.2 adding 200 mul chloroform, shaking rapidly, mixing, standing for 10 min 12000 rpm/15 min;
2.5.3 carefully taking out the supernatant, transferring the supernatant into an EP tube, adding isopropanol with the same volume, reversing, uniformly mixing, standing for 10 min, and centrifuging at 12000 rpm/10 min;
2.5.4 removing the supernatant, adding 1 mL of 75% ethanol for washing, centrifuging at 8000 rpm/5 min once, carefully removing the supernatant, standing at room temperature for 10 min to volatilize the ethanol, and dissolving the precipitate with 40 μL of DEPC treated water when the precipitate becomes transparent;
2.5.5 RNA concentration was measured and DEPC-treated water was diluted to 100 ng/μL
2.6 reverse transcription: Kit Takara (PrimeScript RT reagent Kit (Perfect Real Time)

TABLE 3

Compound induced SCD-1 gene expression content change

| Compound | R1 | R2 | R3 | R4 | R5 | Relative mRNA expression of SCD-1 |
|---|---|---|---|---|---|---|
| XIV | —H | —Cl | —H | —Cl | —H | 0.46 |
| IX | —H | —F | —H | —H | —H | 0.72 |
| X | —H | —Cl | —H | —H | —H | 0.56 |
| XII | —H | —OCH3 | —H | —H | —H | 0.62 |
| XIII | —H | —H | —H | —H | —H | 0.71 |
| II | —H | —CF3 | —H | —H | —H | 0.39 |
| III | —H | —Cl | —Cl | —H | —H | 0.64 |
| IV | —H | —CF3 | —H | —CF3 | —H | 0.42 |
| V | —H | —CF3 | —H | —F | —H | 0.72 |
| VI | —CF3 | —H | —H | —H | —H | 1.03 |
| VII | —H | —H | —CF3 | —H | —H | 1.07 |
| XII | —H | —OCF3 | —H | —H | —H | 0.67 |
| BF175 | | | | | | 0.45 |
| DMSO | | | | | | 1 |
| benzoxaborole | | | | | | 1.02 |
| travaborole | | | | | | 1.08 |

RT-PCR results show that all the compounds except compounds VI and VII can reduce the relative mRNA expression level of the SREBP target gene SCD-1 to different degrees, wherein the activities of compounds II and IV are better than those of BF-175.

Figure 33:
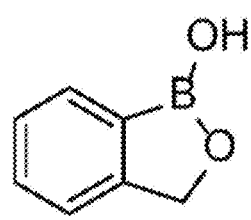
FIG. 33 shows structural formulas of the compounds benzoxaborole and travaborole.
Figure 33:
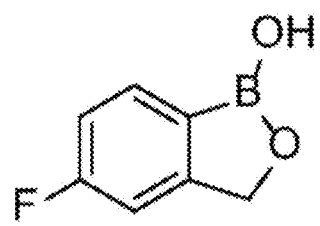

Although benzoxaborole and travaborole also have the structure of benzo borone hetero-oxolane (structural formula shown in FIG. 33), they do not have the activity of reducing the expression of SCD-1 gene (see Table 3). Compared with compounds II, IV, XIV, IX, X, XI, XII, III, etc., benzoxaborole and travaborole do not contain structural fragments of substituted stilbenes. Therefore, the preliminary structure-activity relationship suggests that the structure of the benzo-boron-hetero-oxolane of which the parent nucleus is stilbene is the active structure of the compound.

Example 16. Assay for Cell Clonogenic Assay

1. The experimental steps are as follows:
1.1 AN3CA cell recovery and culture (MEM medium, 10% serum, 1% double antibody);
1.2 Passages (1:2 ratio passage);
1.3 When the cell state is good, laying 6-hole plates, 500/hole, and culturing overnight;
1.4 Adding medicine: diluting the final concentration of the drug with a culture medium to 10 μM, 2 mL/well;
1.5 Adding medicine in a liquid changing mode every two days;
1.6 Frequent observation. The culture was terminated when macroscopic colonies appeared in the culture dish. The supernatant was discarded, carefully rinsed 2 times with PBS and air dried. Cells were fixed with 5 mL of 4% paraformaldehyde for 30 minutes or with methanol for 10 minutes. And (3) removing the stationary liquid after air drying, adding a proper amount of GIMSA, dyeing for 10-30 minutes by using the dyeing liquid, then slowly washing away the dyeing liquid by using running water, and air drying.
1.7 Plates were inverted and overlaid with a piece of transparent film with grid and clones were counted either directly with the naked eye or with a microscope (low power) for clones larger than 10 cells. And finally calculating the clone formation rate.
1.8 Percent colony formation rate (number of clones/number of inoculated cells)×100%

Figure 34:
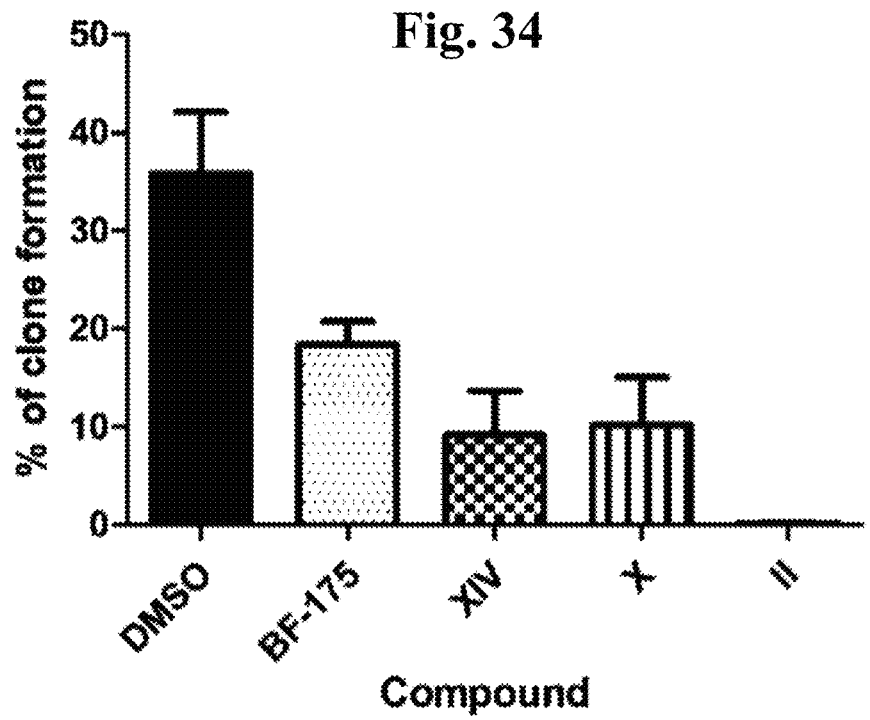
FIG. 34 shows the effect of representative compounds on the clonal formation rate of AN3CA cells.

The results of the clonogenic experiments are shown in FIG. 34, and it can be seen that representative compounds all have different degrees of inhibitory effects on the clonogenic rate of AN3CA cells. The effect of 5 μM compound XIV on inhibiting the clonogenic rate of AN3CA cells was comparable to that of 10 μM BF 175. The compound II has the most obvious effect of inhibiting the clone formation rate of AN3CA cells, and the compound II with the concentration of 10 μM can completely inhibit the clone formation of AN3CA cells.

Example 17. Cell Proliferation Assay

Figure 35:
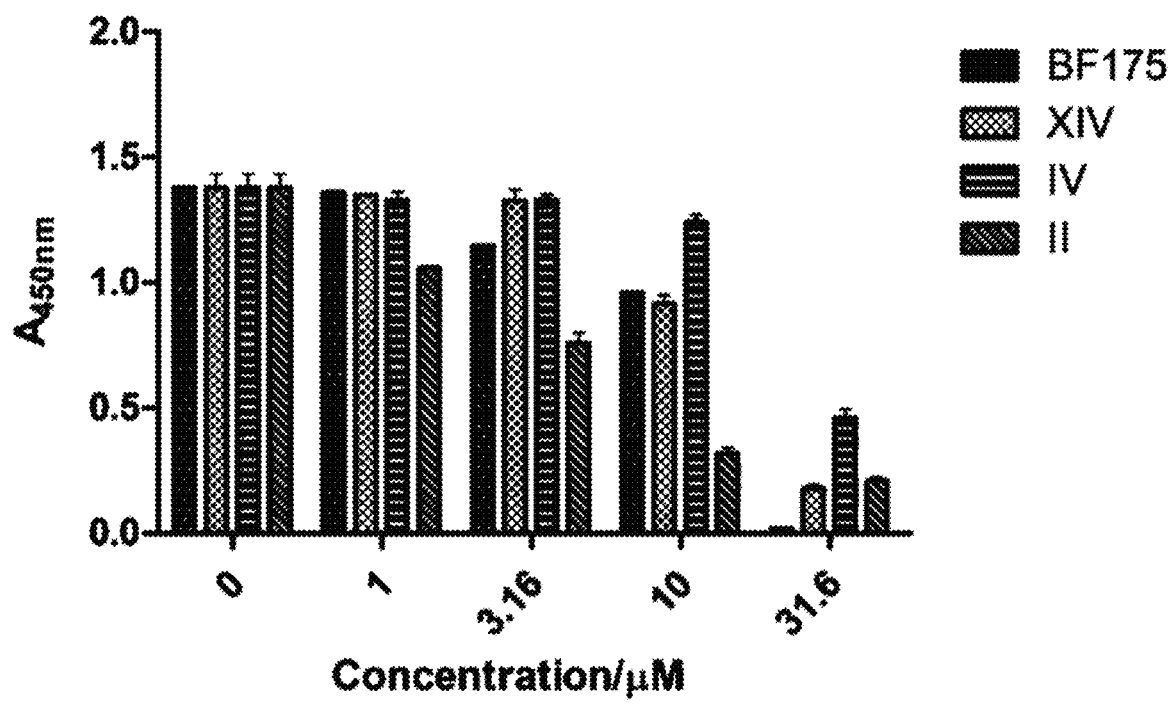
FIG. 35 shows the inhibitory effect of representative compounds on the proliferation of AN3CA cells.

1. The experimental steps are as follows:
1.1 AN3CA cell recovery and culture (MEM medium, 10% serum, 1% double antibody);
1.2 Passages (passage at a ratio of 1:2);
1.3 Place 96-well plate when the cell status is good, $1×10^4$ Well, culture overnight;
culture medium with 10% defatted serum
1.4 Adding medicine: diluting the final concentration of the drug with a culture medium to 10 μM, and treating for 48 h at 100 μL/well;
culture medium with 10% defatted serum
1.5 Addition of 2 μL MTS/well, care taken to prevent bubble formation, 490 nm data after 1-4 h The result is shown in FIG. 35 in the specification. It can be seen that representative compounds II, IV and XIV all have different degrees of inhibition on AN3CA cells, with compound II being superior to BF 175. Compound II inhibited AN3CA cells by 80% at 10 μM.

Example 18. Inhibition of And-1 by Compounds; $IC_{50}$ Values (μM)

TABLE 4

$IC_{50}$ of representative Compounds for inhibition of And-1 in both IGROV1 CR and OV90 CR cells

| | $IC_{50}$ (μM) | |
|---|---|---|
| Compound | IGROV1 CR | OV90 CR |
| III | 7.834 | 13.34 |
| X | 19.17 | 20.57 |
| II | 20.39 | 21.11 |
| XIV | 25.7 | 29.9 |
| IV | 37.57 | 57.89 |
| XIII | 40.99 | 45.64 |
| XII | 34.06 | 37.42 |
| XI | 32.88 | 34.27 |

The results show that the compound has different degrees of inhibition effects on IGROV1 CR and OV90 CR ovarian cancer cells, and the representative compound III has $IC_{50}$ for inhibiting And-1 in IGROV1 CR cells of 7.8 μM.

Example 19. Western Blot Detection of And-1 Protein Expression Experiment

1. Experimental Steps:

Select the A549 cells in good growth condition and inoculate them in a 60 mm petri dish at a density of 500,000. After culturing in a constant temperature incubator at 37° C. and 5% CO2 for 24 hours, add different compounds of the same concentration (5 μM) and continue culturing for 24 hours before collecting Cells were subjected to Western blotting experiments to compare with untreated cells to detect the inhibitory effect of each compound on the expression of And-1 protein.

Figure 36:
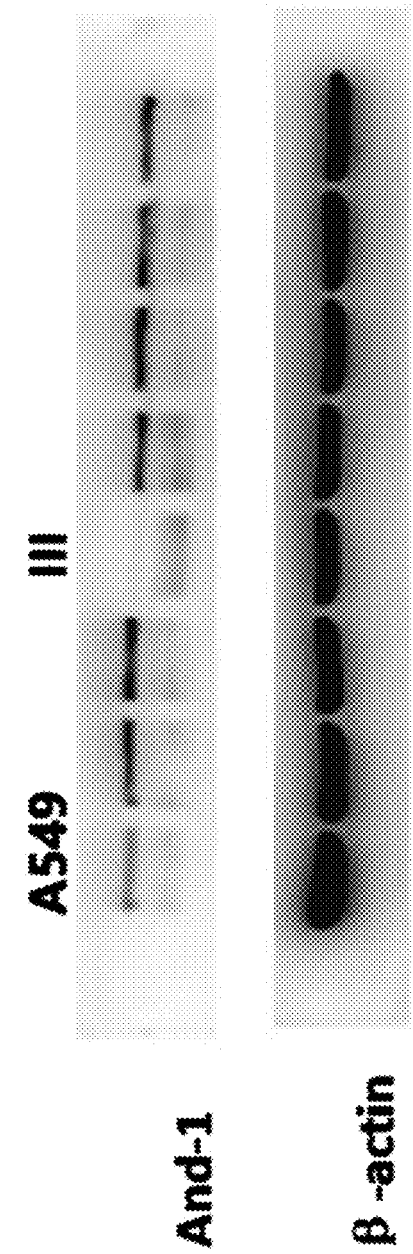
FIG. 36 shows Western Blot results of compound III (A549 cell line).

The results are shown in FIG. 36 of the specification. The representative compound III can significantly inhibit the expression of And-1 protein in A549 cell line.

Therefore, the compounds of Formula I can inhibit the activities of Srebp and And-1 in various cell lines to varying degrees. Among them, the representative compounds III, X, and II have a high inhibitory effect on the Srebp of human endometrial cancer AN3CA cells at 10 μM, and have a good effect on the And-1 protein of human ovarian cancer cells IGROV1, OV90 and lung cancer cell A549. The inhibitory activity. The compound represented by formula I is expected to be an antitumor drug or a radiochemotherapy sensitizer.

What is claimed is:

1. A compound represented by formula I or a pharmaceutically acceptable salt thereof:

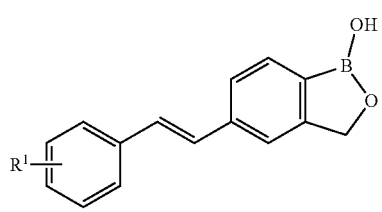

I wherein, $R^1$ is independently mono-or poly-substituted with hydrogen, trifluoromethyl, trifluoromethoxy, nitro, cyano, halogen, C1-C10 alkyl, or —$OR^2$, wherein $R^2$ is independently selected from hydrogen or C1-C10 alkyl.

2. The compound of claim 1, wherein the at least one compound represented by formula I or a pharmaceutically acceptable salt thereof comprises a compound selected from the group consisting of

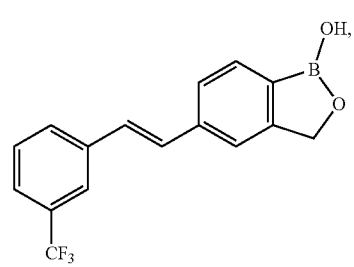

II

-continued

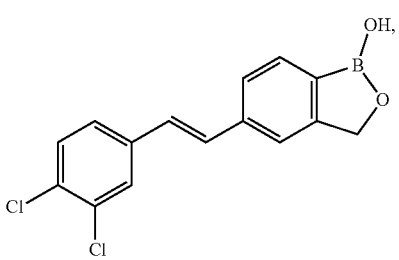

III

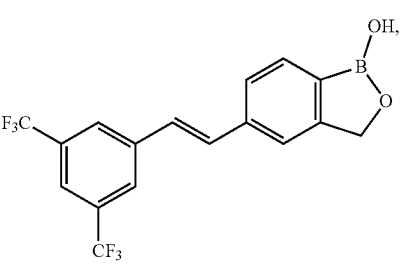

IV

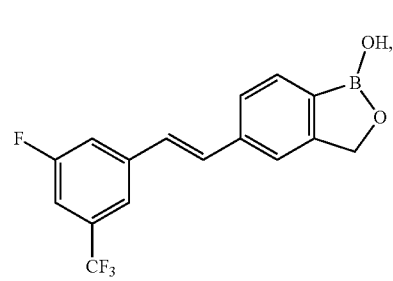

V

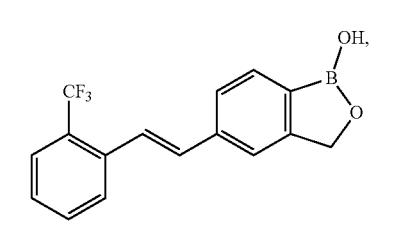

VI

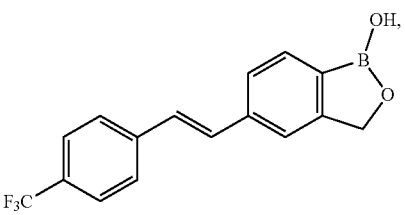

VII

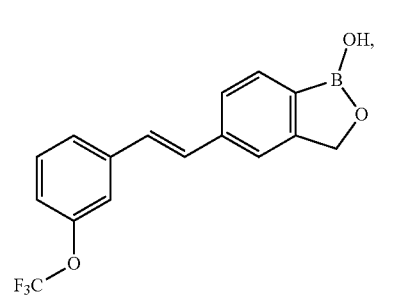

VIII

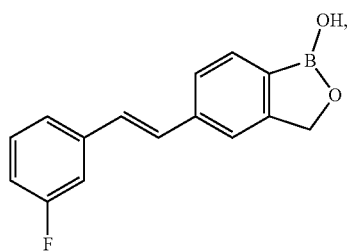

IX

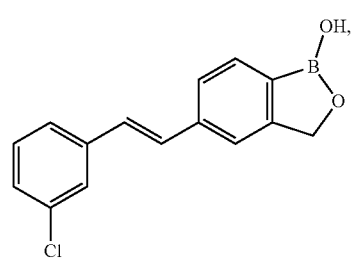

X

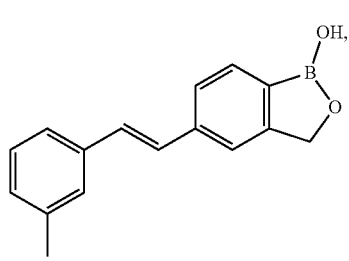

XI

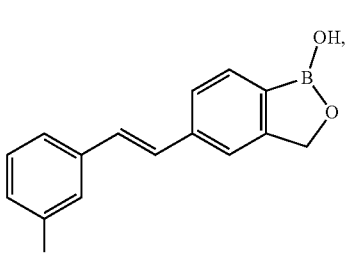

XII

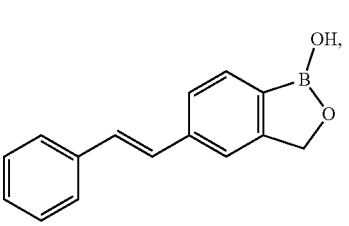

XIII

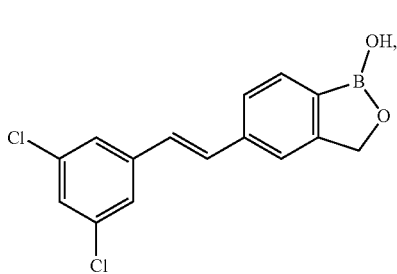

XIV

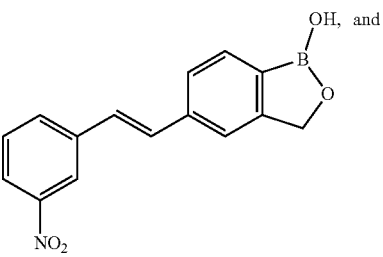

XV

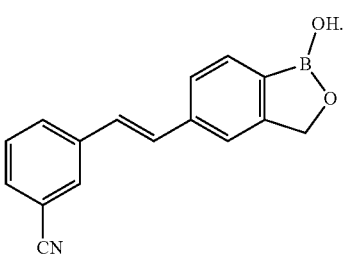

XVI

3. The compound of claim 1, wherein the compound represented by formula I or a pharmaceutically acceptable salt thereof comprises a compound represented by formula III,

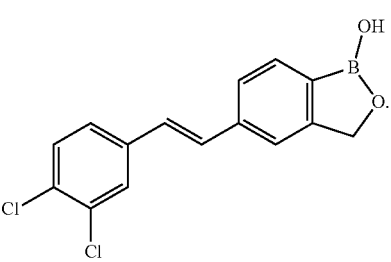

III

4. A method for treating a subject in need thereof, the method comprising: administering to a subject having one or more tumors a therapeutically effective amount of a pharmaceutical composition comprising the compound represented by formula III,

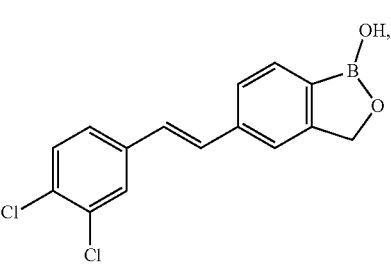

III and at least one pharmaceutically acceptable excipient, wherein, following administration, anti-tumor activity is increased in the subject.

5. The method of claim 4, wherein the one or more tumors comprises a testicular tumor, ovarian tumor, cervical tumor, kidney tumor, bladder tumor, head-and-neck tumor, liver tumor, stomach tumor, lung tumor, endometrial tumor, esophageal tumor, breast tumor, cervical tumor, central nervous system tumor, germ cell tumor, prostate tumor, neuroblastoma, sarcoma, melanoma, mesothelioma, osteogenic sarcoma, or any combination thereof.

6. The method of claim 4 wherein the one or more tumors comprises a breast tumor, an ovarian tumor, or any combination thereof.

7. The method of claim 4, wherein the subject is resistant to at least one anticancer drug therapy.

8. The method of claim 7, wherein the at least one anticancer drug therapy comprises one or more platinum-based chemotherapeutics.

9. A method of preparing at least one compound of claim 1,
the method comprising:
   a. reacting a compound represented by Compound A with concentrated hydrochloric acid and paraformaldehyde to obtain a compound represented by Compound B;
   b. reacting a compound represented by Compound B with triphenylphosphonium in an aprotic solvent to obtain a compound represented by Compound C;
   c. producing a compound represented by Compound E from compounds represented by Compound C and Compound D under strong base conditions;
   d. reacting a compound represented by Compound E with trifluoromethanesulfonic anhydride in dichloromethane to obtain a compound represented by Compound F;
   e. reacting a compound represented by Compound F with pinacol diboronic acid or diboronic acid under palladium salt catalyst to obtain a compound represented by Compound G; and
   f. reacting a compound represented by Compound G with a reducing agent such and adding acid to obtain a compound represented by Compound H, wherein the reducing agent comprises sodium borohydride, tetrahydroaluminum lithium, or any combination thereof;

wherein:

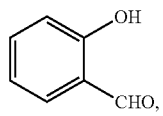
Compound A

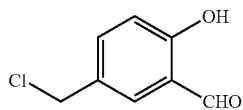
Compound B

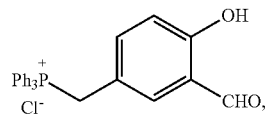
Compound C

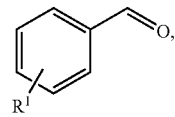
Compound D

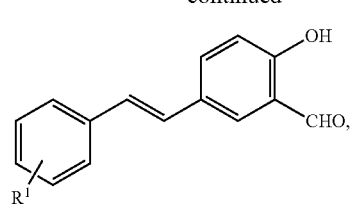
Compound E

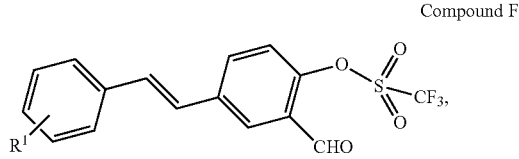
Compound F

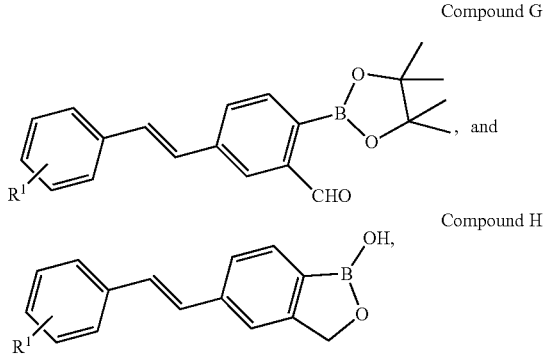
Compound G

Compound H wherein $R^1$ is independently mono-or poly-substituted with hydrogen, trifluoromethyl, trifluoromethoxy, nitro, cyano, halogen, C1-C10 alkyl, or —$OR^2$,
wherein $R^2$ is independently selected from hydrogen or C1-C10 alkyl.

10. The method of claim 9, wherein the strong base conditions of step (iii) are strong alkaline conditions comprising sodium methoxide, sodium ethoxide, sodium tert-butoxide, sodium isopropoxide, butyl lithium, sodium hydroxide, lithium hydroxide, potassium hydroxide, or any combination thereof.

11. The method of claim 9, wherein steps (iii) and (v) are performed at about 80° C.

12. The method of claim 9, wherein steps (iv) and (vi) are performed at about 0° C.

13. The method of claim 9, wherein the palladium salt catalyst of step (v) comprises palladium acetate, palladium chloride, tetrakis(triphenylphosphorus) palladium, bis(acetonitrile) palladium dichloride, bis(triphenylphosphorus) palladium chloride, 1,1'-[bis(diphenylphosphorus)ferrocene]palladium dichloride, bis(benzonitrile)palladium dichloride, 1,1'-[bis(di-tert-butylphosphorus)ferrocene] Palladium dichloride, bis(tricyclohexylphosphorus) palladium dichloride, bis(o-toluene)palladium dichloride, or any combination thereof.

14. The method of claim 9, wherein step (v) is performed under an alkaline condition, wherein the alkaline condition comprises a base comprising sodium acetate, potassium acetate, sodium methoxide, sodium ethoxide, potassium methoxide, potassium ethoxide, sodium fluoride, potassium fluoride, or any combination thereof.

15. The method of claim 9, wherein step (v) is performed in a polar solvent, wherein the polar solvent comprises N,N-dimethylformamide, dimethylsulfoxide, acetonitrile, acetone, methyl ethyl ketone, 1,4-dioxane, water, or any combination thereof.

16. The method of claim 4, further comprising administering to the subject one or more anticancer drugs or one or more platinum-based chemotherapeutics.

17. The method of claim 16, wherein the one or more anticancer drugs comprises gemcitabine, methotrexate, vinblastine, adriamycin, or any combination thereof, and wherein the one or more platinum-based chemotherapeutics comprises cisplatin, carboplatin, nedaplatin, satraplatin, picoplatin, phenanthriplatin, triplatin tetranitrate, or any combination thereof.

18. The method of claim 4, wherein the anti-tumor activity comprises reducing cell proliferation, reducing tumor growth, reducing tumor volume, reducing tumor burden, reducing tumor load, reducing the number of metastatic lesions, or any combination thereof.

\* \* \* \* \*

UNITED STATES PATENT AND TRADEMARK OFFICE
CERTIFICATE OF CORRECTION

PATENT NO. : 12,258,360 B2
APPLICATION NO. : 17/944506
DATED : March 25, 2025
INVENTOR(S) : Wenge Zhu, Jing Li and Yiliang Li Page 1 of 1

It is certified that error appears in the above-identified patent and that said Letters Patent is hereby corrected as shown below:

In the Claims

In Claim 2, Column 63, Line 51, delete "at least one".

Signed and Sealed this
Thirteenth Day of May, 2025

Coke Morgan Stewart
*Acting Director of the United States Patent and Trademark Office*